US008394946B2

(12) United States Patent
Todd et al.

(10) Patent No.: US 8,394,946 B2
(45) Date of Patent: Mar. 12, 2013

(54) MULTICOMPONENT NUCLEIC ACID ENZYMES AND METHODS FOR THEIR USE

(75) Inventors: Alison Velyian Todd, Glebe (AU); Donald John Birkett, Mosman (AU); Tram Bich Doan, Fairfield West (AU); Elisa Mokany, Kirrawee (AU)

(73) Assignee: Speedx Pty Ltd, Eveleigh, NSW (AU)

( * ) Notice: Subject to any disclaimer, the term of this patent is extended or adjusted under 35 U.S.C. 154(b) by 808 days.

(21) Appl. No.: 11/544,926

(22) Filed: Oct. 6, 2006

(65) Prior Publication Data

US 2007/0231810 A1  Oct. 4, 2007

Related U.S. Application Data

(60) Provisional application No. 60/726,291, filed on Oct. 13, 2005, provisional application No. 60/724,567, filed on Oct. 7, 2005.

(51) Int. Cl.
*C07H 21/04* (2006.01)
*C12Q 1/68* (2006.01)
*C12N 5/00* (2006.01)
*C12N 5/02* (2006.01)

(52) U.S. Cl. ........ 536/24.5; 536/23.1; 435/6.1; 435/375

(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,176,995 A | 1/1993 | Sninsky et al. |
| 5,545,729 A | 8/1996 | Goodchild et al. |
| 5,589,332 A | 12/1996 | Shih et al. |
| 5,807,718 A | 9/1998 | Joyce |
| 6,140,055 A | 10/2000 | Todd et al. |
| 6,201,113 B1 | 3/2001 | Todd et al. |
| 6,326,174 B1 | 12/2001 | Joyce et al. |
| 6,365,724 B2 | 4/2002 | Todd et al. |
| 6,861,223 B2 | 3/2005 | Jenne et al. |
| 7,141,665 B1 | 11/2006 | Joyce et al. |
| 7,553,945 B2 | 6/2009 | Leontis |
| 2002/0102568 A1 | 8/2002 | Usman et al. |
| 2003/0013095 A1 | 1/2003 | Taira et al. |
| 2010/0136536 A1 | 6/2010 | Todd et al. |
| 2010/0221711 A1 | 9/2010 | Nauwelaers et al. |
| 2011/0143338 A1 | 6/2011 | Todd et al. |
| 2012/0101267 A1 | 4/2012 | Todd et al. |

FOREIGN PATENT DOCUMENTS

| | | |
|---|---|---|
| AU | PI5911 | 12/1987 |
| AU | 199959817 B2 | 10/2000 |
| EP | 0 552 931 A1 | 7/1993 |
| EP | 1063296 A1 | 12/2000 |
| WO | 9617086 A1 | 6/1996 |
| WO | 9627026 A1 | 9/1996 |
| WO | 9849346 A1 | 11/1998 |
| WO | 9945146 A1 | 9/1999 |
| WO | 9950452 A1 | 10/1999 |
| WO | 0058505 A1 | 10/2000 |
| WO | 03/089650 A2 | 10/2003 |
| WO | 2005/051174 A2 | 6/2005 |
| WO | 2005/073405 A2 | 8/2005 |
| WO | WO 2007/041774 A1 | 4/2007 |
| WO | WO 2007/065926 A1 | 6/2007 |
| WO | WO 2008/040095 A1 | 4/2008 |
| WO | WO 2008/054834 A2 | 5/2008 |
| WO | WO 2009/022125 A1 | 2/2009 |
| WO | WO 2010/017246 A1 | 2/2010 |

OTHER PUBLICATIONS

Achenbach, J., Nutiu, et. al., (2005) Structure-switching allosteric deoxyribozymes. Analytica Chimica Acta. 534(1): 41-51.
Adams, J. (1992) Biotin amplification of biotin and horseradish peroxidase signals in histochemical stains. J Histochem Cytochem. Oct;40(10): 1457-63.
Bobrow, M., Harris, T., et. al., (1989) Catalyzed reporter deposition, a novel method of signal amplification. Application to immunoassays. J Immunol Methods. Dec 20(125(1-2)): 279-85.
Breaker, R.R., and Joyce, G.F., (1994) A DNA enzyme that cleaves RNA. Chem Biol. Dec;1(4): 223-9.
Brown, A., Li, J., et. al., (2003) A lead-dependent DNAzyme with a two-step mechanism. Biochem. Jun 17;42(23): 7152-61.
Cairns, M., King, et. al., (2000) Nucleic acid mutation analysis using catalytic DNA. Nucl Acids Res. 28(3): e9.
Cairns, M., King, et. al., (2003) Optimisation of the 10-23 DNAzyme-substrate pairing interactions enhanced RNA cleavage activity at purine-cytosine target sites. Nucl Acids Res. Jun. 1;31(11): 2883-9.
Carmi, N., Shultz, et. al., (1996) In vitro selection of self-cleaving DNAs. Chem Biol. 3(12): 1039-46.
Chehab, F.F., et. al., (1987) Detection of sickle cell anaemia and thalassaemias [letter] [published erratum appears in Nature 1987 Oct. 22-28;329(6141):678]. Nature. 329(6137): 293-4.
Chen, C., Ridzon, et. al., (2005) MicroRNA quantitation by looped RT-PCR. AACR. poster.
Cheng, S., Merlino, et. al., (1993) A versatile method for coupling of proteins to DNA:synthesis of a2-macroglobin-DNA conjugates. Nucleic Acid Research: 11, 659-669.
Compton, J. (1991) Nucleic acid sequence-based amplification. Nature. 350(6313): 91-2.
Cruz, R. P. et. al., (2004) Dinucleotide junction cleavage versatility of 8-17 deoxyribozyme. Chem. Biol. Jan:11 (1):57-67.
Cuenoud, B., and Szostak, J.W., (1995) A DNA metalloenzyme with DNA ligase activity. Nature. 375(6532): 611-4.

(Continued)

Primary Examiner — Dana Shin
(74) Attorney, Agent, or Firm — Alston & Bird LLP

(57) ABSTRACT

The present invention relates to Multicomponent Nucleic Acid Enzymes (MNAzymes) and methods for their use. MNAzymes comprise two or more oligonucleotide components which self-assemble in the presence of one or more MNAzyme assembly facilitator molecules to form a catalytically active structure. Compositions for making MNAzymes, and collections of MNAzymes are provided. Also provided are methods for using MNAzymes for the detection, identification and/or quantification of one or more targets. The methods can be practiced in solution-based assays or in assays where one or more reaction components are attached to a support structure. The methods allow for multiplexing the MNAzyme detection to detect multiple targets in a single reaction. Also provided are kits for making the compositions, and for practicing the methods provided herein.

25 Claims, 25 Drawing Sheets

OTHER PUBLICATIONS

Eigen, M., and Rigler, R., (1994) Sorting single molecules: application to diagnostics and evolutionary biotechnology. Proc Natl Acad Sci U S A. 91(13): 5740-7.

Elghanian, R., Storhoff, et. al., (1997) Selective colorimetric detection of polynucleotides based on the distance-dependent optical properties of gold nanoparticles. Science. 277: 1078-1079.

Fahy, E., Kwoh, et. al., (1991) Self-sustained sequence replication (3SR): an isothermal transcription-based amplification system alternative to PCR. PCR Methods Appl. Aug;1(1): 25-33.

Fokina, A.A. et al., (2004) Two-Component 10-23 DNA Enzymes. Nucleosides, Nucleotides & Nucleic Acids. vol. 23, Nos. 6 & 7, pp. 1031-1035.

Hall, J.G., et. al., (2000) From the Cover: Sensitive detection of DNA polymorphisms by the serial invasive signal amplification reaction. Proc Natl Acad Sci USA. 97(15): 8272-8277.

Haseloff, J., and Gerlach, W.L., (1988) Simple RNA enzymes with new and highly specific endoribonuclease activities. Nature. Aug 18; 334(6183): 585-91.

Huizenga, D.E., and Szostak, J.W., (1995) A DNA aptamer that binds adenosine and ATP. Biochemistry. 34: 656-665.

Impey, H., Applegate, et, al., (2000) Factors that influence deoxyribozyme cleavage during polymerase chain reaction. Anal Biochem. Nov 15; 286(2): 300-3.

Jonas, V., et. al., (1993) Detection and identification of Mycobacterium tuberculosis directly from sputum sediments by amplification of rRNA. Journal of Clinical Microbiology. 31: 2410-2416.

Kuwabara, T., et. al., (1999) tRNAVal-heterodimeric maxizymes with high potential as gene inactivating agents: Simultaneous cleavage at two sites in HIV-1 tat mRNA in cultured cells. Proc Natl Acad Sci USA. 96(5): 1886-1891.

Kuwabara, T., Warashina, et. al., (2000) Allosterically controllable maxizymes cleave mRNA with high efficiency and specificity. TIBTECH. Nov (18): 462-468.

Lee, J.F., et. al. (2004) Aptamer Database. Nucl Acids Res. 32(90001): D95-100.

Levy, M. and Ellington, A.D., (2003) Exponential growth by cross-catalytic cleavage of deoxyribozymogens. Proc Natl Acad Sci USA. 100(11):6416-21.

Li, J., et al., (2000) In vitro selection and characterization of a highly efficient Zn(II)-dependent RNA-cleaving deoxyribozyme. Nucl. Acids Res. 28(2): 481-488.

Li, Y., and Sen, D., (1996) A catalytic DNA for porphyrin metallation [letter]. Nat. Struc Biol. 3(9):743-7.

Liu, J., and Lu, Y., (2004) Adenosine-dependent assembly of aptazyme-functionalized gold nanoparticles and its application as a colorimetric biosensor. Analytical Chemistry. 76:1627-1632.

Lohse, P.A., and Szostak, J.W., (1996) Ribozyme-catalysed amino-acid transfer reactions. Nature 381(6581): 442-4.

McCall, M., et. al., (1992) Minimal Sequence Requirements for Ribozyme Activity. Proc Natl Acad Sci USA. 89(13): 5710-5714.

Mirkin, C., et. al., (1996) A DNA-based method for rationally assembling nanoparticles into macroscopic materials. Nature 382:607-609.

Nagamine, K., et. al., (2002) Isolation of Single-Stranded DNA from Loop-Mediated Isothermal Amplification Products. Biochemical and Biophysical Research Communications. 290(4): 1195-1198.

Notomi, T., et. al., (2000) Loop-mediated isothermal amplification of DNA. Nucl. Acids Res. Jun 15:28(12): E63.

Oshima, K., et. al., (2003) Maxizymes and Small Hairpin-Type RNAs That Are Driven by a tRNA Promoter Specifically Cleave a Chimeric Gene Associated with Leukemia in Vitro and in Vivo. Cancer Res. 63(20): 6809-6814.

Paul, N. and Joyce, G.F., (2004) Minimal self-replicating systems. Current Opinion in Chemical Biology. 8(6):634-639.

Perreault, J. et. al., (1991) Relationship between 2'-hydroxyls and magnesium binding in the hammerhead RNA domain: a model for ribozyme catalysis. Biochemistry. 30(16):4020-5.

Perreault, J. et. al., (1990) Mixed deoxyribo- and ribo-oligonucleotides with catalytic activity. Nature 344(6266):565-7.

Perriman, R., et. al., (1992) Extended target-side specificity for a hammerhead ribozyme. Gene. 113(2):157-63.

Raap, A., et al., (1995) Ultra-sensitive FISH using peroxidase-mediated deposition of biotin- or fluorochrome tyramides. Hum Mol Genet. Apr; 4(4):529-34.

Raillard, S.A. and Joyce, G.F., (1996) Targeting sites within HIV-1 cDNA with a DNA-cleaving ribozyme. Biochemistry. 35(36):11693-701.

Saiki, R.K., et. al., (1985) Enzymatic amplification of beta-globin genomic sequences and restriction site analysis for diagnosis of sickle cell anemia. Science. 230(4732):1350-4.

Santoro, S.W. and Joyce, G.F., (1997) A general purpose RNA-cleaving DNA enzyme. Proc Natl Acad Sci USA 94:4262-4266.

Santoro, S.W. and Joyce, G.F., (1998) Mechanism and utility of an RNA-cleaving DNA enzyme. Biochem. 37(38):13330-42.

Schubert, S. et. al, (2004) Gaining target access for deoxyribozymes. J. Mol. Biol. May 28:339(2):355-63.

Sidorov, A., et. al., (2004) Sequence-specific cleavage of RNA in the absence of divalent metal ions by a DNAzyme incorporating imidazolyl and amino functionalities. Nucl. Acids Res. Mar 5; 32(4): 1591-601.

Silverman, S. (2004) Breaking up is easy to do (if you're a DNA enzyme that cleaves RNA). Chem. Biol. Jan:11(1):7-8.

Tabor JJ, et. al., (2006) Deoxyribozymes that recode sequence information. Nucleic Acids Research. vol. 34, No. 8, 2166-2172.

Tarasow, T. M. et. al., (1997) RNA-catalysed carbon-carbon bond formation. Nature 389(6646) 54-7.

Todd, A.V., et. al., (2000) DzyNA-PCR: use of DNAzymes to detect and quantify nucleic acid sequences in a real-time fluorescent format. Clin. Chem. May 46(5):625-630.

Urdea, M., (1993) Synthesis and characterization of branched DNA (bDNA) for the direct and quantitative detection of CMV, HBV, HCV and HIV. Clin. Chem. 39:725-726.

Zhang, S. et al. (2002) Aptamer-based multiplexed amplified real-time biochemical detector. Indiana Biosensor Symposium Poster.

Warashina, et al., Working at the Cutting Edge: the Creation of Allosteric Ribozymes, Structure, vol. 8, R207-R212, Nov. 2000, 2000 Elsevier Science Ltd.

Tanabe, et al., Maxizymes, Novel Allosterically Controllable Ribozymes, Can Be Designed to Cleave Various Substrates, Biomacromolecules 2000, vol. 1, pp. 108-117, 2000 American Chemical Society.

Lizardi et al., Mutation detection and single-molecule counting using isothermal rolling-circle amplification, Nature Genetics, vol. 19, Jul. 1998, pp. 225-232.

Breaker et al., DNA Enzymes, Nature Biotechnology, vol. 15, May 1997, pp. 427-431.

Illangasekare et al., Aminoacyl-RNA Synthesis Catalyzed by an RNA, Science, vol. 267, Feb. 3, 1995, pp. 643-647.

U.S. Appl. No. 12/594,656, filed May 17, 2010, Todd, et al.

U.S. Appl. No. 11/697,021, filed Apr. 5, 2007, Todd, et al.

European Supplementary Search Report completed Sep. 10, 2010 for EP 06790343.5.

Kossen, et al. "High-Throughput Ribozyme-Based Assays for Detection of Viral Nucleic Acids" *Chemistry & Biology*. vol. 11, 807-815 Jun. 2004.

Swearingen, et al. "Immobilization of a Catalytic DNA Molecular Beacon on Au for Pb(II) Detection" *Anal. Chem*. 77(2) 442-448 Jan. 15, 2005.

Vaish, et al. "Zeptomole detection of a viral nucleic acid using a target-activated ribozyme" *RNA*. 9: 1058-1072 2003.

Written Opinion and Search Report mailed May 11, 2009 for SG 200802640-3.

Australian Application No. AU2006302729, first Examination Report mailed Jan. 5, 2010.

Australian Application No. AU2006302729, second Examination Report mailed Aug. 5, 2010.

Australian Application No. AU2007304837, first Examination Report mailed Jan. 14, 2010.

Australian Application No. AU2007304837, Notice of Acceptance mailed Sep. 15, 2011.

Australian Application No. AU2007304837, Second Examination Report mailed Mar. 7, 2011.

Australian Application No. AU2007304837, third Examination Report mailed Jun. 27, 2011.

Australian Application No. AU2011202017, first Examination Report mailed Nov. 14, 2011.
Barany, "Genetic disease detection and DNA amplification using cloned thermostable ligase," *PNAS*,88:189-193, (1991).
Benenson et al., "Programmable and autonomous computing machine made of biomolecules" *Nature*, 414(6862):430-434, (2001).
Benenson, et al., "An autonomous molecular computer for logical control of gene expression," *Nature*, 429:423-429, (2004).
Beyer, et al., "A modular DNA signal translator for the controlled release of a protein by an aptamer," *Nucleic Acids Research*, 34(5):1581-1587, (2006).
Chinese application No. 200680045926.6, first Office Action mailed Mar. 9, 2011.
Chinese application No. 200680045926.6, second Office Action mailed May 3, 2012.
Chinese application No. 200780037345.2, Office Action mailed Jan. 18, 2012.
Coppins, et al., "Rational modification of a selection strategy leads to deoxyribozymes that create native 3'-5' RNA linkages," *J. Am. Chem. Soc.*, 126(50):16426-16432, (2004).
Cox, et al., "DNA computation," *Curr Biol*, 11(9):R336, (2001).
Emilsson, et al., "Deoxyribozymes: new activities and new applications," *Cell. Mol. Life Sci*,59:596-607, (2002).
European application No. 06790343.5, first Examination Report mailed Jan. 20, 2010.
European application No. 06790343.5, second Examination Report mailed Aug. 11, 2010.
European application No. 08733324.1, first Examination Report mailed Jun. 30, 2011.
European application No. 08733324.1, first Office Action mailed Feb. 9, 2010.
European application No. 08733324.1, further Examination Report mailed Jan. 31, 2012.
European application No. 08733324.1, second Office Action mailed Jun. 23, 2010.
European application No. EP07815323.6, Office Action mailed Oct. 19, 2011.
European Search Opinion for application EP07815323.6 mailed Jan. 31, 2011.
European Search Report for application EP07815323.6 mailed Jan. 12, 2011.
European Supplementary Search Report/Search Opinion for EP 06790343.5 dated Sep. 16, 2010.
Flynn-Charlebois, et al., "In vitro evolution of an RNA-cleaving DNA enzyme into an RNA ligase switches the selectivity from 3'-5' to 2'-5'," *J. Am. Chem. Soc.*, 125:5346-5350, (2003).
Israel Application No. IL197543, Office Action mailed Jul. 4, 2011.
Israeli application No. IL 201420, first Office Action dated Feb. 23, 2012.
Israeli application No. IL190501, first Office Action dated May 24, 2010.
Israeli application No. IL190501, second Office Action dated Jan. 31, 2012.
Japanese Application No. JP2008-533829, first Office Action mailed Mar. 1, 2012.
Kurata, et al., "MAXIZYMEs: Allosterically controllable ribozymes with biosensor functions," *Journal of Biochemistry and Molecular Biology*, 33(5):359-365, (2000).
Kuwabara, et al., "A Novel Allosterically *tran*-Activated Ribozyme, the Maxizyme, with Exceptional Specificity In Vitro and In Vivo", *Mol. Cell.*, 2:617-627, (1998).
New Zealand Application No. NZ567403, first Examination report mailed Mar. 18, 2010.
New Zealand Application No. NZ567403, second Examination report mailed Aug. 18, 2010.
New Zealand Application No. NZ575802, first Examination Report mailed Sep. 27, 2010.
New Zealand Application No. NZ575802, second Examination Report mailed Nov. 17, 2011.
New Zealand Application No. NZ580129, Examination Report mailed Mar. 8, 2012.
New Zealand Application No. NZ580129, Examination Report mailed Oct. 4, 2010.
New Zealand Application No. NZ580129, second Examination Report mailed Dec. 22, 2011.
PCT Application No. PCT/AU2007/001517, International Search Report, mailed Jan. 19, 2008.
PCT Application No. PCT/AU2007/001517, Written Opinion of the International Searching Authority, mailed Jan. 19, 2008.
PCT Application No. PCT/AU2008/000492, International Search Report, mailed Jul. 4, 2008.
PCT application No. PCT/AU2011/001504, International Search Report, mailed Feb. 17, 2012.
PCT application No. PCT/AU2011/001504, Written Opinion filed Feb. 17, 2012.
PCT International Preliminary Report on Patentability (Chapter 1) for application PCT/AU08/000492 dated Oct. 6, 2009.
PCT International Preliminary Report on Patentability (Chapter 1) for application PCT/AU07/001517 dated Apr. 7, 2009.
Prior et al., "Structure-function correlations derived from faster variants of a RNA ligase deoxyribozyme," *Nucleic Acids Research*, 32(3):1075-1082, (2004).
Sando, et al., "Amplified Nucleic Acid Sensing Using Programmed Self-Cleaving DNAzyme," *J. Am. Chem. Soc.*, 125:15720-15721, (2003).
Schweitzer, et al., "Combining nucleic acid amplification and detection," *Current Opinion in Biotechnology*, 12:21-27, (2001).
Singapore Application No. SG 200901779-9, first Written Opinion mailed Oct. 5, 2010.
Singapore Application No. SG 200901779-9, second Written Opinion mailed May 19, 2011.
Singapore Application No. SG200802640-3, Search and Examination Report mailed Apr. 30, 2010.
Singapore Application No. SG200906638-2, final Examination Report mailed Jun. 16, 2011.
Singapore Application No. SG200906638-2, first Written Opinion mailed Aug. 5, 2010.
Soda, et al., "A novel maxizyme vector targeting a *bcr-abl* fusion gene induced specific cell death in Philadelphia chromosome—positive acute lymphoblastic leukemia," *Blood*104(2):356-363, (2004).
Stojanovic, "Deoxyribozyme-Based Half-Adder," *J. Am. Chem. Soc.*, 125(22):6673-6676, (2003).
Stojanovic, "Deoxyribozyme-Based Ligase Logic Gates and their Initial Circuits," *J. Am. Chem. Soc.*, 127(19):6914-6915, (2005).
Stojanovic, "Deoxyribozyme-Based Logic Gates," *J. Am. Chem. Soc.*, 124(14):3555-3561, (2002).
Stojanovic, et al., "A Deoxyribozyme-Based Molecular Automation," *Nature Biotechnology*, 21(9):1069-1074, (2003).
Supplementary European Search Report and European Search Opinion for application EP08733324.1 mailed Sep. 28, 2010.
U.S. Appl. No. 11/697,021, Non-Final Office Action mailed Dec. 28, 2011.
U.S. Appl. No. 11/697,021, Requirement for Restriction/Election mailed Aug. 23, 2011.
U.S. Appl. No. 12/442,275, Final Office Action mailed Jul. 19, 2012.
U.S. Appl. No. 12/442,275, Non-Final Office Action mailed Nov. 4, 2011.
U.S. Appl. No. 12/442,275, Requirement for Restriction/Election mailed May 4, 2011.
U.S. Appl. No. 12/594,656, Non-Final Office Action mailed Jul. 2, 2012.
U.S. Appl. No. 12/594,656, Requirement for Restriction/Election mailed Mar. 1, 2012.
Van Gijlswijk, R., et. al., (1997) Fluorochrome-labeled tyramides: use in immunocytochemistry and fluorescence in situ hybridization. J. Histochem Cytochem. Mar 45(3):375-82.
Walker, G.T., et. al., (1992) Strand displacement amplification-an isothermal, in vitro DNA amplification technique. Nucl. Acids Res. 20(7):1691-6.
Warashina, M., et. al., (1999) Extremely high and specific activity of DNA enzymes in cells with a Philadelphia chromosome. Chem Biol. Apr 6(6): 237-50.
Xiao, Y. et. al., (2004) Lighting up biochemiluminescence by the surface self-assembly of DNA-hemin complexes. ChemBioChem, 5: 374-379.

Yakimovich, O. et. al., (2003) Influence of DNA aptamer structure on the specificity of binding to Taq DNA polymerase. Biochemistry (Moscow). 68(2):228-235.

Zaborowska, Z, et. al. (2002) Sequence requirements in the catalytic core of the "10-23" DNA enzyme. J. Biol. Chem. 277(43):240617-22.

Hayden, E.J. and Lehman, N. (2006). Self-assembly of a group I intron from inactive oligonucleotide fragments. Chemistry & Biology, vol. 13 (8): 909-18.

International Search Report dated Dec. 4, 2006 for Australian Patent No. PCT/AU2006/001473.

Figure 20
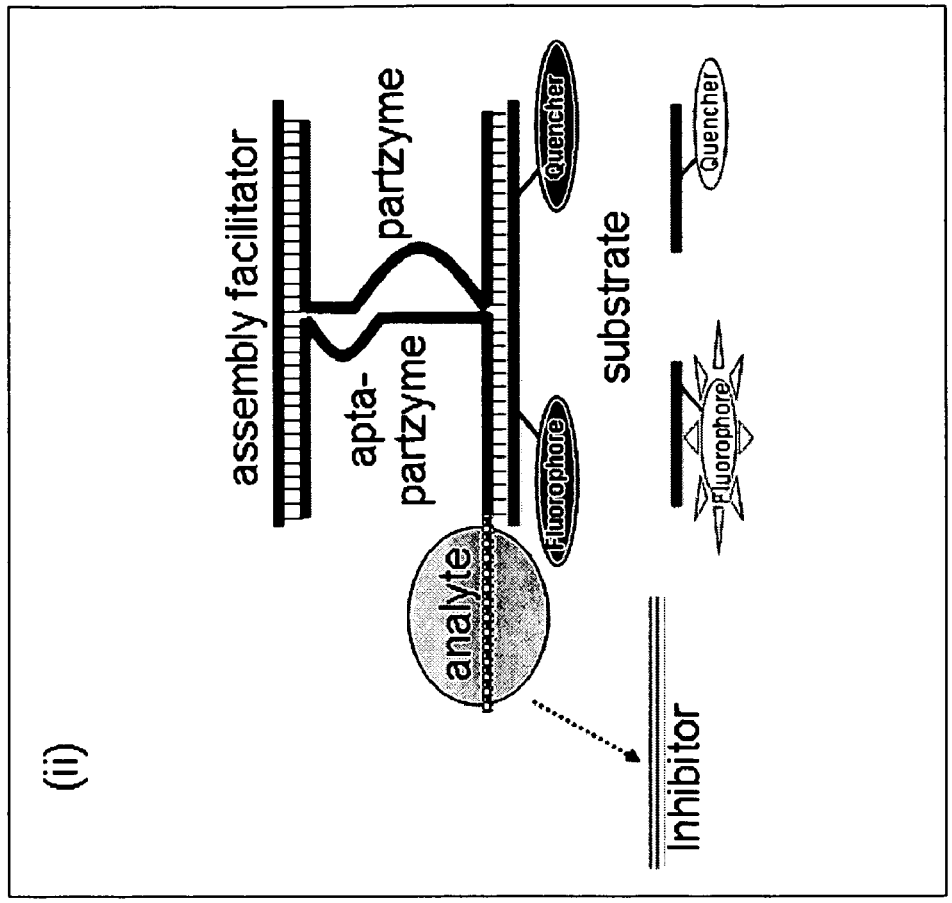
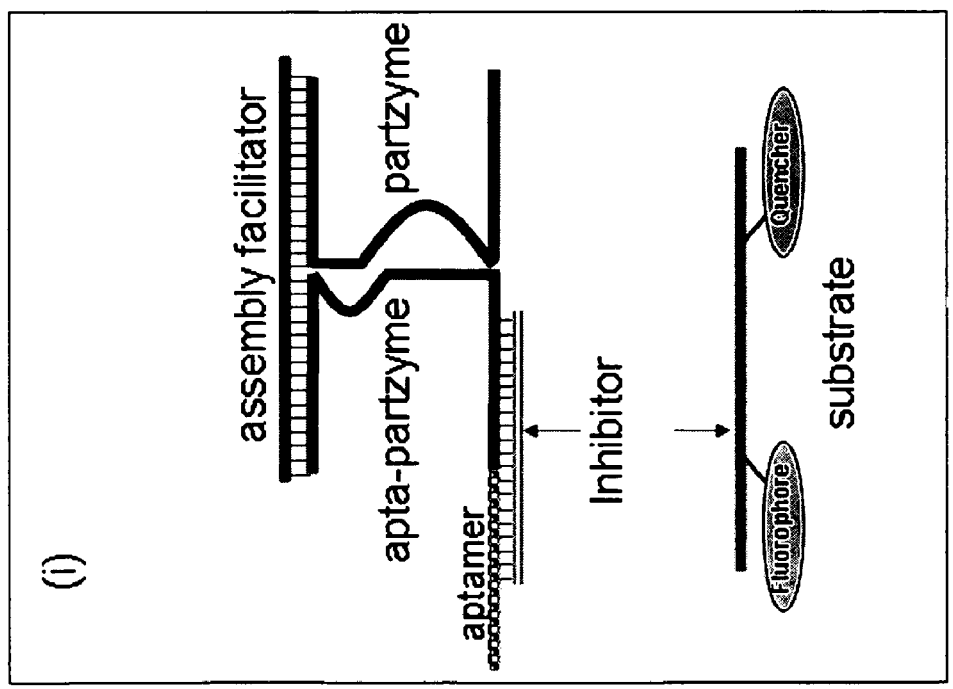

SEQUENCE LISTING

<160> NUMBER OF SEQ ID NOS: 178

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctggtcatc cagcacggtc gaaatagtga gt                                    32

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gctggtcatc cagcagcggt cgaaatagtg agt                                   33

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catctcttct ccgtcgaagt gttcgacaat ggc                                   33

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
catctcttct ccggtgttcg acaatggc                                         28

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catctcttct ccgagcgtgt tcgacaatgg c                                     31

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
actcactata ggaagagatg                                              20

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gctggtcatc cagcacggtc taaatagtga gt                                32

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gccattgtcg aacacctgct ggatgaccag c                                 31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgaccattag gtcgtccaca agctgttacc g                                 31

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tacctgcact acggtcgaaa tagtgagt                                     28

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
catctcttct ccgagctaag cacttta                                      27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
taaagtgctt atagtgcagg ta                                                  22

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caaagtgctt acagtgcagg tagt                                                24

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaagtgctgt tcgtgcaggt ag                                                  22

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaaagtgctt acagtgcagg tagc                                                24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
taaagtgctg acagtgcaga t                                                   21

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caaacgagtc ctggccttgt ccgcacaacg agaggaaacc tt                            42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgcccaggga ggctagctgc ggtggagacg gattacacct tc                            42
```

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caaacgagtc ctggccttgt ctacaacgag aggaaacctt                    40

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcccaggga ggctagctgt ggagacggat tacaccttc                     39

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
aaggtttcct cguccctggg ca                                       22

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaggtgtaa tccgtctcca cagacaaggc caggactcgt ttg                43

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
caagactgga gacaaagtg                                           19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

-continued

```
gcagagtttc ctctgtgata                                              20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
acgtgacgct aaagtgct                                                18

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cgtccgaatg acgtacctgc ac                                           22

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cgaatgacgt acctgcac                                                18

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uaaagugcuu auagugcagg ua                                           22

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: Phosphorylated guanine

<400> SEQUENCE: 29
caaacgagtc ctggccttgt ctacaacgag gttgtgctg                         39

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (39)..(39)
<223> OTHER INFORMATION: Phosphorylated cytosine

<400> SEQUENCE: 30
cggttggtga ggctagctgt ggagacggat tacaccttc                              39

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
cagcacaacc gucaccaacc g                                                 21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cattctatca tcaacgggta                                                   20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caaaggcaga tggatcag                                                     18

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tacctgcact aacaacgaga ggaaacctt                                         29

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgcccaggga ggctagctta agcacttta                                         29

<210> SEQ ID NO 36
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
cagcacaacc gucaccaacc g                                                    21

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: Phosphorylated thymine

<400> SEQUENCE: 37
gaccgtgagg tagtaacaac gagaggaaac ctt                                       33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: Phosphorylated cytosine

<400> SEQUENCE: 38
tgcccaggga ggctagctgg ttgtatagtt gtc                                       33

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugagguagua gguuguauag uu                                                   22

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agcgaagctg agacaactat acaa                                                 24

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 41
cgacgtgacc gtgaggtag                                                19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
catggcacaa gcgaagctga                                               20

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: Phosphorylated guanine

<400> SEQUENCE: 43
gcccccgcct ccaactacaa cgaggttgtg ctg                                33

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Phosphorylated cytosine

<400> SEQUENCE: 44
cggttggtga ggctagcaac gcccgcacct c                                  31

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gttggttacg gtcgcggttc                                               20

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccgaccgtaa ctattcgata cg                                            22

<210> SEQ ID NO 47
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other
<220> FEATURE:
<221> NAME/KEY: modified_base
<222> LOCATION: (3)..(5)
<223> OTHER INFORMATION: a, c, g, t, unknown or other
<220> FEATURE:
<221> NAME/KEY: modified_base
<222> LOCATION: (9)..(11)
<223> OTHER INFORMATION: a, c, g, t, unknown or other
<220> FEATURE:
<221> NAME/KEY: modified_base
<222> LOCATION: (15)..(15)
<223> OTHER INFORMATION: a or g
<220> FEATURE:
<221> NAME/KEY: modified_base
<222> LOCATION: (16)..(16)
<223> OTHER INFORMATION: a or can be missing
<220> FEATURE:
<221> NAME/KEY: modified_base
<222> LOCATION: (17)..(17)
<223> OTHER INFORMATION: a, c, g, t, unknown or other

<400> SEQUENCE: 47
ntnnnagcnn nwcgnnn                                              17

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (11)..(13)
<223> OTHER INFORMATION: a, c, g, t, unknown or other
<220> FEATURE:
<221> NAME/KEY: modified_base
<222> LOCATION: (17)..(17)
<223> OTHER INFORMATION: a, c, g, t, unknown or other

<400> SEQUENCE: 48
nggmtmghnd nnnmgdn                                              17

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggctagctac aacga                                                15

<210> SEQ ID NO 50
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (4)..(6)
<223> OTHER INFORMATION: a, c, g, t, unknown or other
<220> FEATURE:
<221> NAME/KEY: modified_base
<222> LOCATION: (10)..(12)
<223> OTHER INFORMATION: a, c, g, t, unknown or other

<400> SEQUENCE: 50
nntnnnagcn nn                                                       12

<210> SEQ ID NO 51
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: Phosphorylated thymine

<400> SEQUENCE: 51
agatcaagat cattgctcca caacgagagg aaacctt                             37

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(36)
<223> OTHER INFORMATION: Phosphorylated cytosine

<400> SEQUENCE: 52
tgcccaggga ggctagcttc ctgagcgcaa gtactc                              36

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
taaagtgctt atagtgcagg tag                                           23

<210> SEQ ID NO 54
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
```

```
<223> OTHER INFORMATION: a, c, g, t, unknown or other
<220> FEATURE:
<221> NAME/KEY: modified_base
<222> LOCATION: (14)..(16)
<223> OTHER INFORMATION: a, c, g, t, unknown or other

<400> SEQUENCE: 54
nnnnnnacaa cgannn                                                    16

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: Phosphorylated thymine

<400> SEQUENCE: 55
agttcaaatc tgtactgcac cacaacgaga ggcgtgat                             38

<210> SEQ ID NO 56
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: Phosphorylated guanine

<400> SEQUENCE: 56
ctgggaggaa ggctagctct ggaggtggat tcctttgg                             38

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (42)..(42)
<223> OTHER INFORMATION: Phosphorylated adenine

<400> SEQUENCE: 57
actgaataga aatagtgata gatacaacga gtgccatgtt aa                        42

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: Phosphorylated thymine

<400> SEQUENCE: 58
tatcacagcc aaggctagct ccattcctat gactgtagat t                         41

<210> SEQ ID NO 59
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
aaggtttcct cguccctggg ca                                              22

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
cagcacaacc gucaccaacc g                                               21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
atcacgcctc gutcctccca g                                               21

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
ttaacatggc acgutggctg tgata                                           25

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cattgccgac aggatgcaga                                                 20

<210> SEQ ID NO 64
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 64
gagccgccga tccacacg                                                         18

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cactcagcca ctggatttaa                                                       20

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gcgcgtcttt gctttattc                                                        19

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ctttgctgac ctgctggatt a                                                     21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cctgttgact ggtcattaca a                                                     21

<210> SEQ ID NO 69
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: Phosphorylated adenine

<400> SEQUENCE: 69
agatcaagat cattgctcca caacgagtgc catgttaa                                   38

<210> SEQ ID NO 70
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: Phosphorylated cytosine

<400> SEQUENCE: 70
tatcacagcc aaggctagct tcctgagcgc aagtactc                                  38

<210> SEQ ID NO 71
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: Phosphorylated guanine

<400> SEQUENCE: 71
caaacgagtc ctggccttgt ctacaacgag tgcgccatg                                 39

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: Phosphorylated cytosine

<400> SEQUENCE: 72
tacttctccc aaggctagct gtggagacgg attacacctt c                              41

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (12)..(17)
<223> OTHER INFORMATION: a, c, g, t, unknown or other

<400> SEQUENCE: 73
nnrggctagc tnnnnnn                                                         17

<210> SEQ ID NO 74
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
```

```
<223> OTHER INFORMATION: a, c, g, t, unknown or other
<220> FEATURE:
<221> NAME/KEY: modified_base
<222> LOCATION: (12)..(14)
<223> OTHER INFORMATION: a, c, g, t, unknown or other

<400> SEQUENCE: 74
nnnnacaacg annn                                                           14

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: Phosphorylated thymine

<400> SEQUENCE: 75
actgaataga aatagtgata gatacaacga gaggaaacct t                              41

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: Phosphorylated thymine

<400> SEQUENCE: 76
tgcccaggga ggctagctcc attcctatga ctgtagatt                                 39

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: Phosphorylated guanine

<400> SEQUENCE: 77
gctggtcatc cagcagacaa cgaggttgtg ctg                                       33

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(33)
<223> OTHER INFORMATION: Phosphorylated cytosine

<400> SEQUENCE: 78
cggttggtga ggctagctgt gttcgacaat ggc                                       33

<210> SEQ ID NO 79
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
aaggtttcct cguccctggg ca                                           22

<210> SEQ ID NO 80
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (12)..(14)
<223> OTHER INFORMATION: a, c, g, t, unknown or other

<400> SEQUENCE: 80
nnrggctagc tnnn                                                    14

<210> SEQ ID NO 81

<400> SEQUENCE: 81

000

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
taaagtgctt atagtgcagg ta                                           22

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
catggcgcac gutgggagaa gta                                          23

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 84
caagactgga gacaaagtg                                                    19

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcagagtttc ctctgtgata                                                   20

<210> SEQ ID NO 86
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: Phosphorylated thymine

<400> SEQUENCE: 86
ggttgtcgtc agctcgtgta caacgagagg aaacctt                                37

<210> SEQ ID NO 87
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: Phosphorylated guanine

<400> SEQUENCE: 87
tgcccaggga ggctagctcg tgagatgttg ggttaag                                37

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tggtgcatgg ttgtcgtc                                                     18

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ttgcgctcgt tgcggga                                                      17

<210> SEQ ID NO 90
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: Phosphorylated thymine

<400> SEQUENCE: 90
gaagaggcca ataaaggaga gacaacgaga ggcgtgat                              38

<210> SEQ ID NO 91
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: Phosphorylated cytosine

<400> SEQUENCE: 91
ctgggaggaa ggctagctaa caccagcttg ttacacc                               37

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cagggtcatc cattccatgc ag                                              22

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gctagtacca gttgagccag                                                 20

<210> SEQ ID NO 94
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gggctggtca tccagcagta caacgagagg aaacctt                              37

<210> SEQ ID NO 95
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
```
gggctggtca tccagcagta caacaagagg aaacctt        37

<210> SEQ ID NO 96
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gggctggtca tccagcagtt caacgagagg aaacctt        37

<210> SEQ ID NO 97
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gggctggtca tccagcagta catcgagagg aaacctt        37

<210> SEQ ID NO 98
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gggctggtca tccagcagta ctacgagagg aaacctt        37

<210> SEQ ID NO 99
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgcccaggga ggctagcgtg ttcgacaatg gcagca        36

<210> SEQ ID NO 100
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tgcccaggga ggctagagtg ttcgacaatg gcagca        36

<210> SEQ ID NO 101
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgcccaggga ggccagcgtg ttcgacaatg gcagca        36

<210> SEQ ID NO 102
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atgctgccat tgtcgaacac ctgctggatg accagcccaa                              40

<210> SEQ ID NO 103
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aacgtacact gcacgcggtc gaaatagtga gtacctgggg gagtattgcg gaggaaggt        59

<210> SEQ ID NO 104
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
catctcttct ccgagcgtct gtaccgtgta c                                      31

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gtacacggta cagaccgtgc agtgtacgtt                                        30

<210> SEQ ID NO 106
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ccaggtactc actattt                                                      17

<210> SEQ ID NO 107
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: Phosphorylated thymine

<400> SEQUENCE: 107

```
caaacgagtc ctggccttgt cttacaacga gaggaaacct t                 41

<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: Phosphorylated adenine

<400> SEQUENCE: 108
tgcccaggga ggctagcgtg gagacgga                                28

<210> SEQ ID NO 109
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: Phosphorylated adenine

<400> SEQUENCE: 109
tgcccaggga ggctagcgtc gagacgga                                28

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
agcagccaca aaggcaga                                           18

<210> SEQ ID NO 111

<400> SEQUENCE: 111

000

<210> SEQ ID NO 112
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(34)
<223> OTHER INFORMATION: Phosphorylated adenine

<400> SEQUENCE: 112
tgcccaggga ggctagctgt ggagacggat taca                         34

<210> SEQ ID NO 113

<400> SEQUENCE: 113

000
```

<210> SEQ ID NO 114
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (33)..(33)
<223> OTHER INFORMATION: Phosphorylated adenine

<400> SEQUENCE: 114
tgcccaggga ggctagcgtg gagacggatt aca                                33

<210> SEQ ID NO 115
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (37)..(37)
<223> OTHER INFORMATION: Phosphorylated thymine

<400> SEQUENCE: 115
caaacgagtc ctggccttgt ctacgagagg aaacctt                            37

<210> SEQ ID NO 116
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (37)..(37)
<223> OTHER INFORMATION: Phosphorylated adenine

<400> SEQUENCE: 116
tgcccaggga ggctagctac agtggagacg gattaca                            37

<210> SEQ ID NO 117
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (39)..(39)
<223> OTHER INFORMATION: Phosphorylated thymine

<400> SEQUENCE: 117
caaacgagtc ctggccttgt ctcaacgaga ggaaacctt                          39

<210> SEQ ID NO 118
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (35)..(35)

```
<223> OTHER INFORMATION: Phosphorylated adenine

<400> SEQUENCE: 118
tgcccaggga ggctagctag tggagacgga ttaca                                35

<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (42)..(42)
<223> OTHER INFORMATION: Phosphorylated thymine

<400> SEQUENCE: 119
caaacgagtc ctggccttgt ctctacaacg agaggaaacc tt                        42

<210> SEQ ID NO 120
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: Phosphorylated adenine

<400> SEQUENCE: 120
tgcccaggga ggctaggtgg agacggatta ca                                   32

<210> SEQ ID NO 121
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(43)
<223> OTHER INFORMATION: Phosphorylated thymine

<400> SEQUENCE: 121
caaacgagtc ctggccttgt ctgctacaac gagaggaaac ctt                       43

<210> SEQ ID NO 122
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: Phosphorylated adenine

<400> SEQUENCE: 122
tgcccaggga ggctagtgga gacggattac a                                    31

<210> SEQ ID NO 123
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 123
gctacccaac tgttgcatc                                                  19

<210> SEQ ID NO 124
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aacgtacact gcacgcggtc gaaatagtga gtgcggtcgg ctcggggcat tcttagcgtt      60
ttgccccgag ccgaccgc                                                   78

<210> SEQ ID NO 125
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgccccgagc cgaccgaact cactattt                                        28

<210> SEQ ID NO 126
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: Phosphorylated thymine

<400> SEQUENCE: 126
actggatgtc catctgtctg acaacgagag gaaacctt                             38

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: Phosphorylated cytosine

<400> SEQUENCE: 127
tgcccaggga ggctagctta tac                                             23

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
```

```
<223> OTHER INFORMATION: Phosphorylated guanine

<400> SEQUENCE: 128
cttcgtgagg gtgag                                                        15

<210> SEQ ID NO 129
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tgccccctca ccctcacgaa ggtatacaga cagatggaca tccagttggt ga               52

<210> SEQ ID NO 130
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tgccccctca ccctcacgaa ggcatacaga cagatggaca tccagttggt ga               52

<210> SEQ ID NO 131
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(37)
<223> OTHER INFORMATION: Phosphorylated thymine

<400> SEQUENCE: 131
gggctggtca tccagcagta caacgagagg aaacctt                                37

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(36)
<223> OTHER INFORMATION: Phosphorylated adenine

<400> SEQUENCE: 132
tgcccaggga ggctagcgtg ttcgacaatg gcagca                                 36

<210> SEQ ID NO 133
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (37)..(37)
```

```
<223> OTHER INFORMATION: Phosphorylated thymine

<400> SEQUENCE: 133
gggctggtca tccagcagta caacgagagg aaacctt                              37

<210> SEQ ID NO 134
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (37)..(37)
<223> OTHER INFORMATION: Phosphorylated thymine

<400> SEQUENCE: 134
gggctggtca tccagcagta caacgagagg aaacctt                              37

<210> SEQ ID NO 135
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gggctggtca tccagcagua caacgagagg aaacctt                              37

<210> SEQ ID NO 136
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
tgcccaggga ggcuagcgtg ttcgacaatg gcagca                               36

<210> SEQ ID NO 137
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
catctcttct ccgagcgtct gtaccgtgta c                                    31

<210> SEQ ID NO 138
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 138
aaaaaaaagg tttcctcguc cctgggcagc tggtcatcca gcagacaacg aggttgtgct      60
g                                                                      61

<210> SEQ ID NO 139
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
cggttggtga ggctagctgt gttcgacaat ggcaaggttt cctcguccct gggcaaaaaa      60
a                                                                      61

<210> SEQ ID NO 140
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gccattgtcg aacacctgct ggatgaccag c                                     31

<210> SEQ ID NO 141
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gaaggtgtaa tccgtctcca cagacaaggc caggactcgt ttg                        43

<210> SEQ ID NO 142
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tgagctacag tcggtcgaaa tagtgagt                                         28

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
catctcttct ccgagcgctt catctca                                          27
```

```
<210> SEQ ID NO 144
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ggcactaacg tgcctgagct acagtcggtc gaaatagtga gt                          42

<210> SEQ ID NO 145
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
catctcttct ccgagcgctt catctcacga cgataacgtc g                           41

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tgagatgaag cactgtagct ca                                                22

<210> SEQ ID NO 147
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(40)
<223> OTHER INFORMATION: Phosphorylated thymine

<400> SEQUENCE: 147
caaacgagtc ctggccttgt ctacaacgag aggaaacctt                             40

<210> SEQ ID NO 148
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (39)..(39)
<223> OTHER INFORMATION: Phosphorylated cytosine

<400> SEQUENCE: 148
tgcccaggga ggctagctgt ggagacggat tacaccttc                              39

<210> SEQ ID NO 149
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 149 tacaacga                                                                8

<210> SEQ ID NO 150
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150 cggtcgaa                                                                8

<210> SEQ ID NO 151
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151 acaacga                                                                 7

<210> SEQ ID NO 152
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152 tacaacga                                                                8

<210> SEQ ID NO 153
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153 tacaacga                                                                8

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tgcccaggga ggctagcgts gagacgga                                         28

<210> SEQ ID NO 155
<211> LENGTH: 8
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 155 tacaacaa                                                                   8

<210> SEQ ID NO 156
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156 ttcaacga                                                                   8

<210> SEQ ID NO 157
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157 tacatcga                                                                   8

<210> SEQ ID NO 158
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tccgtctcca cagacaaggc caggactcgt ttg                                      33

<210> SEQ ID NO 159
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159 tactacga                                                                   8

<210> SEQ ID NO 160
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
caaacgagtc ctggccttgt cttacaacga gaggaaacct t                             41

<210> SEQ ID NO 161
<211> LENGTH: 6
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 161 caacga                                                              6

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166 ccgagc                                                              6

<210> SEQ ID NO 167
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167 ggctagct                                                            8

<210> SEQ ID NO 168
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168 ggctagc                                                             7

<210> SEQ ID NO 169
<211> LENGTH: 7
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 169 ggctaga                                                                    7

<210> SEQ ID NO 170
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170 ggccagc                                                                    7

<210> SEQ ID NO 171

<400> SEQUENCE: 171

000

<210> SEQ ID NO 172
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172 ggctagcta                                                                  9

<210> SEQ ID NO 173
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
atttcacgaa t                                                              11

<210> SEQ ID NO 174
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
atcacgtcca t                                                              11

<210> SEQ ID NO 175
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggctagctac a                                                              11
```

```
<210> SEQ ID NO 176
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gctacaacga                                                              10

<210> SEQ ID NO 177
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a or g
<220> FEATURE:
<221> NAME/KEY: modified_base
<222> LOCATION: (11)..(11)
<223> OTHER INFORMATION: a or can be missing
<220> FEATURE:
<221> NAME/KEY: modified_base
<222> LOCATION: (12)..(14)
<223> OTHER INFORMATION: a, c, t, g, unknown or other

<400> SEQUENCE: 177
nnnnnnwcgn nnnn                                                         14

<210> SEQ ID NO 178
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a or g
<220> FEATURE:
<221> NAME/KEY: modified_base
<222> LOCATION: (11)..(11)
<223> OTHER INFORMATION: a or can be missing
<220> FEATURE:
<221> NAME/KEY: modified_base
<222> LOCATION: (12)..(14)
<223> OTHER INFORMATION: a, c, t, g, unknown or other

<400> SEQUENCE: 178
nntnnnwcgn nnnn                                                         14
```

MULTICOMPONENT NUCLEIC ACID ENZYMES AND METHODS FOR THEIR USE

CROSS REFERENCE TO RELATED APPLICATIONS

This application claims the benefit of U.S. Provisional Patent Application Nos. 60/726,291 filed Oct. 13, 2005 and 60/724,567 filed Oct. 7, 2005, respectively, which are incorporated herein by reference in their entirety.

REFERENCE TO A SEQUENCE LISTING

The Sequence Listing written in file 402319SEQLIST of 47 kilobytes was created on Sep. 24, 2012 and is hereby incorporated by reference.

TECHNICAL FIELD

The present invention relates to multicomponent catalytic nucleic acids and methods for their use. More particularly, the invention relates to compositions comprising self-assembling multicomponent nucleic acid enzymes, methods for making such compositions, and methods for using such compositions, including for detecting, identifying and/or quantifying targets such as assembly facilitators and other entities by detecting catalytic modification of substrates by said multicomponent nucleic acid enzymes.

BACKGROUND OF THE INVENTION

Various publications, which may include patents, published applications, technical articles and scholarly articles, are cited throughout the specification in parentheses, and full citations of each may be found at the end of the specification. Each of these cited publications is incorporated by reference herein, in its entirety.

Nucleic acid molecules can adopt secondary structural configurations which can confer enzymatic or catalytic activity. In vitro evolution technology has facilitated the discovery and development of such catalytic nucleic acids, often referred to as "DNAzymes" or "ribozymes," that are capable of catalyzing a broad range of reactions including cleavage of nucleic acids (Carmi et al., 1996; Raillard and Joyce, 1996; Breaker, 1997; Santoro and Joyce, 1998), ligation of nucleic acids (Cuenoud and Szostak, 1995), porphyrin metallation (Li and Sen, 1996), and the formation of carbon-carbon bonds (Tarasow et al., 1997), ester bonds (Illangasekare et al., 1995) or amide bonds (Lohse and Szostak, 1996).

In particular, DNAzymes and ribozymes have been characterized which specifically cleave distinct nucleic acid sequences after hybridizing via Watson Crick base pairing. DNAzymes are capable of cleaving either RNA (Breaker and Joyce, 1994; Santoro and Joyce, 1997) or DNA (Carmi et al., 1996) molecules. Catalytic RNA molecules (ribozymes) are also able to cleave both RNA (Haseloff and Gerlach, 1988) and DNA (Raillard and Joyce, 1996) sequences. The rate of catalytic cleavage of most nucleic acid enzymes is dependent on the presence and concentration of divalent metal ions such as $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$ (Santoro and Joyce, 1998; Brown et al., 2003).

Catalytic nucleic acids, such as the hammerhead ribozyme and the 10:23 and 8:17 DNAzymes, have multiple domains. They have a conserved catalytic domain (catalytic core) flanked by two non-conserved substrate binding domains ("hybridizing arms"), which are regions of sequence that specifically bind to the substrate. Haseloff and Gerlach engineered the hammerhead ribozyme, which was so named for the stem-loop structure that brings the two conserved domains together forming the catalytic core (Haseloff and Gerlach, 1988). The "10:23" and "8:17" DNAzymes are capable of cleaving nucleic acid substrates at specific RNA phosphodiester bonds (Santoro and Joyce, 1997). The 10:23 DNAzyme has a catalytic domain of 15 deoxynucleotides flanked by two substrate-recognition arms. The 8:17 DNAzyme has a catalytic domain of 14 deoxynucleotides that is also flanked by two substrate-recognition arms.

A catalytic nucleic acid can cleave a nucleic acid substrate with a target sequence that meets minimum requirements. The substrate sequence must be substantially complementary to the hybridizing arms of the catalytic nucleic acid, and the substrate must contain a specific sequence at the site of cleavage. Specific sequence requirements at the cleavage site include, for example, a purine:pyrimidine ribonucleotide sequence for cleavage by the 10:23 DNAzyme (Santoro and Joyce, 1997), and the sequence uridine:X for the hammerhead ribozymes (Perriman et al., 1992), wherein X can equal A, C, or U, but not G.

Catalytic nucleic acids have been shown to tolerate only certain modifications in the area that forms the catalytic core (Perreault et al., 1990; Perreault et al., 1991; Zaborowska et al., 2002; Cruz et al., 2004; Silverman, 2004)). Examples of sequences responsible for catalytic activity of DNAzymes are listed in Table 1.

TABLE 1

Exemplary sequences for some active DNAzymes and their substrates

| DNAzyme type | DNAzyme sequence | Substrate sequence |
|---|---|---|
| 8:17 | $(N)_x$TNNNAGCNNNWCGN$_a$$(N)_x$ (SEQ ID NO: 47) | $(N')_x(rN)_xG(N')_x$ |
| 10:23 | $(N)_x$GGMTMGHNDNNNMGD$(N)_x$ (SEQ ID NO: 48) | $(N')_x$rRrY$(N')_x$ |

N = A, C, T, G or any analogue; N' = any nucleotide complementary to N; $(N)_x$ or $(N')_x$ = any number of nucleotides; W = A or T; $N_a$ = A, G or AA; rN =any ribonucleotide base; $(rN)_x$ = any number of ribonucleotides; rR = A or G; rY = C or U; M = A or C; H = A, C or T; D = G, A or T The substitution of certain deoxyribonucleotides for certain ribonucleotides in known ribozymes has been attempted under certain conditions (McCall et al., 1992). Ribozymes that have been fully converted into DNA have no activity due to the conformational differences of RNA and DNA (Perreault et al., 1990). These studies demonstrate that RNA enzymes cannot be modified into working DNA enzymes by merely replacing ribonucleotides with deoxyribonucleotides.

There have been some studies which attempted to develop certain homodimeric or heterodimeric ribozymes for therapeutic applications (Kuwabara et al., 1999; Kuwabara et al., 2000; Oshima et al., 2003). In those studies, the catalytic core of the ribozyme comprised solely of ribonucleotides. Moreover, the capacity for DNAzymes to function in dimeric or multimeric formats has not been considered, nor has any information been provided as to how to extrapolate from a dimeric ribozyme to a dimeric DNAzyme in terms of a possible structure of a dimeric DNAzyme and resulting activity.

Catalytic nucleic acids have been used in combination with in vitro amplification protocols as a means of generating a detectable signal, thus allowing real time monitoring of amplified nucleic acid target sequences (Todd et al., 2000) (U.S. Pat. Nos. 6,140,055; 6,201,113; WO 99/45146; PCT/IB99/00848; WO 99/50452). Zymogene detection (U.S. Pat.

Nos. 6,140,055; 6,201,113; WO 99/45146; PCT/IB99/00848; WO 99/50452), also known in the art as DzyNA detection (Todd et al., 2000), results in concurrent target and signal amplification. This occurs because the catalytic DNAzymes or ribozymes co-amplify along with target sequences to produce amplicons that function as true enzymes capable of multiple turnover. As such, each catalytic nucleic acid amplicon cleaves multiple reporter substrates. The DNAzymes and ribozymes are introduced into the amplicons by using primers with 5' tags that are inactive, anti-sense sequences of catalytic nucleic acids. When these sequences are copied during in vitro amplification the catalytically active sense sequences are co-amplified along with target sequence. The zymogene/DzyNA approach is very flexible since catalytic signal amplification can be linked to target amplification methods including PCR (polymerase chain reaction), strand displacement amplification ("SDA"), or rolling circle amplification ("RCA"), producing DNAzyme amplicons; and nucleic acid sequence-based amplification ("NASBA"), self-sustained sequence replication ("3SR"), or transcription-mediated amplification ("TMA") amplification methods producing ribozyme amplicons. Further, since numerous catalytic nucleic acid molecules with a broad range of catalytic activities have been discovered or evolved, the zymogene approach can use a reporter substrate other than a nucleic acid where the readout of the assay is dependent on a chemical modification other than cleavage of a nucleic acid substrate. The zymogene/DzyNA (Todd et al., 2000) or NASBA/ribozyme (WO 00/58505) approach may be considered sensitive and useful, but there is potential for noise due to amplification of primer sequences.

NASBA has been used to produce RNA amplicons containing target nucleic acid and one section of the catalytic core of the hammerhead ribozyme (GAArA), introduced as antisense sequence tagged to a primer and then copied (WO 00/58505). The additional sequence required for catalytic activity (CUrGANrGrA) was introduced as sense sequence on a second molecule, which was labeled with a fluorophore and quencher, and which also served as the reporter substrate. Certain of the ribonucleotide bases (rN above) must remain as ribonucleotides, or catalytic ribozyme activity is lost. Two molecules consisting entirely of DNA were considered unable to form catalytically active heterodimer enzymes (WO 00/58505).

Catalytic nucleic acids have also been used for detection of single nucleotide polymorphisms ("SNPs"). The strict requirement for Watson Crick base pairing between the catalytic nucleic acid binding arms and the substrate has allowed the development of methods that allow discrimination of closely related short sequences. DNAzymes and ribozymes have been shown to discriminate between two sequences differing by as little as a single base (Cairns et al., 2000) (WO 99/50452).

DNAzymes have properties which provide advantages over ribozymes for certain in vitro applications. DNA is inherently more stable than RNA and hence is more robust with a longer shelf life. DNA can be stored for long periods at room temperature either in solution or in a lyophilized form. DNAzymes also are preferable over the majority of protein enzymes in certain applications because, for example, they are not irreversibly denatured by exposure to high temperatures during amplification.

Thus, there is an ongoing need in the art for simple, fast, and cost effective methods for detecting, identifying and quantifying nucleic acid sequences and other entities, which preferably provide catalytic nucleic acids based on DNAzymes and/or ribozymes.

SUMMARY OF THE INVENTION

According to a first aspect of the present invention, there is provided a composition comprising at least two or more oligonucleotide components wherein at least a first oligonucleotide component and a second oligonucleotide component self-assemble in the presence of an MNAzyme assembly facilitator to form a catalytically active multi-component nucleic acid enzyme (MNAzyme), wherein each of said at least first and said second oligonucleotide components comprise a substrate arm portion, a catalytic core portion, and a sensor arm portion;

wherein upon self-assembly, the sensor arm portion of said first and second oligonucleotide components act as sensor arms of the MNAzyme, the substrate arm portion of the first and second oligonucleotide components act as substrate arms of the MNAzyme, and the catalytic core portion of the first and second oligonucleotide components act as a catalytic core of the MNAzyme;

and wherein the sensor arms of the MNAzyme interact with said MNAzyme assembly facilitator so as to maintain the first and second oligonucleotide components in proximity for association of their respective catalytic core portions to form the catalytic core of the MNAzyme, said catalytic core capable of modifying at least one substrate, and wherein said substrate arms of said MNAzyme engage a substrate so that said catalytic core of said MNAzyme can modify said substrate.

At least one of said oligonucleotide components, assembly facilitator or substrate may comprise DNA or an analogue thereof.

The assembly facilitator may be a target to be identified, detected or quantitated. The target may comprise a nucleic acid. The nucleic acid may be selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The ribosomal RNA may be 16S ribosomal RNA.

The source of the nucleic acid may be selected from the group comprising synthetic, mammalian, human, animal, plant, fungal, bacterial, viral, archael or any combination thereof.

The nucleic acid may be amplified. The amplification may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

The composition may further comprise at least a third oligonucleotide component which acts to stabilise at least one of said substrate arm portions or sensor arm portions.

At least one of said assembly facilitator, said oligonucleotide components or substrate or a combination thereof may be comprised of more than one molecule.

The catalytic core portions of the first oligonucleotide component may be selected from the group comprising SEQ ID NOs 149-153, 155-157, 159 and 161, and the catalytic core portions of the second oligonucleotide component may be selected from the group comprising SEQ ID NOs 166-170 and 172.

The composition may further comprise at least one inhibitor of said self assembly of said MNAzyme.

At least one of said oligonucleotide components or assembly facilitator or substrate or a combination thereof may further comprise at least one aptamer or portion thereof. The aptamer or portion thereof may be comprised of at least one of nucleic acid, peptide, polypeptide or protein or a derivative or combination thereof.

The composition may further comprise at least one inhibitor of said self assembly of said MNAzyme.

At least one of said first or said second oligonucleotide components or said assembly facilitator or said substrate may further comprise at least one portion of self complementary sequence capable of forming a hairpin structure. The hairpin structure may inhibit self assembly of said MNAzyme. The inhibition of self assembly may be removed upon contact of an aptamer with a target. The aptamer, or portion thereof, may bind a target selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof.

The substrate may comprise a nucleic acid or a protein. The nucleic acid may comprise at least one of a labeled nucleic acid, RNA, DNA, nucleic acid analogue, peptide nucleic acid, locked nucleic acid, peptide-nucleic acid chimera, or any combination thereof. The protein may comprise at least one of an antibody, polypeptide, glycoprotein, lipoprotein, or any combination thereof. The substrate may further comprise at least one nanoparticle or microparticle, or combination thereof. The substrate may be attached to an insoluble support or be free in solution. The substrate may comprise a detectable portion and a quencher portion, wherein upon modification of said substrate by said MNAzyme, a detectable effect provided by said detectable portion is increased or decreased.

The substrate arms may engage said substrate through complementary base pairing.

The modification of said substrate by said MNAzyme may provide a detectable effect. The modification of said substrate may be selected from the group comprising cleavage, ligation, porphyrin metallation, formation of carbon-carbon bonds, ester bonds or amide bonds, or any combination thereof. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof. The detectable effect may be measured, wherein the magnitude of said measurement is indicative of the quantity of a target.

At least one of said oligonucleotide components, said assembly facilitator or said substrate may be selected from the group comprising DNA, RNA, nucleic acid analogues, peptide nucleic acids, locked nucleic acids, peptide-nucleic acid chimeras, or a combination thereof. The assembly facilitator and said substrate may comprise nucleic acids that are completely or partially complementary to at least part of said first or second oligonucleotide components. At least one of said oligonucleotide components, said assembly facilitator or said substrate may comprise at least one nucleotide substitution or addition selected from the group comprising 4-acetylcytidine, 5-(carboxyhydroxylmethyl)uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl) uridine, beta D-arabinosyl uridine, beta D-arabinosyl thymidine.

The composition may further comprise at least a third oligonucleotide component and a fourth oligonucleotide component that self-assemble in the presence of at least one additional assembly facilitator to form at least one additional catalytically active MNAzyme, wherein each of said at least third and fourth oligonucleotide components comprise a substrate arm portion, a catalytic core portion, and a sensor arm portion;

wherein upon self-assembly of said at least a third oligonucleotide component and a fourth oligonucleotide component, the sensor arm portion of said at least third and said at least fourth oligonucleotide components form sensor arms of said at least one additional catalytically active MNAzyme, the substrate arm portion of said at least third and said at least fourth oligonucleotide components form substrate arms of said at least one additional catalytically active MNAzyme, and the catalytic core portion of said at least third and said at least fourth oligonucleotide components form a catalytic core of said at least one additional catalytically active MNAzyme;

and wherein the sensor arms of said at least one additional MNAzyme interact with said at least one additional assembly facilitator so as to maintain said at least third and said at least fourth oligonucleotide components in proximity for association of their respective catalytic core portions to form the catalytic core of said at least one additional MNAzyme, said catalytic core capable of acting on at least one additional substrate, and wherein the substrate arms of said at least one additional MNAzyme engage at least one additional substrate so that the catalytic core of said at least one additional MNAzyme can act on said at least one additional substrate.

Each of the additional substrates may be the same, different or a combination thereof.

According to a second aspect of the present invention, there is provided a method for detecting the presence of at least one assembly facilitator comprising (a) providing two or more oligonucleotide components, wherein at least a first oligonucleotide component and a second oligonucleotide component self-assemble in the presence of an assembly facilitator to form at least one catalytically active multi-component nucleic acid enzyme (MNAzyme);

(b) contacting the two or more oligonucleotide components with a sample putatively containing the assembly facilitator under conditions permitting:
  (1) the self-assembly of said at least one catalytically active MNAzyme, and
  (2) the catalytic activity of said MNAzyme; and (c) determining the presence of the catalytic activity of said at least one MNAzyme, wherein the presence of the catalytic activity is indicative of the presence of said at least one assembly facilitator.

At least one of said oligonucleotide components or assembly facilitator may be comprised of DNA or an analogue thereof.

The assembly facilitator may be a target to be identified, detected or quantified. The target may comprise a nucleic acid. The nucleic acid may be selected from the group comprising DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. The ribosomal RNA may be 16S ribosomal RNA.

The source of the nucleic acid may be selected from the group comprising synthetic, mammalian, human, animal, plant, fungal, bacterial, viral, archael or any combination thereof.

The method may further comprise a step of amplifying the assembly facilitator. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

At least one of said assembly facilitator, said oligonucleotide components or substrate or a combination thereof may be comprised of more than one molecule.

The method may further comprise determination of the presence of said catalytic activity during or after said amplification.

The self assembly of the MNAzyme may require contact of the assembly facilitator with one or both of said first and second oligonucleotide components.

The method may further comprise providing at least a third oligonucleotide component that contacts at least a portion of either or both of the first and second oligonucleotide components to self-assemble the MNAzyme. The third oligonucleotide component may be comprised of more than molecule.

According to a third aspect of the present invention, there is provided a method for detecting the presence of at least one assembly facilitator comprising
 (a) providing two or more oligonucleotide components, wherein at least a first oligonucleotide component and a second oligonucleotide component self-assemble in the presence of at least a first assembly facilitator to form at least a first catalytically active multi-component nucleic acid enzyme (MNAzyme);
 (b) providing at least a first substrate, said first substrate capable of being modified by said first MNAzyme, wherein said modification of said substrate by said MNAzyme provides a detectable effect;
 (c) contacting said two or more oligonucleotide components with a sample putatively containing said at least first assembly facilitator under conditions permitting:
   (1) the self-assembly of said at least first MNAzyme, and
   (2) the catalytic activity of said at least first MNAzyme; and
 (d) detecting said detectable effect.

At least one of said oligonucleotide components, assembly facilitator or substrate may be comprised of DNA or an analogue thereof.

The assembly facilitator may be a target to be identified, detected or quantified. The target may comprise a nucleic acid. The nucleic acid may be selected from the group comprising DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The ribosomal RNA may be 16S ribosomal RNA.

The source of the nucleic acid may be selected from the group comprising synthetic, mammalian, human, animal, plant, fungal, bacterial, viral, archael or any combination thereof.

The method may further comprise the step of amplifying the nucleic acid. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

At least one of said assembly facilitator, said oligonucleotide components or substrate or combination thereof may be comprised of more than one molecule.

The method may further comprise detecting said detectable effect during or after said amplification. The detectable effect may be indicative of the presence of said assembly facilitator. The detectable effect may be quantitatively or qualitatively measured.

The substrate may be a nucleic acid or a protein. The nucleic acid may comprise at least one of a labeled nucleic acid, RNA, DNA, nucleic acid analogue, peptide nucleic acid, locked nucleic acid, peptide-nucleic acid chimera, or any combination thereof. The protein comprises at least one of an antibody, polypeptide, glycoprotein, lipoprotein, or any combination thereof. The substrate may further comprise at least one of a nanoparticle or microparticle or combination thereof. The substrate may be attached to an insoluble support or be free in solution.

The substrate may comprise a nucleic acid and said substrate arms may engage said substrate through complementary base pairing.

The substrate may comprise a detectable portion and a quencher portion, wherein upon modification of the substrate by the MNAzyme, a detectable effect provided by the detectable portion is increased or decreased. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, V, visible light or infra red spectroscopy, enzymatic methods or any combination thereof.

The method may further comprise amplifying the detectable effect by use of a detectable effect amplification cascade. The detectable effect amplification cascade may comprise one or more of a ribozyme/ligase cascade, a circular nucleic acid enzyme cascade, a protein enzyme cascade, or one or more enzymes attached to a support, or any combination thereof.

The modification of said substrate may be selected from the group comprising cleavage, ligation, porphyrin metallation, formation of carbon-carbon bonds, ester bonds or amide bonds.

The method may further comprise providing at least a third and fourth oligonucleotide component, said at least third and at least fourth oligonucleotide component are capable of self assembling in the presence of at least one additional assembly facilitator to form at least one additional catalytically active MNAzyme, and wherein at least one additional substrate is present in the sample, said additional substrate is capable of being modified by the additional MNAzyme, wherein said modification provides said additional detectable effect.

The at least one additional detectable effect may be independently detectable.

At least one of each additional substrate may be attached to an insoluble support so that only one of a detectable portion and a quencher portion of the additional substrate remain attached to the support when said additional substrate is modified by said additional MNAzyme.

One additional substrate may be attached to at least one insoluble support so that a detectable effect is produced when that substrate is modified by its respective MNAzyme.

According to a fourth aspect of the present invention, there is provided a method for detecting the presence of at least one target comprising (a) providing two or more oligonucleotide components wherein at least a first oligonucleotide component and at least a second oligonucleotide component are capable of self-assembly in the presence of said target to form a catalytically active multi-component nucleic acid enzyme (MNAzyme); and wherein at least one of said first and said second oligonucleotide components further comprises at least one aptamer portion;

(b) contacting said oligonucleotide components with a sample putatively containing said at least one target under conditions permitting:
(1) binding of said target to said aptamer portions and
(2) catalytic activity of the MNAzyme; and (c) determining the presence of the catalytic activity of the MNAzyme, wherein the presence of the catalytic activity is indicative of the presence of said target.

At least one of said oligonucleotide components may be attached to a solid support.

At least one of said oligonucleotide components may be comprised of DNA or an analogue thereof.

The target may be identified, detected or quantified.

The method may further comprise providing at least a third and fourth oligonucleotide component, said at least third and at least fourth oligonucleotide component are capable of self assembling in the presence of at least one additional target to form at least one additional catalytically active MNAzyme and wherein at least one of said third or fourth oligonucleotide components comprises at least one additional aptamer portion which binds said at least one additional target.

According to a fifth aspect of the present invention, there is provided a method for detecting the presence of at least one target comprising (a) providing two or more oligonucleotide components wherein at least a first oligonucleotide component and a second oligonucleotide component are capable of self-assembly in the presence of at least one assembly facilitator and said at least one target to form at least one catalytically active multi-component nucleic acid enzyme (MNAzyme); and wherein at least one of said first or said second oligonucleotide components or said at least one assembly facilitator further comprises at least one aptamer or portion thereof and wherein said target is capable of binding said at least one aptamer or portion thereof;

(b) providing at least one inhibitor of said self assembly of said MNAzyme (c) contacting said oligonucleotide components, assembly facilitator and said inhibitor with a sample putatively containing said at least one target under conditions permitting:
(1) binding of said target to said at least one aptamer or portion thereof and
(2) catalytic activity of said at least one MNAzyme; and
(3) removal of said inhibition of said self assembly of said catalytically active MNAzyme; and (d) determining the presence of the catalytic activity of said MNAzyme, wherein the presence of said catalytic activity is indicative of the presence of said target.

The at least one target may be selected from the group comprising proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof.

At least one of said oligonucleotide components, assembly facilitator or inhibitor may be attached to an insoluble support.

At least one of said oligonucleotide components, assembly facilitator, aptamer or aptamer portion may further comprise said inhibitor.

At least one of said first or said second oligonucleotide components or assembly facilitator may further comprise a portion of self complementary sequence capable of forming a hairpin structure. The hairpin structure may inhibit self assembly of said catalytically active MNAzyme.

The aptamer or portion thereof may be comprised of at least one of nucleic acid, peptide, polypeptide or protein or a derivative or combination thereof.

The inhibition of self assembly of said catalytically active MNAzyme may be removed upon contact of said aptamer or aptamer portion with the target.

The inhibitor may be capable of binding at least one of the group comprising said aptamer or portion thereof.

The inhibitor may be selected from the group comprising RNA, DNA, nucleic acid analogues, peptide nucleic acids, locked nucleic acids, peptide-nucleic acid chimeras, or a combination thereof.

The method may further comprise providing a substrate that can be modified by said MNAzyme to provide a detectable effect. The modification may be selected from the group comprising cleavage, ligation, porphyrin metallation, formation of carbon-carbon bonds, ester bonds or amide bonds. The substrate may be not modified by said first or second oligonucleotide components individually or by both said first and second oligonucleotide components in the absence of said assembly facilitator and said target.

The substrate may comprise a nucleic acid or a protein. The nucleic acid comprises at least one of a labeled nucleic acid, RNA, DNA, nucleic acid analogue, peptide nucleic acid, locked nucleic acid, peptide-nucleic acid chimera, or any combination thereof. The protein may comprise at least one of an antibody, polypeptide, glycoprotein, lipoprotein, or any combination thereof.

The substrate may further comprise at least one nanoparticle or microparticle or combination thereof.

Detection of the detectable effect may be indicative of said catalytic activity of said catalytically active MNAzyme and wherein said catalytic activity is indicative of said target. The detectable effect may be quantitatively or qualitatively measured. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased.

According to a sixth aspect of the present invention, there is provided a method for detecting the presence of at least one target comprising
- (a) providing two or more oligonucleotide components wherein at least a first oligonucleotide component and a second oligonucleotide component are capable of self-assembly in the presence of at least a first assembly facilitator and said at least a first target to form at least a first catalytically active multi-component nucleic acid enzyme (MNAzyme);
- (b) providing at least a first substrate, said first substrate capable of being modified by said at least first MNAzyme, wherein said modification of said substrate by said MNAzyme provides a detectable effect;
- (c) wherein at least one of said first or said second oligonucleotide components or said at least a first assembly facilitator or said at least a first substrate further comprises an aptamer and wherein said target is capable of binding at least a portion of said aptamer, providing at least a first inhibitor which is capable of inhibiting said self-assembly of said catalytically active MNAzyme in the absence of said target;
- (d) contacting said oligonucleotide components, said assembly facilitator, said substrate, and said inhibitor with a sample putatively containing said target under conditions permitting:
  - (1) binding of said target to said aptamer and
  - (2) removal of said inhibition of said self assembly of said catalytically active MNAzyme
  - (3) catalytic activity of the MNAzyme; and
- (e) determining the presence of said detectable effect thereby detecting the presence of said target.

At least one of said oligonucleotide components or assembly facilitator may be comprised of DNA or an analogue thereof.

The aptamer, or portion thereof, may bind a target selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions or any derivatives, portions or combinations thereof.

At least one of said oligonucleotide components, assembly facilitator, substrate, or inhibitor may be attached to an insoluble support.

At least one of said oligonucleotide components, assembly facilitator, aptamer or aptamer portion may further comprise said inhibitor.

The aptamer or portion thereof may be comprised of at least one of nucleic acid, peptide, polypeptide or protein or a derivative or combination thereof.

At least one of said first or said second oligonucleotide components, assembly facilitator or substrate may further comprise a portion of self complementary sequence capable of forming a hairpin structure. The hairpin structure may inhibit self assembly of said catalytically active MNAzyme. The inhibition of self assembly of said catalytically active MNAzyme may be removed upon contact of said aptamer or aptamer portion with the target.

The inhibitor may be capable of binding at least one of the group comprising said aptamer or portion thereof. The inhibitor may be selected from the group comprising RNA, DNA, nucleic acid analogues, peptide nucleic acids, locked nucleic acids, peptide-nucleic acid chimeras, or a combination thereof.

The substrate may comprise a nucleic acid or a protein. The nucleic acid may comprise at least one of a labeled nucleic acid, RNA, DNA, nucleic acid analogue, peptide nucleic acid, locked nucleic acid, peptide-nucleic acid chimera, or any combination thereof. The protein may comprise at least one of an antibody, polypeptide, glycoprotein, lipoprotein, or any combination thereof.

The substrate may further comprise at least one nanoparticle or microparticle or combination thereof.

Detection of said detectable effect may detect the presence of said target. The detectable effect may be quantitatively or qualitatively measured. The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased. The modification may be selected from the group comprising cleavage, ligation, porphyrin metallation, formation of carbon-carbon bonds, ester bonds or amide bonds.

The method may further comprise providing at least a third and fourth oligonucleotide component, wherein said at least third and at least fourth oligonucleotide component are capable of self assembling in the presence of at least one additional assembly facilitator and at least one additional target to form at least one additional catalytically active MNAzyme, and
- wherein at least one additional substrate is present in the sample, said additional substrate is capable of being modified by the additional MNAzyme, wherein said modification provides an additional detectable effect;
- and wherein at least one of said third or fourth oligonucleotide component or said additional assembly facilitator or said additional substrate further comprises at least one additional aptamer which binds said at least one additional target;
- wherein at least one additional inhibitor molecule contacts a portion of said additional aptamer, thereby inhibiting said self-assembly of said catalytically active additional MNAzyme in the absence of said additional target; and
- wherein said at least one additional assembly facilitator contacts at least a portion of said additional oligonucleotide components.

The at least one additional detectable effect may be independently detectable.

Each of the additional substrates may be the same, different or a combination thereof.

At least one of each additional substrate may be attached to an insoluble support so that only one of a detectable portion and a quencher portion of the additional substrate remain attached to the support when said additional substrate is modified by said additional MNAzyme.

According to a seventh aspect of the present invention, there is provided a method for detecting the presence of at least one nucleic acid sequence variant comprising
- (a) providing two or more oligonucleotide components, wherein at least a first oligonucleotide component and a second oligonucleotide component self-assemble in the presence of a sequence variant of a nucleic acid to form a catalytically active multi-component nucleic acid enzyme (MNAzyme);
(b) providing at least one substrate, said substrate capable of being modified by said first MNAzyme, wherein said modification of said substrate by said MNAzyme provides a detectable effect;
(c) contacting the two or more oligonucleotide components with a sample putatively containing said sequence variant under conditions permitting:
 (1) the self-assembly of said catalytically active MNAzyme, and
 (2) the catalytic activity of said MNAzyme; and
(d) determining the presence of said detectable effect thereby detecting the presence of said at least one sequence variant.

The sequence variant may be selected from the group comprising single nucleotide polymorphisms, multiple nucleotide polymorphisms, insertions, deletions, duplications, translocations, frameshift sequence variants, nonsense sequence variants, or any combination thereof. The sequence variant may be present in DNA or RNA.

Either or both of said first oligonucleotide component and said second oligonucleotide components may be comprised of more than one molecule.

The sample containing said sequence variant may be selected from the group comprising bisulfite modified methylated or non-methylated DNA, bisulfite modified methylated or non-methylated RNA, at least one amplicon of bisulfite modified methylated or non-methylated DNA, at least one amplicon of bisulfite modified methylated or non-methylated RNA or a combination thereof.

The self assembly of the multi-component nucleic acid enzyme may require contact of at least a portion of either or both of the first and second oligonucleotide components with the nucleic acid which comprises said sequence variant.

The method may further comprise a step of amplifying the nucleic acid containing said sequence variant. The step of amplifying may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). The method may further comprise determination of the presence of said nucleic acid sequence variant during or after said amplification.

The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased.

The substrate may be attached to an insoluble support or free in solution.

The modification may be selected from the group comprising cleavage, ligation, porphyrin metallation, formation of carbon-carbon bonds, ester bonds or amide bonds.

The method may further comprise
(a) providing at least a third oligonucleotide component and at least a fourth oligonucleotide component that self assemble in the presence of at least one additional nucleic acid sequence variant to form at least one additional catalytically active multi-component nucleic acid enzyme (MNAzyme);
(b) contacting said at least third and at least fourth oligonucleotide components with a sample putatively containing at least one additional nucleic acid sequence variant in the presence of at least one additional substrate capable of being modified by said at least one additional MNAzyme, wherein said modification of said at least one additional substrate provides at least one additional detectable effect under conditions permitting:
 (1) the self-assembly of at least one MNAzyme, and
 (2) the catalytic activity of at least one MNAzyme; and
(c) detecting said at least one additional detectable effect, thereby detecting the presence of said at least one additional sequence variant.

The at least one additional detectable effect may be independently detectable.

Each of the additional substrates may be the same, different or a combination thereof.

The method may further comprise providing an insoluble support having said substrate attached thereto.

At least one of each additional substrate may be attached to an insoluble support so that only one of a detectable portion and a quencher portion of the additional substrate remain attached to the support when said additional substrate is modified by said additional MNAzyme.

According to an eighth aspect of the present invention, there is provided a method for detecting the presence of a sequence variant of a nucleic acid comprising
(a) providing two or more oligonucleotide components comprising at least a first oligonucleotide component and a second oligonucleotide component capable of self assembly in the presence of a nucleic acid to form at least a first catalytically active multi-component nucleic acid enzyme (MNAzyme);
(b) contacting the two or more oligonucleotide components with a sample putatively containing the nucleic acid, in the presence of at least a first substrate modifiable by said at least a first MNAzyme, wherein the substrate comprises a detectable portion capable of providing at least a first detectable effect upon modification of the substrate by said at least a first MNAzyme under conditions permitting:
 (1) the self-assembly of the MNAzyme, and
 (2) the catalytic activity of the MNAzyme; and
(c) wherein the absence of the catalytic activity is indicative of the presence of a sequence variant in said nucleic acid.

According to a ninth aspect of the present invention, there is provided a method for detecting the presence of at least one methylated nucleic acid comprising
(a) providing two or more oligonucleotide components, wherein at least a first oligonucleotide component and a second oligonucleotide component self-assemble in the presence of methylated nucleic acid to form at least one catalytically active multi-component nucleic acid enzyme (MNAzyme);
(b) providing at least a first substrate, said first substrate capable of being modified by said first MNAzyme, wherein said modification of said substrate by said MNAzyme provides at least a first detectable effect;
(c) contacting the two or more oligonucleotide components with a sample putatively containing the methylated nucleic acid under conditions permitting:

(1) the self-assembly of the catalytically active MNAzyme, and
(2) the catalytic activity of the MNAzyme; and
(d) determining the presence of said at least one detectable effect thereby detecting the presence of said at least one methylated nucleic acid.

The conditions may further comprise a temperature that facilitates hybridization of said MNAzyme with said methylated nucleic acid but not with unmethylated nucleic acid.

The method may further comprise amplifying the detectable effect by use of a detectable effect amplification cascade. The detectable effect amplification cascade may comprise one or more of a ribozyme/ligase cascade, a circular nucleic acid enzyme cascade, a protein enzyme cascade, or one or more enzymes attached to a support. or any combination thereof.

The source of said methylated nucleic acid may be selected from the group comprising synthetic, mammalian, human, animal acid, plant, fungal, bacterial, viral, archael or any combination thereof.

The methylated nucleic acid may be selected from the group comprising methylated RNA or methylated DNA.

The self assembly of the multi-component nucleic acid enzyme may require contact of the methylated nucleic acid with one or both of the first and second oligonucleotide components.

The method may further comprise providing an insoluble support having at least one of said substrate or said first or second oligonucleotide components, or a combination thereof attached thereto.

The detectable effect may be detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

The substrate may comprise a detectable portion and a quencher portion, wherein upon modification of said substrate by said MNAzyme, a detectable effect provided by said detectable portion is increased or decreased.

The modification may be selected from the group comprising cleavage, ligation, porphyrin metallation, formation of carbon-carbon bonds, ester bonds or amide bonds.

The method may further comprise providing at least a third and fourth oligonucleotide component, wherein said at least third and at least fourth oligonucleotide component are capable of self assembling in the presence of at least one additional methylated nucleic acid to form at least one additional catalytically active MNAzyme, and
wherein at least one additional substrate is present in the sample, said additional substrate is capable of being modified by said additional MNAzyme, wherein said modification provides said additional detectable effect.

The at least one additional detectable effect may be independently detectable.

Each of the additional substrates may be the same, different or a combination thereof.

At least one of said additional substrate may be attached to an insoluble support so that only one of an additional detectable portion and an additional quencher portion of the additional substrate remain attached to the support when said additional substrate is modified by said additional MNAzyme.

According to a tenth aspect of the present invention, there is provided a method for detecting at least one assembly facilitator using an amplification cascade comprising (a) providing two or more oligonucleotide components comprising at least a first oligonucleotide component and at least a second oligonucleotide component that self assemble in the presence of at least a first assembly facilitator to form at least a first catalytically active multi-component nucleic acid enzyme (MNAzyme);
(b) providing an insoluble support having at least a first substrate attached thereto, said first substrate is capable of being modified by said MNAzyme, wherein said first substrate comprises at least a third molecule comprising at least a first catalytically active enzyme that is released upon modification of said first substrate by said first MNAzyme;
(c) contacting said two or more oligonucleotide components with a sample putatively containing said assembly facilitator, in the presence of said insoluble support having said first substrate attached thereto under conditions permitting:
(1) the self-assembly of said MNAzyme, and
(2) the catalytic activity of said MNAzyme; and
(d) providing an insoluble support having at least a second substrate attached thereto, said second substrate cleavable by said first catalytically active enzyme wherein said second substrate comprises at least a fourth molecule comprising at least a detectable moiety which is released upon modification of said second substrate by said first enzyme; and
(e) wherein said first catalytically active enzyme modifies a plurality of said second substrate thereby releasing a plurality of detectable moieties
(f) wherein said detectable moieties are detectable after modification of said second substrate by said first catalytically active enzyme, and;
(g) wherein detection of said detectable moieties is indicative of the presence of said assembly facilitator.

The detectable moieties may further comprise an additional second catalytically active enzyme capable of modifying said first substrate thereby releasing additional catalytically active enzyme. At least one of said first or said second catalytically active enzyme may be selected from the group comprising MNAzymes, DNAzymes, ribozymes, hydrolytic enzymes, restriction endonucleases, exonucleases, proteases, proteinases, hydrolases, lyticases, peptidases, dipeptidases, esterases, caspases, cathepsisns, desulfhydrases, amidases, glycosidases.

The assembly facilitator may comprise a target to be identified, detected or quantified. The target may be selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof. The nucleic acid may be selected from the group comprising DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof.

According to an eleventh aspect of the present invention, there is provided a method for detecting a target using an MNAzyme mediated signal amplification cascade comprising
(a) providing a first oligonucleotide component and a second oligonucleotide component that self assemble in the presence of said target to form a first catalytically active multi-component nucleic acid enzyme (MNAzyme);

(b) providing an insoluble support having a first and a second substrate attached thereto, said first and second substrates are capable of being modified by said first MNAzyme, wherein said first and second substrates comprise at least a third and a fourth oligonucleotide component respectively, capable of forming a second catalytically active MNAzyme, wherein said third and fourth oligonucleotide components are released upon modification of said first and second substrates by said first MNAzyme;

(c) providing said insoluble support having a third and a fourth substrate attached thereto, said third and fourth substrates are capable of being modified by said second MNAzyme, wherein said third and fourth substrates comprise at least a fifth and a sixth oligonucleotide component respectively, capable of forming a third catalytically active MNAzyme, wherein said fifth and said sixth oligonucleotide components are released upon modification of said third and fourth substrates by said second MNAzyme, and;

(d) providing an assembly facilitator capable of facilitating the assembly of said second and said third MNAzyme, and;

(e) providing a fifth substrate which is capable of being modified by said second MNAzyme to provide a detectable effect;

(f) contacting said first and second oligonucleotide components with a sample putatively containing said target, in the presence of said assembly facilitator, and in the presence of said insoluble support having said first, second, third and fourth substrates attached thereto under conditions permitting:
  (1) self-assembly of said first, second and third, MNAzymes, and
  (2) catalytic activity of said first, second and third, MNAzymes; and (g) wherein said third MNAzyme modifies said first and second substrates thereby further providing said second MNAzyme wherein said second MNAzyme further modifies at least one of said third, fourth and fifth substrates thereby further providing said third MNAzyme thereby further providing said detectable effect, and;

(h) wherein detection of said detectable effect is indicative of the presence of said target.

The target may be identified, detected or quantified. The target may be selected from the group comprising nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, nucleic acids or any derivatives, portions or combinations thereof. The nucleic acid may be selected from the group comprising DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof.

The fifth substrate may be the same as or different to any one of said first, second, third or fourth substrates.

Each of said first, second, third or fourth substrates may be present on the same solid support or different solid supports or any combination thereof.

The modification of at least one of said first, second, third or fourth substrates may further provide a detectable effect.

According to a twelfth aspect of the present invention, there is provided a method for making a plurality of multi-component nucleic acid enzymes (MNAzymes) that each recognize at least one assembly facilitator and modify a substrate, the method comprising:

(a) providing a plurality of assembly facilitators to be identified, detected or quantified, (b) designing two or more oligonucleotide components wherein at least a first oligonucleotide component and a second oligonucleotide component self-assemble in the presence of an assembly facilitator to form a catalytically active multi-component nucleic acid enzyme (MNAzyme), wherein each of the at least first and second oligonucleotide components comprise a substrate arm portion, a catalytic core portion, and a sensor arm portion, wherein upon self-assembly, the sensor arm portion of the first and second oligonucleotide components form sensor arms of the MNAzyme, the substrate arm portion of the first and second oligonucleotide components form substrate arms of the MNAzyme, and the catalytic core portion of the first and second oligonucleotide components form a catalytic core of the MNAzyme;

and wherein the sensor arms of the MNAzyme interact with an assembly facilitator so as to maintain the first and second oligonucleotide components in proximity for association of their respective catalytic core portions to form the catalytic core of the MNAzyme, said catalytic core capable of acting on at least one substrate, and wherein the substrate arms of the MNAzyme engage a substrate so that the catalytic core of the MNAzyme can modify said substrate;

(c) altering said two or more oligonucleotide components such that the substrate arm portion and the catalytic core portion of the first and second oligonucleotide components is constant, and the sensor arm portion of at least one of the first and second oligonucleotide components is adapted to recognize another of the plurality of assembly facilitators, and (d) repeating the altering step for each of the plurality of assembly facilitators.

According to a thirteenth aspect of the present invention, there is provided a kit for detecting the presence of a plurality of targets comprising a plurality of oligonucleotide components designed to assemble a plurality of MNAzymes each corresponding to at least one of a plurality of targets, and at least one substrate.

According to a fourteenth aspect of the present invention, there is provided a kit for assembling a plurality of MNAzymes comprising a plurality of assembly facilitators, a plurality of oligonucleotide components designed to assemble a plurality of MNAzymes each one corresponding to each of the plurality of assembly facilitators, and at least one substrate.

According to a fifteenth aspect of the present invention, there is provided a kit for detecting a target comprising a plurality of oligonucleotide components designed to assemble an MNAzyme corresponding to the target, and a substrate.

BRIEF DESCRIPTION OF THE DRAWINGS

A preferred embodiment of the present invention will now be described, by way of an example only, with reference to the accompanying drawings wherein:

FIG. 20: MNAzyme detection of targets using an aptamer: One exemplary strategy for the detection of a target is depicted. In this strategy, an aptamer sequence is incorporated at the end of a partzyme (apta-partzyme) in a configuration whereby an active MNAzyme is only formed in the presence of the target. The oligonucleotide components required for the MNAzyme detection strategy illustrated include: (a) a standard partzyme; (b) an apta-partzyme which is a partzyme with an aptamer incorporated into one of its ends; (c) an assembly facilitator which binds to both the apta-partzyme and the partzyme enabling assembly of an active MNAzyme (in the presence of target); (d) a reporter probe substrate: and (e) an assembly inhibitor which hybridises to the apta-partzyme in a region which spans at least part of the aptamer sequence and part of the substrate binding arm of the partzyme sequence. In the absence of a target analyte (panel (i)), the assembly inhibitor binds to the apta-partzyme thus blocking binding (and cleavage) of the reporter probe substrate. In the presence of a target analyte (panel (ii)), the target binds to the aptamer sequence of the apta-partzyme, preventing the binding of the assembly inhibitor and allowing the binding and cleavage of the reporter probe substrate. As such, MNAzymes can only form and cause fluorescent signal generation in the presence of target.

DEFINITIONS

Figure 1:
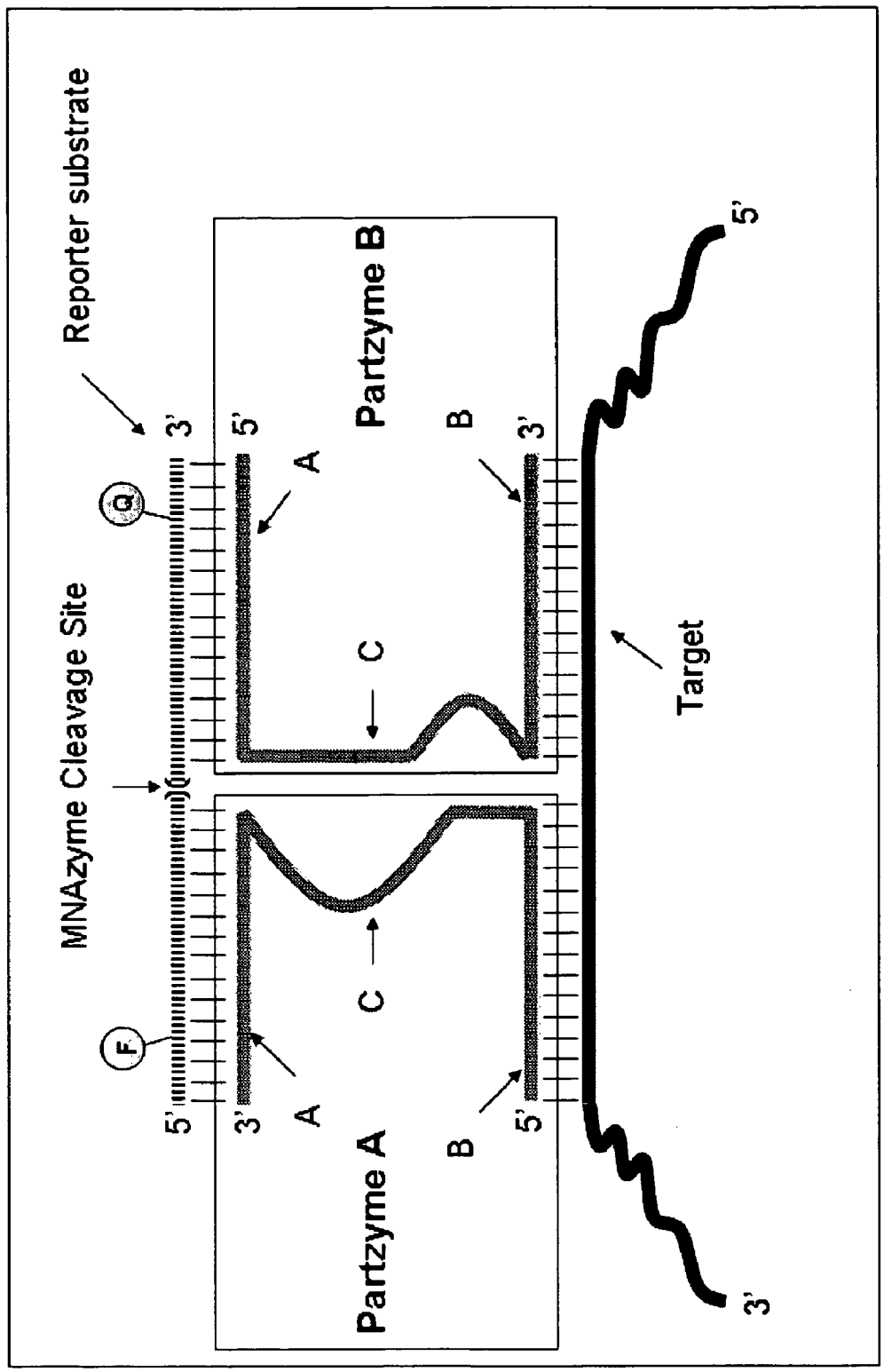
FIG. 1: Design for an MNAzyme: shown is a depiction of an exemplary design for an MNAzyme, wherein substrate arm portions (A) of partzymes A and B bind to a Reporter substrate, to which is attached a fluorescent tag (left) and a quencher (right). Catalytic core portions (C) are located between substrate arm portions (A) and sensor arm portions (B). Upon binding of sensor arm portions (B) to a Target, the Reporter substrate is cleaved at the MNAzyme Cleavage Site, thereby increasing fluorescence.

Certain terms are used herein which shall have the meanings set forth as follows.

The term "comprising" means "including principally, but not necessarily solely". Furthermore, variations of the word "comprising", such as "comprise" and "comprises", have correspondingly varied meanings.

The terms "polynucleotide", "nucleic acid" and "oligonucleotide" may be used interchangeably and refer to a single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael or any combination thereof.

The terms "oligonucleotide" and "primer" typically denote a segment of DNA or a DNA-containing nucleic acid molecule, or RNA or RNA-containing molecule, or a combination thereof. Examples of oligonucleotides include nucleic acid targets; substrates, for example, those which can be modified by an MNAzyme; primers such as those used for in vitro target amplification by methods such as PCR; and components of MNAzymes. MNAzyme assembly facilitators, in certain embodiments, may comprise oligonucleotides as defined herein. Partzymes as used herein may also comprise oligonucleotides.

The terms "polynucleotide", "nucleic acid" and "oligonucleotide" include reference to any specified sequence as well as to the sequence complementary thereto, unless otherwise indicated. Oligonucleotides may comprise at least one addition or substitution, including but not limited to the group comprising 4-acetylcytidine, 5-(carboxyhydroxylmethyl) uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl) threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine, beta D-arabinosyl thymidine.

The terms "catalytic nucleic acid molecule", "catalytic nucleic acid", "nucleic acid enzyme" and "catalytic nucleic acid sequence" are used herein interchangeably and shall mean a DNA molecule or DNA-containing molecule (also known in the art as a "DNA enzyme", "deoxyribozyme" or "DNAzyme") or an RNA or RNA-containing molecule (also known in the art as a "RNA enzyme" or "ribozyme") or a combination thereof, being a DNA-RNA hybrid molecule, which may recognize a substrate and catalyze a modification of the substrate. The nucleotide residues in the catalytic nucleic acids may include the bases A, C, G, T, and U, as well as derivatives and analogues thereof.

The term "derivative" when used in relation to a nucleic acid or nucleotide of the present invention includes any functionally-equivalent nucleic acids or nucleotides, including any fusion molecules produced integrally (e.g., by recombinant means) or added post-synthesis (e.g., by chemical means). Such fusions may comprise oligonucleotides of the invention with RNA or DNA added thereto or conjugated to a polypeptide (e.g., puromycin or other polypeptide), a small molecule (e.g., psoralen) or an antibody.

The term "analogue" when used in relation to a nucleic acid or nucleotide includes a compound having a physical structure that is related to a DNA or RNA molecule or residue, and may be capable of forming a hydrogen bond with a DNA or RNA residue or an analogue thereof (i.e., it is able to anneal with a DNA or RNA residue or an analogue thereof to form a base-pair), but such bonding is not so required for said compound to be encompassed within the term "analogue". Such analogues may possess different chemical and biological properties to the ribonucleotide or deoxyribonucleotide residue to which they are structurally related. Methylated, iodinated, brominated or biotinylated residues are examples of analogues. Active DNAzymes have been described which contain nucleotide analogues, including deoxyinosine, C-5-immidazole deoxyuridine, 3-(aminopropynyl)-7-deaza-dATP, 2'-O-methyl RNA, 2' O-methyl cap (Warashina et al., 1999; Cairns et al., 2003; Schubert et al., 2004; Sidorov et al., 2004). Other analogues are compatible with catalytic activity of DNAzymes. Alteration of a catalytic nucleic acid sequence, for example by substitution of one base for another, by substitution of an analogue for a base, or alteration of the sugar component or phosphodiester backbone, can be straight forward for the skilled artisan. For example, alterations can be made during synthesis, or by modification of specific bases after synthesis. Empirical testing of catalytic nucleic acids incorporating alterations such as base changes or base analogues allows for assessment of the impact of the altered sequences, or specific analogues, on catalytic activity. Analogues of the bases A, C, G, T and U are known in the art, and a subset is listed in Table 2.

TABLE 2

Examples of nucleotide analogues useful herein

| Abbreviation | Name |
| --- | --- |
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl thiouridine |
| D | Dihydrouridine |
| Fm | 2'-O-methylpseudouridine |
| Galq | beta, D-galactosylqueosine |
| Gm | 2'-O-methylguanosine |
| I | Inosine |
| i6a | N6-isopentenyladenosine |
| m1a | 1-methyladenosine |
| m1f | 1-methylpseudouridine |
| m1g | 1-methylguanosine |
| Ml1 | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| Manq | beta, D-mannosylmethyluridine |
| mcm5s2u | 5-methoxycarbonylmethyluridine |
| Mo5u | 5-methoxyuridine |
| Ms2i6a | 2-methylthio-N6-isopentenyladenosine |
| Ms2t6a | N-((9-beta-ribofuranosyl-2-methylthiopurine-6-yl)carbamoyl)threonine |
| Mt6a | N-((9-beta-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |
| AraU | beta D-arabinosyluridine |
| AraT | beta D-arabinosylthymidine |

The term "fragment" when used in relation to a nucleic acid refers to a constituent of that nucleic acid. Typically the fragment possesses qualitative biological activity in common with the nucleic acid, although this does not necessarily have to be the case. Fragments of a nucleic acid do not necessarily need to encode polypeptides which retain biological activity. Rather, a nucleic acid fragment may, for example, be useful as a hybridization probe or PCR oligonucleotide. The fragment may be derived from a nucleic acid of the invention or alternatively may be synthesized by some other means, for example chemical synthesis.

The term "variant" as used herein refers to substantially similar nucleic acid or polypeptide sequences. Generally, sequence variants possess qualitative biological activity in common. Further, such sequence variants may share at least 50%, 55%, 60%, 65%, 70%, 75%, 80%, 85%, 90%, 95%, 96%, 97%, 98% or 99% sequence identity. Also included within the meaning of the term "variant" are homologues, which are typically a polypeptide or nucleic acid from a different species but sharing substantially the same biological function or activity as the corresponding polypeptide or nucleic acid disclosed herein.

The term "high stringency" as used herein refers to the conditions under which two nucleic acids may be hybridized, and may include, for example, the concentration of salts and/or detergents in a solution, the temperature of a solution that is used during the hybridization of the two nucleic acids and time period of the hybridization. Accordingly, the term "high stringency" as used herein refers to conditions in a solution that are conducive to hybridization of two nucleic acids only where such nucleic acids share a high degree of complementarity. The degree of complementarity may include, but not be limited to, a range of from about 50% to 99%. Thus, "high stringency" conditions may involve, but are not limited to, the use of a varying temperature and a buffer comprising various concentrations of detergents, salts, and divalent cations.

The terms "assembly facilitator molecule", "assembly facilitator", "MNAzyme assembly facilitator molecule", "facilitator" and "MNAzyme assembly facilitator" as used herein refer to entities that can facilitate the self-assembly of component partzymes to form a catalytically active MNAzyme. In preferred embodiments an assembly facilitator is required for the self assembly of an MNAzyme. An assembly facilitator in some embodiments comprises a target such as a nucleic acid or non-nucleic acid analyte. Assembly facilitator molecules may comprise one or more regions or molecules that may pair with, or bind to, one or more oligonucleotide "partzymes," which constitute components or portions of an "MNAzyme". It is not required that the assembly facilitator interact with, pair with, or bind to each component partzyme or oligonucleotide provided that it interacts with, pairs with, or binds to, at least one of the component partzymes of an MNAzyme. As used herein, MNAzyme assembly facilitator molecules are intended to encompass the broadest range of constituents which can facilitate self-assembly of an MNAzyme. In some embodiments, an assembly facilitator may comprise a nucleic acid. In other embodiments, an assembly facilitator may comprise any cell or any portion thereof, for example, any eukaryotic or prokaryotic cell, a virus, prion, yeast or fungus, or any other molecule, for example, including but not limited to a protein, polypeptide, peptide or nucleic acid. In other embodiments, an assembly facilitator may comprise a virus, prion, yeast or fungus, or any other molecule, for example, including but not limited to glycoproteins, lipids, lipoproteins, entire organisms, cells, viruses, bacteria, archaea, fungi, antibodies, metabolites, pathogens, toxins, contaminants, poisons, small molecules, polymers, metal ions, metal salts, prions or any derivatives, portions or combinations thereof.

The term "target" as used herein includes any natural or synthetic entity, constituent or analyte which is sought to be detected, identified or quantified by a particular MN Azyme(s). Targets therefore encompass the broadest range of detectable entities, constituents or analytes for which methods of sensitive detection, identification and/or quantification are desirable. In some embodiments, a target comprises an assembly facilitator. Some exemplary targets include, but are not limited to, protein, polypeptide, peptide or nucleic acid, glycoproteins, lipids, lipoproteins, entire organisms, cells, viruses, bacteria, archaea, yeast, fungi, antibodies, metabolites, pathogens, toxins, contaminants, poisons, small molecules, polymers, metal ions, metal salts, prions or any derivatives, portions or combinations thereof. Other targets are also contemplated for use herein.

The terms "substrate", "substrate molecule" and "chemical substrate" as used herein include any molecule which is capable of being recognized, and acted upon or chemically modified by a catalytic molecule. In particular embodiments, a substrate may be recognized and modified by an enzyme. In other embodiments, a substrate may be recognized and modified by a catalytic nucleic acid molecule. The chemical modification of a substrate can be measured by the appearance of, or increase in, a product of the modification reaction, or by the disappearance of, or decrease in, a substrate of the modification reaction(s). A particular catalytic molecule may recognize one or more different substrate molecules provided each substrate molecule has at least a minimum structure which is recognizable for catalytic activity by the catalytic molecule.

A "reporter substrate", "reporter probe" or "reporter probe substrate" as used herein is a substrate that is particularly adapted to facilitate measurement of either the disappearance of a substrate or the appearance of a product in connection with a catalyzed reaction. Reporter substrates can be free in solution or bound (or "tethered"), for example, to a surface, or to another molecule. A reporter substrate can be labeled by any of a large variety of means including, for example, fluorophores (with or without one or more additional components, such as quenchers), radioactive labels, labeling with biotin (e.g. biotinylation) or chemiluminescent labels. Reporter substrates for catalytic nucleic acids may also include protein or nucleic acid enzymes, for example, covalently attached to their termini.

As used herein, "generic" or "universal" substrates are substrates, for example reporter substrates, that are recognized by and acted on catalytically by a plurality of MNAzymes, each of which can recognize a different target. The use of such substrates facilitates development of separate assays for detection, identification or quantification of a wide variety of targets using structurally-related MNAzymes all of which recognize a universal substrate. These universal substrates can each be independently labeled with one or more labels. In preferred embodiments, independently detectable labels are used to label one or more generic substrates to allow the creation of a convenient system for independently or simultaneously detecting a variety of targets using MNAzymes.

As used herein, the terms "partzyme", "component partzyme" and "component oligonucleotide" refer to a DNA-containing or RNA-containing or DNA-RNA-containing oligonucleotide, two or more of which, only in the presence of a MNAzyme assembly facilitator molecule, can together form an "MNAzyme." In certain preferred embodiments, one or more component partzymes, and preferably at least two, may comprise three regions or domains: a "catalytic" domain, which forms part of the MNAzyme's catalytic core that catalyzes a chemical modification; a "sensor arm" domain, which may associate with and/or bind to an assembly facilitator (e.g. a target); and a "substrate arm" domain, which may associate with and/or bind to a substrate. A depiction of these regions or domains can be seen, for example, in FIG. 1. A partzyme may comprise one or more molecules. Partzymes may comprise at least one additional component including but not limited to an aptamer, referred to herein as an "apta-partzyme." A partzyme may also include a substrate, as can be seen, for example, in FIG. 25.

The term "MNAzyme" as used herein, refers to two or more oligonucleotide sequences (e.g. partzymes) which, only in the presence of MNAzyme assembly facilitator molecule (for example, a target), form an active nucleic acid enzyme that is capable of catalytically modifying a substrate. An exemplary MNAzyme comprising partzyme A and partzyme B is depicted in FIG. 1. With reference to FIG. 1, DNA partzymes A and B each bind to a target (e.g., through Watson-Crick base pairing with a nucleic acid target). The MNAzyme only forms when the sensor arms of partzymes A and B hybridize adjacent to each other on the target. The substrate arms of the MNAzyme engage the reporter substrate, the cleavage of which is catalyzed by the catalytic core of the MNAzyme, formed by the interaction of the catalytic domains of partzymes A and B. The MNAzyme cleaves the substrate between a fluorophore and a quencher dye pair, thus generating signal. Cleavage of a DNA/RNA chimera (reporter substrate) is exemplified in the drawing. The terms "multi-component nucleic acid enzyme" and "MNAzyme" are used herein interchangeably and comprise bipartite structures, composed of two molecules, or tripartite structures, composed of three nucleic acid molecules, or other multipartite structures, for example those formed by four or more nucleic acid molecules. An MNAzyme may also comprise a stabilizing oligonucleotide which provides stability of the MNAzyme by interacting with an assembly facilitator or substrate. It is apparent that formation of an MNAzyme requires the assembly of at least the partzyme components with the assembly facilitator, as well as the binding of a substrate, for catalytic activity to be detectable, and that the absence of any of these components will result in a lack of catalytic activity.

As used herein an "aptamer" may comprise a structure that has the ability to recognize one or more ligands. For example, the recognition may have a high degree of specificity due to higher level structure of the aptamer, such as, a 3-dimensional binding domain or pocket. Aptamers may therefore bind protein, polypeptide, peptide or nucleic acid, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof, or any other entity. Preferred aptamers herein may comprise short single-stranded DNA or RNA oligomers that can be isolated from complex libraries of synthetic nucleic acid by an iterative process of adsorption, recovery, and reamplification. Aptamers may therefore be generated against almost any target, ranging from small molecules such as amino acids, or antibiotics to protein and nucleic acid structures.

As used herein, the term "cascade" refers to any succession of processes or operations that occur in successive stages, wherein the occurrence of each stage is typically dependent on the occurrence of a preceding stage. A cascade may therefore include, but is not limited to, an enzymatic cascade or any other signal transduction cascade. In some embodiments, a cascade may comprise amplification of a signal resulting from catalytic activity of an MNAzyme. In preferred embodiments, such an amplification cascade may involve repeated and therefore cyclic amplification of a signal, wherein catalytic activity of a first MNAzyme makes available a required molecule for catalytic activity of a second MNAzyme, which in turn makes available a required molecule for catalytic activity of the first MNAzyme. In some embodiments, the required molecule may comprise a partzyme, an enzyme, an assembly facilitator, a substrate, a target, a portion or fragment thereof or a combination thereof. In some embodiments, a cascade may therefore involve production of a cumulative effect, and thus detect a target of low abundance by generating a signal to a level at which it may be detected. In other embodiments, more than two catalytic stages may be employed. The cascade may be linear. In a preferred embodiment, the cascade may be exponential.

As used herein, the terms "inhibitor" or "assembly inhibitor" include, but are not limited to, any protein, polypeptide, peptide or nucleic acid, RNA, DNA, nucleic acid analogues, peptide nucleic acids, locked nucleic acids, peptide-nucleic acid chimeras, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivative, portion or combination thereof, or any other entity or molecule that interacts with one or more components of an MNAzyme as defined herein, or that interacts with a substrate or assembly facilitator, so as to prevent assembly of an MNAzyme. An "inhibitor" or "assembly inhibitor" need not be in physical proximity to an MNAzyme, but, by way of non-limiting example, may competitively bind a component part of an MNAzyme, substrate or assembly facilitator, thereby preventing such component part from being available for MNAzyme assembly. Such binding may include, for example, an inhibitory nucleic acid that is complementary to an oligonucleotide comprising a component part of an MNAzyme.

The following abbreviations are used herein and throughout the specification:

MNAzyme: multi-component nucleic acid enzyme, or multipartite nucleic acid enzyme;
DNAzyme: deoxyribonucleic acid enzyme;
RNAzyme: ribonucleic acid enzyme, or ribozyme;
PCR: polymerase chain reaction;
SDA: strand displacement amplification;
LAMP: loop-mediated isothermal amplification;
RCA: rolling circle amplification;
TMA: transcription-mediated amplification;
3SR: self-sustained sequence replication;
NASBA: nucleic acid sequence based amplification;
$dH_2O$: deionized distilled water;
LNA: locked nucleic acid;
PNA: peptide nucleic acid;
bDNA: branched DNA assay;
FCS: fluorescence correlation spectroscopy;
TSA: tyramide signal amplification;
An: analyte or target;
F: fluorophore;
Q: quencher;
miR: microRNA;
N=A, C, T, G, or any analogue thereof;
N'=any nucleotide complementary to N, or able to base pair with N;
$(N)_x$: any number of N;
$(N')_x$: any number of N';
W: A or T;
K: A, G, or AA;
rN: any ribonucleotide base;
$(rN)_x$: any number of rN;
rR: A or G;
rY: C or U;
M: A or C;
H: A, C, or T;
D: G, A, or T;
JOE or 6-JOE: 6-carboxy-4',5'-dichloro-2',7'-dimethoxy-fluorescein;
FAM or 6-FAM: 6-Carboxyfluorescein.
BHQ1: Black Hole Quencher 1
BHQ2: Black Hole Quencher 2

M-MLV RT (H-): Moloney Murine Leukemia Virus Reverse Transcriptase,
  RNase H Minus
  shRNA: short hairpin RNA
  siRNA: short interfering RNA
  mRNA: messenger RNA
  tRNA: transfer RNA
  snoRNA: small nucleolar RNA
  stRNA: small temporal RNA
  smRNA: small modulatory RNA
  pre-microRNA: precursor microRNA
  pri-microRNA: primary microRNA

DETAILED DESCRIPTION OF ILLUSTRATIVE EMBODIMENTS

It is to be understood at the outset, that the figures and examples provided herein are to exemplify, and not to limit the invention and its various embodiments.

In accordance with the present invention, compositions, methods and kits are provided for the detection, identification and/or quantification of a target. The methods generally comprise the use of compositions comprising multi-component or multipartite nucleic acid enzymes which are preferably formed by multiple nucleic acid components that self assemble to form an active nucleic acid enzyme in the presence of an assembly facilitator. In preferred embodiments, the assembly facilitator is the target and therefore the multi-component nucleic acid enzymes form only in the presence of the target.

1. Compositions—MNAzymes

The Multi-component Nucleic Acid enzymes (also referred to herein equally as multipartite nucleic acid enzymes or "MNAzymes") are capable of self-assembling from two or more oligonucleotide components, also referred to herein as partzymes. The partzyme oligonucleotides self-assemble in the presence of an MNAzyme self assembly facilitator to form an MNAzyme. MNAzymes are therefore catalytically active nucleic acid enzymes. In some embodiments, the presence of an MNAzyme can be detected, and is indicative of the presence of a target, because the MNAzyme forms only in the presence of the target, wherein the target comprises the assembly facilitator. A wide variety of assays based on the basic principles outlined above are provided herein. Compositions comprising oligonucleotides capable of forming MNAzymes, and MNAzymes of various sequences are also provided herein. In some embodiments at least one of the oligonucleotide components, assembly facilitator or substrate may also include/comprise an aptamer which is capable of binding to a target.

In preferred embodiments, the MNAzyme structures are based on one or more DNAzymes and/or ribozymes. More preferred are those MNAzyme structures which are based on a particular DNAzyme structure. Presently preferred structures are based on DNAzymes including the 10:23 and 8:17 DNAzymes. In various embodiments the MNAzymes comprise either or both ribonucleotide bases and deoxyribonucleotide bases. In more preferred embodiments, an MNAzyme structure is based at least in part on the structure of a DNAzyme. In other preferred embodiments, MNAzymes comprise at least some deoxyribonucleotide bases or analogues thereof. In more preferred embodiments, the catalytic core of an MNAzyme comprises one or more deoxyribonucleotide bases or analogues thereof. In still more preferred embodiments, one or more deoxyribonucleotide bases or analogues thereof are involved in the catalysis of a substrate. In other embodiments, at least one deoxyribonucleotide base, or its analogue, in the catalytic core improves catalytic activity. In yet other embodiments, there is a strict requirement for at least one deoxyribonucleotide base, or its analogue, in the catalytic core of the MNAzyme for catalysis to occur at a measurable rate, relative to that of a comparable MNAzyme without the deoxyribonucleotide base present.

As provided herein, MNAzymes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions, as demonstrated herein, such that the molecule retains catalytic activity. Substitutions and modifications to arms that bind the substrate or assembly facilitator may be well tolerated and in fact are the basis of allowing tailoring of the molecules to different substrates/assembly facilitators. For example, modification of the sensor arms will allow tailoring to different assembly facilitators, while modification of the substrate arms will allow tailoring to different substrates.

Therefore, in certain preferred embodiments, the invention envisages MNAzymes with catalytic activity that are comprised of deoxyribonucleotides or which are derived from such molecules by certain modifications/substitutions etc. As a general rule, replacement of the whole molecule with, for example, ribonucleotides, will render the molecule inactive because it relies for its activity on certain key deoxyribonucleotides. In a corresponding fashion, some ribonucleotides in a ribozyme may be substituted with deoxyribonucleotides but replacement of the whole molecule with, for example, deoxyribonucleotides, will render the molecule inactive.

The skilled artisan will appreciate that MNAzymes comprise either deoxyribonucleotides or ribonucleotides, or even both. Those MNAzymes comprising at least one and more preferably, all, deoxyribonucleotide component oligonucleotides are presently preferred. Also preferred are those MNAzymes comprising at least one deoxyribonucleotide base, or its analogue, within the catalytic core of the MNAzyme. Even more preferred are those embodiments where such a base is required for catalytic activity.

The skilled artisan will also appreciate that multipartite DNAzymes have advantages over multipartite ribozymes, for example with respect to stability and ease of use. Thus, the multi-component MNAzymes provided herein can provide a presently preferred alternative to multi-component ribozymes, which are also provided in accordance with various embodiments. It is also to be appreciated that in certain embodiments, MNAzymes offer advantages over uni-molecular nucleic acid enzymes, for example DNAzymes, which can only recognize one substrate, whereas a single MNAzyme can recognize two molecules, namely an assembly facilitator (e.g. a target) and a substrate. For example, these properties of MNAzymes make them adaptable for example, for detection of targets, including in situ, in vivo or in vitro detection.

2. Methods Using MNAzymes for Detecting, Identifying or Quantifying Targets

The present invention provides various methods employing the use of one or more MNAzymes for the detection, identification or quantification of at least one target. In one embodiment, first and second oligonucleotide components self-assemble only when contacted with a sample containing an assembly facilitator, said self-assembly of the catalytically active MNAzyme thereby indicating the presence of the assembly facilitator, wherein the assembly facilitator is the target. In other embodiments, such as for example those involving an aptamer, the assembly facilitator may not be the target, and thus may comprise only an element required for self-assembly of the MNAzyme.

Several of the various embodiments of the invention may be better understood by way of pictorial representations. Therefore, with reference to the figures, and in accordance with the compositions and methods herein, generally provided are MNAzyme-based methods that allow detection of at least one target using only nucleic acid enzymes (for example, FIGS. 1, 3, 4, 7-13, 20, 21, 24, 25) without any need for protein enzymes such as polymerases. Although the use of protein enzymes in conjunction with MNAzymes is not excluded herein, and in certain embodiments herein the inclusion of protein enzymes is permissible, or even preferred, the reaction conditions for methods that do not require protein enzymes are generally less restrictive and more readily optimized, for example for the efficiency of MNAzyme cleavage. The lack of requirement for protein enzymes also generally decreases the cost of reagents.

As further provided herein, some methods of employing MNAzymes for target detection do not require thermocycling and/or denaturation of a target. Isothermal methods are more flexible than methods requiring thermocycling and can also enable differentiation between targets comprising single stranded and double-stranded nucleic acid. Further, the lack of a need for thermocycling may make such methods easier and less expensive. Provided in accordance with the methods herein are simple, fast, cost effective, isothermal, and procedurally-flexible methods of detecting targets of interest in a sample, which may be synthetic or natural.

Certain of the examples provided herein demonstrate detection of a nucleic acid target by target-specific assembly of an MNAzyme leading to MNAzyme-mediated cleavage of, for example, a fluorescent reporter substrate. Furthermore, due to the nature of the MNAzyme molecule, reactions can be performed over a wide range of temperatures, subject only to the requirements for the assembly of MNAzyme and catalytic modification (e.g. cleavage) of the substrate utilized.

A basic example of a MNAzyme structure is depicted in FIG. 1. The structure shown comprises partzyme A and partzyme B which have base-paired with an MNAzyme assembly facilitator molecule, shown here simply as Target. Partzymes A and B by interacting with Target, have allowed the catalytic core to come into close proximity and thereby form. The substrate arms of the MNAzyme have interacted with and base-paired with a substrate, here Reporter Substrate. Thus the MNAzyme has self-assembled and this process is facilitated through the presence of the MNAzyme assembly facilitator molecule Target. In the absence of Target, no MNAzyme will form. Modification (in this case, cleavage) of the substrate is catalyzed by the catalytic core of the MNAzyme at the MNAzyme Cleavage Site within the substrate denoted by the vertical arrow. The substrate in this particular embodiment of the invention comprises a detectable portion having a detectable signal, for example fluorophore F, and a quencher portion having a quenching effect on the detectable signal F through the action of quencher Q. Upon cleavage at the MNAzyme Cleavage Site, there is a substantial increase in detectable signal, here fluorescence, which is readily detected or quantified.

FIG. 1 can further be understood to depict an example of a basic method of using MNAzymes to detect a target, which in some embodiments comprises an assembly facilitator. Strategy 1 (see FIG. 2) uses MNAzymes adapted for detection of the targets including DNA, RNA and proteins. The reporter substrate can be either free in solution (FIG. 1) or bound to a support (FIG. 3). Signal can be generated by various means such as separation of fluorophore F and quencher Q dye pairs (FIGS. 1 and 3).

More specifically, partzyme A and partzyme B are shown in FIG. 1, each comprising a substrate arm portion, catalytic core portion, and a sensor arm portion. In the presence of a target, the sensor arm portions of partzyme A and partzyme B can begin to hybridize to, and base pair with complementary portions of the target, for example a DNA or RNA sequence. Upon contacting the target in this fashion, the MNAzyme self-assembles forming a catalytic core which can modify a substrate which is bound by the substrate arms. Preferably the presence of the MNAzyme is detected through the detection or measurement of its catalytic activity. The substrate arms of the thus assembled MNAzyme can engage a substrate, for example the reporter substrate shown in FIG. 1, through the interaction of the complementary sequences on the substrate arms and the substrate. Once the substrate is so engaged with the substrate arms, the catalytic core can promote the modification (eg. cleavage) of the substrate, which can in turn be measured or detected, directly or indirectly.

Figure 2:
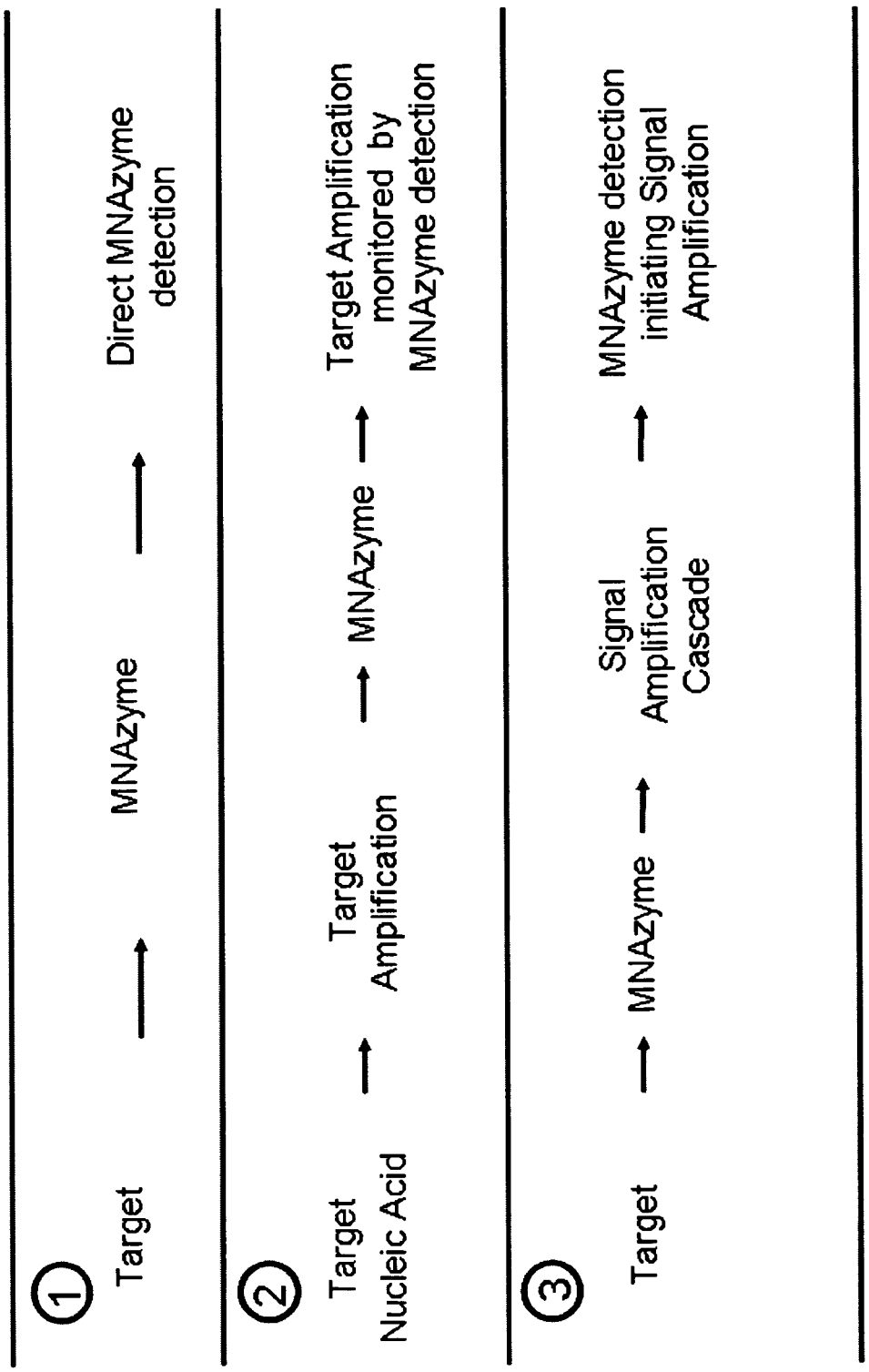
FIG. 2: Strategies for MNAzyme mediated target detection: shown is a flow chart showing exemplary applications of methods for target detection using MNAzymes. MNAzymes can be used for (1) direct detection; (2) detecting amplicons generated, for example, by PCR, SDA, LAMP, RCA, TMA, 3SR or NASBA either during, or following, amplification; and (3) initiating a signal amplification cascade.
Figure 3:
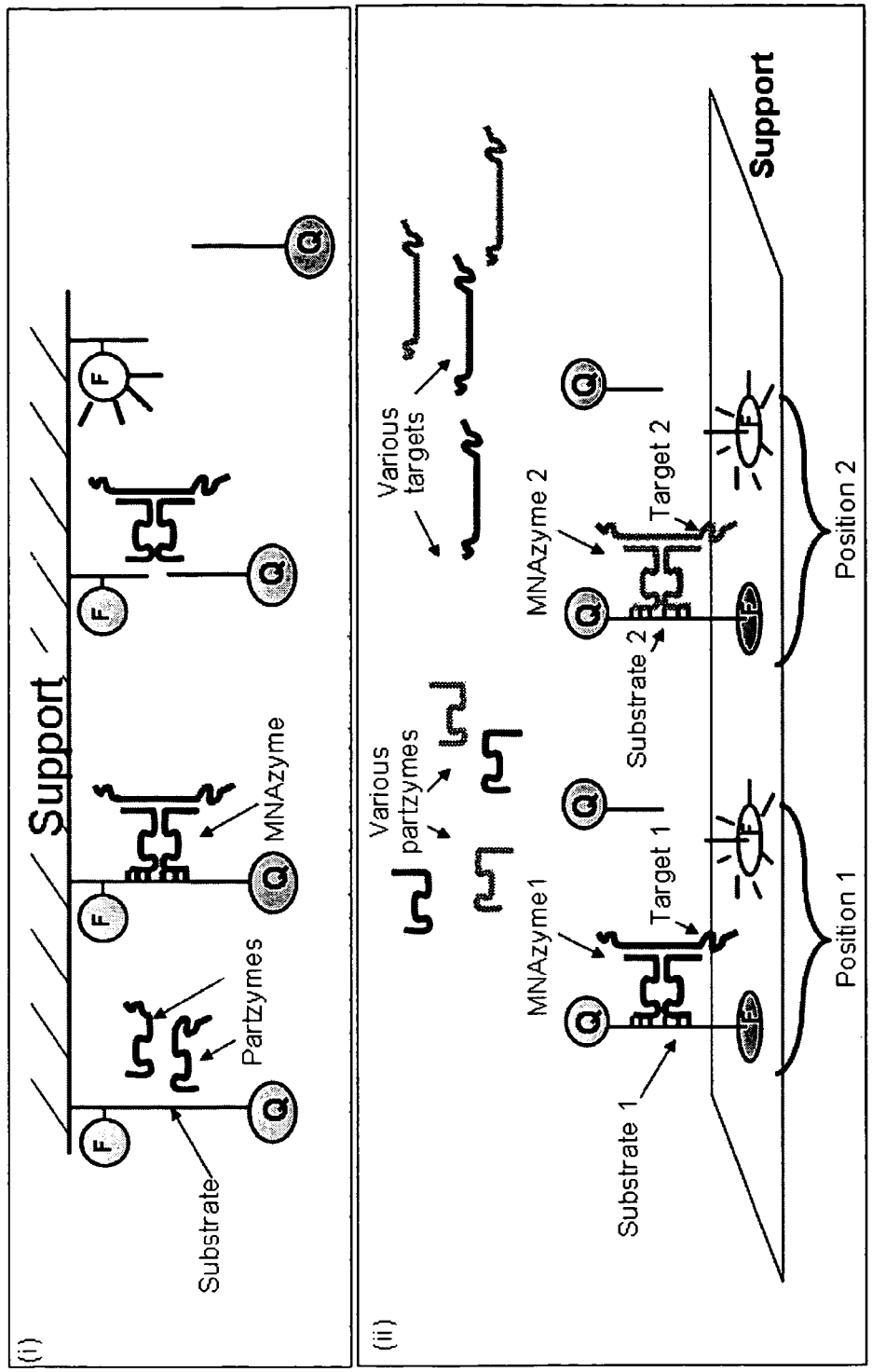
FIG. 3: Method for detection of targets using an MNAzyme and anchored generic substrates: shown is a depiction of exemplary MNAzymes and a method for target detection using MNAzymes that cleave substrates tethered to a support. In this embodiment, the MNAzyme forms only in the presence of an assembly facilitator (target). When the MNAzyme cleaves the tethered substrate between a fluorophore and quencher, a signal is generated. As shown here, upon cleavage between fluorophore F and quencher Q, there is a resultant increase in fluorescence. In general, the method may be designed such that either fluorophore F or quencher Q may stay attached to the support once cleavage occurs. Panel (i): The support shown has only one substrate tethered to it. Panel (ii): There may be multiple substrates tethered in different positions. Each substrate can be cleaved only by an MNAzyme formed in the presence of a specific MNAzyme assembly facilitator molecule—here, Targets 1 and 2 facilitate the self-assembly of MNAzymes 1 and 2 respectively. Thus, in this example MNAzyme 1 only self-assembles in the presence of Target 1 and only cleaves Substrate 1. Similarly, MNAzyme 2 only self-assembles in the presence of Target 2 and only cleaves Substrate 2. The signal can be localised by positioning of the substrate on the surface, thus allowing specific detection of different assembly facilitators.

With further reference to the figures, FIG. 2 provides a stylized overview of several example applications of an MNAzyme assay. Strategy 1 exemplifies a basic application of the MNAzyme assay as described above. An MNAzyme composed of two separate oligonucleotides with recognition sequences for both a target and a substrate forms when the oligonucleotides recognize and bind a target. The substrate, e.g. reporter substrate, is modified by the catalytic action of the MNAzyme and causes generation of a detectable signal, either directly (Strategy 1), during or after target amplification (Strategy 2) or via a signal cascade (Strategy 3). In some embodiments, both target and signal amplification occur simultaneously.

One skilled in the art would recognise that MNAzymes can be used in strategies for detection, identification or quantification of assembly facilitators that cover a broad range of application areas. These areas include, but are not limited to, medical, veterinary, agricultural, food technology, imaging and bioterrorism applications.

It will also be readily apparent to a skilled artisan that MNAzymes can be used to detect, identify and/or quantify targets in solution. For example, strategies involving detecting, identifying and/or quantifying single targets using a single substrate are applicable to such detection. In some embodiments this may involve the use of a generic substrate. Multiple targets can also be detected in solution using multiple MNAzymes which modify a series of generic substrates, the modification of each substrate resulting in a distinctly detectable signal e.g. different fluorescence.

3. Methods Using Multiple MNAzymes

The skilled artisan will recognize that the various assays provided herein can generally be used to detect a single target per reaction or assay, or to detect multiple targets in a single reaction or assay. When detecting multiple targets, one or more MNAzymes can be used depending on the assay and what is to be detected. For example, a single MNAzyme may suffice where detecting multiple related structures, for example a group of sequences sharing a critical sequence (recognized by the MNAzyme) and varying only for example, in length, or in sequence outside of the critical sequence. Any sequence with the critical sequence could be detected. Multiple MNAzymes would be useful where detecting related sequences differing by as little as a single nucleotide or even where vastly different targets are being detected, and it desirable to know the presence or absence of each. Similarly, in some embodiments a single substrate will suffice, while in others a unique substrate is required to detect each of several targets. In some cases, to multiplex the method requires the use of a distinct or unique detectable signal for each substrate to facilitate the design of the method. A distinct or unique detectable signal for each substrate may not be required when the substrates are affixed to a support or supports and can be distinguished by virtue of their localization on the support or supports. These design features will be readily understood by one skilled in the art. In some embodiments, the methods allow detection of a variety of different types of target in one reaction, eg a nucleic acid target and a protein.

4. Methods Using Target Amplification

The skilled artisan will readily appreciate that the methods described herein may involve amplification of a target before, during or after MNAzyme catalytic activity. Such target amplification finds particular application in embodiments of the present invention where the amount of target being sought to be detected, identified or quantified is of such quantum so as to provide a signal that may otherwise not be detectable. Such amplification may comprise one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

Strategy 2 (FIG. 2) exemplifies the use of an MNAzyme adapted to monitor the accumulation of amplicons during, or following, in vitro amplification of nucleic acid targets. Techniques for in vitro amplification of nucleic acid sequences are known in the art. These include techniques mediated by a DNA polymerase, such as the polymerase chain reaction ("PCR") (see, for example, U.S. Patent Nos. 4,683,202; 4,683,195; 4,800,159; 4,965,188; 5,176,995) (Saiki et al., 1985; Chehab et al., 1987), strand displacement amplification ("SDA") (Walker et al., 1992), rolling circle amplification ("RCA") (Lizardi et al., 1998), reverse transcription polymerase chain reaction (RT-PCR) and loop-mediated isothermal amplification ("LAMP") (Notomi et al., 2000; Nagamine et al., 2002). Other target amplification techniques are mediated by an RNA polymerase, for example, transcription-mediated amplification ("TMA") (Jonas et al., 1993), self-sustained sequence replication ("3SR") (Fahy et al., 1991) and nucleic acid sequence replication based amplification ("NASBA") (Compton, 1991).

The amplification products ("amplicons") produced by PCR, RT-PCR, SDA, RCA and LAMP are composed of DNA, whereas RNA amplicons are produced by TMA, 3SR and NASBA.

With further reference to strategy 2 as exemplified in FIG. 2, in one of its several aspects, the invention provides methods of using MNAzymes in conjunction with target amplification methods which include, for example, the aforementioned PCR, RT-PCR, SDA, RCA, LAMP, TMA, 3SR and NASBA. Examples 4, 5, 6, and 9 demonstrate the detection of PCR amplicons. In Examples 4, 5, 6, and 9, end point analysis following PCR facilitated rapid determination of the presence or absence of the target nucleic acids. Examples 8, 10, 11, 13, 14, 15, 16, 19, and 20 exemplify real time monitoring of PCR amplification, thus permitting quantification of the target nucleic acid. The accumulation of amplicons produced by PCR using either asymmetric or symmetric primer ratios can be monitored using MNAzymes.

As can be seen in FIG. 2 (strategy 2) a target nucleic acid is amplified in accordance with a procedure for amplifying that nucleic acid (i.e. DNA or RNA). Preferably, standard methods of in vitro amplification are used. The amplicons generated during the amplification serve as targets for an MNAzyme, thus MNAzyme activity is indicative of the presence of the target. The skilled artisan will appreciate that such monitoring can be conducted in a single vessel under conditions that permit both the amplification and the MNAzyme assembly and catalytic activity, or the MNAzyme assay can be conducted subsequent to, or at time points throughout, the amplification, by removing samples at the end or during the course of the amplification reactions.

It is also to be appreciated that methods or protocols that combine target amplification with catalytic nucleic acid activity may require specific reaction conditions. Preferably, reaction conditions are compatible with both polymerase activity (for amplification), and catalytic nucleic acid modification of a substrate (for detection). Protocols for determining conditions for concurrent catalytic activity and polymerase activity at high temperature, such as during PCR, have been described for DNAzymes (Impey et al., 2000). The influence of factors including DNAzyme arm length, buffer, temperature, divalent ion concentration and effects of additives was demonstrated in this paper. DNA enzymes are suited for use in combination with in vitro amplification strategies. For example, they are not irreversibly denatured by exposure to high temperatures during amplification.

5. Methods Using Insoluble and Solid Supports

It is also to be understood that generally the methods, whether multiplexed or not, are applicable in solution, or combined with an insoluble support or solid support on which one or more of substrate, enzyme or portion thereof, MNAzyme assembly facilitator and/or target are bound, attached or tethered. Again the features of such assay systems will be generally understood by the skilled artisan provided with the methods and variations exemplified herein and the working examples. Thus, the invention is not to be considered limited to the literal teachings herein, but is capable of being modified and varied consistent with the principles and scope of the teachings provided herein and the knowledge in the art.

With reference to FIG. 3, Panel (i), an exemplary method for detecting targets using an MNAzyme and a substrate anchored to a support is depicted. In this embodiment, the substrate is preferably a substrate as shown with a detectable portion comprising a detectable signal, for example a fluorophore, and a quencher portion which diminishes or eliminates the detectable signal while the detectable portion and the quencher portion of the substrate remain in close proximity, for example, until the substrate is modified eg. by cleavage. The substrate is attached to a support. Preferably the support is an insoluble material, or a matrix which retains the substrate and excludes it from freely moving in the bulk of the reaction mixture. Such supports are known in the art for immobilizing or localizing substrates, including nucleic acid targets. The skilled artisan will appreciate that the support can be selected from a wide variety of matrices, polymers, and the like in a variety of forms including beads convenient for use in microassays, as well as other materials compatible with the reaction conditions. In certain preferred embodiments, the support can be a plastic material, such as plastic beads or wafers, or that of the well or tube in which a particular assay is conducted.

The attachment of the substrate to the support is designed such that upon modification, e.g. by cleavage, of the substrate by the MNAzyme, either the detectable portion or the quencher portion, but not both, remains attached to the support, while the other is freed to move into the bulk of the reaction mixture, away from the portion remaining attached. Thus, in a cleavage example, the detectable signal vastly increases as the quencher portion and the detectable portion are separated upon cleavage. In the embodiment shown in FIG. 3, Panel (i), the fluorophore-containing detectable portion remains attached after cleavage. This has the benefit of allowing localization of the signal on the support but in certain instances, the fluorophore/s may be released into solution. In a further embodiment where, for example, ligation occurs, the quencher may be ligated to a fluorophore thus decreasing the detectable signal.

With reference to FIG. 3, Panel (ii), a multiplexed method comprising multiple MNAzyme components for making multiple MNAzymes (two shown) specific for different targets is shown. This embodiment encompasses a structure which comprises a substrate in a particular known position, e.g. a "chip", where multiple positions are available to bind numerous substrates, e.g. Substrate 1, Substrate 2. The detectable portion of each substrate can be traced to its position and is tethered at that location. For each MNAzyme, e.g. MNAzyme 1, MNAzyme 2, if the target, e.g. Target 1, Target 2, is present in, for example, a test solution, the MNAzyme corresponding to and specific for that target will self-assemble and be able to catalyze the cleavage of its corresponding substrate, resulting in the production of a signal at that location. The position of the detectable signal will thus identify which MNAzyme has cleaved its substrate, and thus which target(s) is present in the test solution. In this embodiment, the modification of the substrate results in an identifiable signal by virtue of its location. The substrate does not need an independently identifiable detection mechanism, eg, a different fluorophore, although persons skilled in the art would recognize that such contemplation is within the scope of the present invention.

Embodiments of the present invention encompassing an insoluble support in the form of a "chip", otherwise known as an array or microarray, typically comprise a plurality of substrates coupled, tethered or otherwise attached to the chip. In particular embodiments, the substrates comprise a nucleic acid. A plurality of nucleic acids may be positioned upon the chip by any suitable method known in the art, for example, by pipette, ink-jet printing, contact printing or photolithography. The chip may be comprised of at least one element, with each element comprising at least one nucleic acid. The at least one element may be comprised of a plurality of nucleic acids of the same sequence. The number of elements comprising a chip may be any number, and where a plurality of elements is positioned on a chip, the elements may be spaced apart at a uniform or a variable distance, or a combination thereof. In some embodiments, the elements may be positioned randomly, with the respective location of each element then determined. The size and shape of the elements will depend upon the particular application of the present invention, and different sized and shaped elements may be combined into a single chip. The surface of the chip may be substantially planar or may have features such as depressions or protuberances, and the elements may be positioned either into the depressions or onto the protuberances. Such depressions may provide a reservoir for solutions into which the elements are immersed, or such protuberances may facilitate drying of the elements. For example, elements may be placed in each well of a 96 well plate. In some embodiments, the chip may include unique identifiers such as indicia, radio frequency tags, integrated devices such as microprocessors, barcodes or other markings in order to identify each of the elements. The unique identifiers may additionally or alternatively comprise the depressions or protuberances on the surface of the array. Furthermore, the unique identifiers can provide for correct orientation or identification of the chip. The unique identifiers may be read directly by a data capture device or by an optical scanner or detector.

6. Reporter Substrate Systems Used in the Methods

Also provided in accordance with the present invention are generic reporter substrate systems, which allow rapid assay development by allowing facile design changes to create new MNAzymes which recognize different targets. As discussed herein, the substrate arm portion and the catalytic core portion of the partzymes may remain unchanged, with changes only to the sensor arm portion of one or more partzymes required for new targets. Generic substrate sequences are provided and the same substrate can therefore be incorporated in assays for many different targets. Further, the same substrate can be incorporated into the methods in various embodiments herein, including assays where the substrate is free in solution or is tethered or attached to a support. A series of generic substrates can be used in a multiplex reaction allowing simultaneous detection of multiple targets.

MNAzyme strategies using generic substrates offer a major advantage over technologies such as TaqMan® or Beacons which require the design and use of probes specific for each new target.

7. Substrates Used in the Methods

As described in more detail below, MNAzymes have an advantageous property in certain embodiments of being able to utilize a universal or generic substrate. Such a substrate is shown in FIG. 1 in a presently preferred configuration wherein the substrate comprises both a detectable portion and a quencher portion. The quencher portion is adapted to diminish or eliminate a detectable signal from the detectable portion of the substrate until the substrate is cleaved by the MNAzyme. For example, the quencher portion may comprise "Black Hole Quencher 1" (BHQ1) or "Black Hole Quencher 2" (BHQ2).

Thus, the MNAzyme cleaves the substrate between the detectable portion and the quencher portion allowing the two portions to separate in solution, thereby allowing the detectable signal to appear or increase as the quencher portion is distanced from, or effectively removed from the local environment of the detectable portion.

The use of the generic or universal substrate is enabled through the design of the MNAzyme's component partzymes. By altering only the sensor arms of the partzymes, but by leaving the substrate arms unchanged, a large variety of MNAzymes specific for each of a plurality of targets can be designed all of which utilize a universal substrate for detection. The skilled artisan will appreciate the advantages that this offers in terms of eliminating the need for customized or unique substrates for each target. Each new target requires only one or more changes in one or more of the sensor arm portions; the substrate arm portion and the catalytic core portion can remain constant. Thus, a single reporter substrate can be used for a single target using an MNAzyme, and multiple targets in a series of assays using altered MNAzymes. A plurality of reporter substrates allows multiplexing to detect multiple targets in a single assay using multiple MNAzymes, one for each target. Such multiplexed methods of using MNAzymes are readily accomplished in solution (FIG. 18) or with attachment to a support system (FIG. 3). It is contemplated herein that multiplexed assays can thus be accomplished in systems involving attaching one or more of the substrate, or the MNAzyme partzymes or assembly facilitator, or additional enzyme activities, to a support as described herein.

Further, the substrates may incorporate additional entities such as labeled nucleic acids, nanoparticles, microparticles, proteins, antibodies, RNA, DNA, nucleic acid analogues, proteins, glycoproteins, lipoproteins, peptide nucleic acids, locked nucleic acids, peptide-nucleic acid chimeras, or any combination thereof. For instance, the nanoparticles may be gold nanoparticles, wherein these gold nanoparticles are associated with a plurality of targets, such as nucleic acids.

Substrates can be modified by an MNAzyme thereby providing a detectable effect. In the detection process, the substrate modification by an MNAzyme may involve, for example, cleavage, ligation, porphyrin metallation, formation of carbon-carbon bonds, ester bonds or amide bonds. As a consequence of substrate modification by an MNAzyme, a detectable effect is generated and the magnitude of the effect may therefore be indicative of the quantity of the target sought to be measured. The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

Several groups have reported detection of nucleic acid targets, and other analytes with colourimetric readouts (Elghanian et al., 1997, Mirkin et al, 1996, and Liu and Lu, 2004). The strategy involves preparation of batches of gold nanoparticles, each of which has a distinct DNA oligonucleotide sequence attached to its surface. Gold particles can then be aggregated by the addition of a "bridging oligonucleotide", which has complementarity with the sequences that are attached to the gold particles. Particle aggregation results in a concomitant change in colour from red to blue (Mirkin et al, 1996). More recent work has shown that the inclusion of a DNAzyme substrate sequence within the bridging oligonucleotide can provide a mechanism for reversing the aggregation of the gold particles (Liu and Lu, 2004). Activation of the DNAzymes, and subsequent cleavage of the substrate/bridging oligonucleotide, resulted in the dissociation of the gold particles and a change in colour from blue to red.

A simple lead detector based on the above concept was devised which functioned by exploiting the dependence of a specific DNAzyme on lead for its catalytic activity. The DNAzyme was designed to cleave a bridging oligonucleotide used to aggregate gold particles (Liu and Lu, 2004). Similarly, an aptazyme containing an aptamer specific for adenosine, and a DNAzyme capable of cleaving a bridging oligonucleotide only in the presence of adenosine, allowed detection of adenosine in a colourimetric format.

8. Optimization of the Methods

The skilled artisan will readily understand that the methods described herein may be optimized using a variety of experimental parameters in order to optimize the detection, identification and/or quantification of a target. The particular experimental parameters that are optimized, and the level of such optimization, will depend upon the particular method being employed and the particular target being sought to be detected, identified and/or quantified. Such parameters include, but are not limited to, time, temperature, concentration of salts, detergents, cations and other reagents including but not limited to dimethylsulfoxide (DMSO), and length, complementarity, GC content and melting point (Tm) of nucleic acids.

In some embodiments, for example those methods involving detection of sequence variation and/or detection of methylated DNA, the experimental parameters, and preferably including the temperature at which the method is performed, may be optimized so as to discriminate between binding of an MNAzyme component nucleic acid to a target nucleic acid that does or does not comprise a sequence variation or a methylated nucleotide, respectively. The temperature at which such methods may be performed may be in the range of about 20° C. to about 96° C., about 20° C. to about 75° C., 20° C. to about 60° C. or about 20 to about 55° C., In one preferred embodiment, optimized reactions for practicing the methods of using MNAzymes are provided herein. In such optimized reactions, catalytic activity is increased by up to 10, 20, or 30% above unoptimized reactions. More preferred reaction conditions improve catalytic activity by at least 35%, or 40%, and preferably up to 50% or more. In still more preferred embodiments, optimized reactions have an increase of catalytic activity of more than 50%, and up to 66%, 75% or even 100%. In yet more preferred embodiments, a fully optimized reaction method will offer 100, 200 or even 300% or more increase in catalytic activity. Other preferred reaction conditions can improve the catalytic activity by up to 1000% or more over methods practiced with unoptimized reaction conditions. A highly preferred reaction condition for optimizing the methods provided herein is the inclusion of certain divalent cations. The catalytic activity of most nucleic acid enzymes may be influenced in a concentration-dependent fashion by the concentration of divalent cations. Preferred optimized reactions are optimized for one or more of $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$.

9. Methods Using Aptamers

Persons skilled in the art will readily appreciate that the methods described herein may be performed with aptamers, wherein said aptamers may facilitate the detection, identification and/or quantification of targets including targets other than nucleic acids.

Figure 4:
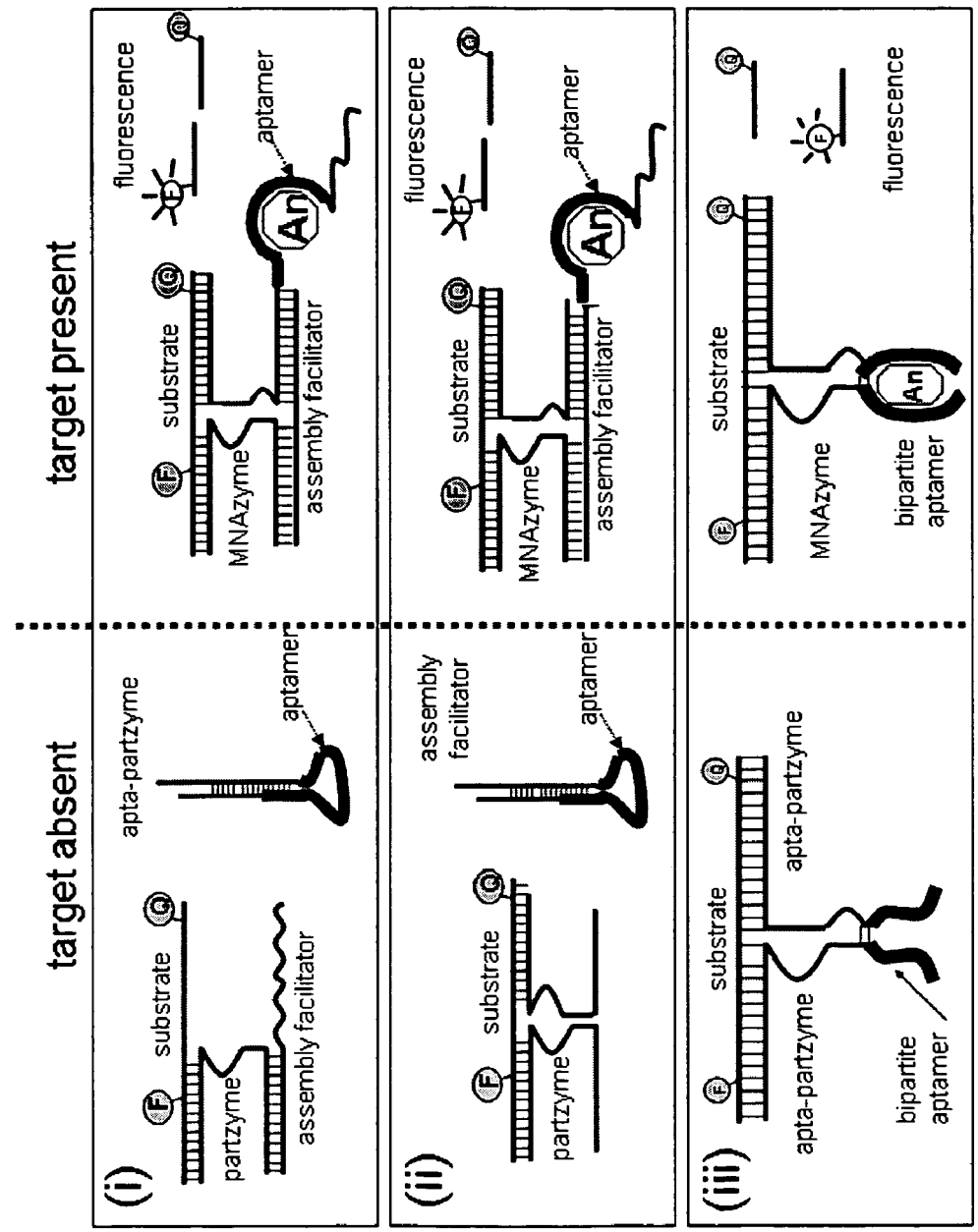
FIG. 4: Exemplary methods for target detection: shown are examples of methods that use an MNAzyme to detect a target analyte (An), for example, including but not limited to a protein or small molecule. This example shows generation of a signal by MNAzyme cleavage of a substrate labelled with a fluorophore (F) and a quencher (Q). The general designs could be used in other formats, whereby the signal is generated by a modification other than cleavage and/or where the readout is not fluorescent, but, for example, is colourimetric, radioactive etc. Three general strategies are illustrated in this figure. (i) An aptamer for binding a target analyte is linked to one partzyme (an apta-partzyme). This molecule has self-complementarity, and cannot contribute to active MNAzyme assembly in the absence of target analyte. A second partzyme, a substrate and an assembly facilitator are also provided. When a specific target analyte binds to the aptamer domain, the complementary bases within the apta-partzyme separate, enabling the apta-partzyme to adopt a conformation whereby it can contribute to active MNAzyme assembly. The active MNAzyme can cleave the substrate and generate fluorescence. (ii) An aptamer for binding a target analyte is linked to an assembly facilitator. This molecule has self-complementarity, and cannot direct the partzymes to align and assemble an active MNAzyme in the absence of target analyte. Two partzymes and a substrate are also provided. When a specific target analyte binds to the aptamer domain, the complementary bases within the assembly facilitator separate, enabling the assembly facilitator to adopt a conformation whereby it can direct the assembly of active MNAzymes. The active MNAzyme can cleave the substrate and generate fluorescence. (iii) Two apta-partzymes, each of which contains a portion of an aptamer, are incubated in the presence of a substrate. In the absence of target analyte, the two apta-partzymes cannot assemble to form an active MNAzyme. When a specific target analyte is present, and binds to both of the domains that contain a portion of the aptamer, the two apta-partzymes are brought into close proximity and can assemble into an active MNAzyme. The active MNAzyme can cleave the substrate and generate fluorescence.

With reference to FIGS. 4 and 20, a method of using MNAzymes to detect targets, including non-nucleic acid entities is exemplified. This method uses aptamers which may comprise a nucleic acid or protein, polypeptide, or peptide or combination thereof that has the ability to recognize one or more ligands. Aptamers may bind, for example, proteins, polypeptides, peptides or nucleic acids, glycoproteins, lipids, lipoproteins, cells, viruses, bacteria, archaea, fungi, antibodies, metabolites, pathogens, toxins, contaminants, poisons, entire organisms, small molecules, polymers, metal ions, metal salts, prions or any derivatives, portions or combinations thereof, or any other entity (Lee et al., 2004).

Preferred aptamers herein may comprise short single-stranded DNA or RNA oligomers or peptides that can be isolated from complex libraries of synthetic nucleic acids or peptides by an iterative process of adsorption, recovery, and reamplification. Aptamers may therefore be generated against almost any target, ranging from small molecules such as amino acids or antibiotics, to protein and nucleic acid structures. In preferred embodiments, aptamers include, for example, nucleic acid binding molecules which are preferably generated by evolution and selection techniques. Preferably, aptamers may comprise DNA or RNA molecules, or a combination of both, including but not limited to the nucleotide analogues as per, for example, Table 2 above.

Strategies for combining the use of aptamers with MNAzymes are illustrated in FIGS. 4 and 20. With reference to FIG. 4 panel (i), the nucleic acid oligonucleotides required for this MNAzyme detection strategy may include; (a) a standard partzyme; (b) an apta-partzyme which is a partzyme that incorporates an aptamer (bold sequence) as well as a complementary sequence capable of forming a hairpin and therefore inhibiting MNAzyme assembly; (c) an assembly facilitator which can bind to both the apta-partzyme and the partzyme, thus enabling assembly of an active MNAzyme; and (d) a substrate. In the absence of a target analyte (An), the apta-partzyme adopts a hairpin structure which inhibits assembly of an active MNAzyme. In the presence of target analyte, the target analyte binds to the aptamer domain of the apta-partzyme, thus disrupting the hairpin structure and allowing the apta-partzyme to participate in assembly of an active MNAzyme. The active MNAzyme can then modify a substrate causing, for example, fluorescent signal generation.

With reference to FIG. 4 panel (ii), the nucleic acid oligonucleotides required for this MNAzyme detection strategy may include; (a) two standard partzymes; (b) an assembly facilitator that incorporates an aptamer (bold sequence) as well as complementary inhibitor sequence capable of forming a hairpin structure; and (c) a substrate. In the absence of a target analyte, the assembly facilitator adopts a hairpin structure which inhibits the ability of this component to direct the assembly of active MNAzymes. In the presence of target analyte, the target analyte binds to the aptamer domain of the assembly facilitator, thus disrupting the hairpin structure and allowing the component to direct the assembly of an active MNAzyme. The active MNAzyme can then modify a substrate causing, for example, fluorescent signal generation.

One skilled in the art will appreciate that the aptamer may be incorporated into either end of the assembly facilitator molecule or molecules. Further it will be appreciated that multiple aptamers could be incorporated into one or more of the partzyme oligonucleotide components. The assembly facilitator in the strategies illustrated in FIG. 4 panels (i) and (ii) can comprise DNA, RNA, LNA, PNA or a sequence containing one or more nucleotide base analogues. In other embodiments, the target An is a nucleic acid. In such embodiments, a sequence complementary to the target nucleic acid replaces the bold aptamer sequence in FIG. 4.

With reference to —FIG. 4 panel (iii), the nucleic acid oligonucleotides required for this MNAzyme detection strategy may include two apta-partzymes, each of which contains a portion of an aptamer. In the absence of a target analyte, active MNAzymes cannot assemble. In the presence of target analyte, the target analyte serves as the assembly facilitator bringing the oligonucleotide components together thus directing the assembly of an active MNAzyme. The active MNAzyme can then modify a substrate causing, for example, fluorescent signal generation.

A related strategy, which combines aptamer binding and MNAzyme assembly, is illustrated in FIG. 20. In this strategy, an aptamer sequence is incorporated at the end of a partzyme (apta-partzyme) in a configuration whereby an active MNAzyme is only formed in the presence of the target analyte. The oligonucleotide components required for the MNAzyme detection strategy illustrated include; (a) a standard partzyme; (b) an apta-partzyme which is a partzyme with an aptamer incorporated into one of its ends; (c) an assembly facilitator which binds to both the apta-partzyme and the partzyme enabling assembly of an active MNAzyme (in the presence of target); (d) a reporter probe substrate; and (e) an assembly inhibitor which hybridises to the apta-partzyme in a region which spans at least part of the aptamer sequence and part of the substrate binding arm of the partzyme sequence. In the absence of a target (left hand panel), the assembly inhibitor binds to the apta-partzyme thus blocking binding (and cleavage) of the reporter probe substrate. In the presence of a target (right hand panel), the target binds to the aptamer sequence of the apta-partzyme, preventing the binding of the assembly inhibitor and allowing the binding and cleavage of the reporter probe substrate. As such, an active MNAzyme can only form and cause fluorescent signal generation in the presence of target.

Further, it will be appreciated by one skilled in the art that the strategy as illustrated in FIG. 20 is similar to that illustrated in FIG. 4 panel (i), with the difference being that the complementary inhibitor sequence, which prevents active MNAzyme formation, is either incorporated into an oligonucleotide partzyme component (FIG. 4 panel (i)) or into a separate molecule (FIG. 20). As such, an inhibitor sequence can be a separate molecule or can be incorporated into one of the components that participate in the MNAzyme complex.

It will also be appreciated by one skilled in the art that one or more aptamers could be incorporated into any of the oligonucleotide components, including the partzymes, the assembly facilitator or the substrate. Further the aptamer could be incorporated into either end of any one of these oligonucleotides.

The invention may be better understood by reference to examples 18 and 21 where the aptamer/MNAzyme strategy is used to detect a small molecule (ATP) and a protein (Taq polymerase) respectively.

10. Methods for Detection, Identification and Quantification of MicroRNA

Figure 5:
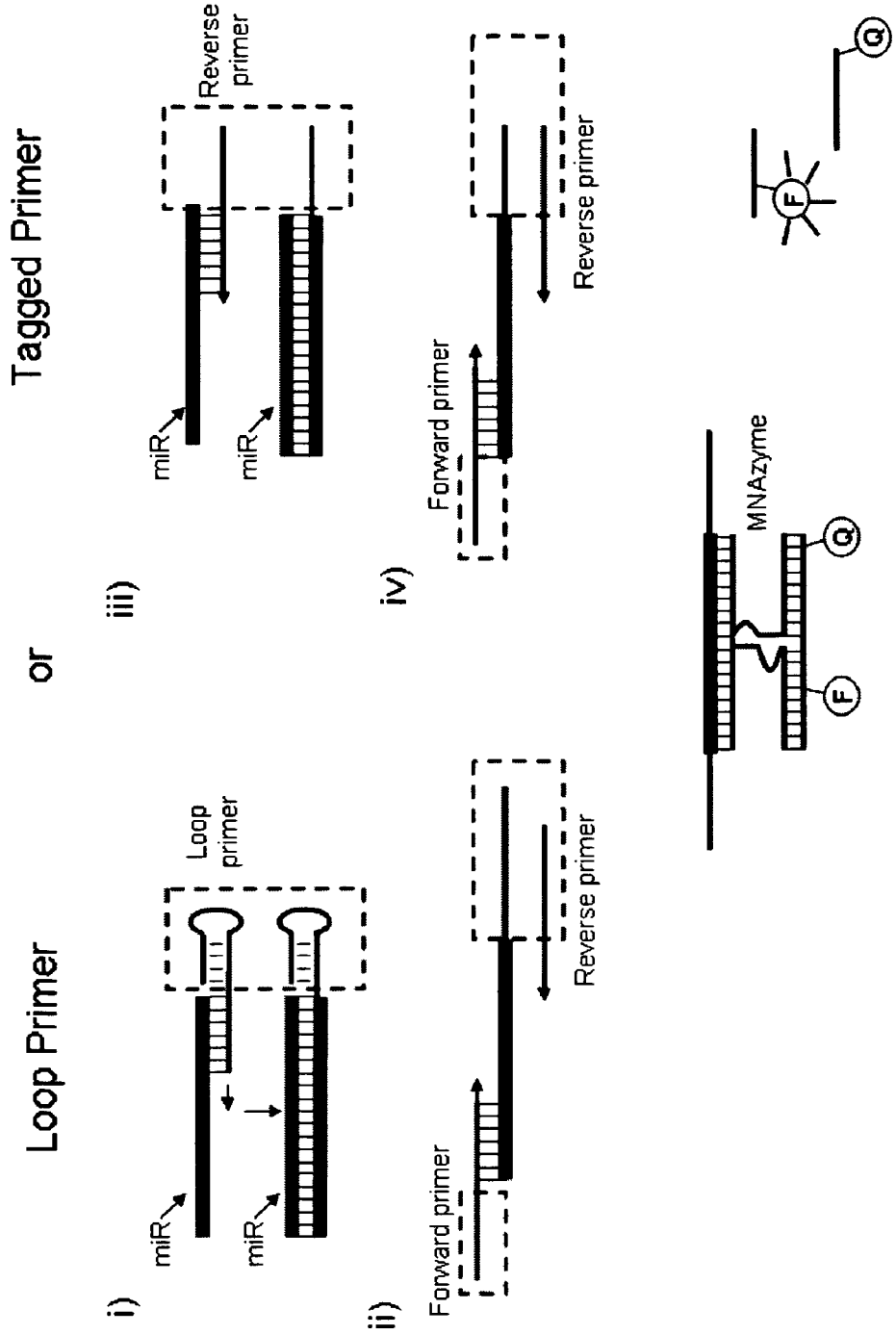
FIG. 5: PCR amplification of microRNAs and detection using MNAzymes: shown is a depiction of an MNAzyme strategy for amplification and detection of short sequences such as micro-RNA (miR) species. The method uses a 3' primer that binds to the miR at the 3' end and which has an unrelated extension sequence (shown in dashed boxes) which may (parts (i) and (ii), Loop Primer, left), or may not (parts (iii) and (iv), Tagged primer, right), form a stem-loop structure at the 5' end. The 3' miR primer is extended in the presence of reverse transcriptase (parts (i) and (iii)), followed by amplification via PCR using 5' and 3' primers with miR specific sequence at the 3' ends and unrelated extension sequence at the 5' ends (parts (ii) and (iv)). The amplicons can be detected by MNAzymes, which hybridize to the amplicon, including the region between the 5' and 3' primers. A requirement for strict complementarity of the MNAzyme sensor arms and the target nucleic acid allows discrimination of closely related sequences. F: fluorophore; Q: quencher.

The skilled artisan will understand that the detection, identification and/or quantification of microRNA represents a particular embodiment of the methods described herein. With reference to FIG. 5, a strategy for amplification of short nucleic acid sequences (e.g. microRNAs (miRs)) and detection of amplicons using MNAzymes is exemplified.

Detection of short nucleic acid sequences such as microRNAs (miRs) requires additional strategies primarily due to the small size of these targets. MiRs are non-coding RNA molecules of approximately 22 nucleotides in length. They can be detected by cloning or northern blot analysis, but these methods are laborious and require larger amounts of total RNA than techniques such as RT-PCR. The small size of miRs provides insufficient sequence to accommodate two PCR primers of standard design. Further, even if miR amplification is accomplished, it is difficult to distinguish genuine amplicons from primer-dimers using either size (ascertained by electrophoresis), or fluorescence from the intercalation of non-specific dyes, such as Sybr Green or Ethidium Bromide. This limitation could be overcome by probing the miR amplicons with internal hybridization probes such as TaqMan® or Beacon probes, however, again the small size of the amplicons prohibits use of probes of standard designs.

A modified TaqMan® RT-PCR method (Chen et al., 2005) for miR analysis initiates reverse transcription using 3' primers which have miR specific 3' termini and additional unrelated sequences at their 5' termini which can form stem-loops. The cDNA generated is amplified using these 3' primers and 5' primers, which also have miR specific 3' termini and additional unrelated sequences at their 5' termini. The amplification is monitored in real time using TaqMan® probes that bind to both miR sequences and unrelated sequences introduced by the primers. However, due to the primer design, and the size and positioning of the TaqMan® probe there is a still the likelihood that specific miRs may not be distinguished from closely related sequences.

As shown in FIG. 5, the method employed here preferably employs a 3' primer that binds to a miR at its 3' end and has an extension sequence, unrelated to the miR, which may, or may not, form a stem-loop at the 5' end. As FIG. 5 depicts, the unrelated sequence of the primer may create a loop structure (FIG. 5, left-hand side) or may merely create a tag structure (FIG. 5, right-hand side). In either example, the 3' miR primer is extended in the presence of reverse transcriptase, followed by PCR amplification using 5' and 3' primers with miR-specific sequence at the 3' end with unrelated extension sequence at the 5' ends. The amplicons are readily detected by MNAzymes, which recognize and hybridize to the amplicon including the region between the 5' and 3' primers. The strict requirement for complementarity between the MNAzyme sensor arm and the target nucleic acid allows discrimination of even closely related sequences. Example 5 and Example 10 in the Examples below demonstrates the results of using MNAzymes to detect amplicons generated by amplification of short nucleic acid sequences (see also strategy 2 in FIG. 2, above). Further, the example 5 demonstrates the capacity of methods using MNAzymes to distinguish between two sequences having only a single nucleotide difference. This provides a major advantage in that, even when the amplification process is unable to discriminate between closely related sequences, the MNAzymes allow discrimination between minor sequence variation in the resulting amplicons.

11. Methods Using Cascades

Figure 25:
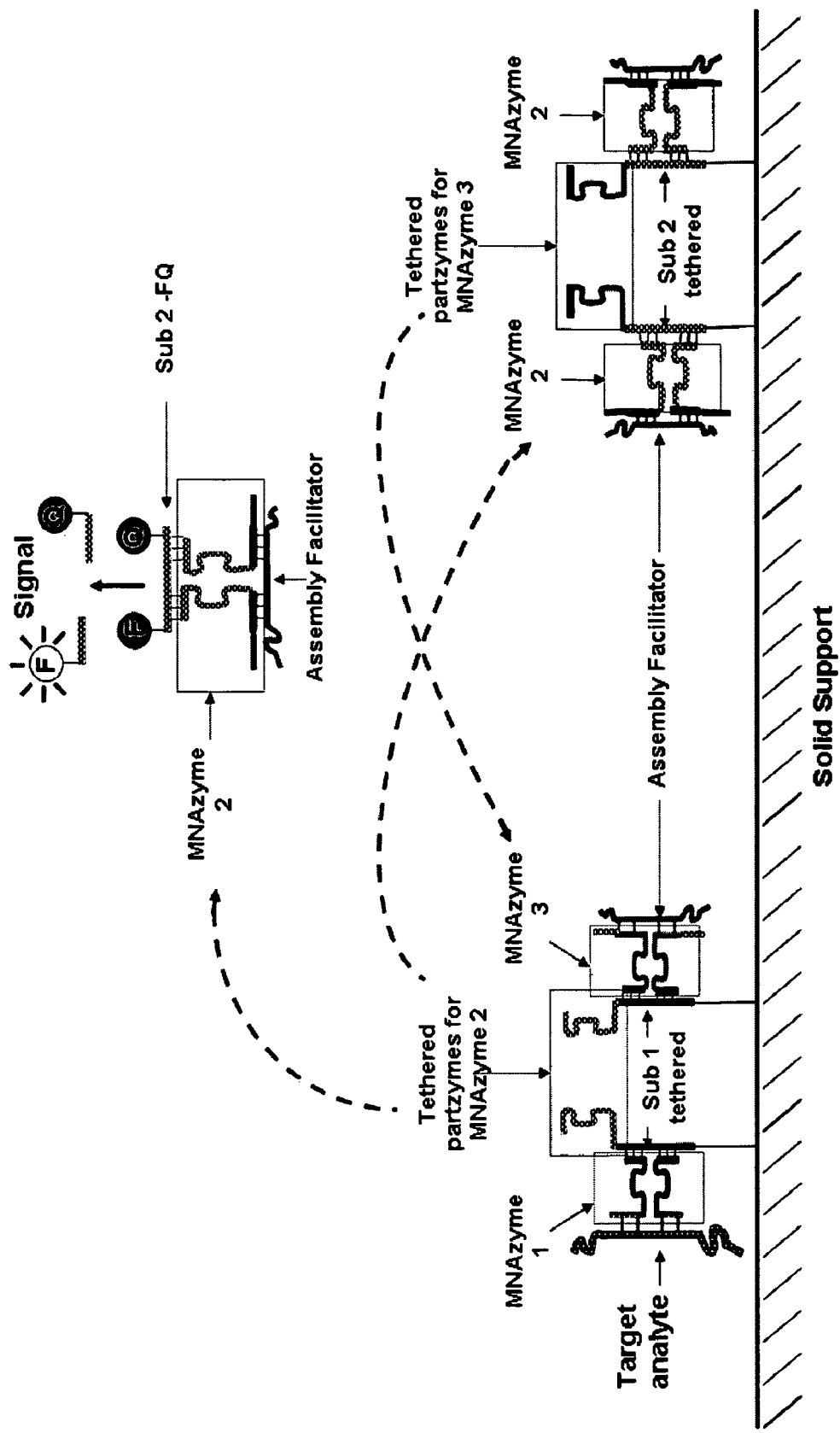
FIG. 25: Example of an MNAzyme cascade using tethered partzymes: MNAzymes can be used to initiate signal amplification cascades as illustrated in this diagram. The reaction contains the following elements: (i) partzymes for MNAzyme 1 which are free in solution; (ii) an assembly facilitator for MNAzymes 2 and 3 (which have the same sensor arms) which is either free in solution (as illustrated) or tethered to an insoluble support by substrate, Sub 1; (iii) partzymes for MNAzyme 2 which are tethered to an insoluble support by the substrate, Sub 1. Sub 1 can be cleaved by either MNAzyme 1 (in the presence of a target) or MNAzyme 3 (in the presence of an assembly facilitator), and cleavage results in the release of the partzymes for MNAzyme 2 into solution; (iv) partzymes for MNAzyme 3 which are tethered to an insoluble support by the substrate, Sub 2. Sub 2 can be cleaved by MNAzyme 2 (in the presence of assembly facilitator) and cleavage results in the release of the partzymes for MNAzyme 3 into solution; (v) Sub 2-FQ, which has the same sequence as Sub 2, but is free in solution and is dual labelled with a fluorophore (F) and a quencher (Q). Sub 2-FQ can be cleaved by MNAzyme 2 to generate a fluorescent signal. In the presence of the target, active MNAzyme 1 forms from partzymes that are free in solution. MNAzyme 1 cleaves its Sub 1 thus releasing partzymes for MNAzyme 2. Once free, these partzymes hybridize with the assembly facilitator and form MNAzyme 2, which cleaves free Sub 2-FQ (generating a fluorescent signal), or tethered Sub 2 (releasing partzymes for MNAzyme 3). Since MNAzyme 3 shares the same substrate arms as MNAzyme 1, it can also cleave tethered Sub1, thus releasing more partzymes for MNAzyme 2. This results in a cascade of enzymatic generation of the components (partzymes) for more enzymes (MNAzymes) and a concomitant signal amplification cascade.

Persons skilled in the art will appreciate that the methods described herein may be used to perform a cascade as herein defined. Particular embodiments of performing such methods as disclosed herein include, but are not limited to (1) use of an MNAzyme to cleave a substrate only in the presence of a target, wherein said substrate is then made available for involvement in a second event such as generation of a detectable signal, as depicted in FIG. 6 wherein cleavage of a substrate makes available an enzyme that may then cleave an anchor, thereby resulting in fluorescent tag dissociating from a quencher; or (2) use of an MNAzyme to cleave a substrate only in the presence of a target, wherein said substrate is then made available for involvement in a second event, wherein performance of said second event in turn makes available a further substrate for involvement in any number of subsequent events, such that a subsequent event makes available a substrate for involvement in the performance of an earlier event, thereby creating a cyclic cascade, such as depicted in FIGS. 7 and 25, wherein such cyclic cascades may be employed to amplify a signal, for example, in applications where the low abundance of a target may not otherwise provide for a signal that is detectable.

A detectable effect amplification cascade may comprise one or more of a ribozyme/ligase cascade, a circular nucleic acid enzyme cascade, a protein enzyme cascade, or one or more enzymes attached to a support, or any combination thereof.

With reference to FIG. 2, strategy 3 shows an overview of a method of using an MNAzyme to amplify a signal through the use of a signal cascade. This is discussed in more detail with reference to FIGS. 6, 7 and 25.

Figure 6:
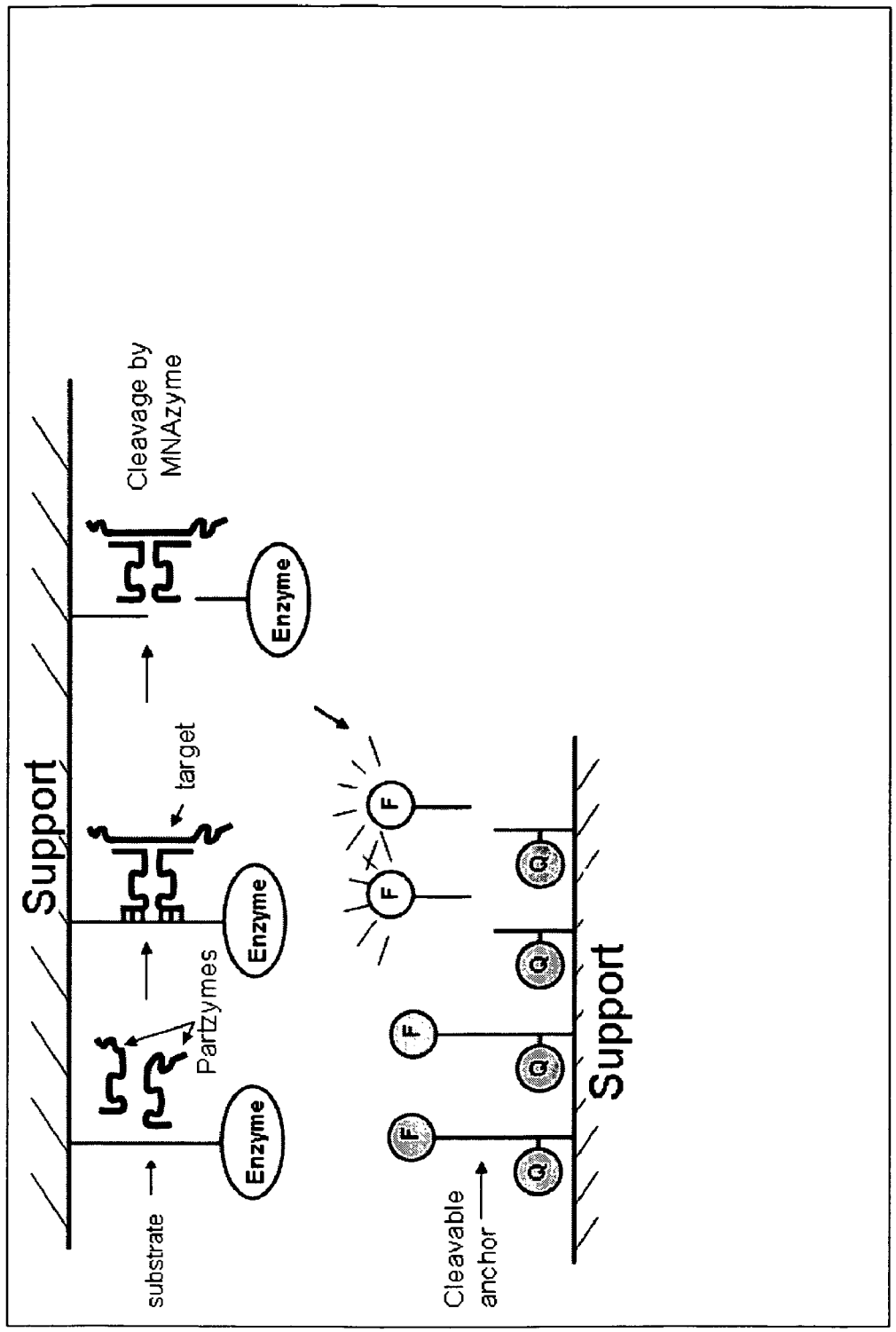
FIG. 6: MNAzyme detection coupled to enzyme mediated signal amplification: shown is a depiction of an MNAzyme for initiating a signal amplification cascade. In this embodiment MNAzymes trigger a downstream cascade of signal generation, wherein (from left to right, top panel) an MNAzyme forms only in the presence of a target and then releases an enzyme from a tethered position on a support. As shown in the bottom panel, the freed enzyme then cleaves a fluorescent substrate molecule. The fluorescent substrate is readily detected. F: fluorophore; Q: quencher.
Figure 7:
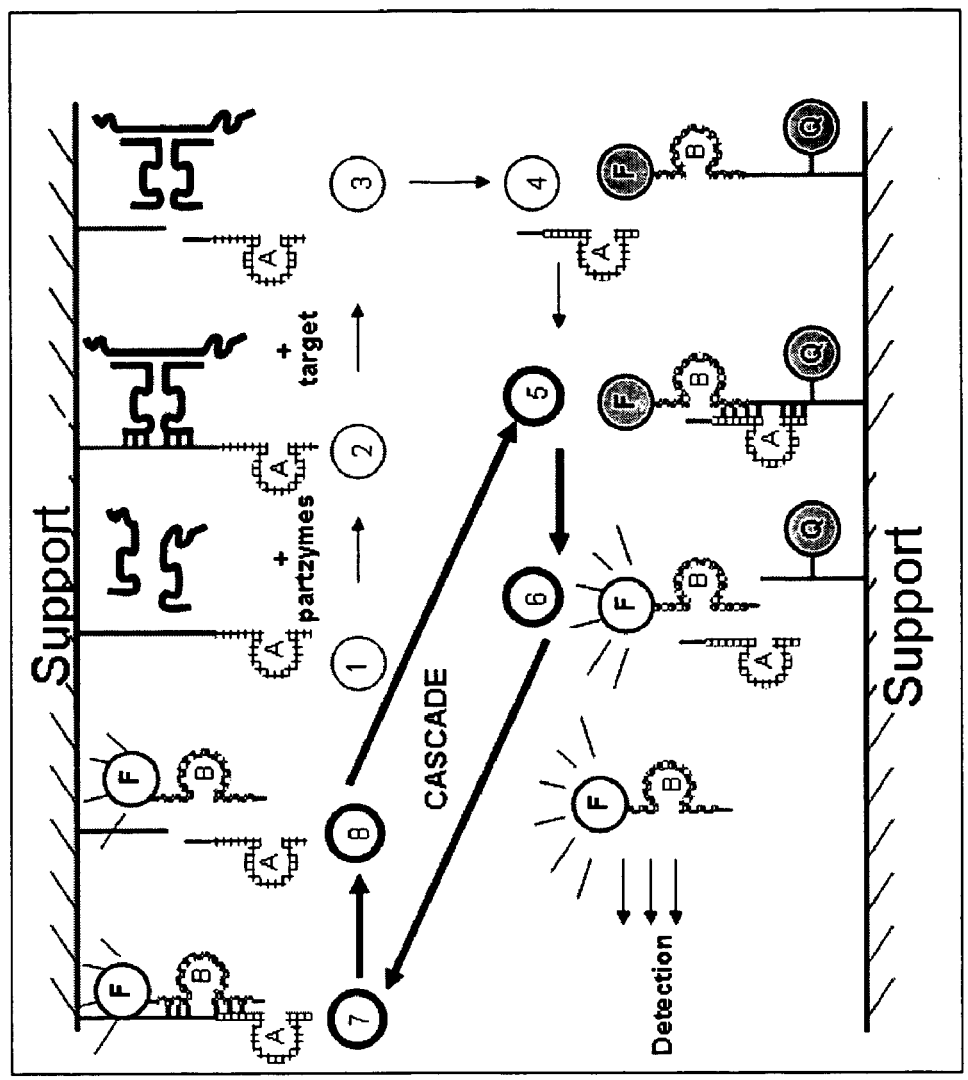
FIG. 7: Detection of analytes using MNAzymes and signal amplification: An MNAzyme can trigger a cascade generated using spatially separated DNAzymes. As shown in the sequentially numbered steps, an initial MNAzyme cleavage event, which occurs only in the presence of target, can cleave immobilized substrate, thereby releasing a first tethered DNAzyme A ("A") (steps 1-3). DNAzyme A, once freed, then cleaves and releases second tethered DNAzyme B ("B") (labeled with fluorophore) (steps 4-6) that, in turn, cleaves and releases additional DNAzyme A (steps 7-8), resulting in initiation of a cascade. Exponential signal amplification makes measurement facile as DNAzyme B with fluorophore is released in the ensuing cascade. F: fluorophore; Q: quencher.

FIG. 6 depicts an exemplary method of MNAzyme detection of target coupled with enzyme mediated signal amplification. As discussed above, the invention provides for methods of using MNAzyme detection wherein a target is amplified as well as methods wherein a signal generated is amplified. In some embodiments, combining MNAzyme technology with signal amplification strategies provides an alternative to MNAzyme assays combined with target amplification, although in some instances both target amplification and signal amplification can be used together. Preferred methods of amplifying signals involve cascade mechanisms, which as the skilled artisan will appreciate are often involved in amplifying signals in biological systems.

Several examples of amplification cascades, which use catalytic nucleic acids, are known in the art and are contemplated for use herein. Ligation cascades (Paul and Joyce, 2004) use a first ribozyme (A) which ligates two RNA containing oligonucleotides to form a second ribozyme (B). Ribozyme (B) then ligates two other RNA containing oligonucleotides to form a new first ribozyme (A), thus triggering a cascade reaction.

A second amplification cascade suitable for use herein uses circularized DNAzyme/substrate molecules (Levy and Ellington, 2003). A DNAzyme (A) is inactive when circular, but becomes activated by linearization by a second DNAzyme (B), which cleaves the circular DNAzyme (A). Active linear DNAzyme (A) then cleaves circular DNAzyme (B) molecules thus linearizing and activating them. The two DNAzymes capable of cleaving/linearizing each other result in a cascade of catalytic nucleic acid activity.

Persons of skill in the art will understand that other approaches are available—for example combining the use of DNAzymes with the versatility of aptamers and/or with the catalytic power of traditional protein enzymes (see e.g. Zhang et al., 2005). Zhang's method results in the release of a protein enzyme that can, in turn, catalyze the formation of detectable molecules thereby generating and amplifying signal. Zhang's approach allows sensitive detection, but it is expensive as it requires highly customized molecules for each assay. Methods for coupling of peptides to nucleic acids are known in the art (see e.g. Cheng et al., 1993), as are methods for attaching DNA to support structures. For example, Asher (PCT/US96/02380) described tethering an enzyme (ribozyme) to an insoluble support, which upon release, cleaved a substrate thereby initiating amplification of a signal using two spatially separated ribozymes.

Other examples of signal amplification for in vitro methods are known in the art, and yet other strategies for amplifying signals can be created using techniques similar to those that have proven successful. For example, the branched DNA assay (bDNA) (Urdea, 1993) amplifies a signal by employing a secondary reporter molecule (e.g. alkaline phosphatase) attached to labeled probes mediating the reaction. Fluorescence correlation spectroscopy (FCS) employs electronic amplification of the signal (Eigen and Rigler, 1994). Tyramide signal amplification (TSA) (Bobrow et al., 1989; Adams, 1992; Raap et al., 1995; van Gijlswijk et al., 1997), uses horseradish peroxidase to convert tyramiside to its active form, which binds to tyrosine residues in proteins. TSA is used for various applications of cell immunochemistry. The Invader assay (Hall et al., 2000) employs two oligonucleotides that bind to a target sequence in a manner that allows for nuclease cleavage leading to greater than 1000 cleavage events per target molecule over time, and the cleavage reaction can be coupled to a fluorescent probe. However, there are limitations to the known signal amplification methods. For example, the bDNA assay is not as sensitive as the target amplification methods.

Thus, with further attention to FIG. 6, depicted is an example of a method employing an enzyme released by MNAzymes as part of a signal amplification strategy. The signal can be generated, for example, by enzyme cleavage of a substrate between a fluorophore moiety and a quencher moiety, thus allowing a signal to be generated. Enzymes contemplated for use herein include, but are not limited to, DNAzymes, MNAzymes, ribozymes, and protein enzymes with measurable activity, such as proteases, restriction endonucleases and other hydrolytic enzymes. Preferred targets are nucleic acid sequences including, but not limited to, human, animal, plant, viral, bacterial DNA or RNA. Other preferred targets may include, prion, yeast or fungus, or any other molecule, for example, including but not limited to glycoproteins, lipids, lipoproteins, entire organisms, cells, viruses, bacteria, archaea, fungi, antibodies, metabolites, pathogens, toxins, contaminants, poisons, small molecules, polymers, metal ions, metal salts, prions or any derivatives, portions or combinations thereof.

As can be seen in FIG. 6, an exemplary enzyme, herein designated "Enzyme" is attached to a first insoluble support, through a cleavable molecule, preferably a nucleic acid. As shown in the example in FIG. 6, the cleavable molecule acting as the attachment for the enzyme "Enzyme" is a generic or universal MNAzyme substrate. Also attached to an insoluble support not in contact with the first insoluble support is a "Cleavable anchor" substrate for the enzyme "Enzyme". "Enzyme" is any enzyme with a detectable activity, for example an MNAzyme, DNAzyme, ribozyme, or protein enzyme as described above. In preferred embodiments, MNAzymes or DNAzymes are particularly useful. In the presence of the oligonucleotide components, or partzymes, that self assemble to form an MNAzyme capable of cleaving the universal or generic substrate, and in the presence of the target for the MNAzyme, the MNAzyme forms and catalytically cleaves "Enzyme" from the support, thereby freeing it and allowing it to access the "Cleavable anchor" substrate and cleave it. Cleavage of "Cleavable anchor" releases the fluorophore from the attached substrate. The fluorophore is readily detected and measured.

The physical separation of an immobilized or attached enzyme from its substrate, which is preferably also immobilized or attached to a support, is sometimes referred to herein as "spatial separation." One or more enzymes can be "spatially separated" from their respective substrates, and from each other. A signal amplification cascade can result, particularly where the cleavage of the substrate for the first enzyme releases the second enzyme, which in turn releases more first enzyme when the substrate for the second enzyme is cleaved (see FIG. 7).

In preferred embodiments, the substrate for the enzyme "Enzyme" is a bifunctional substrate as shown, comprising both a quencher portion and detectable portion. Particularly preferred are embodiments wherein the substrate for enzyme "Enzyme" is a molecule with no detectable signal while in the uncleaved substrate, and whose detectable signal increases by one to many orders of magnitude upon cleavage.

With reference now to FIG. 7, an example of an assay using MNAzymes and a signal amplification using two "spatially-separated" enzymes is shown. A signal amplification cascade can also be generated using such "spatially separated" DNAzymes as described above. An initial MNAzyme cleavage event cleaves an immobilized tethered substrate, thereby releasing DNAzyme A. DNAzyme A then migrates to a second sequence where a second DNAzyme B is tethered. DNAzyme A releases DNAzyme B that, in turn, releases more of DNAzyme A. A cascade is initiated that results in signal amplification. In various embodiments, the target can be nucleic acid sequences including, but not limited to, human, viral, bacterial DNA or RNA; or the target can be proteins, viruses, prions, antibodies, whole cells or small molecules.

In particular, it can be seen from the example in FIG. 7 that DNAzyme A is attached to a support through a first universal MNAzyme substrate or generic substrate, which is also cleaved by DNAzyme B. DNAzyme B is attached to an insoluble support through a second generic substrate that is a substrate for DNAzyme A. Both DNAzymes are retained such that their respective substrates are inaccessible to them. In the presence of the partzymes that self assemble to form an MNAzyme that cleaves the universal substrate, and in the further presence of the target, the MNAzyme is formed and cleaves the universal MNAzyme substrate retaining DNAzyme A, thereby releasing DNAzyme A. DNAzyme A can now migrate to the second generic substrate. Upon cleavage of the second generic substrate by DNAzyme A, DNAzyme B is released along with its attached detectable signal, shown here as a fluorophore F. Fluorophore F is now detectable as it separates from a retained quencher portion Q. Freed DNAzyme B, now able to access its substrate does so, cleaving it (the first generic substrate) and thereby releasing additional DNAzyme A, which in turn releases more DNAzyme B and detectable signal F. Thus, a powerful signal amplification cascade is established, with exponentially increasing amounts of detectable signal F.

An example of an MNAzyme cascade using tethered partzymes can be better understood by reference to FIG. 25. MNAzymes can be used to initiate signal amplification cascades as illustrated in this diagram. The reaction contains the following elements; (i) partzymes for MNAzyme 1 which are free in solution; (ii) an assembly facilitator for MNAzymes 2 and 3 (which have the same sensor arms) which is either free in solution (as illustrated) or tethered to an insoluble support by substrate, Sub 1; (iii) partzymes for MNAzyme 2 which are tethered to an insoluble support by the substrate, Sub 1. Sub 1 can be cleaved by either MNAzyme 1 (in the presence of a target analyte) or MNAzyme 3 (in the presence of an assembly facilitator), and cleavage results in the release of the partzymes for MNAzyme 2 into solution; (iv) partzymes for MNAzyme 3 which are tethered to an insoluble support by the substrate, Sub 2. Sub 2 can be cleaved by MNAzyme 2 (in the presence of assembly facilitator) and cleavage results in the release of the partzymes for MNAzyme 3 into solution; (v) Sub 2-FQ, which has the same sequence as Sub 2, but is free in solution and is dual labelled with a fluorophore (F) and a quencher (Q). Sub 2-FQ can be cleaved by MNAzyme 2 to generate a fluorescent signal.

In the presence of the target analyte, active MNAzyme 1 forms from partzymes that are free in solution. MNAzyme 1 cleaves its Sub 1 thus releasing partzymes for MNAzyme 2. Once free, these partzymes hybridize with the assembly facilitator and form MNAzyme 2, which cleaves free Sub 2-FQ (generating a fluorescent signal), or tethered Sub 2 (releasing partzymes for MNAzyme 3). Since MNAzyme 3 shares the same substrate arms as MNAzyme 1, it can also cleave tethered Sub1, thus releasing more partzymes for MNAzyme 2. This results in a cascade of enzymatic generation of the components (partzymes) for more enzymes (MNAzymes) and a concomitant signal amplification cascade.

12. Methods for the Detection, Identification and Quantification of Methylated Nucleic Acid MNAzyme mediated signal generation allows discrimination between fully matched nucleic acid sequences and those containing mismatches. This capacity enables MNAzymes to be used for the detection, identification and quantification of methylated nucleic acid.

Alterations in methylation pattern occur frequently in association with diseases such as cancer, diabetes, autoimmune diseases, and psychiatric disorders. The vast majority of protocols currently used for methylation analysis begin with bisulphite modification of genomic DNA. Bisulphite modification converts unmethylated, but not methylated, cytidines to uridines. If the bisulphite modified nucleic acid is then amplified, for example by PCR, the uridines are replaced with thymidines and the methylated cytidine is replaced by cytidine. The modified amplicons can be analysed by various methods that allow discrimination of the sequences containing T (in positions originally containing unmethylated C) and C (in positions originally containing methylated C).

The capacity for MNAzymes to discriminate between closely related sequence variants makes this technology well suited for discriminating between bisulphite modified sequences which were originally either methylated or unmethylated. The approach may be better understood by reference to example 11.

Further, MNAzymes can provide a new approach allowing the direct analysis of methylated and unmethylated DNA without the need for bisulphite modification. This provides a significant advantage because bisulphite modification is laborious, time consuming and destructive to the nucleic acid to be analysed.

The use of a stabiliser arm with a partzyme that has a truncated sensor arm has been used to demonstrate the capacity of MNAzymes to detect single nucleotide polymorphisms present in assembly facilitators (Example 22). Under the experimental conditions used in that example, a partzyme with a truncated (five base) sensor arm was functional at a temperature well above its expected melting temperature. Systems with stabiliser arms, and partzymes that have truncated sensor arms, are very sensitive to small changes in the target, and are amenable to use at highly stringent temperatures. This detection strategy can be further extended to discriminate directly between targets, which are either methylated or unmethylated at specific cytosine residues, without the need for prior bisulphite modification.

The presence of 5-methylcytosine(s) increases the melting temperature of DNA by 1.3° C. per methylated base, relative to unmethylated cytosine(s). When partzymes, a stabiliser arm, and a substrate are incubated at a temperature, which is suitable for hybridization and active MNAzyme assembly in the presence of a methylated target, but which is too high for MNAzyme assembly in the presence of an unmethylated target, a signal would be generated only in the presence of the methylated target. This provides a new strategy for direct analysis of methylation patterns that can provide a method for detection of methylation bases as markers of cancer and other diseases.

Skilled artisans will therefore readily appreciate and understand that the optimization of experimental parameters including temperature as herein disclosed is contemplated as being within the scope of the methods of the present invention, and that such optimization finds particular application in the performance of methods relating to detection of methylated DNA either directly or after bisulphite modification.

13. Methods for the Detection and Identification of Nucleic Acid Sequence Variants The present invention further provides for methods for the detection and identification of sequence variants on the basis that MNAzyme mediated signal generation allows discrimination between fully matched nucleic acid sequences and those containing mismatches.

Sequence variations capable of detection by the methods of the present invention include, but are not limited to, additions, deletions, substitutions, conversions, duplications, translocations, frame-shift sequence variants, nonsense sequence variants, or any combination thereof.

The methods may be applied in any situation in which it is desirable to detect and/or identify a nucleic acid sequence variation, including but not limited to diagnosis of diseases or predispositions thereto, identification of polymorphisms, or assessment of nucleic acid replication fidelity. In addition, larger alterations such as translocations associated with various cancer types, which result in fusion transcripts, may also be detected. These occur frequently in association with leukaemia. For example, PML/RARα fusion transcripts are associated with acute promyelocytic leukaemia and bcr/abl fusion transcripts are associated with chronic granulocytic leukaemia.

MNAzyme-mediated target detection can occur via Watson-Crick base recognition of the partzyme sensor arms and the assembly facilitator. The requirement for complementarity can be exploited to detect small sequence variations, including but not limited to, single base mismatches between the partzyme sensor arm and the assembly facilitator. The capacity for discrimination of sequence variants may be better understood by reference to examples 5, 19 and 22.

Those examples all demonstrate the capacity of MNAzymes to discriminate between situations where the sensor arm and assembly facilitator are fully matched, and situations where there is at least a single base mismatch or polymorphism.

The capacity to discriminate single base mismatches is dependent on several factors including (a) the stringency of the reaction conditions, which can be influenced by many factors including temperature, salt concentration, cation concentration, (b) the type of mismatch, (c) the position of the mismatch within the partzyme arm, and (d) the length of the partzyme arm. Depending on the application, the stringency of the reaction can be tailored to be either intolerant, or tolerant, to some degree of mismatch between the sensor arm and the assembly facilitator. Stringent conditions allow discrimination of closely related sequence variants, such as a single nucleotide difference. Lower stringency conditions may not discriminate between assembly facilitators with closely related sequences. Therefore, this could be exploited to detect simultaneously a group of closely related sequences in a single reaction with a single MNAzyme.

Figure 23:
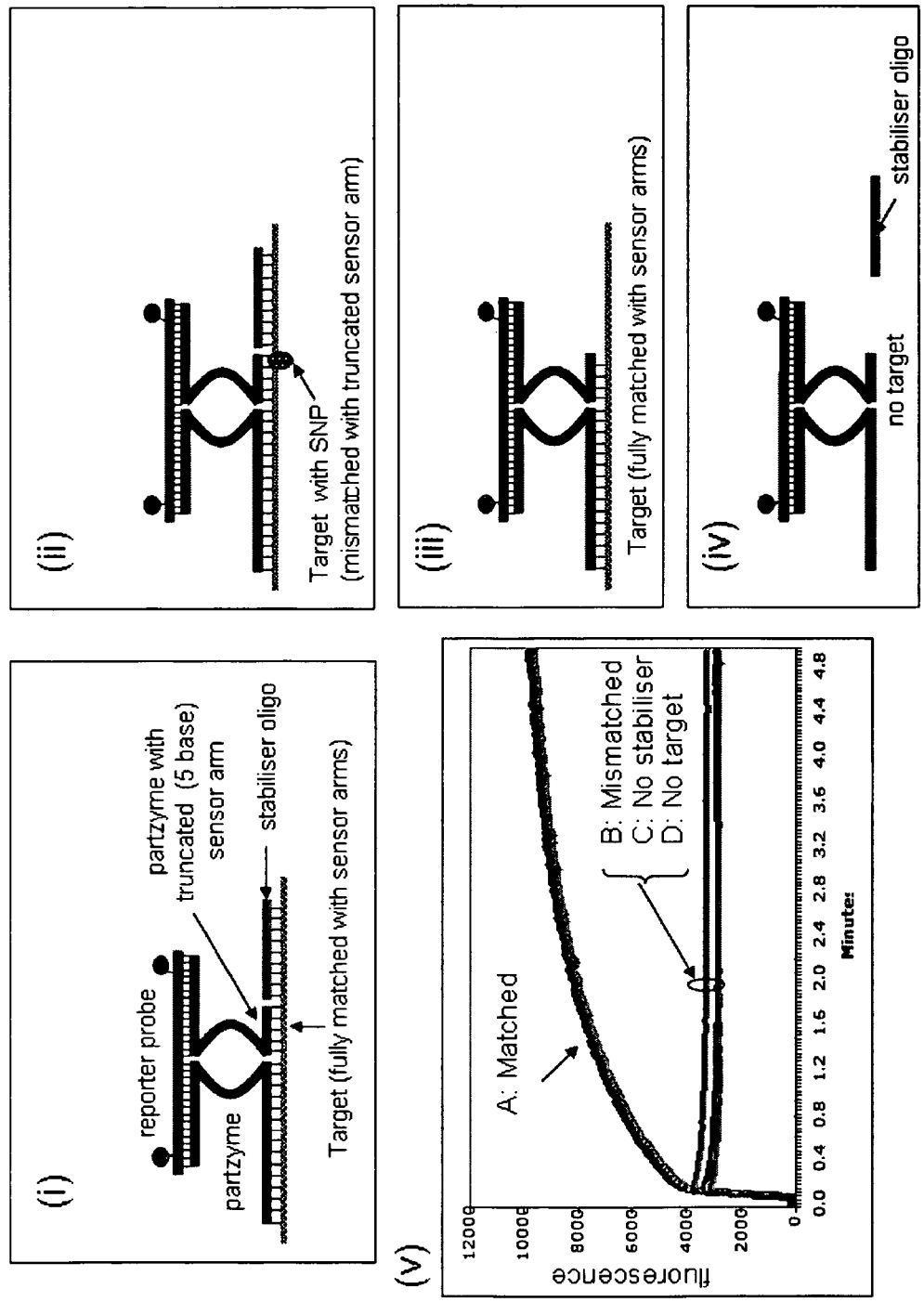
FIG. 23: The MNAzyme strategy and results for SNP detection: The method uses a truncated partzyme B sensor arm which is fully matched to one version of the SNP, and stabiliser oligonucleotide which facilitates MNAzyme assembly in the presence of the fully-matched target. The requirement for strict complementarity of the partzyme B sensor arm and the target nucleic acid allows discrimination of closely related sequences. Panel (i): Fully matched 5-base sensor arm plus stabiliser oligonucleotide; Panel (ii): Mismatched 5-base sensor arm plus stabiliser oligonucleotide; Panel (iii): No stabiliser control; Panel (iv): No target control; Panel (v): Results of MNAzyme SNP detection with fully-matched target, mismatched target, no stabiliser control and no target control.

The discrimination of single nucleotide polymorphisms can be extended by the use of partzymes with truncated sensor arms (FIG. 23 and Example 22). Truncated sensor arms can be stabilised by a stabiliser oligonucleotide component, which although a separate molecule, can be considered as a second component of the truncated partzyme, to which it binds adjacently.

14. MNAzymes for Detection, Identification and/or Quantification of Bacteria and Viruses The present invention encompasses methods for the detection of bacteria, viruses or any other microorganism, for example, through design of MNAzyme sensor arms that are adapted to hybridize to any molecule such as a nucleic acid that is unique to the microorganism that is sought to be detected, identified and/or quantified. Additionally or alternatively, a class of microorganism may be detected, for example, including but not limited to Gram positive or Gram negative bacteria. Further variations of the methods that are within the scope of contemplation of the person skilled in the art include, but are not limited to, use of an aptamer adapted to bind a protein, small molecule, cell, cellular component or cellular product such as a toxin that is unique to the microorganism that is sought to be detected, identified and/or quantified.

Bacteria and viruses contain DNA and/or RNA which can provide a template for their rapid and sensitive identification, detection and/or quantification using MNAzyme technology. Sequence variation between bacterial and viral species and strains can be used to allow sensitive discrimination between individual species and strains. Multiplex MNAzyme approaches are particularly preferred for the simultaneous detection and/or discrimination of multiple bacterial or viral species, strains or isolates.

Alternatively, regions of sequence similarity across bacterial or viral species and strains can be used to identify the presence or absence of any of a group of individual species and strains in a single MNAzyme assay. This latter approach is exemplified in Example 15 where a conserved region found in bacterial ribosomal 16S sequence was used as the basis of an assay to replace the bacterial test of a Gram stain for a rapid release test for sterility and/or mycoplasma contamination.

Example 16, which illustrates the use of MNAzymes for the detection and quantification of HIV-1 viral RNA, demonstrates the use of MNAzymes as a sensitive tool for viral detection and quantification.

15. Kits

The present invention also provides kits for practicing the methods disclosed herein. Typically, kits for carrying out the methods of the present invention contain all the necessary reagents to carry out the method. For example, in one embodiment a kit may comprise a first container containing at least a first and second oligonucleotide component comprising a first and second partzyme, and a second container comprising a substrate, wherein self-assembly of the first and second partzymes, and the substrate, into an MNAzyme requires association of an assembly facilitator present in a test sample. Accordingly, in such embodiment, the first and second partzymes, and the substrate, may be applied to the test sample in order to determine the presence of the assembly facilitator, wherein the assembly facilitator comprises the target.

Typically, the kits of the present invention will also comprise one or more other containers, containing for example, wash reagents, and/or other reagents as required in the performance of the methods of the invention.

In the context of the present invention, a compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the reagents used in the assay, containers which contain wash reagents, and containers which contain a detection reagent. Typically, a kit of the present invention will also include instructions for using the kit components to conduct the appropriate methods. Kits and methods of the invention may be used in conjunction with automated analysis equipment and systems, for example, including but not limited to, real time PCR machines.

For application to detection, identification or quantitation of different targets, a single kit of the invention may be applicable, or alternatively different kits, for example containing reagents specific for each target, may be required. Methods and kits of the present invention find application in any circumstance in which it is desirable to detect, identify or quantitate any entity.

The present invention will now be further described in greater detail by reference to the following specific examples, which should not be construed as in any way limiting the scope of the invention.

EXAMPLES

In the following examples, several MNAzyme designs, based on splitting the catalytic core of either the 10:23 or the 8:17 DNAzyme, were adapted for a variety of target nucleic acids and substrates (Table 3). These target substrate systems have been tested under a variety of reaction conditions and have proven robust.

Example MNAzyme designs and specific partzymes used in the following examples are listed in Table 3. The partzymes are named such that the name (e.g. RO4A1/1) incorporates the reference to the target domain (e.g. RO4 for RPLPO exon 4), the domain required for MNAzyme catalytic activity (e.g. A1) and the substrate domain (e.g. 1 for SubBi-1).

TABLE 3

Exemplary MNAzymes and substrates. Specific partzymes used in working examples

| MNAzyme Designs (Catalytic core) | Partzymes A and B | Specific Partzymes Targets Substrates | Examples (FIGS.) |
|---|---|---|---|
| 1 (8:17) | A1:B1 | RO4A1/1:RO4B1/1 RPLPO exon 4 (RO4) SubBi-1-FB (1) | 1 (8) |
| 2 (8:17) | A1:B2 | RO4A1/1:RO4B2/1 RPLPO exon 4 (RO4) SubBi-1-FB (1) | 1 (8) |
| 3 (8:17) | A1:B3 | RO4A1/1:RO4B3/1 RPLPO exon 4 (RO4) SubBi-1-FB (1) | 1 (9, 10) |
| 4 (8:17) | A2:B3 | RO4A2/1:RO4B3/1 RPLPO exon 4 (RO4) SubBi-1-FB (1) | 1 and 4 (10, 14) |
|  |  | miR20A2/1:miR20B3/1 MiR-20 SubBi-1-FB (1) | 2, 5 and 6 (11, 12, 15, 16) |
|  |  | AtpA2/1:Atp B3/1 ATP and dATP SubBi-1-FB (1) | 18 |
|  |  | TaqA2/1:AtpB3/1 Taq polymerase SubBi-1-FB (1) | 21 |
|  |  | miR143 A2/1:miR143 B3/1 miR143 SubBi-1-FB (1) | 12 |
|  |  | miR143 A2/1:miR143 B3H/1 miR143 | 12 |

TABLE 3-continued

Exemplary MNAzymes and substrates. Specific partzymes used in working examples

| MNAzyme Designs (Catalytic core) | Partzymes A and B | Specific Partzymes Targets Substrates | Examples (FIGS.) |
|---|---|---|---|
| | | SubBi-1-FB (1) miR143 A2H/1:miR143 B3/1 miR143 | 12 |
| | | SubBi-1-FB (1) miR143 A2H/1:miR143 B3H/1 miR143 | 12 |
| 5 (10:23) | A3:B4 | SubBi-1-FB (1) RO5A3/2:RO5B4/2 RPLPO exon 5 (RO5) | 3 (13) |
| 6 (10:23) | A4:B5 | SubBi-2-FB (2) RO5A4/2:RO5B5/2 RPLPO exon 5 (RO5) | 3 (13) |
| | | SubBi-2-FB (2) RO5A4/3-P:RO5B5/3-P RPLPO exon 5 (RO5) | 8 (17) |
| | | SubBi-3-FB (3) RO5A4/3-P:RO5B5/3-P RPLPO exon 5 (RO5) | 13 |
| | | SubBi-3-Q6B2 (3) RO5A4/3-P:RO5B5/3-P RPLPO exon 5 (RO5) | 9 (19) |
| | | SubBi-3-JB (3) RO5A4/4-P:RO5B5/4-P RPLPO exon 5 (RO5) | 14 |
| | | SubBi-4-JB (4) RO5A4/2-P:RO5B5(16)/2-P RPLPO exon 5 (RO5) | 20 |
| | | SubBi-2-FB (2) RO5A4/2-P:RO5B5/2-P RPLPO exon 5 (RO5) | 24 |
| | | SubBi-2 (2) miR20A4/2:miR20B5/2 miR-20 | 9 (19) |
| | | SubBi-2-FB (2) PCR7aA4/2-P:PCR7aB5/2-P Let-7a | 10 |
| | | SubBi-2-FB (2) BaA4/2-P:BaB5/2-P B-actin | 13 |
| | | SubBi-2-JB (2) BaA4/7-P:BaB5/7-P B-actin | 14 |
| | | SubBi-7-FB (7) BCRA4/6-P:BCRB5/6-P BCR | 13 and 14 |
| | | SubBi-6-TRB2 (6) HPRTA4/7-P:HPRTB5/7-P HPRT | 13 |
| | | SubBi-7-FB (7) HPRTA4/2-P:HPRTB5/2-P HPRT | 14 |
| | | SubBi-2-A350B (2) RO4A4/3-P:RO4B5/3-P RPLPO exon 4 (RO4) | 14 |
| | | SubBi-3-Q6B2 (3) RO4A4/3-5b:RO4B5/3-3b RPLPO exon 4 (RO4) | 24 |
| | | SubBi-3-FB (3) NefA4/6-P:NefB5/6-P HIV-1 Nef | 16 |
| | | SubBi-6-TRB2 (6) XdA4/2-P:XdB5/2-P Xd | 22 (23) |
| 7 (10:23) | A5:B6 | SubBi-2-FB (2) p16A5/3-P:p16B6/3-P p16 | 11 |
| | | SubBi-3-FB (3) 16S1A5/2-P:16S1B6/2-P Bacterial.ribosomal 16 S | 15 |
| | | SubBi-2-FB (2) RO5A5/2(22)-P:RO5B6/2(11G)-P RPLPO exon 5 (RO5) | 19 (22) |
| | | SubBi-2-FB (2) | |

TABLE 3-continued

Exemplary MNAzymes and substrates. Specific partzymes used in working examples

| MNAzyme Designs (Catalytic core) | Partzymes A and B | Specific Partzymes Targets Substrates | Examples (FIGS.) |
|---|---|---|---|
| | | RO5A5/2(22)-P:RO5B6/2(11C)-P RPLPO exon 5 (RO5) SubBi-2-FB (2) | 19 (22) |
| | | RO5A5/2(22)-P:RO5B6(16)/2-P RPLPO exon 5 (RO5) SubBi-2-FB (2) | 20 |
| | | RO4A5/2:RO4B6/2 RPLPO exon 4 (RO4) SubBi-2-FB (2) | 17 |
| | | RO4A5/2-G14A:RO4B6/2 RPLPO exon 4 (RO4) SubBi-2-FB (2) | 17 |
| | | RO4A5/2-A12T:RO4B6/2 RPLPO exon 4 (RO4) SubBi-2-FB (2) | 17 |
| | | RO4A5/2-A11T:RO4B6/2 RPLPO exon 4 (RO4) SubBi-2-FB (2) | 17 |
| | | RO4A5/2-A9T:RO4B6/2 RPLPO exon 4 (RO4) SubBi-2-FB (2) | 17 |
| | | RO4A5/2:RO4B6/2-C7A RPLPO exon 4 (RO4) SubBi-2-FB (2) | 17 |
| | | RO4A5/2:RO4B6/2-T4C RPLPO exon 4 (RO4) SubBi-2-FB (2) | 17 |
| | | RO4A5(18)/2-P:RO4B6 (19)/2-P RPLPO exon 4 (RO4) SubBi-2-FB (2) | 23 |
| | | RO4A5(18)/2-rA9-P:RO4B6 (19)/2-P RPLPO exon 4 (RO4) SubBi-2-FB (2) | 23 |
| | | RO4A5(18)/2-rG14-P:RO4B6 (19)/2-P RPLPO exon 4 (RO4) SubBi-2-FB (2) | 23 |
| | | RO4rA5(18)/2:RO4B6 (19)/2-P RPLPO exon 4 (RO4) SubBi-2-FB (2) | 23 |
| | | RO4A5(18)/2-P:RO4rB6(19)/2 RPLPO exon 4 (RO4) SubBi-2-FB (2) | 23 |
| | | RO4rA5(18)/2:RO4rB6(19)/2 RPLPO exon 4 (RO4) SubBi-2-FB (2) | 23 |
| 8 (10:23) | A6:B7 | RO5A6(22)/2-P:RO5B7(16)/2-P RPLPO exon 5 (RO5) SubBi-2-FB (2) | 20 |
| 9 (10:23) | A7:B8 | RO5A7(22)/2-P:RO5B8(16)/2-P RPLPO exon 5 (RO5) SubBi-2-FB (2) | 20 |
| 10 (10:23) | A8:B9 | RO5A8(22)/2-P:RO5B9(16)/2-P RPLPO exon 5 (RO5) SubBi-2-FB (2) | 20 |
| 11 (10:23) | A9:B10 | RO5A9(22)/2-P:RO5B10(16)/2-P RPLPO exon 5 (RO5) SubBi-2-FB (2) | 20 |

Example 1

Application of MNAzymes to the Direct Detection of a Target Nucleic Acid (Human RPLPO Sequence)

1.1. Partzyme Oligonucleotides

Figure 8:
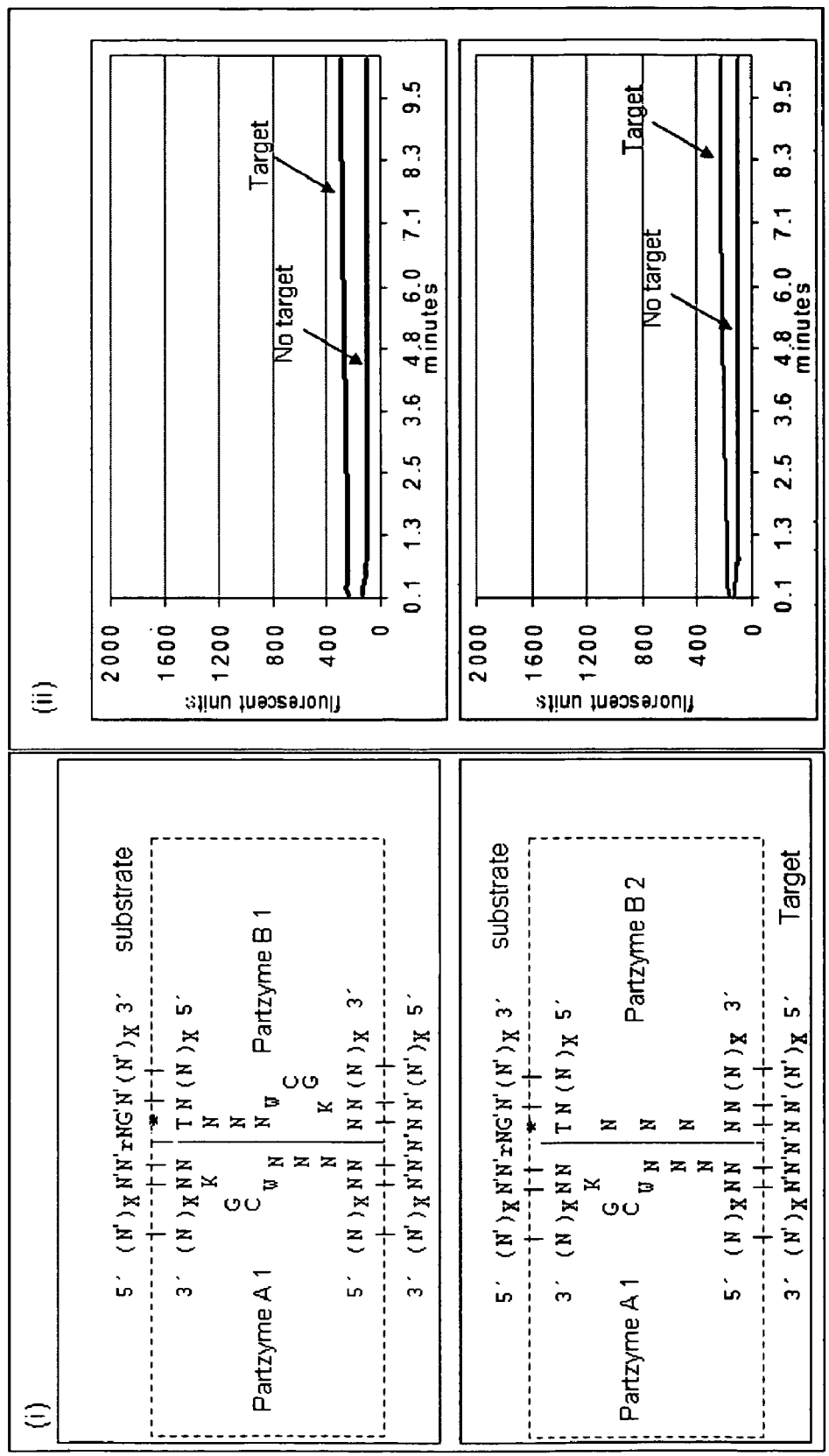
FIG. 8: MNAzyme design for RPLPO target: Panel (i): Exemplary sequences for designs 1 (upper panel) and 2 (lower panel) for MNAzymes; "Partzyme A 1" disclosed as SEQ ID NO: 177 and "Partzyme B1" disclosed as SEQ ID NO: 178. Panel (ii): Results of target-dependent cleavage of a reporter substrate by MNAzyme designs 1 (upper panel) and 2 (lower panel). N=A, G, C, T or any analogue; N'=any nucleotide complementary to N; (N or N')$_x$=any number of nucleotides or analogues; K=A, G or AA; W=A or T; rN=any ribonucleotide and/or any number of ribonucleotides; *=wobble base.
Figure 9:
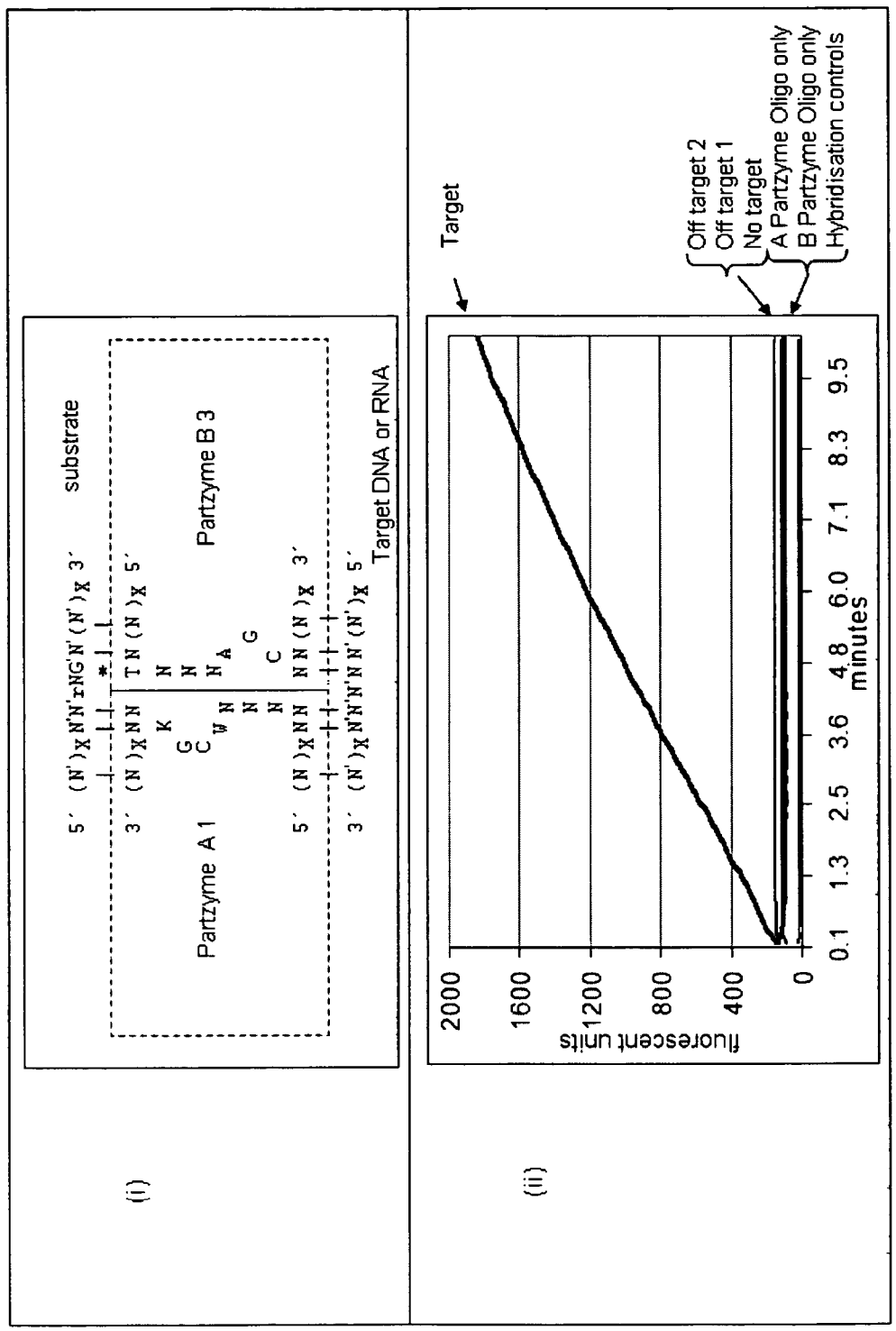
FIG. 9: MNAzyme design for RPLPO target: Panel (i): Exemplary sequence for design 3 for an MNAzyme; Partzyme B3 disclosed as SEQ ID NO: 50; Panel (ii): Results for target-dependent cleavage of a reporter substrate. Control reactions shown include no-target, hybridization control, two off-target controls and reactions containing either partzyme A or partzyme B oligonucleotides, but not both. N=A, G, C, T or any analogue; N'=any nucleotide complementary to N; (N or N')$_x$=any number of nucleotides or analogues; K=A, G or AA; W=A or T; rN=any ribonucleotide and/or any number of ribonucleotides; *=wobble base.
Figure 10:
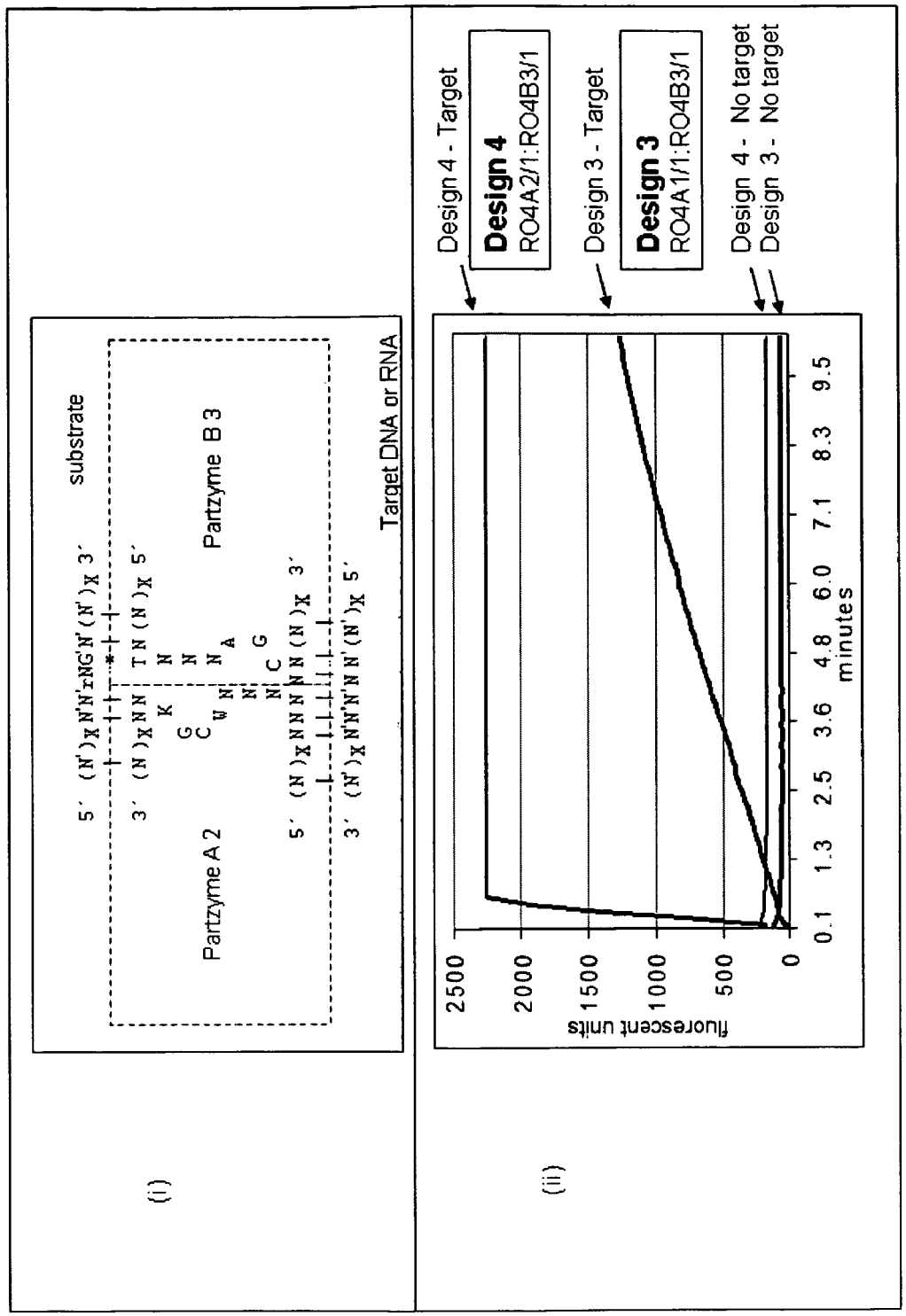
FIG. 10: MNAzyme design for RPLPO target: Panel (i): Exemplary sequence for design 4 for an MNAzyme; Partzyme B3 disclosed as SEQ ID NO: 50; Panel (ii): The efficiency of target-dependent cleavage for designs 3 and 4. Results are shown for reactions containing the target RPLPO oligonucleotides, and controls lacking target. N=A, G, C, T or any analogue; N'=any nucleotide complementary to N; (N or N')$_x$=any number of nucleotides or analogues; K=A, G or AA; W=A or T; rN=any ribonucleotide and/or any number of ribonucleotides; *=wobble base.

Four designs for MNAzymes (FIGS. 8-10) based on the 8:17 DNAzyme were tested. Those skilled in the art will appreciate that the sensor arm (target binding) sequences designated by "N" may be replaced by target-specific sequences for any known nucleic acid target (FIGS. 8-10). The substrate arm sequences, which bind the reporter substrate, can be generic and used for many targets. Those skilled in the art will appreciate that the substrate sequences designated by "N'" in FIGS. 8-10 may be replaced by DNA, RNA or DNA/RNA chimeric sequences and those designated by "r" may be replaced by other and/or a different number of ribonucleotide sequences.

In the experiments conducted to measure the catalytic activity of the RPLPO MNAzymes described in FIGS. 8-10, the A and B oligonucleotide partzymes were designed to target exon 4 of the RPLPO gene. The sequences of the A and B partzymes are listed below from 5' to 3' where the bases underlined form at least part of the active catalytic core of the assembled MNAzyme, bases in bold hybridize with the target, and bases in italics hybridize to the substrate.

```
SEQ ID NO:1: Partzyme A1 RO4A1/1:
GCTGGTCATCCAGCACGGTCGAAATAGTGAGT

SEQ ID NO:2: Partzyme A2 RO4A2/1:
GCTGGTCATCCAGCAGCGGTCGAAATAGTGAGT

SEQ ID NO:3: Partzyme B1 RO4B1/1:
CATCTCTTCTCCGTCGAAGTGTTCGACAATGGC

SEQ ID NO:4: Partzyme B2 RO4B2/1:
CATCTCTTCTCCGGTGTTCGACAATGGC

SEQ ID NO:5: Partzyme B3 RO4B3/1:
CATCTCTTCTCCGAGCGTGTTCGACAATGGC
```

1.2. Reporter Substrate

MNAzyme activity is monitored by cleavage of a dual labelled nucleic acid reporter substrate. The substrate sequence is a chimeric sequence containing both RNA and DNA bases which has been used previously as an 8:17 DNAzyme substrate (Li et al., 2000). In the current example, the reporter substrate is designated SubBi-1-FB and has internal labels, namely 6-carboxyfluorescein ("6-FAM") attached to a nucleotide 5' to the RNA base, and a Black Hole Quencher 1 ("BHQ1") moiety attached to a nucleotide 3' to the RNA base. Cleavage of SubBi-1-FB by MNAzymes was monitored at 530 nm (FAM emission wavelength) with excitation at 485 nm (FAM excitation wavelength). The labelled sequence of SubBi-1-FB is as follows, 5' to 3', with the underlined bases indicating the position of the 6-FAM and BHQ1 moieties. The lower case bases represent RNA and the upper case bases represent DNA.

```
SEQ ID NO: 6: SubBi-1-FB:
ACTCACTATaGGAAGAGATG
```

1.3. Control MNAzyme Sequence

The hybridization control (inactive MNAzyme) was inactivated by mutating a single base in the A1 oligonucleotide that is essential for formation of the catalytic core. Although both the reporter substrate and target sequences can still bind to the MNAzymes, the substrate cannot be cleaved due to the modification in the catalytic core of the MNAzyme. The binding of the reporter substrate to the partzyme molecules could in itself generate a measure of fluorescence due to conformational change of the reporter substrate upon hybridisation. A control that uses a mutated A1 partzyme molecule (RO4A1mut) was included and designated the Hybridisation Control. The mutated MNAzyme sequence is illustrated below and the position of the G base that was changed to a T is underlined.

```
SEQ ID NO: 7: Mutant Partzyme A
RO4A1mut/1: GCTGGTCATCCAGCACGGTCTAAATAGTGAGT
```

1.4. Target

The target sequence for this example was an oligonucleotide, RO4/1Target, which has the same sequence as a section of exon 4 of the human RPLPO gene. The sequence of RO4/1Target is as follows, written 5' to 3'.

```
SEQ ID NO: 8 RO4/1Target:
GCCATTGTCGAACACCTGCTGGATGACCAGC
```

To ensure a signal cannot be detected when an incorrect target sequence is present the "off-target" effect was determined by using 3 μg of lambda DNA (PROMEGA) or a synthetic negative control oligonucleotide of unrelated sequence (RO4/1mutTarget).

```
SEQ ID NO: 9 RO4/1mutTarget:
CGACCATTAGGTCGTCCACAAGCTGTTACCG
```

1.5. Reaction Components

Detection of the target sequence was measured by an increase in fluorescent signal caused by cleavage of the reporter substrate by the catalytically active MNAzyme. Reactions were initiated by the addition of substrate and the total volume of all reactions was 25 μL. All reactions were conducted at 40° C. in a SmartCycler® System thermocycler (Cepheid). Fluorescence for each reaction was read every 7 seconds for a total of 10 minutes. All reactions in Table 4 contained the bulk mix of 1 μM SubBi-1-FB in Tris HCl (pH 9.0 at 25° C.) and 25 mM MgCl$_2$.

TABLE 4

Reaction components for the detection of a nucleic acid

| | | Partzymes | | | |
|---|---|---|---|---|---|
| MNAzyme Design | Reaction | A | B | Target | FIGURE |
| 1 | Target | 1 μM RO4A1/1 | 1 μM RO4B1/1 | 1 μM RO4/1Target | FIG. 8 |
| | No target | 1 μM RO4A1/1 | 1 μM RO4B1/1 | H$_2$0 | |
| 2 | Target | 1 μM RO4A1/1 | 1 μM RO4B2/1 | 1 μM RO4/1Target | |
| | No target | 1 μM RO4A1/1 | 1 μM RO4B2/1 | H$_2$0 | |
| 3 | Target | 1 μM RO4A1/1 | 1 μM RO4B3/1 | 1 μM RO4/1Target | FIG. 9 |
| | No target | 1 μM RO4A1/1 | 1 μM RO4B3/1 | H$_2$0 | |
| | Off-target 1 | 1 μM RO4A1/1 | 1 μM RO4B3/1 | 1 μM RO4/1mutTarget | |
| | Off-target 2 | 1 μM RO4A1/1 | 1 μM RO4B3/1 | 3 μg Lambda DNA | |
| | Hybridisation Control | 1 μM RO4A1mut/1 | 1 μM RO4B3/1 | 1 μM RO4/1Target | |

TABLE 4-continued

Reaction components for the detection of a nucleic acid

| Design | MNAzyme Reaction | Partzymes A | Partzymes B | Target | FIGURE |
|---|---|---|---|---|---|
|  | Partzyme A only | 1 µM RO4A1/1 | — | 1 µM RO4/1Target |  |
|  | Partzyme B only | — | 1 µM RO4B3/1 | 1 µM RO4/1Target |  |
| 3 | Target | 1 µM RO4A1/1 | 1 µM RO4B3/1 | 1 µM RO4/1Target | FIG. 10 |
|  | No Target | 1 µM RO4A1/1 | 1 µM RO4B3/1 | H$_2$0 |  |
| 4 | Target | 1 µM RO4A2/1 | 1 µM RO4B3/1 | 1 µM RO4/1Target |  |
|  | No Target | 1 µM RO4A2/1 | 1 µM RO4B3/1 | H$_2$0 |  |
| All | Background | — | — | — | — |

Each reaction well on the SmartCycler® System thermocycler (Cepheid) utilised during an experiment was first tested for its background level of fluorescence, as this is known to vary between wells. This was measured by reading the fluorescence of the bulk mix alone. This value was then subtracted from all other reactions performed in that well to allow comparisons between wells.

1.6. Results: Detection of Cleavage of SubBi-1-FB Reporter Substrate

Design 1 and 2 MNAzymes showed little evidence of target-dependent cleavage of the reporter substrate under the conditions of this experiment (FIG. 8). The fluorescence was similar for reactions with, and without, target RPLPO oligonucleotide target. The addition of target RPLPO oligonucleotide resulted in an increase of fluorescence for design 3 (FIGS. 9 and 10) and design 4 (FIG. 10). This is consistent with the formation of active MNAzymes in the presence of target nucleic acid resulting in cleavage of the reporter substrate between the fluorophore and quencher dye pair causing an increase in fluorescence. The fluorescence of the no-target controls was lower than that in the target-containing reactions and none of the control reactions showed an increase in fluorescence over time (FIGS. 8-10). This demonstrates that the increase in fluorescence produced in target-containing reactions is due to target-dependent assembly of a catalytically active MNAzyme that then cleaved the reporter substrate. The cleavage efficiency of design 4 was greater than design 3 for the RPLPO system (FIG. 10).

The off-target, hybridization, Partzyme A only and Partzyme B only control reactions are shown for design 3 (FIG. 9). The fluorescence levels of these controls were either lower than or similar to that of the no-target reactions. None of the control reactions showed an increase in fluorescence over time. These results further demonstrate that cleavage of the reporter substrate is dependent on the presence of both the Partzyme A and the Partzyme B oligonucleotides that are required for assembly of an active MNAzyme, as well as the target nucleic acid sequence.

Example 2

MNAzymes for Detection of miR-20 or Short DNA Sequences Homologous to miR-20

2.1. Partzyme Oligonucleotides

Detection using MNAzymes can also be used for the analysis of miRs. In this example, the MNAzyme only forms when the correct miR sequence is present. This MNAzyme can distinguish between related miR sequences e.g. hsa-miR-20 and hsa-miR-93.

Figure 11:
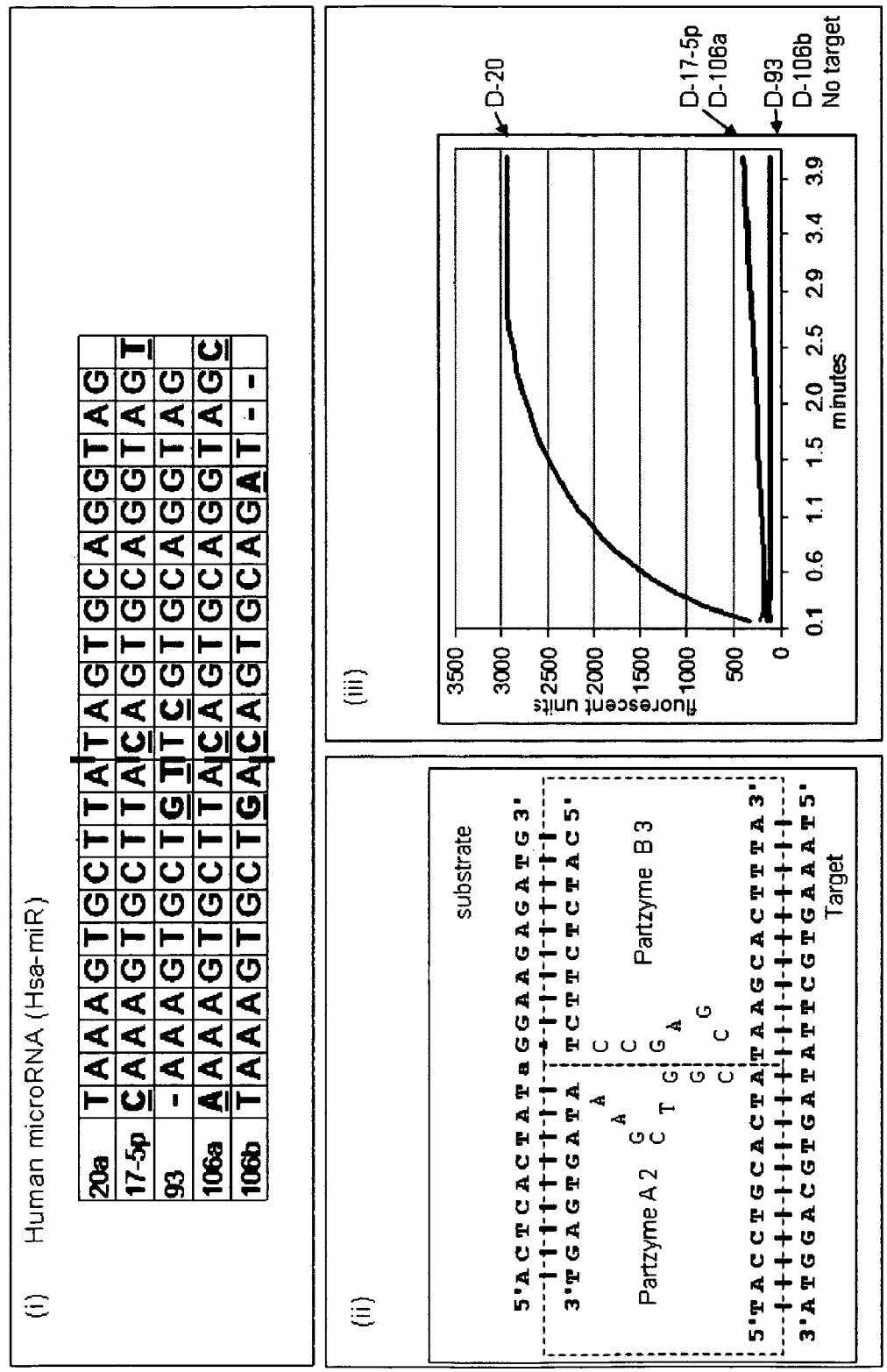
FIG. 11: Use of MNAzymes to discriminate between closely related sequences: Panel (i): DNA sequences (SEQ ID NOS 53 and 13-16, respectively, in order or appearance) homologous to the hsa-miR-20 and related miR sequences, used as target sequence in the experiments in FIGS. 11 and 12 are illustrated. The differences in sequence between D-20 and related D-miRs are underlined. The vertical bold dashed line separates the regions of the oligonucleotides recognized by the two sensor arms. Panel (ii): Depicts exemplary sequences for an MNAzyme of design 4 for detection of miR-20. Substrate, Partzyme A2, Partzyme B3 and Target sequences disclosed as SEQ ID NO 6 and 10-12, respectively. Panel (iii): Results for D-20 MNAzyme target-dependent cleavage of a reporter substrate. Control reactions shown: "off-target" oligonucleotides (D-17-5p, D-106a, D-106b, D-93), and "no-target" (dH$_2$O) control reactions.

In the experiments conducted to measure the catalytic activity of the MNAzyme described in FIG. 11, the A and B partzyme oligonucleotides were designed to target hsa-miR-20. The sequences of the partzymes A and B oligonucleotides are listed below from 5' to 3'. In the following sequences, the bases underlined form part of the catalytic core of the assembled MNAzyme, bases in bold hybridize with the target, and bases in italics hybridize to the substrate.

```
SEQ ID NO: 10: Partzyme A2:
miR20A2/1: TACCTGCACTACGGTCGAAATAGTGAGT

SEQ ID NO: 11: Partzyme B3:
miR20B3/1: CATCTCTTCTCCGAGCTAAGCACTTTA
```

2.2. Reporter Substrate

MNAzyme activity is monitored by cleavage of a dual labelled nucleic acid reporter substrate. The reporter substrate for this example is SubBi-1-FB with the sequence, 5' to 3', as below. The lower case bases represent RNA and the upper case bases represent DNA. The underlined bases indicate the position of a 6-FAM moiety at the 5' end and a BHQ1 moiety at the 3' end. Changes in fluorescence due to cleavage of SubBi-1-FB at the ribonucleotide between the FAM and BHQ1 were monitored at 530 nm (FAM emission wavelength) with excitation at 485 nm (FAM excitation wavelength).

```
SEQ ID NO: 6: SubBi-1-FB:
ACTCACTATaGGAAGAGATG
```

2.3. Target

The target sequence for this example was a DNA oligonucleotide, D-20, which has sequence which is homologous to the RNA hsa-miR-20 species (FIG. 11 (i)). The sequence of D-20Target is as follows, written 5' to 3'.

```
SEQ ID NO: 12: D-20Target:
TAAAGTGCTTATAGTGCAGGTA
```

2.4. Control Sequences

Any assay developed to detect microRNAs must specifically distinguish the desired miR sequence e.g. hsa-miR-20 from related sequences such as hsa-miR-17-5p, which may differ from the target miR by one or more bases (FIG. 11 (i)). The hsa-miR-20 related "off-target" 17-5p, 93, 106a and 106b miR oligonucleotides were also synthesized as DNA and are written 5' to 3' below.

```
SEQ ID NO: 13: D-17-5pTarget:
CAAAGTGCTTACAGTGCAGGTAGT

SEQ ID NO: 14: D-93Target:
AAAGTGCTGTTCGTGCAGGTAG

SEQ ID NO: 15: D-106aTarget:
AAAAGTGCTTACAGTGCAGGTAGC

SEQ ID NO: 16: D-106bTarget:
TAAAGTGCTGACAGTGCAGAT
```

2.5. Reaction Conditions

Detection of the target sequence was measured by an increase in fluorescent signal caused by cleavage of the reporter substrate by the catalytically active MNAzyme. Reactions were initiated by the addition of substrate and the total volume of all reactions was 25 µL. All reactions were conducted at 40° C. in a SmartCycler® System thermocycler (Cepheid). Fluorescence for each reaction was read every 7 seconds for a total of 4 minutes. All reactions in Table 5 contained the bulk mix consisting of 1 µM SubBi-1-FB, Tris HCl (pH 9.0 at 25° C.) and 25 mM $MgCl_2$.

TABLE 5

Components of reactions for the detection of a nucleic acid target as shown in FIG. 11

| MNAzyme Reaction | Template | Partzyme A | Partzyme B |
|---|---|---|---|
| Target | 1 µM D-20 | 1 µM miR20A2/1 | 1 µM miR20B3/1 |
| No-Target | $H_2O$ | | |
| Off-target17-5p | 1 µM D-17-5p | | |
| Off-targetD-93 | 1 µM D-93 | | |
| Off-targetD-106a | 1 µM D-106a | | |
| Off-targetD-106b | 1 µM D-106b | | |
| A Partzyme only | 1 µM D-20 | 1 µM miR20A2/1 | — |
| B Partzyme only | 1 µM D-20 | — | 1 µM miR20B3/1 |

Each reaction well on the SmartCycler® System thermocycler (Cepheid) used during the experiment was first tested for its background level of fluorescence, as this is known to vary between wells. This was measured by reading the fluorescence of the bulk mix alone. This value was then subtracted from all other reactions performed in each well to allow between well comparisons.

Figure 12:
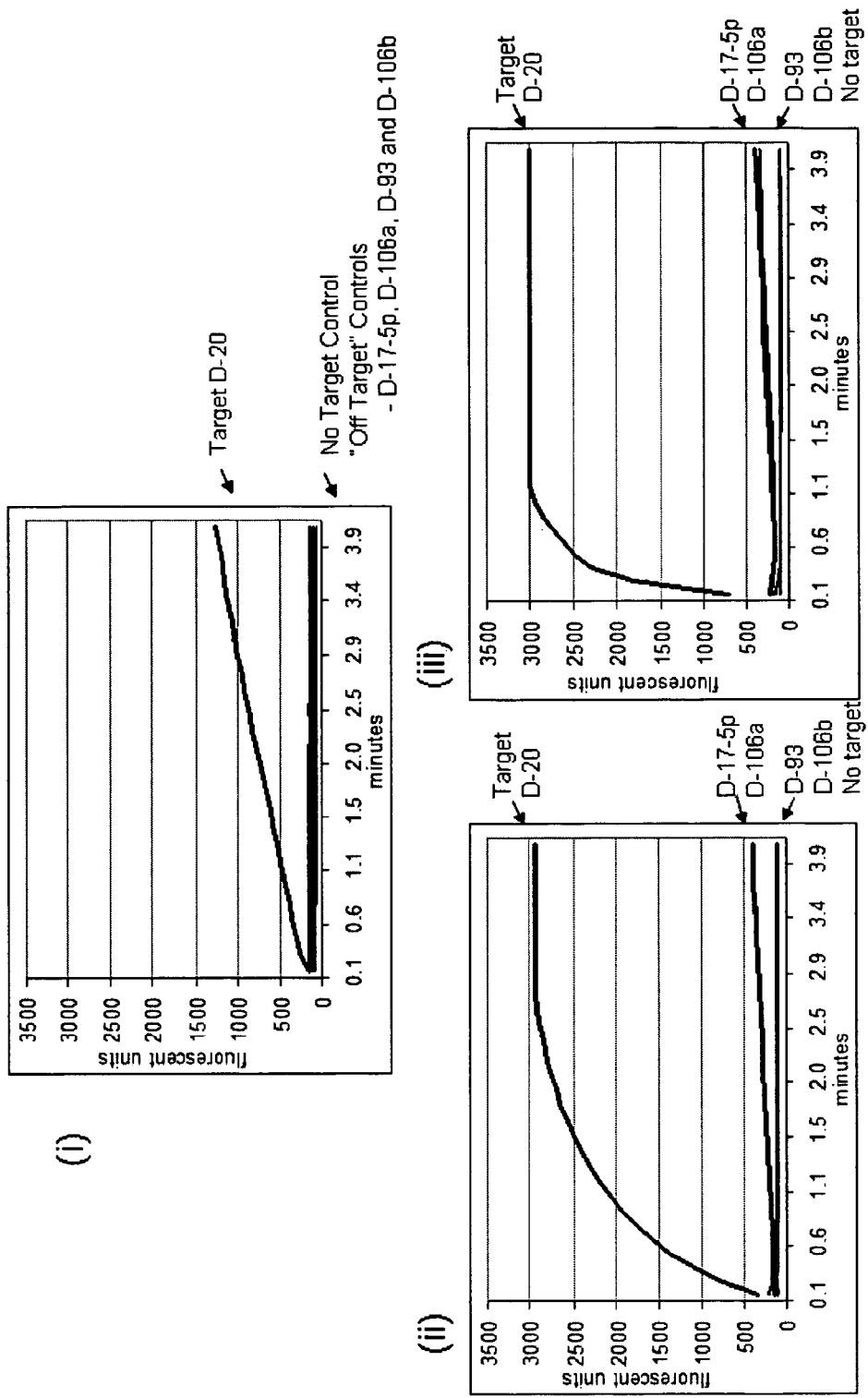
FIG. 12: MgCl$_2$ optimization of the MiR-20 MNAzyme system: Results obtained using an exemplary design 4 MNAzyme system for miR-20 detection. Target (D-20)-dependent cleavage of a reporter substrate. Control reactions containing "off target" sequences (D-17-5p, D-106a, D-06b, D-93) or "no-target" (dH$_2$O), are shown for reactions containing (i) 5 mM, (ii) 25 mM or (iii) 100 mM MgCl$_2$, respectively.

The target-containing, "no-target" and "off-target" reactions were also performed in the presence of 5 mM and 100 mM $MgCl_2$ concentrations and compared to 25 mM $MgCl_2$ (FIG. 12).

2.6. Results: Detection of Cleavage of SubBi-1-FB Reporter Substrate

The partzyme A and B oligonucleotides of the MNAzyme assemble into a catalytically active MNAzyme to cleave the reporter substrate only in the presence of the target sequence. In this example the off-target controls have as little as two mismatched bases with the sensor arms (miR-20 target binding sequence). The "off-target" D-17-5p has two mismatched bases, only one of which occurs in the most discriminatory region located in the middle of the miR-20 sequence. The cleavage reaction containing the target sequence D-20 gave a 26-fold increase in signal compared to the no-target control (FIG. 11(iii)). This compares with the off-target controls, D-17-5p and D-106a, which give a 3,5-fold increase in signal compared to the no-target control, and D-93 and D-106b which give no increase in signal compared to the no-target control (FIG. 11(iii)). Thus, differentiation of D-20 from related sequences demonstrates the capacity of the MNAzyme system to discriminate sequences that differ by only a few bases. Previous studies using uni-molecular DNAzymes have demonstrated that DNAzymes have the capacity to distinguish single base mutations (Impey et al., 2000). MNAzymes also allow discrimination of single base changes (see example 5 below).

The "partzyme A only" and "partzyme B only" controls had a similar fluorescence to that of the background fluorescence (data not shown).

The use of protein enzymes requires other reagents in the reaction to be at concentrations that are optimal for protein enzyme activity. For example, the concentration of the metal ion cofactor that aids a DNAzyme in cleaving the reporter substrate is kept at a minimum in protocols that utilize enzymes like polymerases. Direct detection using MNAzymes does not require any protein enzymes and therefore reaction conditions can be optimized for rapid substrate cleavage. In these reactions the metal ion cofactor e.g. $Mg^{2+}$ can be increased to optimize the MNAzyme catalytic rate. FIG. 12 shows how the concentration of $MgCl_2$ can be increased to levels that cannot normally be tolerated in target detection protocols. At high $MgCl_2$ (100 mM) the catalytic efficiency of the MNAzyme is higher. Furthermore, when detecting D-20Target an increase in the $MgCl_2$ did not affect the specificity of the reaction, since D-20Target is still clearly distinguishable from the related sequences D-17-5p, Target D-106aTarget, D-93Target and D-106bTarget.

Example 3

Figure 13:
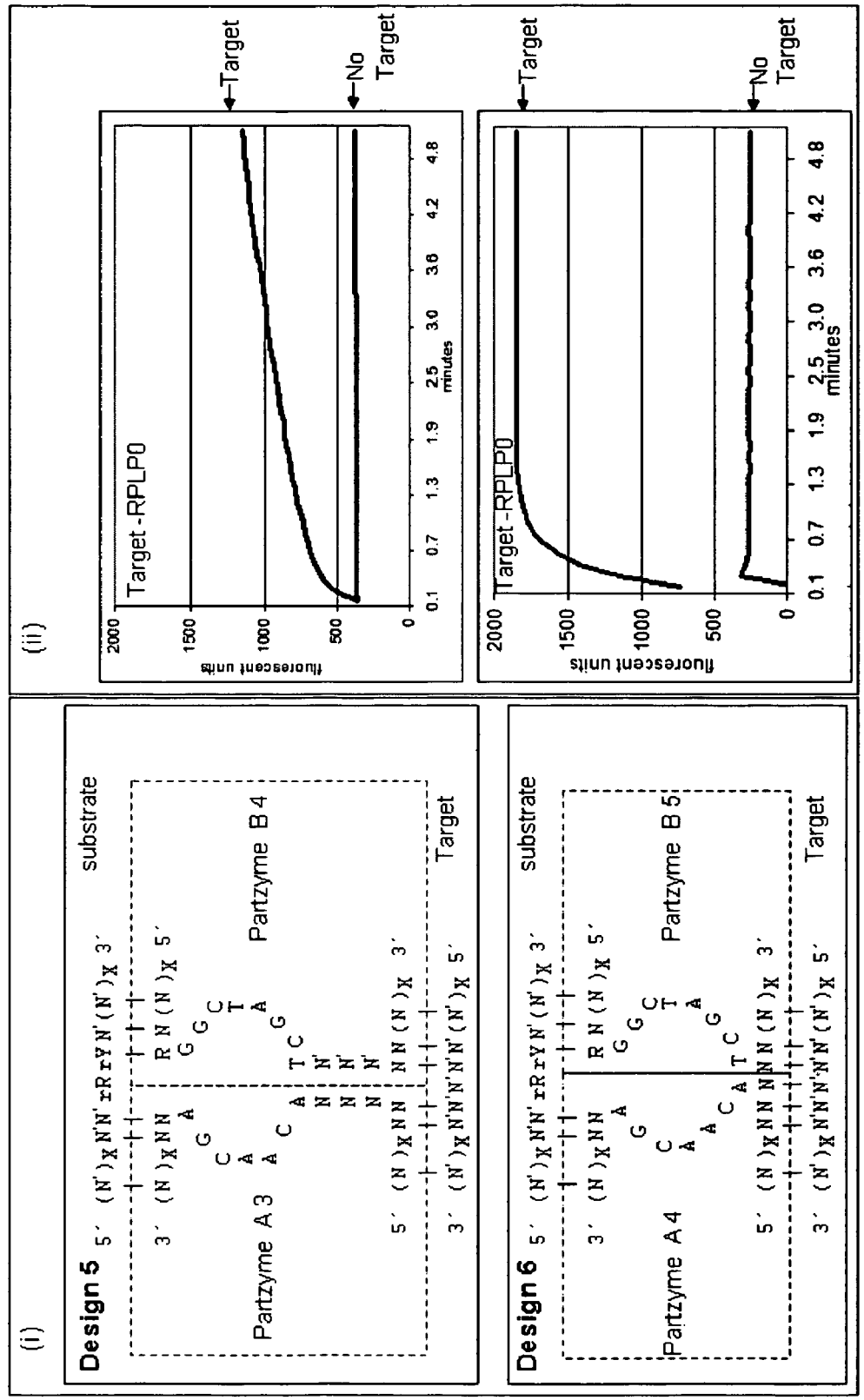
FIG. 13: MNAzyme design for RPLPO target: Panel (i): Exemplary sequences for designs 5 and 6 for MNAzymes. Partzyme A3, Partzyme B4, Partzyme A4 and Partzyme B5 sequences disclosed as SEQ ID NOS 54, 73-74 and 80 respectively. Panel (ii): Results for target-dependent cleavage of a reporter substrate using designs 5 and 6, and their "no-target" controls. N=A, G, C, T or any analogue; N'=any nucleotide complementary to N; (N or N')$_x$=any number of nucleotides or analogues; R=A or G; Y=C or U; rN= ribonucleotide base.

MNAzymes (Designs 5 and 6) for Direct Detection of a Nucleic Acid Target 3.1. Partzyme Oligonucleotides The designs 5 and 6 for MNAzymes, based on the 10:23 DNAzyme, were tested for catalytic activity (FIG. 13). Those skilled in the art will appreciate that the sensor arm (target binding) sequences designated by "N" may be replaced by target-specific sequences for any known nucleic acid target. The substrate arm sequences, which bind the reporter substrate, can be generic and used for many targets. Those skilled in the art will appreciate that the substrate sequences designated by "N" in FIG. 13 may be replaced by DNA, RNA or DNA/RNA chimeric sequences.

In the experiments conducted to measure the catalytic activity of the RPLPO MNAzymes described in FIG. 13, the A and B oligonucleotide partzymes were designed to target exon 5 of the RPLPO gene. The sequences of the A and B partzymes are listed below from 5' to 3' where the bases underlined form part of the catalytic core of the assembled MNAzyme, bases in bold hybridize with the target, and bases in italics hybridize to the substrate. Sequences which are neither underlined, bolded, or italicized in SEQ ID NO: 17 and SEQ ID NO: 18 preferably form a stem structure such as that depicted in FIG. 13 (see e.g., Design 5).

```
SEQ ID NO: 17 partzyme A3 R05A3/2:
CAAACGAGTCCTGGCCTTGTCCGCACAACGAGAGGAAACCTT SEQ ID NO: 18 partzyme B4 R05B4/2:
TGCCCAGGGAGGCTAGCTGCGGTGGAGACGGATTACACCTTC
```

-continued

SEQ ID NO: 19 partzyme A4 RO5A4/2:
CAAACGAGTCCTGGCCTTGTCTACAACGA*GAGGAAACCTT*

SEQ ID NO: 20 partzyme B5 RO5B5/2:
*TGCCCAGGGA*GGCTAGCTGTGGAGACGGATTACACCTTC

3.2. Reporter Substrate

The reporter substrate for this example is SubBi-2 with the sequence, 5' to 3', as below. In the current example, SubBi-2 was end labelled with a 6-FAM moiety at the 5' end and a BHQ1 moiety at the 3' end and was designated SubBi-2-FB. Cleavage of SubBi-2-FB was monitored at 530 nm (FAM emission wavelength) with excitation at 485 nm (FAM excitation wavelength). The lower case bases represent RNA and the upper case bases represent DNA.

SEQ ID NO: 21 SubBi-2-FB:
AAGGTTTCCTCguCCCTGGGCA

3.3. Target Sequences

The target sequence for this example was a synthetic oligonucleotide RO5/1Target with the sequence, 5' to 3', as below. This target sequence has the same sequence as a section of the RPLPO gene, exon 5.

SEQ ID NO: 22 RO5/1Target:
GAAGGTGTAATCCGTCTCCACAGACAAGGCCAGGACTCGTTTG

3.4. Reaction Components

Detection of the target sequence was measured by an increase in fluorescent signal caused by cleavage of the reporter substrate by the catalytically active MNAzyme. Reactions were initiated by the addition of substrate and the total volume of all reactions was 25 µL. All reactions were conducted at 55° C. in a SmartCycler® System thermocycler (Cepheid). Fluorescence for each reaction was read every 7 seconds for a total of 5 minutes. All reactions in Table 6 contained 1 µM SubBi-2-FB, Tris HCl (pH 9.0 at 25° C.) and 25 mM MgCl$_2$.

TABLE 6

Components of reactions for detection of a nucleic acid target as shown in FIG. 13

| Design | Partzyme A (1 µM) | Partzyme B (1 µM) | MNAzyme Reaction | Target |
|---|---|---|---|---|
| 5 | RO5A3/2 | RO5B4/2 | Target | 1 µM RO5/1 |
|   |         |         | No Target | H$_2$0 |
| 6 | RO5A4/2 | RO5B5/2 | Target | 1 µM RO5/1 |
|   |         |         | No Target | H$_2$0 |

Each reaction well on the SmartCycler® System thermocycler (Cepheid) used during the experiment was first tested for its background level of fluorescence, as this is known to vary between wells. This was measured by reading the fluorescence of the bulk mix alone. This value was then subtracted from all other reactions performed in that well to allow between well comparisons.

3.5. Results: Detection and Cleavage of Substrate

The target-containing reactions, with the MNAzymes of designs 5 and 6, showed an increase in fluorescence over time compared to the no-target control (FIG. 13ii), upper and lower panels, respectively. This demonstrates that the partzyme oligonucleotides assemble into a catalytically active MNAzyme and cleave the reporter substrate only in the presence of the target sequence. The no-target controls did not show an increase in fluorescence indicating that no cleavage was occurring. The cleavage rate for design 6 was considerably faster than design 5.

Example 4

Detection of Amplicons from In Vitro PCR Amplification of a Nucleic Acid Sequence Using MNAzymes

4.1. Partzyme Oligonucleotides

MNAzymes can also be used to detect amplicons from in vitro amplified nucleic acid sequence. For this example, detection of amplicons is performed as a two-step process but may also be performed in a single reaction. In this instance, the oligonucleotides used to detect the amplicons were based on design 4 using oligonucleotides RO4A2/1 and RO4B3/1 (FIG. 10), which detects the human RPLPO gene. The A and B partzyme oligonucleotides are listed below. In the following sequences, the bases underlined form part of the catalytic core of the assembled MNAzyme, bases in bold hybridize with the target, and bases in italics hybridize to the substrate.

SEQ ID NO: 2 Partzyme A2 RO4A2/1:
GCTGGTCATCCAGCAGCGGTCGAAA*TAGTGAGT*

SEQ ID NO: 5 Partzyme B3 RO4B3/1:
*CATCTCTTCT*CCGAGCGTGTTCGACAATGGC

4.2. Reporter Substrate

The reporter substrate for this example is SubBi-1-FB with the sequence, 5' to 3', as below. The lower case bases represent RNA and the upper case bases represent DNA. The underlined bases indicate the position of a 6-FAM moiety at the 5' end and a BHQ1 moiety at the 3' end. Cleavage of SubBi-1-FB was monitored at 530 nm (FAM emission wavelength) with excitation at 485 nm (FAM excitation wavelength).

SEQ ID NO: 6 SubBi-1-FB:
ACTCACTATaGGAAGAGATG

4.3. Primers for Amplification of Human RPLPO Gene by PCR

The target sequence for this example was generated by in vitro PCR amplification of sequence from exon 4 of the RPLPO gene from human genomic DNA extracted from the K562 (PROMEGA) cell line, using the PCR primers listed below.

SEQ ID NO: 23 Primer 5RO4/3:
CAAGACTGGAGACAAAGTG

SEQ ID NO: 24 Primer 3RO4/2:
GCAGAGTTTCCTCTGTGATA

4.4. Control Target Oligonucleotide

An oligonucleotide was synthesised and used as a positive control for RPLPO sequence. The control oligonucleotide was not amplified by PCR in these experiments.

SEQ ID NO: 8 RO4/1Target:
GCCATTGTCGAACACCTGCTGGATGACCAGC

4.5. Reaction Components: PCR Amplification of the RPLPO Gene

PCR amplification of the RPLPO gene was performed in total reaction volume of 25 µL. All amplification reactions were conducted in a GeneAmp® PCR System 9700 thermocycler (Applied Biosystems). The cycling parameters were 95° C. for 7 minutes, 10 cycles of 95° C. for 5 seconds and 65° C. for 30 seconds (with a 1° C. decrease in temperature per cycle), and finally 50 cycles of 95° C. for 5 seconds and 55° C. for 30 seconds. All reactions contained 40 nM 5RO4/3 and 200 nM of 3RO4/2, 3 mM $MgCl_2$, 200 μM of each dNTP, 1×Immobuffer (Bioline) and 1 unit of Immolase (Bioline) with or without 500 ng of K562 human genomic DNA (PROMEGA).

4.6. Reaction Components: Detection of Target Sequence

Detection of the target sequence was measured by an increase in fluorescent signal caused by cleavage of the reporter substrate by the catalytically active MNAzyme. Reactions were initiated by the addition of substrate and the total volume of all reactions was 25 μL. All reactions were conducted at 40° C. in a SmartCycler® System thermocycler (Cepheid). Fluorescence for each reaction was read every 7 seconds for a total of 10 minutes. All reactions in Table 7 contained the bulk mix of 1 μM SubBi-1-FB, Tris HCl (pH 9.0 at 25° C.) and 25 mM $MgCl_2$. Concentrations of oligonucleotide Partzymes A and B are 1 μM.

TABLE 7

Reaction components for the detection of RPLPO DNA amplicons following in vitro PCR. The MNAzyme systems used Design 4 (RO4A2/1:RO4B3/1)

| RPLPO MNAzyme Reaction | Target |
|---|---|
| Target-oligo (Positive Control RPLPO) | $10^{12}$ copies RO4/1Target Oligo |
| Target-PCR product RPLPO (Test) | 5 μL of RPLPO PCR product (equivalent to 100 ng of genomic DNA) |
| No-Target (Negative Control RPLPO) | 5 μL $H_2O$ |
| Non amplified genomic DNA (Negative Control) | 5 μL containing 500 ng of genomic DNA |

Each reaction well on the SmartCycler® System thermocycler (Cepheid) used during the experiment was first tested for its background level of fluorescence, as this is known to vary between wells. This was measured by reading the fluorescence of the bulk mix alone. This value was then subtracted from all other reactions performed in that well to allow between well comparisons.

4.7. Results: Detection of Cleavage of SubBi-1-FB Reporter Substrate

Figure 14:
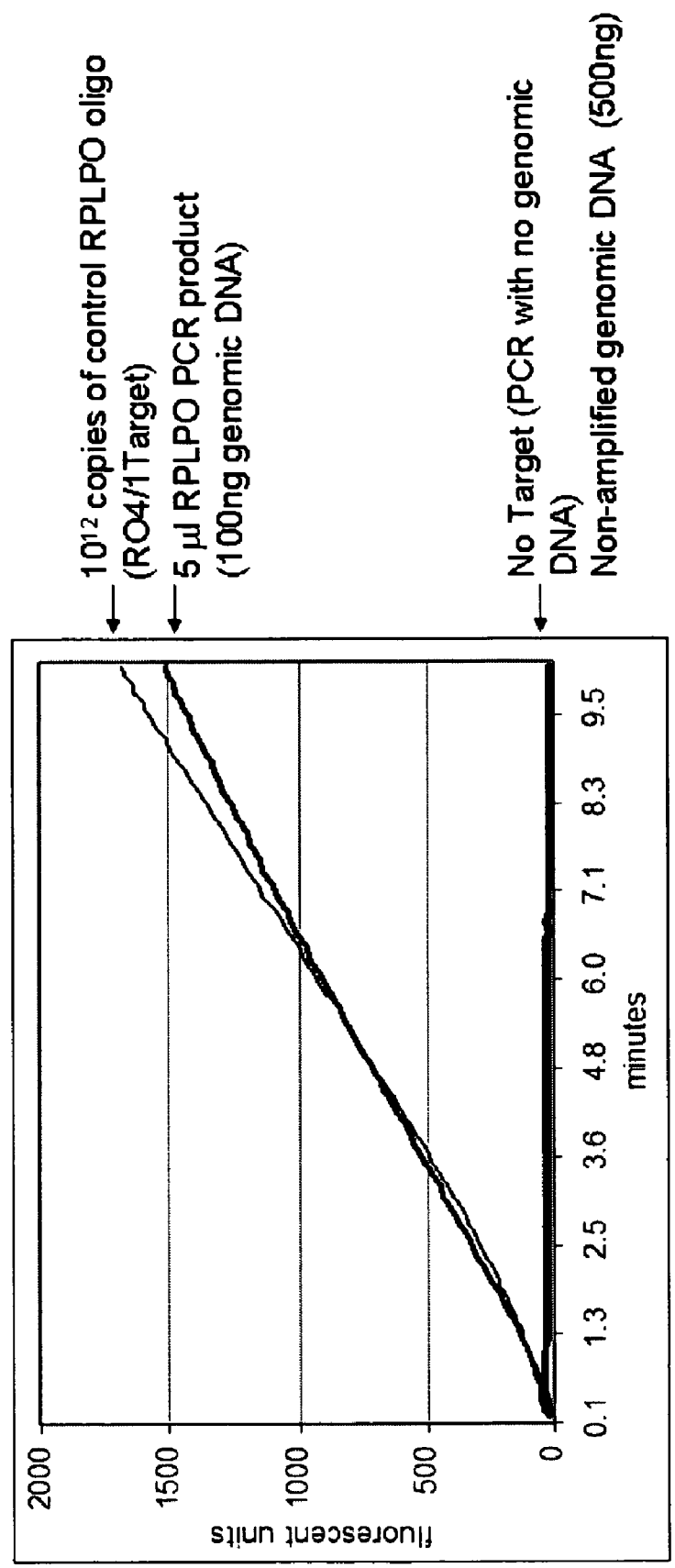
FIG. 14: Detection of PCR amplified RPLPO: Results for target-dependent cleavage of a reporter substrate and various control reactions by the design 4 MNAzyme system targeting the human RPLPO gene. RPLPO MNAzyme reaction contained either (i) control RPLPO oligonucleotides, (ii) RPLPO PCR amplicons (5 µl) produced by amplification of human genomic DNA (100 ng) using primers complementary to the RPLPO gene, (iii) "no target" RPLPO PCR reactions which lack genomic DNA or (iv) unamplified human genomic DNA (500 ng).

The MNAzyme design 4 for the detection of RPLPO, exon 4, showed an increase in fluorescence over time when the target RPLPO sequence was amplified from human genomic DNA by PCR (FIG. 14). The increase in fluorescence seen for RPLPO amplicons was similar to that seen for $10^{12}$ copies of the positive control RO4/1Target oligonucleotides. The fluorescence of the no-target controls was lower than that in the target-containing reactions and none of the negative control reactions showed an increase in fluorescence over time. This demonstrates that the increase in fluorescence produced in target-containing reactions is due to target-dependent assembly of a catalytically active MNAzyme that then cleaved the reporter substrate.

Example 5

Use of MNAzymes for Detection of Amplicons Produced by In Vitro PCR Amplification of Short Nucleic Acid Sequences 5.1. Partzyme Oligonucleotides MNAzymes can be used to detect amplicons from in vitro amplified nucleic acid sequence. In this example amplification and detection are performed in a three-step process (FIG. 5) but reverse transcription, PCR amplification and detection could also be performed concurrently in a single reaction tube. For this example the oligonucleotides used to detect the amplicons used design 4, miR partzyme A and B oligonucleotides (FIG. 11), which are designed to detect hsa-miR-20. The MNAzyme partzyme oligonucleotides are listed below such that the bases underlined form part of the catalytic core of the assembled MNAzyme, bases in bold hybridize with the target, and bases in italics hybridize to the substrate.

SEQ ID NO: 10 Partzyme A2 miR2OA2/1:
TACCTGCACTA<u>CGGTCGAAA</u>*TAGTGAGT*

SEQ ID NO: 11 Partzyme B3 miR20B3/1:
*CATCTCTTCT*<u>CCGAGC</u>TAAGCACTTTA

5.2. Reporter Substrate

The reporter substrate for this example is SubBi-1-FB with the sequence, 5' to 3', as below. The lower case bases represent RNA and the upper case bases represent DNA. The underlined bases indicate the position of a 6-FAM moiety at the 5' end and a BHQ1 moiety at the 3' end. Cleavage of SubBi-1-FB was monitored at 530 nm (FAM emission wavelength) with excitation at 485 nm (FAM excitation wavelength).

SEQ ID NO: 6 SubBi-1-FB:
AC<u>T</u>CAC<u>T</u>ATaGGAAGAGA<u>T</u>G 5.3. PCR Primers for Amplification of 22 Mer D-20 Oligonucleotide Target Sequences The target sequence for this example was generated by in vitro amplification of the D-20 oligonucleotide using the oligonucleotides PCR primers listed below SEQ ID NO: 25 Primer 5miR20/1:
ACGTGACGCTAAAGTGCT SEQ ID NO: 26 Primer 3miR20/L1:
CGTCCGAATGACGTACCTGCAC SEQ ID NO: 27 Primer 3miR20/P1:
CGAATGACGTACCTGCAC 5.4. Target Sequences and Controls The DNA sequence (D-20Target) with homology to miR-20 was used as template for demonstrating amplification and detection of a short sequence using PCR and MNAzymes.

SEQ ID NO: 12 D-20Target:
TAAAGTGCTTATAGTGCAGGTA

Furthermore, to ensure that any closely related "off-target" sequences erroneously amplified can not be detected with the miR-20 system, the control target DNA oligonucleotide D-17-5pTarget was also tested with the miR-20 partzyme A and B oligonucleotide system.

SEQ ID NO: 13 D-17-5pTarget:
CAAAGTGCTTACAGTGCAGGTAGT 5.5 Reaction Components: Amplification of Target Sequence Amplification of the target sequence was performed in a total reaction volume of 25 μL. All amplification reactions were conducted in a GeneAmp® PCR System 9700 thermocycler (Applied Biosystems). The cycling parameters for steps 1 and 2 (reverse transcription and PCR) were 42° C. for 30 minutes, 95° C. for 7 minutes, 10 cycles of 95° C. for 5 seconds and 30° C. for 30 seconds (plus 2° C. per cycle), and finally 50 cycles of 95° C. for 5 seconds and 50° C. for 30 seconds. The reactions initially only contained 10 nM 3miR20/L1, after 42° C. for 30 minutes the reaction was paused and 30 nM 3miR20/P1 and 200 nM of 5miR20/1 were added. All other reagents listed were in the initial reaction mix, 3 mM $MgCl_2$, 200 µM of each dNTP, 1×Immobuffer (Bioline) and 1 unit of Immolase (Bioline) and either a) $10^8$ copies of D-20Target, b) no target ($dH_2O$) or c) $10^8$ copies of off target DNA (D-17-5pTarget).

5.6. Reaction Components: Detection of Target Sequence

Detection of the target sequence was measured by an increase in fluorescent signal caused by cleavage of the reporter substrate by the catalytically active MNAzyme. Reactions were initiated by the addition of substrate and the total volume of all reactions was 25 µL. All reactions were conducted at 40° C. in a SmartCycler® System thermocycler (Cepheid). Fluorescence for each reaction was read every 7 seconds for a total of 10 minutes. All reactions in Table 8 contained the bulk mix of 1 µM SubBi-1-FB, Tris HCl (pH 9.0 at 25° C.) and 25 mM $MgCl_2$. Concentrations of partzyme A and B were 1 µM.

TABLE 8

Reaction components for the detection of in vitro amplified short (20-25mer) nucleic acid sequences. The MNAzyme system used Design 4 (miR20A2/1:miR20B3/1).

| MNAzyme Reaction | Target |
|---|---|
| miR-20 Target-oligonucleotide (Positive Control miR20) | $10^{12}$ copies D-20Target in 5 µL (not amplified) |
| miR-20 Target-PCR product (Test) | D-20 PCR product (5 µL from 25 µL reaction) (equivalent to 2 × $10^7$ copies of D-20Target amplified by PCR) |
| miR-20 Target-oligonucleotide (Control unamplified D-20) | $10^8$ copies D-20Target in 5 µL (not amplified) |
| No-Target (Negative Control miR20) | 5 µL $H_2O$ |
| Off-target (Off Target Control for miR20) | D-17-5p PCR product (5 µL from 25 µL reaction) (equivalent to 2 × $10^7$ copies of D-17-5pTarget amplified by PCR) |

Each reaction well on the SmartCycler® System thermocycler (Cepheid) used during the experiment was first tested for its background level of fluorescence. This value was then subtracted from all other reactions performed in that well to allow between well comparisons.

5.7. Results: Detection of Cleavage of SubBi-1-FB Reporter Substrate

Figure 15:
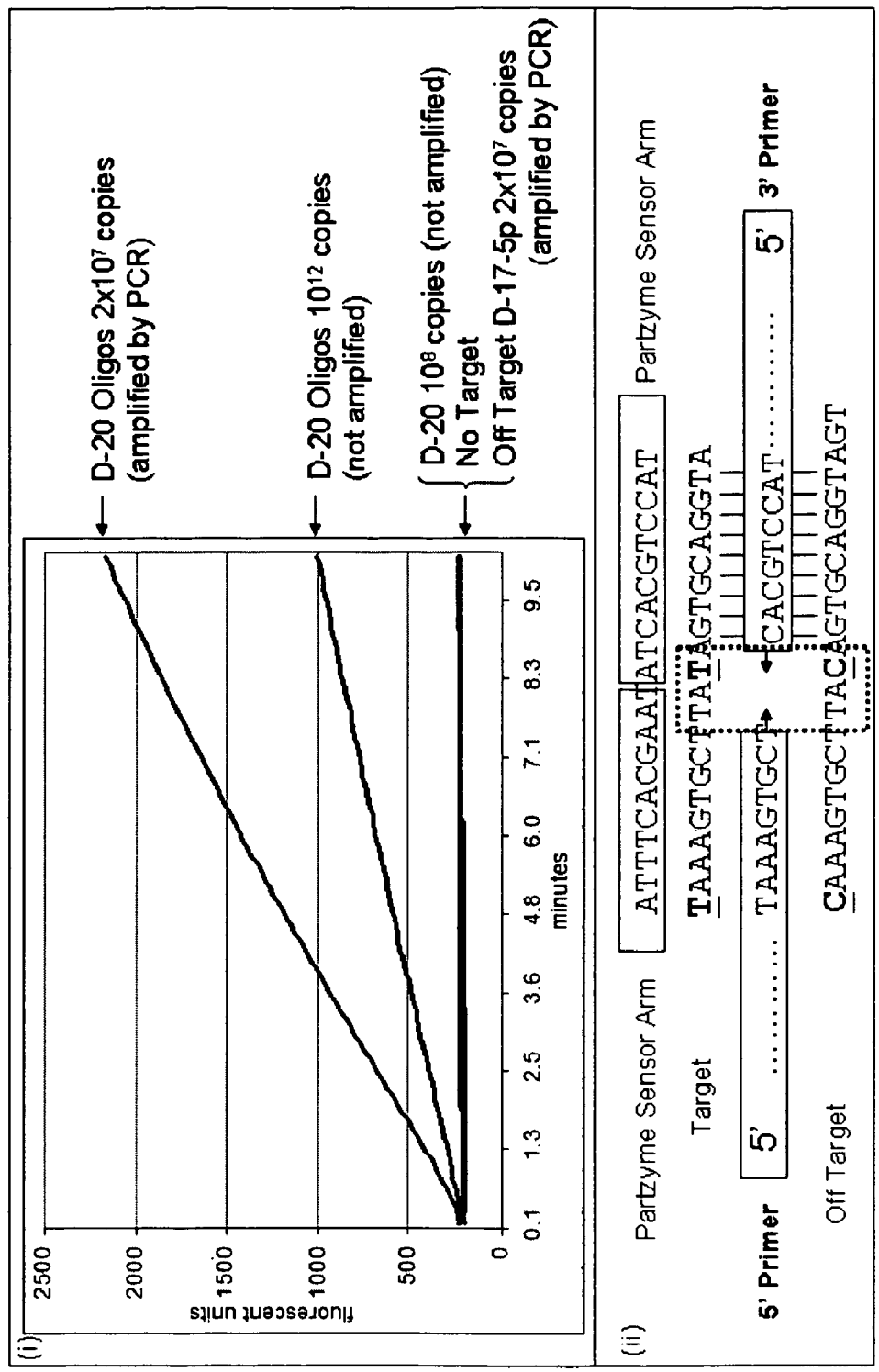
FIG. 15: Detection of amplified short (22mer) sequences: Panel (i): Results for target-dependent cleavage of a reporter substrate by a design 4 MNAzyme system targeting the human miR-20 sequence. MiR-20 MNAzyme reactions were performed with either (i) $10^{12}$ (1E+12) copies of the control D-20Target oligonucleotide (not amplified); (ii) PCR amplicons (5µ1) produced by amplification of 2×$10^7$ (2 E+7) copies of the D-20 target oligonucleotide using primers complementary to the miR-20 sequences; (iii)"no target" PCR reactions which lack D-20Target oligonucleotide; (iv) $10^8$ (1 E+8) copies of D-20Target oligonucleotide (not amplified); and (v) an "off target" control D-17-5p Target (2×$10^7$ (2 E+7) copies amplified by PCR). Panel (ii): Comparison of D-20Target sequence and off target sequence, D-17-5p. The D-17-5p oligonucleotide has one mismatch within the PCR primer binding region relative to the D-20 Target sequence, and one mismatch within the region (located between the primers) that is interrogated by the sensor arms of the MNAzymes. Partzyme Sensor Arms, Target and Off Target sequences disclosed as SEQ ID NOS 173, 174, 82 and 13, respectively.

The MNAzyme design 4 for the detection of miR-20, showed an increase in fluorescence over time when the target sequence used was D-20Target amplified via PCR (FIG. 15(*i*)).

The fluorescence of the no-target control was lower than that in the target-containing reactions, and none of the negative control reactions showed an increase in fluorescence over time. This demonstrates that the increase in fluorescence produced in target-containing reactions is due to target-dependent assembly of catalytically active MNAzymes that then cleaved the reporter substrate.

The off target control (D-17-5p) in this example was also amplified with the miR-20 primers since it only has one mismatch in the terminal position within the regions that hybridize with the miR-20 primers. Amplification of both D-20Target and D-17-5pTarget was confirmed by electrophoresis. Since both amplicons incorporate the primer sequences at their termini, they now only differ by a single base in the middle of the amplicons. The MNAzyme successfully discriminated between the D-20 and D-17-5p amplicons. This discrimination is a result of the single nucleotide difference in the D-20 and D-17-5p amplicons in the region that lies between the primers as illustrated in FIG. 15(ii). The MNAzyme requires the four bases between the primers to be present (thus allowing discrimination between primer dimer and genuine amplicons) and those four bases must be exact with no substitutions tolerated. This example illustrates the capacity for MNAzymes to discriminate between closely related sequences including those which differ by only a single nucleotide polymorphism.

Example 6

Use of MNAzymes for Detection of MicroRNA Amplicons Produced by In Vitro PCR Amplification of Total RNA 6.1. Partzyme Oligonucleotides MNAzymes can be used to detect amplicons from in vitro amplified nucleic acid sequences. In this example amplification and detection are performed in a two-step process (FIG. 5) where reverse transcription and PCR amplification occur in a first tube, followed by MNAzyme mediated detection in a second tube. For this example the oligonucleotides used to detect the amplicons were design 4, miR partzyme A and B oligonucleotides (FIG. 11), which are designed to detect hsa-miR-20. The MNAzyme partzyme oligonucleotides are listed below such that the bases underlined form part of the catalytic core of the assembled MNAzyme, bases in bold hybridize with the target, and bases in italics hybridize to the substrate.

```
SEQ ID NO: 10 Partzyme A2 miR20A2/1:
TACCTGCACTACGGTCGAAATAGTGAGT

SEQ ID NO: 11 Partzyme B3 miR20B3/1:
CATCTCTTCTCCGAGCTAAGCACTTTA
```

6.2. Reporter Substrate

The reporter substrate for this example is SubBi-1-FB with the sequence, 5' to 3', as below. The lower case bases represent RNA and the upper case bases represent DNA. The underlined bases indicate the position of a 6-FAM moiety at the 5' end and a BHQ1 moiety at the 3' end. Cleavage of SubBi-1-FB was monitored at 530 nm (FAM emission wavelength) with excitation at 485 nm (FAM excitation wavelength).

```
SEQ ID NO: 6 SubBi-1-FB:
ACTCACTATaGGAAGAGATG
```

6.3. PCR Primers for Amplification of hsa-miR-20

The target sequence for this example was generated by in vitro amplification of human thymus total RNA (Ambion) using the oligonucleotide PCR primers listed below.

```
SEQ ID NO: 25 Primer 5miR20/1:
ACGTGACGCTAAAGTGCT

SEQ ID NO: 26 Primer 3miR20/L1:
CGTCCGAATGACGTACCTGCAC
```

6.4. Target Sequences and Controls

Human thymus total RNA (Ambion) was used as template for amplification of miR-20 and amplicons were subsequently detected using MNAzymes (section 6.6).

The RNA sequence (R-20Target) with homology to miR-20 was used as a positive control for demonstrating amplification of short sequences, followed by detection of resultant amplicons using MNAzymes.

SEQ ID NO: 28 R-20Target:
uaaagugcuuauagugcaggua 6.5. Reaction Components: Amplification of Target Sequence Reverse transcription and PCR amplification of the target sequence was performed in total reaction volume of 25 µL. All amplification reactions were conducted in a GeneAmp® PCR System 9700 thermocycler (Applied Biosystems). The cycling parameters were 40° C. for 30 minutes, 95° C. for 7 minutes, 10 cycles of 95° C. for 5 seconds and 30° C. for 30 seconds (with a 2° C. increase in temperature per cycle), and finally 50 cycles of 95° C. for 5 seconds and 50° C. for 30 seconds. The reactions contained 40 nM 3miR20/L1 and 200 nM of 5miR20/1, 3 mM $MgCl_2$, 200 µM of each dNTP, 10 units Rnasin (Promega), 30 units of MMLV(-H) Reverse Transcriptase (Promega), 1× Immobuffer (Bioline) and 0.5 units of Immolase (Bioline) and either a) 1 µg of total RNA, b) no target ($dH_2O$) or c) $10^{14}$ copies (5 µM) of R-20Target Oligonucleotide.

6.6. Reaction Components: Detection of Target Sequence

Detection of the target sequence was measured by an increase in fluorescent signal caused by cleavage of the reporter substrate by the catalytically active MNAzyme. Reactions were initiated by the addition of substrate and the total volume of all reactions was 25 µL. All reactions were conducted at 40° C. in a SmartCycler® System thermocycler (Cepheid). Fluorescence for each reaction was read every 30 seconds for a total of 5 minutes. All reactions in Table 9 contained the bulk mix of 1 µM SubBi-1-FB, 1 µM partzyme A, 1 µM partzyme B, 50 mM Tris HCl (pH 9.0 at 25° C.), 25 mM $MgCl_2$ and target (as indicated in Table 9).

TABLE 9

Reaction components for the detection of in vitro amplified total RNA. The MNAzyme system used Design 4 (miR20A2/1:miR20B3/1).

| MNAzyme Reaction | Target |
| --- | --- |
| miR-20 Target - RNA oligonucleotide (Positive Control miR-20) | R-20Target PCR-product (5 µL from a 25 µL reaction) (equivalent to 2 × $10^{13}$ copies of R-20Target oligonucleotide amplified) |
| miR-20 Target - total RNA (Test) | PCR product (5 µL from a 25 µL reaction) (equivalent to 200 ng of total RNA amplified) |
| No-Target RNA (Negative Control miR20) | PCR product (5 µL from a 25 µL reaction) from the "no-target control" reaction containing $dH_2O$. |
| Non-amplified total RNA (Negative Control miR20) | Total RNA (1 µg) in a total volume of 5 µl |

The background level of fluorescence was measured for each reaction well on the SmartCycler® System thermocycler (Cepheid). This value was then subtracted from all other reactions performed in that well to allow comparison between wells.

6.7. Results: Detection of Cleavage of SubBi-1-FB Reporter Substrate

Figure 16:
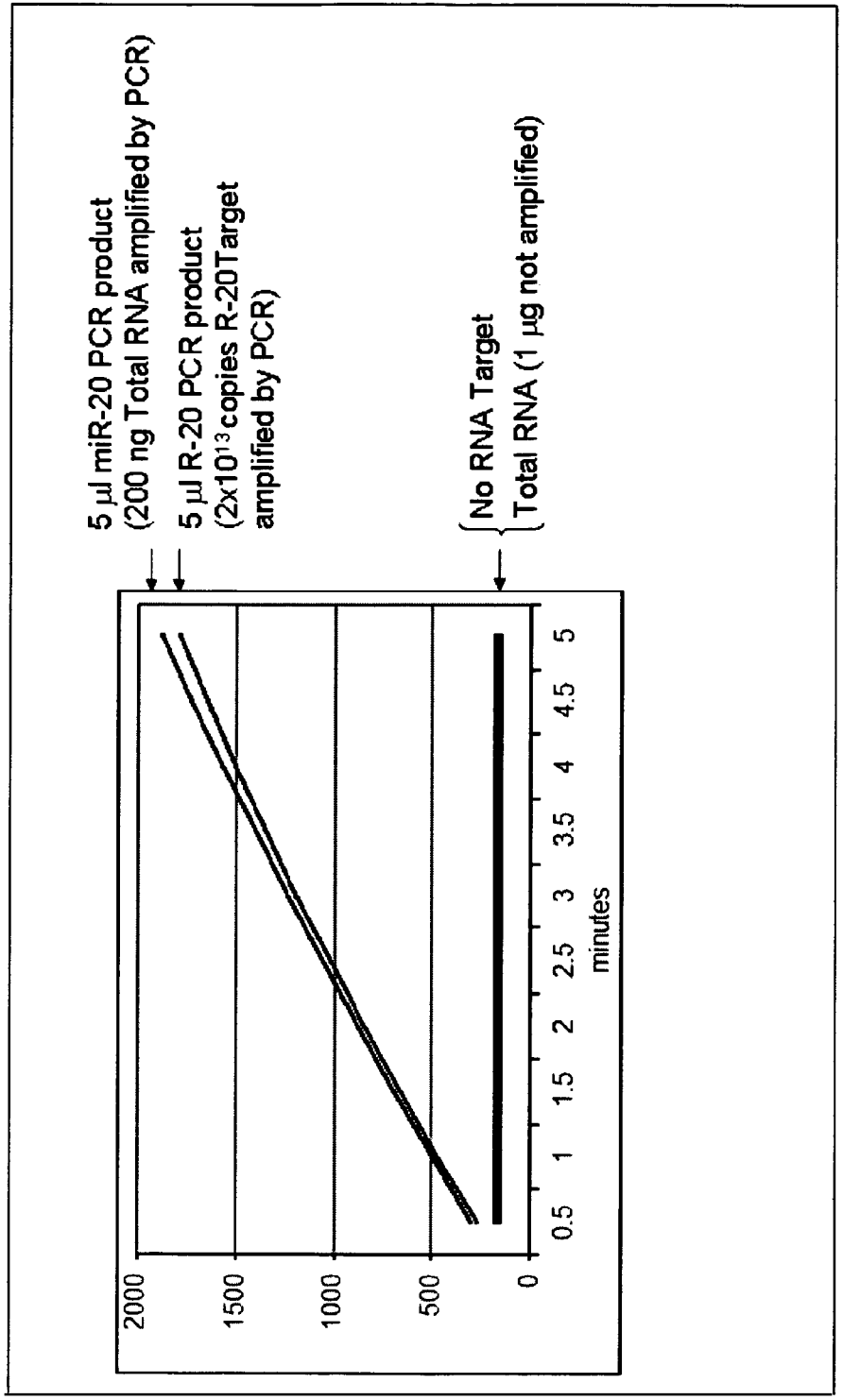
FIG. 16: Detection of amplified miR-20 amplicons: Example of end point detection of amplicons using MNAzymes following PCR amplification. PCR was used to amplify mir-20 microRNA present in total RNA from human thymus cells, and detected using MNAzyme methodology. Amplified samples and controls are as shown.

The MNAzyme design 4 for the detection of miR-20, showed an increase in fluorescence over time when the target sequence used was total RNA amplified via PCR (FIG. 16).

The fluorescence of the no-RNA target control was lower than that in the RNA target-containing reactions, and none of the negative control reactions showed an increase in fluorescence over time. This demonstrates that the increase in fluorescence produced in target-containing reactions is due to PCR amplified target dependent assembly of catalytically active MNAzymes that then cleaved the reporter substrate. While this experiment was performed in two steps (reverse transcription/PCR then MNAzyme end point detection), all steps could be performed concurrently in a single reaction tube allowing the reaction to be monitored in real time.

Example 7

Target Detection by MNAzymes Coupled to a Nucleic Acid Signal Cascade 7.1. MNAzyme Initiated Signal Amplification Cascades It is possible to lower the limit of detection of nucleic acids by coupling MNAzyme detection to a signal amplification cascade reaction, as illustrated in FIG. 7. MNAzymes also allow a highly specific triggering mechanism for initiation of a cascade.

7.2. Spatially Separated DNAzyme Cascade

DNAzymes can be tethered to a support using a variety of methods including attachment to plastic wafers coated with streptavidin that allow attachment of biotin labeled DNAzymes. The sequences used for attachment can also serve as generic MNAzyme/DNAzyme substrates. Targets (e.g. nucleic acid sequences) can be detected following hybridization to partzyme sequences allowing the formation of active MNAzymes. The MNAzymes can then cleave tethered generic substrates thus releasing DNAzyme A. DNAzyme A can then migrate to a second generic sequence on a second solid surface where DNAzyme B is tethered. DNAzyme A can cleave the second generic sequence thus releasing DNAzyme B. Cleavage of this substrate between fluorophore/quencher dye pairs can result in increased fluorescence. The released DNAzyme B can in turn cleave more of the first substrate thus releasing more of DNAzyme A and initiating a signal cascade which results in signal amplification (FIG. 7).

This example describes one mechanism for generating a signal cascade using spatially separated DNAzymes, however, other methods exist which would also allow signal amplification using catalytic nucleic acids. The skilled artisan will appreciate that any such method should be fully functional herewith, provided that by some means of attachment or physical separation, a substrate is kept "inaccessible" to an enzyme that would act on it. Other examples of nucleic acid signal amplification which could be coupled to MNAzyme initiated reactions include, but are not limited to, ligation cascades (Paul and Joyce, 2004) and circular DNAzyme cascades (Levy and Ellington, 2003), each of which involve the base principle of maintaining a "separation" of an enzyme from its substrate, whereupon when the enzyme and substrate come into contact such that catalytic activity can result, directly or indirectly an amplified signal, or signal cascade results.

Example 8

Figure 17:
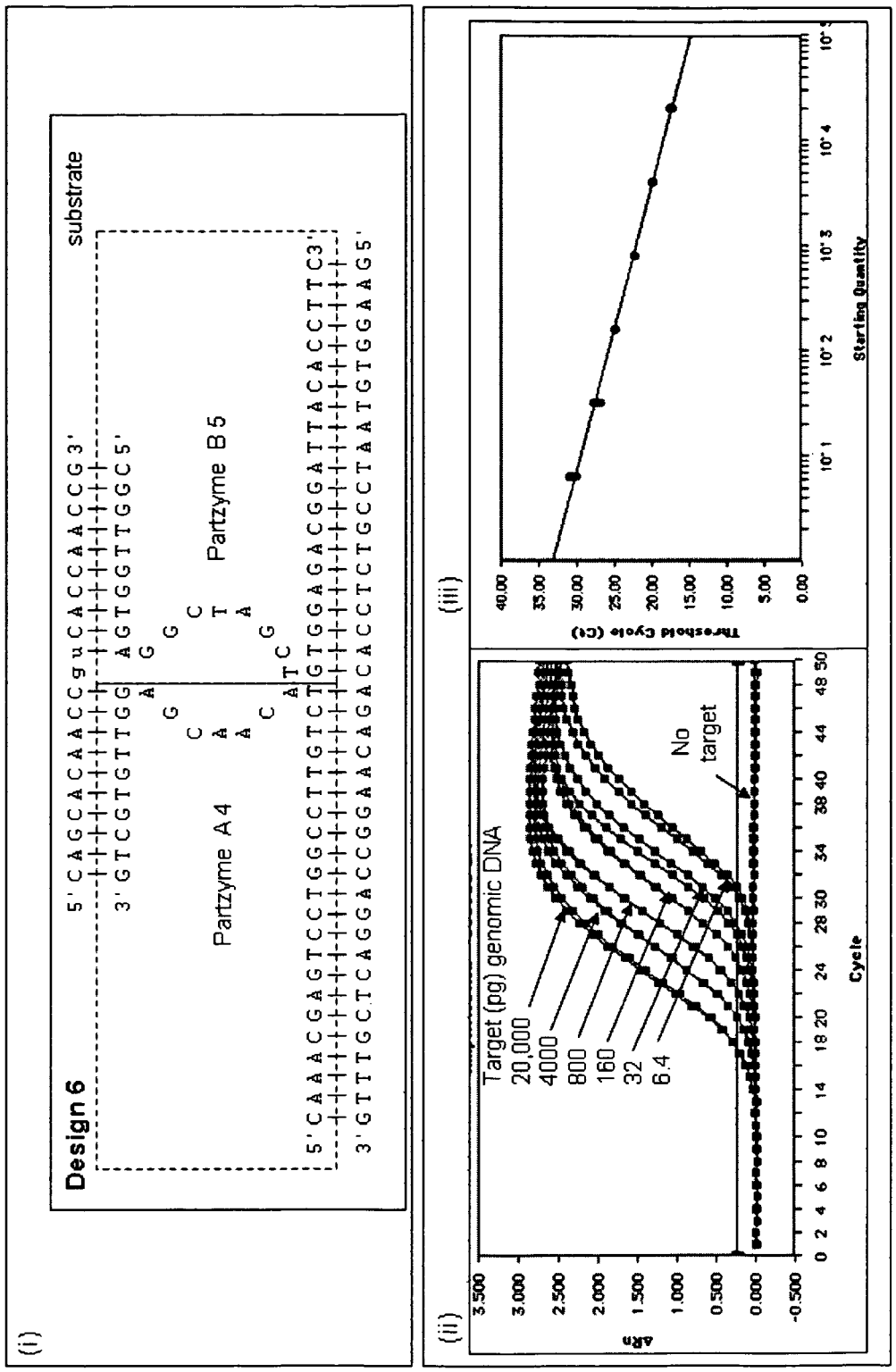
FIG. 17: Quantitative real time PCR analysis of RPLPO exon 5 by MNAzyme design 6: Example of real-time detection and quantification using MNAzyme methodology, wherein the RPLPO gene was detected using MNAzymes to monitor accumulation of exon 5 of RPLPO. Panel (i): MNAzyme design 6; Partzyme A4, Partzyme B5, Substrate and bottom sequence disclosed as SEQ ID NOS 29-31 and 22, respectively. Panel (ii): fluorescence signal indicating real time PCR for different template amounts as shown; Panel (iii): standard curve and quantitation of amplified material. Results show time-dependent increase in fluorescence for MNAzyme detection of human genomic DNA amplified via PCR. $R^2$=0.995; slope=-3.698

Use of MNAzymes for the Quantitation of a Nucleic Acid Target 8.1. Partzyme Oligonucleotides MNAzymes can be used to monitor amplification of target nucleic acids in real time using in vitro target amplification methods such as PCR. Further, real time monitoring allows the amount of target initially present in the reaction to be quantified. In this example amplification and detection are performed in a one-step process, wherein PCR amplification and MNAzyme-mediated detection occur simultaneously in a single tube. Partzyme oligonucleotides A and B used design 6 with sensor arms complementary to exon 5 of the human RPLPO gene (FIG. 17(i)). The partzyme oligonucleotides are listed below with the "-P" indicating 3' phosphorylation of the oligonucleotide.

```
SEQ ID NO: 29 Partzyme A4 RO5A4/3-P:
CAAACGAGTCCTGGCCTTGTCTACAACGAGGTTGTGCTG-P SEQ ID NO: 30 Partzyme B5 RO5B5/3-P:
CGGTTGGTGAGGCTAGCTGTGGAGACGGATTACACCTTC-P
```

8.2. Reporter Substrate

The reporter substrate for this example is SubBi-3 with the sequence, 5' to 3', as below. In the current example, SubBi-3-FB was end-labelled with a 6-FAM moiety at the 5' end and a BHQ1 moiety at the 3' end. Cleavage of SubBi-3-FB was monitored at 530 nm (FAM emission wavelength) with excitation at 485 nm (FAM excitation wavelength). The lower case bases represent RNA and the upper case bases represent DNA.

```
SEQ ID NO: 31 SubBi-3-FB:
CAGCACAACCguCACCAACCG
```

8.3. PCR Primers for Amplification of RPLPO Exon 5

The target sequence for this example was generated by in vitro amplification of human genomic DNA using the oligonucleotide PCR primers listed below.

```
SEQ ID NO: 32 Primer 5RO5/1:
CATTCTATCATCAACGGGTA

SEQ ID NO: 33 Primer 3RO5/1:
CAAAGGCAGATGGATCAG
```

8.4. Target Sequence

Human genomic DNA extracted from the K562 cell line (Promega) was used as template for amplification of RPLPO gene.

8.5. Reaction Components: Amplification and Quantitation of Target Sequence

Real time amplification and quantitation of the target sequence was performed in a total reaction volume of 25 µL. All reactions were conducted in an ABI7700 thermocycler (Applied Biosystems). The cycling parameters were, 95° C. for 7 minutes, 10 cycles of 95° C. for 5 seconds and 60° C. for 30 seconds (with a 1° C. decrease in temperature per cycle), and finally 50 cycles of 95° C. for 5 seconds and 50° C. for 30 seconds. The reactions contained 40 nM 5RO5/1 and 200 nM of 3RO5/1, 200 nM RO5A4/3-P and 200 nM RO5B5/3-P, 200 nM SubBi-3-FB, 10 mM MgCl$_2$, 200 µM of each dNTP, 10 units Rnasin (Promega), 1×ROX reference (Invitrogen), 1×Immobuffer (Bioline), 0.25 units of Immolase (Bioline) and either genomic DNA template (20,000 pg, 4000 pg, 800 pg, 160 pg, 32 pg, and 6.4 pg) or no target (dH$_2$O).

8.6. Results: Amplification of Target and Cleavage of SubBi-3-FB Reporter Substrate The MNAzyme design 6 for the real time detection and quantification of RPLPO exon 5, showed an increase in fluorescence over time when the target sequence used was human genomic DNA amplified via PCR (FIG. 17(ii)).

The fluorescence of the no-DNA target control was lower than that in the DNA target-containing reactions and did not increase during the reaction. This demonstrates that the increase in fluorescence produced in target-containing reactions is due to target dependent assembly of catalytically active MNAzymes that then cleaved the reporter substrate. A standard curve was generated by plotting the log of the DNA concentrations against the threshold cycle resulting in a linear plot with a correlation coefficient of 0.995. In the reaction containing 6.4 pg of genomic DNA, approximately 10 copies of the target would be present. This example demonstrates the high sensitivity of this approach.

While this experiment used asymmetric primer ratios subsequent experiments using real time PCR (data not shown) demonstrated that MNAzyme detection was also compatible with PCR using symmetric primer ratios.

Example 9

Figure 18:
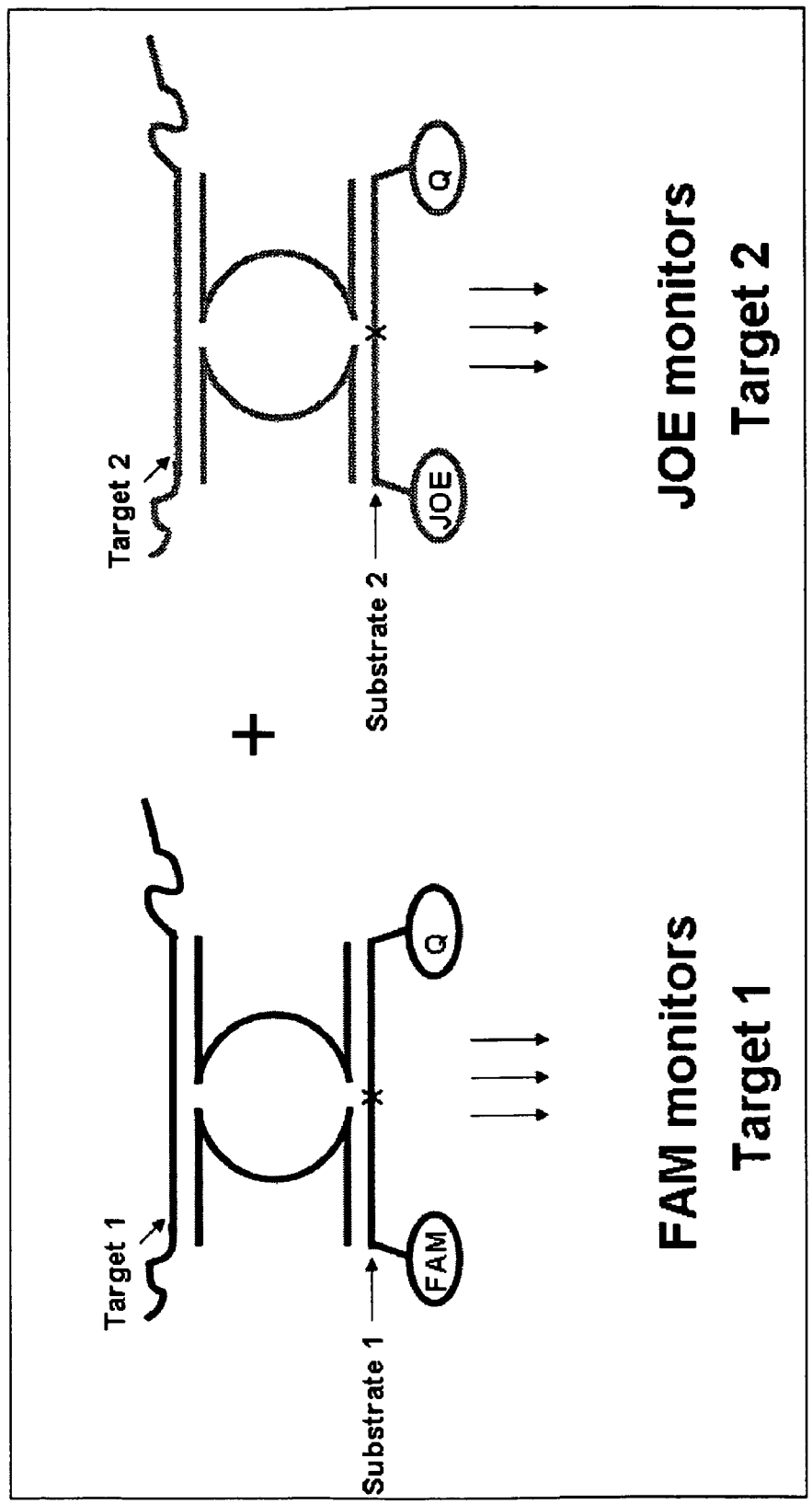
FIG. 18: Schematic representation of an exemplary multiplex analysis of multiple targets: Two or more targets can be simultaneously detected using two or more substrates, each specific for one MNAzyme. Substrates are preferably labeled with different fluorophores. In this example, Target 1 can be detected by monitoring the increase in FAM fluorescence and Target 2 can be detected by monitoring the increase in JOE fluorescence. Q: quencher; FAM, JOE: fluorophores.

Multiplex Reaction Using Multiple MNAzymes Targeting Multiple Targets Simultaneously 9.1. Partzyme Oligonucleotides Multiple targets can be simultaneously detected in one multiplexed reaction that comprises multiple unique MNAzymes. Each MNAzyme has sensor arms specific for one target and substrate arms specific for a unique member of a series of generic substrates, each one of which is labeled with a different fluorophore (FIG. 18). In the following example, MNAzymes were designed to detect two different targets, namely RPLPO and D-20 sequences. It will be appreciated that any number of targets can be used in accordance with the method. The sequences of the partzymes A and B are listed below from 5' to 3'. In the following sequences the bases underlined form part of the catalytic core of the assembled MNAzyme, bases in bold hybridize with the target and bases in italics hybridize to the substrate.

```
SEQ ID NO: 29 Partzyme A4 RO5A4/3-P:
CAAACGAGTCCTGGCCTTGTCTACAACGAGGTTGTGCTG-P SEQ ID NO: 30 Partzyme B5 RO5B5/3-P:
CGGTTGGTGAGGCTAGCTGTGGAGACGGATTACACCTTC-P SEQ ID NO: 34 Partzyme A4 miR20A4/2:
TACCTGCACTAACAACGAGAGGAAACCTT SEQ ID NO: 35 Partzyme B5 miR20B5/2:
TGCCCAGGGAGGCTAGCTTAAGCACTTTA
```

9.2. Reporter Substrates

The two reporter substrates used in this example were SubBi-2 and SubBi-3 with the sequences, 5' to 3', as below. In the current example, SubBi-2 was end labeled with a 6-FAM moiety at the 5' end and a BHQ1 moiety at the 3' end and was designated SubBi-2-FB. SubBi-3 was end labeled with a 6-JOE moiety at the 5' end and a BHQ1 moiety at the 3' end and was designated SubBi-3-JB.

Cleavage of SubBi-2-FB was monitored at 530 nm (FAM emission wavelength) with excitation at 485 nm (FAM excitation wavelength) and the cleavage of SubBi-3-JB was monitored at 548 nm (JOE emission wavelength) with excitation at 520 nm (JOE excitation wavelength). The lower case bases represent RNA and the upper case bases represent DNA.

```
SEQ ID NO: 21 SubBi-2-FB:
AAGGTTTCCTCguCCCTGGGCA
```

```
SEQ ID NO: 36 SubBi-3-JB:
CAGCACAACCguCACCAACCG
```

9.3. Target Sequences

The target sequences for this example were synthetic oligonucleotides RO5/1Target and D-20Target with the sequences, 5' to 3', as below. The RO5/1Target sequence has the same sequence as a section of the RPLPO gene, exon 5 and the D-20Target sequence is a DNA homolog of the RNA hsa-miR-20.

```
SEQ ID NO: 22 RO5/1Target:
GAAGGTGTAATCCGTCTCCACAGACAAGGCCAGGACTCGTTTG

SEQ ID NO: 12 D-20Target:
TAAAGTGCTTATAGTGCAGGTA
```

9.4. Reaction Conditions

Detection of the target sequences was measured by monitoring the increase in fluorescent signal caused by cleavage of the reporter substrates by the catalytically active MNAzymes. Reactions were initiated by the addition of substrate and the total volume of all reactions was 25 µL. All reactions were conducted at 55° C. in a SmartCycler® System thermocycler (Cepheid). Fluorescence for each reaction was read every 7 seconds for a total of 5 minutes. All reactions in Table 10 contained PCRII buffer (Applied Biosystems) and 25 mM $MgCl_2$.

TABLE 10

Components of reactions for the simultaneous detection of two different nucleic acid targets.

| Reaction Type | Partzymes A (1 µM) | Partzymes B (1 µM) | Target |
|---|---|---|---|
| Singleplex D-20 | miR20A4/2 | miR20B5/2 | 1 µM D-20Target<br>No Target ($H_2O$) |
| Singleplex RPLPO | RO5A4/3-P | RO5B5/3-P | 1 µM RO5/1Target<br>No Target ($H_2O$) |
| Multiplex D-20 and RPLPO | miR20A4/2 and RO5A4/3-P | miR20B5/2 and RO5B5/3-P | 1 µM D-20Target and 1 µM RO5/1Target<br>No Target ($H_2O$) |

Each reaction well on the SmartCycler® System thermocycler (Cepheid) used during the experiment was first tested for its background level of fluorescence, as this is known to vary between wells. This was measured by reading the fluorescence of the bulk mix alone. This value was then subtracted from all other reactions performed in that well to allow between well comparisons.

9.5. Results: Detection and Cleavage of Substrate

Figure 19:
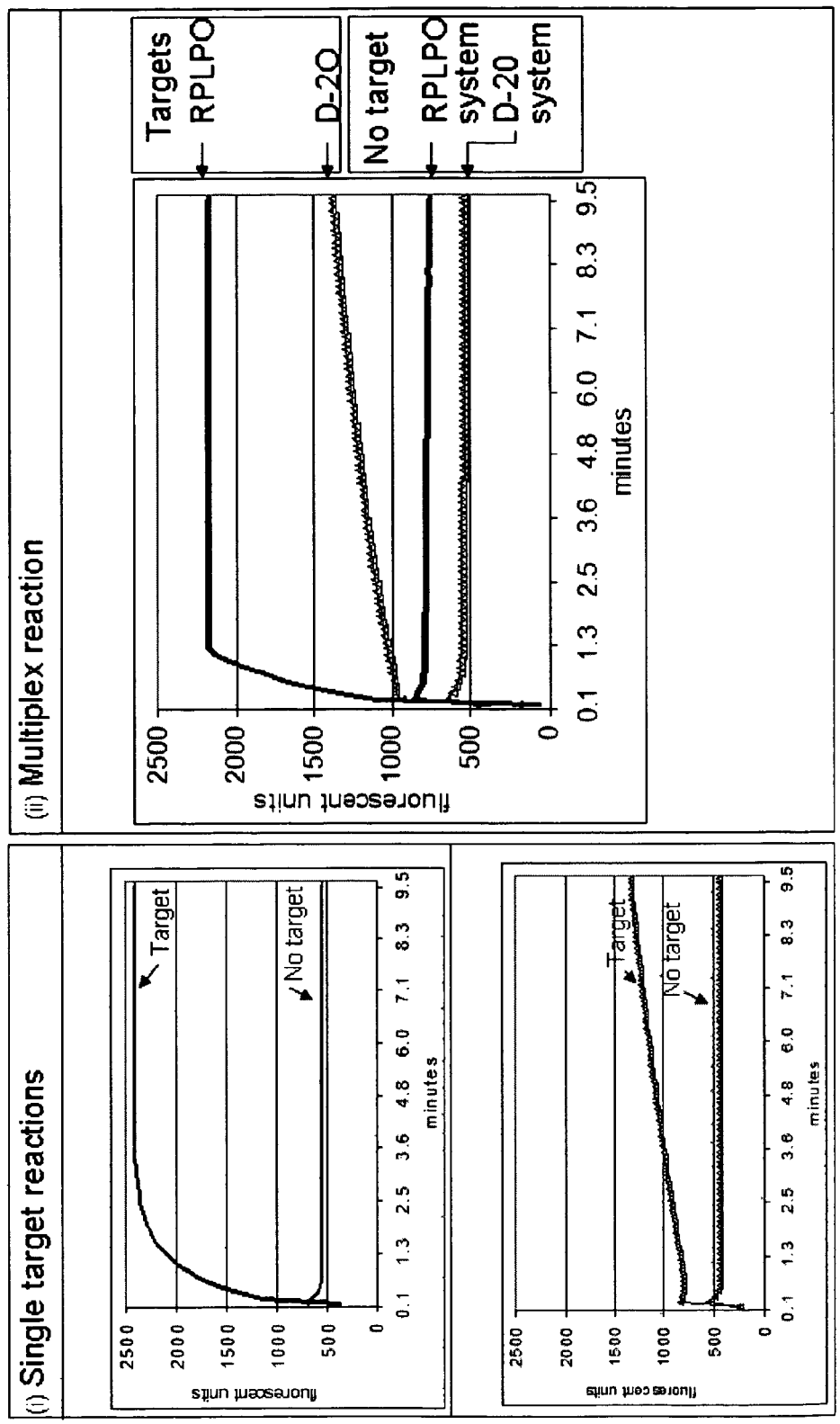
FIG. 19: Single and multiplex detection of RPLPO and D-20 sequences: Detection of RPLPO was monitored using a JOE-labeled substrate and detection of D-20Target sequence was monitored using a FAM-labeled substrate. Panel (i): MNAzyme design 6 comprises partzymes for only one MNAzyme system, either for RPLPO (upper panel) or D-20 (lower panel); Panel (ii): MNAzyme design 6 contains partzymes for MNAzymes targeting both RPLPO and D-20.

Singleplex reactions containing target D-20 or RPLPO showed an increase in fluorescence over time compared to the no-target control (FIG. 19 (i)). This demonstrates that the partzymes assemble into a catalytically active MNAzyme and cleave the reporter substrate only in the presence of the target sequence. The "no-target" (dH2O) controls did not increase in fluorescence indicating that no cleavage occurred in the absence of target. The multiplex reaction for the simultaneous detection of RPLPO and D-20 (FIG. 19 (ii)) produced similar results for each target as those observed in the singleplex reactions for each target. No increase in fluorescence was observed in the "no target" control reaction. These results demonstrate simultaneous detection of multiple targets in a single reaction without loss of specificity.

Example 10

Use of MNAzymes for the Quantification of Amplicons Produced by In Vitro Amplification of MicroRNA

10.1. Partzyme Oligonucleotides

MNAzymes can be used to monitor amplification of target nucleic acids in real time using in vitro target amplification methods such as RTPCR. Further, real time monitoring allows the amount of target initially present in the reaction to be quantified. In this example, amplification and detection are performed in a two-step process, wherein the first step involves production of cDNA via reverse transcription, and then PCR amplification and MNAzyme-mediated detection of the cDNA occur simultaneously in the second step. Partzyme oligonucleotides A and B used design 6 with sensor arms complementary to human microRNA hsa-let-7a. The partzyme oligonucleotides are listed below with the "-P" indicating 3' phosphorylation of the oligonucleotide. In the following sequences the bases underlined form part of the catalytic core of the assembled MNAzyme, bases in bold hybridize with the target and bases in italics hybridize to the substrate.

```
SEQ ID NO: 37 Partzyme A4 PCR7aA4/2-P:
GACCGTGAGGTAGTAACAACGAGAGGAAACCTT-P

SEQ ID NO: 38 Partzyme B5 PCR7aB5/2-P:
TGCCCAGGGAGGCTAGCTGGTTGTATAGTTGTC-P
```

10.2. Reporter Substrate

The reporter substrate for this example is SubBi-2 with the sequence, 5' to 3', as below. In the current example, SubBi-2 was end-labelled with a 6-FAM moiety at the 5' end and a BHQ1 moiety at the 3' end and was designated SubBi-2-FB. Cleavage of SubBi-2-FB was monitored at 516 nm (FAM emission wavelength) with excitation at 492 nm (FAM excitation wavelength). In the following sequence the lower case bases represent RNA and the upper case bases represent DNA.

```
SEQ ID NO: 21 SubBi-2-FB:
AAGGTTTCCTCguCCCTGGGCA
```

10.3. Target Sequences

The standard curve for this example was generated by a two-step RTPCR of a synthetic RNA oligonucleotide R-let7a, which has sequence homologous to the RNA hsa-let-7a species. The sequence of R-let7a, written 5' to 3, ' is as follows.

```
SEQ ID NO: 39 R-let7a:
ugagguaguagguuguauaguu
```

Samples of human total RNA from colon cells (Ambion), K562 leukaemic cells, HeLa cervical cancer cells (Ambion) and spleen cells (Clontech) were amplified and analysed for the abundance of hsa-let-7a.

10.4. PCR Primers for Amplification of hsa-let-7a

The following primers were used for the amplification of hsa-let-7a. The primer 3let7a was used for reverse transcription and the primers 5let7a and 3PCR7a were used for PCR amplification.

```
SEQ ID NO: 40 Primer 3let7a:
AGCGAAGCTGAGACAACTATACAA

SEQ ID NO: 41 Primer 5let7a:
CGACGTGACCGTGAGGTAG

SEQ ID NO: 42 Primer 3PCR7a:
CATGGCACAAGCGAAGCTGA
```

10.5. Reaction Components: Reverse Transcription of Target Sequence

Reverse transcription of the target sequence was performed in a total reaction volume of 25 µL. Reactions were incubated on a 2720 Thermal Cycler (Applied Biosystems) for 20 minutes at 20° C., followed by 20 minutes at 30° C. and then 20 minutes at 40° C. The reactions contained 10 nM 3let7a, 5 mM MgCl$_2$, 300 µM of each dNTP, 20 units Rnasin (Promega), 1×Immobuffer (Bioline), 100 units of M-MLV RT(H-) and 5 µL of either R-let7a ($6\times10^{11}$ copies) or human total RNA from normal colon (0.1 µg), K562 (0.1 µg), HeLa (0.2 µg) or spleen (0.2 µg). A control reaction contained all reagents as above but lacked RNA target instead containing 5 µL of dH$_2$O only.

10.6. Reaction Components: Amplification and Quantification of Target Sequence

Real time amplification and quantification of the target sequence was performed in total reaction volume of 25 µL. All reactions were conducted on a Mx3005P™ QPCR System (Stratagene). The cycling parameters were, 95° C. for 7 minutes, 10 cycles of 95° C. for 15 seconds and 40° C. for 30 seconds (with a 1° C. increase in temperature per cycle), and finally 50 cycles of 95° C. for 15 seconds and 50° C. for 30 seconds. The reactions contained 200 nM 3PCR7a and 40 nM of 5let7a, 400 nM PCR7aA4/2-P and 400 nM PCR7aB5/2-P, 200 nM SubBi-2-FB, 10 mM MgCl$_2$, 200 µM of each dNTP, 20 units Rnasin (Promega), 1×Immobuffer (Bioline), 1 unit of Immolase (Bioline) and 5 µL of either R-let7a cDNA (containing $5\times10^8$, $5\times10^7$, $5\times10^6$, $5\times10^5$, $5\times10^4$ copies) or human total RNA template (normal colon, 0.5 µg; K562, 0.5 µg; HeLa, 1 µg; spleen, 1 µg) or no target (dH$_2$O).

10.7. Results: Amplification of Target and Cleavage of SubBi-2-FB Reporter Substrate The MNAzyme for the real time detection and quantification of hsa-let-7a showed an increase in fluorescence over time when the target sequence used was cDNA generated from synthetic RNA oligonucleotide or human total RNA. There was no signal detected for the no-target control reaction (Table 11). This demonstrates that the increase in fluorescence produced in target-containing reactions was due to target dependent assembly of catalytically active MNAzymes that then cleaved the reporter substrate. A standard curve was generated by plotting the log of the initial RNA concentrations against the threshold cycle, resulting in a linear plot with a correlation coefficient of 0.999. Four human total RNA samples were also amplified and the amount of hsa-let-7a in each was estimated by extrapolating from the standard curve (Table 11).

TABLE 11

Results of reactions for the amplification and detection of hsa-let-7a amplicons.

| Sample | Threshold (Ct) Average of Duplicates | Copy number Known Standard (S) or Estimated (E) | Comments |
|---|---|---|---|
| Standard 1 | 19.4 | $5 \times 10^8$ (S) | Standard Curve |
| Standard 2 | 23.1 | $5 \times 10^7$ (S) | (average of duplicate |
| Standard 3 | 26.9 | $5 \times 10^6$ (S) | reactions) |
| Standard 4 | 30.9 | $5 \times 10^5$ (S) | $R^2$ = 0.999 |
| Standard 5 | 34.7 | $5 \times 10^4$ (S) | Slope = −3.829 |
|  |  |  | Efficiency = 83% |
| No RNA target control | No signal | 0 | No signal |
| Colon RNA | 20 | $4 \times 10^8$ (E) | hsa-let-7a detected and |
| K562 RNA | 31 | $3.5 \times 10^5$ (E) | quantified in all |
| HeLa RNA | 22 | $1.3 \times 10^8$ (E) | test samples |
| Spleen RNA | 22 | $7.6 \times 10^7$ (E) |  |

This example demonstrates the ability of MNAzymes to detect and quantify amplicons generated by RTPCR amplification of human microRNA species. MicroRNA are difficult to amplify and detect due to their small size of around 22 bases. MNAzymes are suitable for this application.

Example 11

Use of MNAzymes to Detect DNA Methylation 11.1. Partzyme Oligonucleotides

It is shown in example 19 that real time PCR and MNAzyme mediated signal generation allows discrimination between fully matched nucleic acid sequences and those containing mismatches with C opposite C. This capacity enables MNAzymes to be used for analysis of methylation status of cells. Alterations in methylation pattern occur frequently in association with cancer. The majority of protocols for methylation analysis begin with bisulphite modification of genomic DNA which converts unmethylated, but not methylated, cytidines to uridines. PCR amplification of the modified DNA then replaces the uridines with thymidines and various methods can be used to distinguish the sequences containing T (originally unmethylated C) and C (originally methylated C). In the following example, an MNAzyme was used to determine the methylation status of specific CpG doublets in the promoter region of the p16 gene in bisulphite modified DNA.

In this example, the partzymes were designed to match the sequence produced following bisulphite modification of a methylated p16 gene. The sequences of the partzymes are listed below (5' to 3'). In the following sequences, the bases underlined form part of the catalytic core of the assembled MNAzyme, bases in bold hybridise with the bisulphite modified target and bases in italics hybridise to the substrate. The "-P" indicates 3' phosphorylation of the oligonucleotide.

```
SEQ ID NO: 43 Partzyme A5 p16A5/3-P:
GCCCCCGCCTCCAACTACAACGAGGTTGTGCTG-P

SEQ ID NO: 44 Partzyme B6 p16B6/3-P:
CGGTTGGTGAGGCTAGCAACGCCCGCACCTC-P
```

11.2. Reporter Substrate

The reporter substrate used in this example was SubBi-3. In the current example, SubBi-3 was end labeled with a 6-FAM moiety at the 5' end, a BHQ1 moiety at the 3' end and designated SubBi-3-FB. Cleavage of SubBi-3-FB was monitored at 530 nm (FAM emission wavelength) with excitation at 485 nm (FAM excitation wavelength). The sequence of SubBi-3-FB is shown below (5' to 3'); the lower case bases represent RNA and the upper case bases represent DNA.

```
SEQ ID NO: 31 SubBi-3-FB:
CAGCACAACCguCACCAACCG
```

11.3. PCR Primers for Amplification of Bisulphite Modified p16

In this example, the PCR primers were designed to match the bisulphite-modified target, which was originally methylated. The target sequence for this example was generated by in vitro amplification of bisulphite modified human genomic DNA using the oligonucleotide PCR primers listed below (5' to 3').

```
SEQ ID NO: 45 Primer 5p16:
GTTGGTTACGGTCGCGGTTC

SEQ ID NO: 46 Primer 3p16:
CCGACCGTAACTATTCGATACG
```

11.4. Target Sequences and Controls.

Human genomic DNA extracted from the K562 cell line was used as negative control genomic DNA containing an unmethylated p16 gene promoter. Universal CpG methylated genomic DNA (Chemicon) was used as a control for a methylated p16 gene promoter. Genomic DNA was bisulphite modified overnight using the MethylEasy kit (Human Genetic Signatures), according to the manufacturer's instructions. Methylated DNA and unmethylated DNA were then serially diluted to yield samples containing varying proportions of DNA methylated at the p16 gene promoter namely; 100%, 20%, 4%, 0.8%, 0.16% and 0.032%. Nuclease-free dH$_2$0 was used in place of genomic DNA as a no-target control.

11.5. Reaction Components: Amplification and Quantification of Target Sequence

Real time amplification and quantification of the target sequence was performed in a total reaction volume of 25 µl. All reactions were conducted on a Stratagene MX3005p QPCR System. The cycling parameters were 95° C. for 7 minutes, 10 cycles of 95° C. for 15 seconds and 56° C. for 30 seconds, and finally 50 cycles of 95° C. for 15 seconds and 52° C. for 30 seconds. The reactions contained 200 nM 5p16 and 40 nM of 3p16, 200 nM p16A5/3-P and 200 nM p16B6/3-P, 200 nM SubBi-3-FB, 7.5 mM MgCl$_2$, 200 µM of each dNTP, 10 units Rnasin (Promega), 1×Immobuffer (Bioline), 1 unit of Immolase (Bioline) and either 150 ng of bisulphite-modified genomic DNA (containing 100%, 20%, 4%, 0.8%, 0.16% or 0.032% methylated DNA) or dH$_2$O only (no target control reaction). All reactions were performed in duplicate.

11.6. Results: Detection of Methylation by an MNAzyme

The methylation-specific MNAzyme showed an increase in fluorescence over time when the target sample contained 100% down to 0.16% methylated DNA (Table 12). In contrast, when the target sample contained 0.032% and 0% methylated DNA, the reaction showed a low level of fluorescence, similar to that seen in the no target control, and the fluorescence did not increase over time. As the percentage of methylated target decreased, the Ct of the reaction increased and a standard curve was plotted with an R$^2$ value of 0.996. The experimental results are summarised in table 12 below.

TABLE 12

Use of MNAzymes to detect DNA methylation in bisulphite modified genomic DNA samples.

| % Methylation | Ct (average of duplicates) | Comments |
|---|---|---|
| 100 | 19.36 | The standard curve generated using these values had an R$^2$ = 0.996, an efficiency of 133% and a slope of −2.72. |
| 20 | 20.94 | |
| 4 | 23.33 | |
| 0.8 | 24.83 | |
| 0.16 | 27.02 | |
| 0.032 | No Ct | Not detected |
| 0 (100% Unmethylated) | No Ct | No signal for unmethylated control |
| No target control | No Ct | No signal for no target control |

The methylated p16-specific primers and MNAzyme were able to discriminate between a methylated and unmethylated target under the conditions used in this example. Further, the system allowed the detection of 0.16% methylated target in a background of unmethylated target. 100% efficiency in a PCR reaction implies a doubling at each cycle. The observed efficiency in this experiment of 133% indicates that there is both target amplification (by PCR) and amplicon detection amplified by the catalytic activity of the MNAzyme.

Example 12

MNAzymes that Assemble from Partzymes which have Sensor Arms that Form Hairpin Structures The structure of partzymes, which are capable of assembling into active MNAzymes, is flexible. This example demonstrates additional structures which are compatible with MNAzyme activity.

12.1. Partzyme Oligonucleotides

Detection using MNAzymes can also be performed when the sensor arm region of partzyme A, or partzyme B, or both partzyme A and B, is followed by an arbitrary hairpin sequence. In the following experiments, the partzymes A and B were designed to target the sequence of a human microRNA, hsa-miR-143. The sequences of the partzyme A and partzyme B oligonucleotides are listed below from 5' to 3'. In the following sequences, the bases underlined form part of the catalytic core of the assembled MNAzyme, bases in bold hybridize with the target, bases in italics hybridize to the substrate and bases that are plain text form the hairpin.

```
SEQ ID NO: 142 Partzyme A2 miR143 A2/1:
TGAGCTACAGTCGGTCGAAATAGTGAGT

SEQ ID NO: 143 Partzyme B3 miR143 B3/1:
CATCTCTTCTCCGAGCGCTTCATCTCA

SEQ ID NO: 144 Partzyme A2 miR143 A2H/1:
GGCACTAACGTGCCTGAGCTACAGTCGGTCGAAATAGTGAGT SEQ ID NO: 145 Partzyme B3 miR143 B3H/1:
CATCTCTTCTCCGAGCGCTTCATCTCACGACGATAACGTCG
```

12.2. Reporter Substrate

MNAzyme activity was monitored by cleavage of a dual-labelled nucleic acid reporter substrate. The reporter substrate for this example was SubBi-1-FB with the sequence, 5' to 3', as written below. The lower case bases represent RNA and the upper case bases represent DNA. The underlined bases indicate the position of a 6-FAM moiety at the 5' end and a BHQ1 moiety at the 3' end. Changes in fluorescence due to cleavage of SubBi-1-FB at the deoxyribonucleotide between the FAM and BHQ1 were monitored at 530 nm (FAM emission wavelength) with excitation at 485 nm (FAM excitation wavelength).

SEQ ID NO: 6 SubBi-1-FB:
ACTCAC*TA*TaGGAAGAGA*TG*

12.3. Target

The target sequence for this example was a DNA oligonucleotide, D-143Target, which has sequence homologous to the human microRNA, hsa-miR-143. The sequence of D-143Target was as follows, written 5' to 3'.

SEQ ID NO: 146 D-143Target:
TGAGATGAAGCACTGTAGCTCA 12.4 Reaction Conditions

Detection of the target sequence was measured by an increase in fluorescent signal caused by cleavage of the reporter substrate by the catalytically active MNAzyme. Reactions were initiated by the addition of substrate and the total volume of all reactions was 25 μL. All reactions were conducted at 40° C. in a SmartCycler® System thermocycler (Cepheid). Fluorescence for each reaction was read every seven seconds for a total of 10 minutes. All reactions in Table 13 contained the bulk mix consisting of 1 μM SubBi-1-FB, 10 mM Tris HCl (pH 9.0 at 25° C.) and 25 mM MgCl$_2$.

TABLE 13

Components of reactions for the detection of a nucleic acid target.

| Reaction Type | Partzyme A miR143 (0.8 μM) | Partzyme B miR143 (0.8 μM) | MNAzyme Reaction | Template (D-143 Target) |
|---|---|---|---|---|
| Neither partzyme had a hairpin | A2/1 | B3/1 | Target No-Target | 0.1 μM Nil (H$_2$0 only) |
| One partzyme contained a hairpin | A2H/1 A2/1 | B3/1 B3H/1 | Target Target | 0.1 μM 0.1 μM |
| Both partzymes contained a hairpin | A2H/1 | B3H/1 | Target No-Target | 0.1 μM Nil (H$_2$0 only) |

Each reaction well on the SmartCycler® System thermocycler (Cepheid) used during the experiment was first tested for its background level of fluorescence, as this is known to vary between wells. This was measured by reading the fluorescence of the bulk mix alone. This value was then subtracted from all other reactions performed in each well to allow between well comparisons.

12.5. Results: Detection of Cleavage of SubBi-1-FB Reporter Substrate

The various combinations of designs of the partzymes A and B were all capable of being assembled into active MNAzymes. These cleaved the reporter substrate, as evidenced by an increase in fluorescence, only in the presence of the target sequence. In this example, the sensor arms of the partzymes had been extended with sequence that formed a hairpin. Reactions, which contained one partzyme with a hairpin (either partzyme A or partzyme B), or where both partzymes (A and B) contained hairpins, gave similar fluorescent signals as that seen when partzymes which lacked hairpins were used. No increase in signal was observed in any of the control reactions lacking target.

The design of partzymes containing hairpins provides a strategy suitable for detection of short sequences such as microRNA. The DNA oligonucleotide detected in this experiment was only 22 bases. This sequence was detected using partzymes, which either do, or do not, contain hairpins. The hairpin design provides a more stable structure and provides further flexibility in the design of partzymes known to be compatible with MNAzyme assembly and catalytic activity.

Example 13

Use of MNAzymes for the Simultaneous Quantification of Four Nucleic Acid Sequences Via Real Time RTPCR 13.1. Partzyme Oligonucleotides for a Quadruplex RTPCR Assay Multiple targets can be simultaneously amplified in real time using in vitro target amplification methods such as RTPCR. Further, the amplification of the targets can be simultaneously monitored in real time in one multiplexed reaction that comprises multiple unique MNAzymes. Each MNAzyme has sensor arms specific for one target and substrate arms specific for a unique member of a series of generic substrates, each one of which is labeled with a different fluorophore (FIG. 18). In this example, MNAzymes were designed to detect four different targets, namely human BCR, RPLPO, β-actin and HPRT transcripts. It will be appreciated that any number of targets can be used in accordance with the method. The sequences of the partzymes A and B for each target are listed below from 5' to 3'. In the following sequences the bases underlined form part of the catalytic core of the assembled MNAzyme, bases in bold hybridize with the target and bases in italics hybridize to the substrate.

SEQ ID NO: 51 Partzyme A4 BaA4/2-P:
AGATCAAGATCATTGCTCCACAACGAGAGGAAACCTT-P

SEQ ID NO: 52 Partzyme B5 BaB5/2-P:
*TGCCCAGGGA*GGCTAGCTTCCTGAGCGCAAGTACTC-P SEQ ID NO: 29 Partzyme A4 R05A4/3-P:
CAAACGAGTCCTGGCCTTGTCTACAACGAGGTTGTGCTG-P SEQ ID NO: 30 Partzyme B5 R05B5/3-P:
*CGGTTGGTGA*GGCTAGCTGTGGAGACGGATTACACCTTC-P SEQ ID NO: 55 Partzyme A4 BCRA4/6-P:
AGTTCAAATCTGTACTGCACCACAACGAGAGGCGTGAT-P SEQ ID NO: 56 Partzyme B5 BCRB5/6-P:
*CTGGGAGAA*GGCTAGCTCTGGAGGTGGATTCCTTTGG-P SEQ ID NO: 57 Partzyme A4 HPRTA4/7-P:
ACTGAATAGAAATAGTGATAGATACAACGAGTGCCATGTTAA-P SEQ ID NO: 58 Partzyme B5 HPRTB5/7-P:
*TATCACAGCCAA*GGCTAGCTCCATTCCTATGACTGTAGATT-P 13.2. Reporter Substrates For this example, four different reporter substrates, each one labeled with a different fluorophore, were used. The sequences of the substrates are written 5' to 3' below. In the current example, SubBi-2 was end-labeled with a 6-JOE moiety at the 5' end and a BHQ1 moiety at the 3' end and was designated SubBi-2-JB. Cleavage of SubBi-2-JB was monitored at 555 nm with excitation at 535 nm. SubBi-3 was end-labeled with a Quasar 670 moiety at the 5' end and a BHQ2 moiety at the 3' end and was designated SubBi-3-Q6B2. Cleavage of SubBi-3-Q6B2 was monitored at 665 nm with excitation at 635 nm. SubBi-6 was end-labeled with Texas Red moiety at the 5' end and a BHQ2 moiety at the 3' end and was designated SubBi-6-TRB2. Cleavage of SubBi-6-TRB2 was monitored at 610 nm with excitation at 585 nm. The fourth substrate, SubBi-7, was end-labeled with a 6-FAM moiety at the 5' end and a BHQ1 moiety at the 3' end and was designated SubBi-7-FB. Cleavage of SubBi-7-FB was monitored at 516 nm with excitation at 492 nm. The lower case bases represent RNA and the upper case bases represent DNA.

```
SEQ ID NO: 59 SubBi-2-JB:
AAGGTTTCCTCguCCCTGGGCA

SEQ ID NO: 60 SubBi-3-Q6B2:
CAGCACAACCguCACCAACCG

SEQ ID NO: 61 SubBi-6-TRB2:
ATCACGCCTCguTCCTCCCAG

SEQ ID NO: 62 SubBi-7-FB:
TTAACATGGCACguTGGCTGTGATA
```

13.3. Target Sequences and PCR Primers for Amplification of the Four Amplicons Human total RNA extracted from K562 leukaemic cells was used as template for in vitro amplification of all four of the target transcripts. The amplicons were generated by RTPCR using the oligonucleotide PCR primers listed below.

```
SEQ ID NO: 32 5' Primer 5RO5/1:
CATTCTATCATCAACGGGTA

SEQ ID NO: 33 3' Primer 3RO5/1:
CAAAGGCAGATGGATCAG

SEQ ID NO: 63 5' Primer 5Bactin:
CATTGCCGACAGGATGCAGA

SEQ ID NO: 64 3' Primer 3Bactin:
GAGCCGCCGATCCACACG

SEQ ID NO: 65 5' Primer 5BCR14:
CACTCAGCCACTGGATTTAA

SEQ ID NO: 66 3' Primer 3BCR15/6:
GCGCGTCTTTGCTTTATTC

SEQ ID NO: 67 5' Primer 5HPRT/5:
CTTTGCTGACCTGCTGGATTA

SEQ ID NO: 68 3' Primer 3HPRT/8:
CCTGTTGACTGGTCATTACAA
```

13.4. Reaction Components: Amplification and Quantification of Target Sequence Real time amplification and quantification of the target sequences was performed in total reaction volume of 25 μL. All reactions were conducted on an Mx3005P™ QPCR System (Stratagene). The cycling parameters were, 50° C. for 30 minutes, 95° C. for 7 minutes, 10 cycles of 95° C. for 15 seconds and 65° C. for 30 seconds (with a 1° C. decrease in temperature per cycle), and finally 40 cycles of 95° C. for 15 seconds and 54° C. for 30 seconds. The reactions contained 40 nM of each 5' primer and 200 nM of each 3' primer, 200 nM of each A partzyme and 200 nM of each B partzyme, 200 nM of each substrate, 10 mM $MgCl_2$, 200 μM of each dNTP, 10 units Rnasin (Promega), 20 units M-MLV RT (H-), 1×Immobuffer (Bioline), 1.5 units of Immolase (Bioline) and either total RNA template (100 ng, 20 ng, 4 ng, 800 pg, 160 pg or 32 pg) or no target ($dH_2O$).

TABLE 14

Components of reactions for the simultaneous detection of four different nucleic acid targets.

| Reaction Type | Primers 5'(40 nM) 3'(200 nM) | Partzyme A (200 nM) | Partzyme B (200 nM) | Substrate (200 nM) | Target |
|---|---|---|---|---|---|
| Multiplex β-actin | 5Bactin 3Bactin | BaA4/2-P | BaB5/2-P | SubBi-2-JB | Human total RNA |
| RPLPO | 5RO5/1 3RO5/1 | RO5A4/3-P | RO5B5/3-P | SubBi-3-Q6B2 | 100 ng 20 ng |
| BCR | 5BCR14 3BCR15/6 | BCRA4/6-P | BCRB5/6-P | SubBi-6-TRB2 | 4 ng 800 pg |
| HPRT | 5HPRT/5 3HPRT/8 | HPRTA4/7-P | HPRTB5/7-P | SubBi-7-FB | 160 pg 32 pg or no RNA ($H_2O$) |

13.5. Results: Simultaneous Amplification of Four Different Target Sequences and Detection Via Cleavage of Four Different Reporter Substrates The four MNAzymes used for the real time detection and quantification of β-actin, RPLPO, BCR, and HPRT transcripts showed an increase in fluorescence over time when the target sequence used was human total RNA amplified via RTPCR (Table 15). The fluorescence of the no-RNA target control for all four reactions was lower than that in the RNA target-containing reactions and did not increase during the reaction (Table 15). This demonstrates that the increase in fluorescence produced in target-containing reactions was due to target dependent assembly of catalytically active MNAzymes that then cleaved the reporter substrate.

Standard curves were generated for all four targets by plotting the log of the RNA concentrations against the threshold cycle resulting in a linear plot. The threshold (Ct) of each standard is shown in Table 15. The Ct values shown in the table are an average of the results for duplicate reactions. The correlation coefficient ($R^2$), slope and reaction efficiency for each target are also shown in Table 15.

TABLE 15

Results of reactions for the simultaneous amplification and detection of four different nucleic acid targets

| Template (total RNA) | Threshold (Ct) | | | |
|---|---|---|---|---|
| | β-actin (JOE) | RPLPO (Quasar 670) | BCR (Texas Red) | HPRT (FAM) |
| 100 ng | 11.2 | 12.8 | 17.6 | 16.2 |
| 20 ng | 13.8 | 15.2 | 19.9 | 18.5 |
| 4 ng | 16.7 | 17.5 | 22.4 | 20.9 |
| 800 pg | 19.1 | 20.1 | 25.0 | 23.5 |
| 160 pg | 21.5 | 22.7 | 27.1 | 26.0 |
| 32 pg | 23.8 | 25.2 | 29.1 | 27.7 |
| no-RNA control | No Ct | No Ct | No Ct | No Ct |
| Standard Curve | $R^2 = 0.998$ | $R^2 = 1.000$ | $R^2 = 0.998$ | $R^2 = 0.997$ |
| | Slope = −3.599 | Slope = −3.561 | Slope = −3.320 | Slope = −3.370 |
| | Efficiency = 90% | Efficiency = 91% | Efficiency = 100% | Efficiency = 98% |

The MNAzyme RTPCR reaction in this example allowed simultaneous detection and generation of standard curves for the quantification of four targets in a single multiplex reaction which included four generic substrates. These generic substrates are suitable for monitoring other combinations of four targets in a single reaction.

Example 14

Use of MNAzymes for the Simultaneous Quantification of Five Nucleic Acid Sequences in a Real Time Multiplex RTPCR 14.1. Partzyme Oligonucleotides for Quintuplex RTPCR Assay Multiple targets can be simultaneously amplified in real time using in vitro target amplification methods such as RTPCR. Further, the amplification of the targets can be simultaneously monitored in real time in one multiplexed reaction that comprises multiple unique MNAzymes. Each MNAzyme has sensor arms specific for one target and substrate arms specific for a unique member of a series of generic substrates, each one of which is labeled with a different fluorophore (FIG. 18). In this example, MNAzymes were designed to detect five different targets, namely BCR, RPLPO exon 4, β-actin, RPLPO exon 5 and HPRT mRNA sequences. It will be appreciated that any number of targets can be used in accordance with the method. The sequences of the partzymes A and B are listed below from 5' to 3'. In the following sequences the bases underlined form part of the catalytic core of the assembled MNAzyme, bases in bold hybridize with the target and bases in italics hybridize to the substrate.

```
SEQ ID NO: 69 Partzyme A4 BaA4/7-P:
AGATCAAGATCATTGCTCCACAACGAGTGCCATGTTAA-P SEQ ID NO: 70 Partzyme B5 BaB5/7-P:
TATCACAGCCAAGGCTAGCTTCCTGAGCGCAAGTACTC-P SEQ ID NO: 71 Partzyme A4 RO5A4/4-P:
CAAACGAGTCCTGGCCTTGTCTACAACGAGTGCGCCATG-P SEQ ID NO: 72 Partzyme B5 RO5B5/4-P:
TACTTCTCCCAAGGCTAGCTGTGGAGACGGATTACACCTTC-P SEQ ID NO: 55 Partzyme A4 BCRA4/6-P:
AGTTCAAATCTGTACTGCACCACAACGAGAGGCGTGAT-P SEQ ID NO: 56 Partzyme B5 BCRB5/6-P:
CTGGGAGGAAGGCTAGCTCTGGAGGTGGATTCCTTTGG-P SEQ ID NO: 75 Partzyme A4 HPRTA4/2-P:
ACTGAATAGAAATAGTGATAGATACAACGAGAGGAAACCTT-P SEQ ID NO: 76 Partzyme B5 HPRTB5/2-P:
TGCCCAGGGAGGCTAGCTCCATTCCTATGACTGTAGATT-P SEQ ID NO: 77 Partzyme A4 RO4A4/3-P:
GCTGGTCATCCAGCAGACAACGAGGTTGTGCTG-P SEQ ID NO: 78 Partzyme B5 RO4B5/3-P
CGGTTGGTGAGGCTAGCTGTGTTCGACAATGGC-P
```

14.2. Reporter Substrates

For this example, five different reporter substrates were used, each of which was labeled with one of five different fluorophores. The substrate sequences are written 5' to 3'. In the current example, SubBi-2 was end-labeled with a Alexa 350 moiety at the 5' end and a BHQ1 moiety at the 3' end and was designated SubBi-2-A350B. Cleavage of SubBi-2-A350B was monitored at 440 nm with excitation at 350 nm. SubBi-3 was end-labeled with a Quasar 670 moiety at the 5' end and a BHQ2 moiety at the 3' end and was designated SubBi-3-Q6B2. Cleavage of SubBi-3-Q6B2 was monitored at 665 nm with excitation at 635 nm. SubBi-6 was end-labeled with a Texas Red moiety at the 5' end and a BHQ2 moiety at the 3' end and was designated SubBi-6-TRB2. Cleavage of SubBi-6-TRB2 was monitored at 610 nm with excitation at 585 nm. SubBi-7 was end-labeled with a 6-FAM moiety at the 5' end and a BHQ1 moiety at the 3' end and was designated SubBi-7-FB. Cleavage of SubBi-7-FB was monitored at 516 nm with excitation at 492 nm. SubBi-4 was end-labeled with a 6-JOE moiety at the 5' end and a BHQ1 moiety at the 3' end and was designated SubBi-4-JB. Cleavage of SubBi-4-JB was monitored at 555 nm with excitation at 535 nm. The lower case bases represent RNA and the upper case bases represent DNA.

```
SEQ ID NO: 79 SubBi-2-A350B:
AAGGTTTTCCTCguCCCTGGGCA

SEQ ID NO: 60 SubBi-3-Q6B2:
CAGCACAACCguCACCAACCG

SEQ ID NO: 61 SubBi-6-TRB2:
ATCACGCCTCguTCCTCCCAG
```

-continued

SEQ ID NO: 62 SubBi-7-FB:
TTAACATGGCACguTGGCTGTGATA

SEQ ID NO: 83 SubBi-4-JB:
CATGGCGCACguTGGGAGAAGTA 14.3. Target Sequences and PCR Primers for Amplification of the Five mRNA Target Sequences.

Human total RNA extracted from K562 cells was used as template for in vitro amplification of all five targets. The amplicons were generated by in vitro amplification using the oligonucleotide PCR primers listed below.

SEQ ID NO: 32 5' Primer 5RO5/1:
CATTCTATCATCAACGGGTA

SEQ ID NO: 33 3' Primer 3RO5/1:
CAAAGGCAGATGGATCAG 14.4. Reaction Components: Amplification and Quantification of Target Sequence Real time amplification and quantification of the target sequences was performed in a total reaction volume of 25 µL. All reactions were conducted on a Mx3005P™ QPCR System (Stratagene). The cycling parameters were, 50° C. for 30 minutes, 95° C. for 7 minutes, 10 cycles of 95° C. for 15 seconds and 65° C. for 30 seconds (with a 1° C. decrease in temperature per cycle), and finally 40 cycles of 95° C. for 15 seconds and 54° C. for 30 seconds. The reactions contained 40 nM of 5Bactin, 5BCR14, 5HPRT/5 and 80 nM 5RO4/3, 5RO5/1 and 200 nM 3Bactin, 3BCR15/6, 3HPRT/8 and 400 nM 3RO4/2 and 3RO5/1. There was 200 nM of each A partzyme and B partzyme for βactin, BCR, RPLPO exon 4 and HPRT and 400 nM of each A partzyme and B partzyme for RPLPO exon 5. There was 200 nM of SubBi-2-A350B, SubBi-3-Q6B2, SubBi-6-TRB2 and SubBi-7-FB, and 400 nM of SubBi-4-JB. Also there was 10 mM $MgCl_2$, 200 µM of each dNTP, 10 units Rnasin (Promega), 20 units M-MLV RT (H-) (Promega), 1× Immobuffer (Bioline), 2 units of Immolase (Bioline) and 5 µl of either total RNA template (100 ng, 20 ng, 4 ng, 800 pg, or 160 pg) or no target ($dH_2O$).

TABLE 16

Components of reactions for the simultaneous detection of five different nucleic acid targets

| Reaction Type | Primers | Partzyme A & B | Substrate | Amount of Partzyme/ substrate | Amount of Primer 3'/5' |
|---|---|---|---|---|---|
| β-actin, RPLPO exon 5, BCR, HPRT, RPLPO exon 4. | 5Bactin 3Bactin | BaA4/7-P BaB5/7-P | SubBi-7-FB | 200 nM/200 nM | 200 nM/40 nM |
| | 5RO5/1 3RO5/1 | RO5A4/4-P RO5B5/4-P | SubBi-4-JB | 400 nM/400 nM | 400 nM/80 nM |
| | 5BCR14 3BCR15/6 | BCRA4/6-P BCRB5/6-P | SubBi-6-TRB2 | 200 nM/200 nM | 200 nM/40 nM |
| | 5HPRT/5 3HPRT/8 | HPRTA4/2-P HPRTB5/2-P | SubBi-2-A350B | 200 nM/200 nM | 200 nM/40 nM |
| | 5RO4/3 3RO4/2 | RO4A4/3-P RO4B5/3-P | SubBi-3-Q6B2 | 200 nM/200 nM | 400 nM/80 nM |

-continued

SEQ ID NO: 63 5' Primer 5Bactin:
CATTGCCGACAGGATGCAGA

SEQ ID NO: 64 3' Primer 3Bactin:
GAGCCGCCGATCCACACG

SEQ ID NO: 65 5' Primer 5BCR14:
CACTCAGCCACTGGATTTAA

SEQ ID NO: 66 3' Primer 3BCR15/6:
GCGCGTCTTTGCTTTATTC

SEQ ID NO: 67 5' Primer 5HPRT/5:
CTTTGCTGACCTGCTGGATTA

SEQ ID NO: 68 3' Primer 3HPRT/8:
CCTGTTGACTGGTCATTACAA

SEQ ID NO: 84 5' Primer 5R04/3:
CAAGACTGGAGACAAAGTG

SEQ ID NO: 85 3' Primer 3R04/2:
GCAGAGTTTCCTCTGTGATA 14.5. Results: Simultaneous Amplification of Five Different Target Sequences and Detection Via Cleavage of Five Different Reporter Substrates The five MNAzymes used for the real time detection and quantification of RNA sequences within RPLPO exon 4, BCR, β-actin, RPLPO exon 5 and HPRT showed an increase in fluorescence over time when the target sequence used was human total RNA amplified by RTPCR (Table 17). The fluorescence of the no-RNA target control for all five reactions was lower than that in the RNA target-containing reactions and did not increase during the reaction (Table 17). This demonstrates that the increase in fluorescence produced in target-containing reactions was due to target dependent assembly of catalytically active MNAzymes that then cleaved the reporter substrate.

Standard curves were generated for all five targets by plotting the log of the RNA concentrations against the threshold cycle, resulting in a linear plot. The threshold (Ct) of each standard is shown in Table 17. The Ct values are the average of the duplicate reactions. The correlation coefficient ($R^2$), slope and reaction efficiency for each target are also shown in Table 17.

TABLE 17

Results of reactions for the simultaneous amplification and detection of five different nucleic acid targets

|  | Threshold (Ct) | | | | |
| --- | --- | --- | --- | --- | --- |
|  | β-actin (FAM) | RPLPO exon 5 (JOE) | BCR (Texas Red) | HPRT (Alexa 350) | RPLPO exon 4 (Quasar 670) |
| 100 ng RNA | 13.8 | 13.7 | 17.2 | 21.4 | 17.2 |
| 20 ng RNA | 16.3 | 17.0 | 19.5 | 23.5 | 19.8 |
| 4 ng RNA | 19.0 | 20.8 | 22.0 | 25.8 | 23.2 |
| 800 pg RNA | 21.9 | 24.0 | 24.3 | 28.6 | 26.0 |
| 160 pg RNA | 24.1 | 26.8 | 26.8 | 30.8 | 28.8 |
| no-RNA control | No signal | No signal | No signal | No signal | No signal |
| Standard Curve | $R^2 = 0.998$ | $R^2 = 0.997$ | $R^2 = 1.000$ | $R^2 = 0.997$ | $R^2 = 0.999$ |
|  | Slope = −3.729 | Slope = −4.750 | Slope = −3.425 | Slope = −3.440 | Slope = −4.192 |
|  | Efficiency = 85% | Efficiency = 62% | Efficiency = 96% | Efficiency = 95% | Efficiency = 73% |

The MNAzyme RTPCR reaction in this example allowed simultaneous detection and generation of standard curves for the quantification of five targets in a single multiplex reaction which included five generic substrates. These generic substrates are suitable for monitoring other combinations of five targets in a single reaction.

Example 15

Use of MNAzymes for the Quantification of Ribosomal 16S in Bacteria

To replace the bacterial test of a Gram stain, MNAzymes can be used for a rapid release test for sterility and/or mycoplasma contamination based on conserved nucleic acid sequences found in bacterial species. MNAzymes can be used to monitor amplification of target bacterial nucleic acids in real time using in vitro target amplification methods such as RTPCR. In this example, a conserved region found in bacterial ribosomal 16S sequence is used, wherein reverse transcription, PCR amplification and MNAzyme-mediated detection occur simultaneously in the one tube.

A system was designed to target a region of the ribosomal 16S sequence which is common to several bacterial species including *Staphylococcus capitis*, *Staphylococcus epidermidis*, *Staphylococcus warneri*, *Staphylococcus aureus*, *Bacillus subtilis*, *Streptococcus pyogenes*, *Clostridium sporogenes*, *Acinetobacter woffii*, *Propionibacterium acnes*, *Pseudomonas aeruginosa* and *Pseudomonas fluorescens*.

15.1. Partzyme Oligonucleotides

Partzyme oligonucleotides A and B used design 7 with sensor arms complementary to a conserved region amongst bacterial species. The partzyme oligonucleotides are listed below with the "-P" indicating 3' phosphorylation of the oligonucleotide. In the following sequences the bases underlined form part of the catalytic core of the assembled MNAzyme, bases in bold hybridize with the target and bases in italics hybridize to the substrate

```
SEQ ID NO: 86 Partzyme A5 16S1A5/2-P:
GGTTGTCGTCAGCTCGTGTACAACGAGAGGAAACCTT-P SEQ ID NO: 87 Partzyme B6 16S1B6/2-P:
TGCCCAGGGAGGCTAGCTCGTGAGATGTTGGGTTAAG-P
```

15.2. Reporter Substrate

The reporter substrate for this example is SubBi-2 with the sequence, 5' to 3', as below. In the current example, SubBi-2 was end-labeled with a 6-FAM moiety at the 5' end and a BHQ1 moiety at the 3' end and was designated SubBi-2-FB. Cleavage of SubBi-2-FB was monitored at 516 nm (FAM emission wavelength) with excitation at 492 nm (FAM excitation wavelength). The lower case bases represent RNA and the upper case bases represent DNA.

```
SEQ ID NO: 21 SubBi-2-FB:
AAGGTTTCCTCguCCCTGGGCA
```

15.3. PCR Primers for Amplification of Ribosomal 16S in Bacteria

The target sequence for this example was generated by in vitro amplification of *Bacillus Subtilis* using the oligonucleotide PCR primers listed below.

```
SEQ ID NO: 88 5' Primer 516S1-1:
TGGTGCATGGTTGTCGTC

SEQ ID NO: 89 3' Primer 316S1-1:
TTGCGCTCGTTGCGGGA
```

15.4. Target Sequence and Control

Bacterial ribosomal RNA was extracted from *Bacillus Subtilis* cells and was used as template for amplification of the 16S region. Nuclease free dH$_2$O was used in place of RNA as a no target control.

15.5. Reaction Components: Amplification and Quantification of Target Sequence

Real time amplification and quantification of the—target sequence was performed in a total reaction volume of 25 μL. All reactions were conducted on a Mx3005p QPCR system (Stratagene). The cycling parameters were, 50° C. for 30 minutes, 95° C. for 7 minutes, 10 cycles of 95° C. for 15 seconds and 65° C. for 30 seconds (with a 1° C. decrease in temperature per cycle), and finally 40 cycles of 95° C. for 5 seconds and 55° C. for 30 seconds. The reactions contained 40 nM 516S1-1 and 200 nM of 316S1-1, 200 nM 16S1A5/2-P and 200 nM 16S1B6/2-P, 200 nM SubBi-2-FB, 7.5 mM MgCl$_2$, 200 μM of each dNTP, 10 units Rnasin (Promega), 1×Immobuffer (Bioline), 1 unit of Immolase (Bioline) and either RNA template (500 ng, 50 ng, 5 ng or 500 pg) or no target (dH$_2$O).

15.6. Results: Amplification of Target and Cleavage of SubBi-2-FB Reporter Substrate The MNAzyme for the real time detection and quantification of bacterial ribosomal 16S, showed an increase in fluorescence over time when the target sequence used was bacterial RNA amplified by RTPCR. The fluorescence of the no-template control was lower than that in the RNA containing reactions and did not increase during the reaction. This demonstrates that the increase in fluorescence produced in target-containing reactions is due to target dependent assembly of catalytically active MNAzymes that then cleaved the reporter substrate. A standard curve was generated by plotting the log of the RNA concentrations against the threshold cycle resulting in a linear plot with a correlation coefficient of 0.992.

TABLE 18

Results of reactions for the amplification and detection of bacterial ribosomal 16S amplicons

| Sample (pg) | Threshold Cycle (Ct) Average of duplicates | Results |
| --- | --- | --- |
| 500,000 | 12.5 | Standard Curve |
| 50,000 | 16.4 | (average of duplicate reactions) |
| 5000 | 20.5 | $R^2 = 0.992$ |
| 500 | 26.0 | Slope = −4.461 |
|  |  | Efficiency = 68% |
| No RNA target control | No signal | No signal |

This example demonstrates the ability of MNAzymes to detect and quantify amplicons generated by RTPCR amplification of bacterial ribosomal 16S RNA. The MNAzymes used in this example target a region of bacterial 16S which is 100% conserved between *Staphylococcus capitis*, *Staphylococcus epidermidis*, *Staphylococcus warneri*, *Staphylococcus aureus*, *Bacillus subtilis*, *Streptococcus pyogenes*, *Clostridium sporogenes*, *Acinetobacter woffii*, *Propionibacterium acnes*, *Pseudomonas aeruginosa* and *Pseudomonas fluorescens*. As such a single MNAzyme and reporter substrate could be used to screen a sample for the presence of any of the above bacteria. Detection of a signal (eg FAM) would be indicative of the presence of one or more of these bacterial species in the sample.

Example 16

Use of MNAzymes for the Detection and Quantification of Viral RNA Via Single-Tube RT-PCR MNAzymes can be used to monitor amplification of target nucleic acids in real time using in vitro target amplification methods such as RTPCR. Further, real time monitoring allows the amount of target initially present in the reaction to be quantified. This example illustrates the use of MNAzyme for the detection and quantification of HIV viral RNA. Reverse transcription, PCR amplification and MNAzyme detection were performed in a one-tube reaction.

16.1. Partzyme Oligonucleotides

Partzymes were designed to specifically target the Nef gene of HIV-1. In the following sequences the bases underlined form part of the catalytic core of the assembled MNAzyme, bases in bold hybridize with the target and bases in italics hybridize to the substrate. The "-P" indicates 3' phosphorylation of the oligonucleotide.

SEQ ID NO: 90 Partzyme A4 NefA4/6-P:
GAAGAGGCCAATAAAGGAGAG<u>ACAACGA</u>*GAGGCGTGAT*-P SEQ ID NO: 91 Partzyme B5 NefB5/6-P:
*CTGGGAGGAA*<u>GGCTAGCT</u>AACACCAGCTTGTTACACC-P 16.2. Reporter Substrate The reporter substrate for this example is SubBi-6 with the sequence, 5' to 3', as below. In the current example, SubBi-6 was end-labelled with a Texas Red moiety at the 5' end and a BHQ2 moiety at the 3' end and was designated SubBi-6-TRB2. Cleavage of SubBi-6-TRB2 was monitored at 610 nm (Texas Red emission wavelength) with excitation at 585 nm (Texas Red excitation wavelength). In the following sequence the lower case bases represent RNA and the upper case bases represent DNA.

SEQ ID NO: 61 SubBi-6-TRB2:
ATCACGCCTCguTCCTCCCAG 16.3. Target Sequences

The standard curve in this experiment was generated by RTPCR amplification of HIV-1 viral RNA. A QIAGEN Ultrasens Virus Kit HIV-1 was used to isolate viral RNA from medium collected from human CEMT4 cells infected with HIV-1. Nuclease-free (NF) water was used in place of viral RNA as a no target control.

16.4. PCR Primers for Amplification of the HIV-1 Nef Transcripts.

The following primers were used for amplification of HIV-1 Nef transcripts. The 3' primer, Nef/3PCR, was used for reverse transcription and then this primer and the 5' primer Nef/5PCR facilitated PCR amplification.

SEQ ID NO: 92 Primer Nef/3PCR:
CAGGGTCATCCATTCCATGCAG

SEQ ID NO: 93 Primer Nef/5PCR:
GCTAGTACCAGTTGAGCCAG 16.5. Reaction Components: Amplification and Quantification of Target Sequence Real time amplification and quantification of the target sequence was performed in a total reaction volume of 25 µL. All reactions were conducted on an Mx3005p QPCR System (Stratagene). The cycling parameters were, 50° C. for 30 minutes, 95° C. for 7 minutes, 10 cycles of 95° C. for 15 seconds and 65° C. for 30 seconds (with a 1° C. decrease in temperature per cycle), and finally 50 cycles of 95° C. for 15 seconds and 55° C. for 30 seconds. The reactions contained 200 nM of the 3' primer Nef/3PCR and 40 nM of the 5' primer Nef/5PCR, 200 nM of partzyme NefA4/6-P and 200 nM of partzyme NefB5/6-P, 200 nM SubBi-6-TRB2, 10 mM MgCl$_2$, 200 µM of each dNTP, 10 units Rnasin (Promega), 1×Immobuffer (Bioline), 0.5 unit of Immolase (Bioline), 10 units MMLV RT (H-) and 5 µL of either total RNA template (containing 45,000 pg, 4,500 pg, 450 pg, 45 pg, 4.5 pg, or 0.45 pg) or no target (water only).

16.6. Results: Amplification of Target and Cleavage of SubBi-6-TRB2 Reporter Substrate The MNAzyme for the real time detection and quantification of HIV-1 Nef transcripts showed an increase in fluorescence over time when the target sequence used was HIV-1 viral RNA amplified via RTPCR. There was no increase in signal for the control reaction lacking target (water only). This demonstrates that the increase in fluorescence produced in target containing reactions was due to target dependent assembly of catalytically active MNAzymes that then cleaved the reporter substrate.

A standard curve was generated by plotting the log of the quantity of RNA template in each reaction against the threshold cycle (Ct) resulting in a linear plot. The Ct of each standard, together with the correlation coefficient ($R^2$), slope and reaction efficiency are shown in Table 19.

TABLE 19

Results of the amplification and detection of HIV Nef transcripts

| Sample | Threshold Cycle (Ct) (average of duplicate reactions) | HIV viral RNA (pg) | Results |
|---|---|---|---|
| Standard 1 | 5.22 | 45,000 | Calibration Curve |
| Standard 2 | 9.96 | 4,500 | $R^2 = 0.996$ |
| Standard 3 | 13.78 | 450 | Slope = −4.271 |
| Standard 4 | 17.22 | 45 | Efficiency = 71.4% |
| Standard 5 | 22.09 | 4.5 | |
| Standard 6 | 27.15 | 0.45 | |
| no target control | No signal | 0 | No signal |

This example demonstrates the capacity of MNAzymes to be used for detection and quantification of viral sequences, including HIV-1.

Example 17

Sequence Requirements of the Catalytic Activity of MNAzymes 17.1. Partzyme Oligonucleotides The catalytic core of the 10:23 DNAzyme as originally discovered comprises 15 nucleotides (Santoro & Joyce, 1997). Later studies of the critical bases within the catalytic core have shown that certain specific base substitutions significantly decrease catalytic activity, while others are well tolerated (Zaborowska et al).

In this example, a series of partzymes were designed and tested to investigate tolerance of the MNAzyme catalytic core to sequence variation within the partial cores of the two partzymes. The unmodified partzymes A and B for the MNAzyme detecting the human RPLPO gene were used as the control and were compared to various mutated partzyme sequences wherein a single base substitution had been made in the partial catalytic core region. Partzyme oligonucleotides used to detect the target were based on design 7 (see Example 20) and are listed below, 5' to 3'. In the following sequences the bases underlined form part of the catalytic core of the assembled MNAzyme, the bases which are underlined, italicized and bold are mutated compared to control (unmutated) partial core sequences, the bases in bold hybridize with the target and the bases in italics hybridize to the substrate.

SEQ ID NO: 94 partzyme A5 RO4A5/2:
GGGCTGGTCATCCAGCAG<u>TACAACGA</u>GAGGAAACCTT

SEQ ID NO: 95 partzyme A5 RO4A5/2-G14A:
GGGCTGGTCATCCAGCAG<u>TACAACA</u>AGAGGAAACCTT SEQ ID NO: 96 partzyme A5 RO4A5/2-A9T:
GGGCTGGTCATCCAGCAG<u>TTCAACGA</u>GAGGAAACCTT SEQ ID NO: 97 partzyme A5 RO4A5/2-A12T:
GGGCTGGTCATCCAGCAG<u>TACATCGA</u>GAGGAAACCTT SEQ ID NO: 98 partzyme A5 RO4A5/2-A11T:
GGGCTGGTCATCCAGCAG<u>TACTACGA</u>GAGGAAACCTT SEQ ID NO: 99 partzyme B6 RO4B6/2:
TGCCCAGGGA<u>GGCTAGC</u>GTGTTCGACAATGGCAGCA

SEQ ID NO: 100 partzyme B6 RO4B6/2-C7A:
TGCCCAGGGA<u>GGCTAGA</u>GTGTTCGACAATGGCAGCA

SEQ ID NO: 101 partzyme B6 RO4B6/2-T4C:
TGCCCAGGGA<u>GGGCAGC</u>GTGTTCGACAATGGCAGCA

17.2. Reporter Substrate

The reporter substrate for this example is SubBi-2 with the sequence, 5' to 3', as below. In the current example, SubBi-2 was end-labelled with a 6-FAM moiety at the 5' end and a BHQ1 moiety at the 3' end and was designated SubBi-2-FB. Cleavage of SubBi-2-FB was monitored at 530 nm (FAM emission wavelength) with excitation at 485 nm (FAM excitation wavelength). In the following sequence the lower case bases represent RNA and the upper case bases represent DNA.

SEQ ID NO: 21 SubBi-2-FB:
AAGGTTTCCTCguCCCTGGGCA 17.3. Target Sequence

A synthetic DNA oligonucleotide was used as the target template in this experiment. The sequence of the target is shown below, 5' to 3'.

SEQ ID NO: 102 RO4/2Target:
ATGCTGCCATTGTCGAACACCTGCTGGATGACCAGCCCAA 17.4. Reaction Conditions Analysis of the catalytic activity of various partzyme pairs was performed using a SmartCycler System thermocycler (Cepheid). Reactions were initiated by the addition of substrate and the total volume of all reactions was 25 μL. Each reaction contained 1×PCR Buffer II (Applied Biosystems), 10 mM MgCl$_2$, 0.2 μM of SubBi-2FB, 2 μM of RO4/2Target and a pair of A and B partzymes each at 2 μM. The partzyme pairs in each reaction were as in Table 20 below.

TABLE 20

Components of reactions for detection of a nucleic acid target

| Reaction | Partzyme A | Partzyme B | Number of replicates |
|---|---|---|---|
| Control (unmutated) partzymes A and B | RO4A5/2 | RO4B6/2 | 6 |
| Mutated partzyme A (G14A) and control partzyme B | RO4A5/2-G14A | RO4B6/2 | 3 |
| Mutated partzyme A (A12T) and control partzyme B | RO4A5/2-A12T | RO4B6/2 | 3 |
| Mutated partzyme A (A11T) and control partzyme B | RO4A5/2-A11T | RO4B6/2 | 3 |
| Mutated partzyme A (A9T) and control partzyme B | RO4A5/2-A9T | RO4B6/2 | 3 |
| Control partzyme A and mutated partzyme B (C7A) | RO4A5/2 | RO4B6/2-C7A | 3 |
| Control partzyme A and mutated partzyme B (T4C) | RO4A5/2 | RO4B6/2-T4C | 3 |

Reactions were incubated at 54° C. for 20 minutes and fluorescent data was collected at 12 second intervals. Since the starting fluorescence can vary for individual wells on the SmartCycler System thermocycler, the initial fluorescence value was subtracted from the fluorescence at each time point for each reaction to allow comparison between reactions in different wells. The averages of replicate reactions, containing either a mutated partzyme A or a mutated partzyme B, were then expressed as a percentage of the fluorescence for control replicates.

17.5. Results: Detection of Cleavage of SubBi-2-FB Reporter Substrate.

Cleavage of the substrate by the various partzyme pairs was measured by the change in fluorescence over time. The normalized fluorescent values for each reaction were then expressed as a percentage of the fluorescence observed in control reactions at the equivalent time point (Table 21).

As such, information in the literature about other sequence substitutions, which are compatible with DNAzyme activity (for example 10:23 DNAzyme or 8:17 DNAzymes), could predict the catalytic activity expected when the same sequence variation is introduced into one of the partzymes. Further, one skilled in the art could use empirical testing to identify additional partzyme partial catalytic core sequence variants, which are compatible with active MNAzyme formation.

TABLE 21

Cleavage activity of various partzyme sequence variants (*this example) and comparison to the activity of variant 10:23 DNAzymes (**Zaborowska). Table 21 discloses the 10:23 core sequence as SEQ ID NO: 49.

| Position number within catalytic core from 5' to 3' | Sequences of partzyme partial core (control) Partzyme B | Sequences of partzyme partial core (control) Partzyme A | Sequence 10:23 core (Santoro & Joyce 1997) | Substituted base (& name) within the (**) 10:23 DNAzyme | Cleavage activity (percentage of control) for DNA enzymes with substitutions *MNAzymes (54° C. for 10 min) | **10:23 DNAzyme (37° C. for 20 min) |
|---|---|---|---|---|---|---|
| 1 | G | | G | | | |
| 2 | G | | G | | | |
| 3 | C | | C | | | |
| 4 | T | | T | C (T4C) | 17% | <10% |
| 5 | A | | A | | | |
| 6 | G | | G | | | |
| 7 | C | | C | A (C7A) | 40% | <80% |
| 8 | | T | T | | | |
| 9 | | A | A | T (A9T) | 70% | 90% |
| 10 | | C | C | | | |
| 11 | | A | A | T (A11T) | 86% | 80% |
| 12 | | A | A | T (A12T) | 80% | 80% |
| 13 | | C | C | | | |
| 14 | | G | G | A (G14A) | 3% | <10% |
| 15 | | A | A | | | |

The experiment shows that various substitutions within the partial catalytic core of either partzyme A or B were compatible with active MNAzyme formation. In contrast other substitutions were not well tolerated and produced structures with little or no catalytic activity. When results obtained using MNAzymes were compared with those reported for the equivalent substitution within the 10:23 DNAzyme catalytic core (Zaborowska et al), a similar pattern was observed (Table 21) above. For example, substitution of A for G at position 14 (G14A) within partzyme A, or within the 10:23 core, resulted in >90% loss of cleavage activity. In contrast, substitution of T for A at position 12 (A12T) within partzyme A, or within the 10:23 core, resulted in molecules which retained approximately 80% cleavage activity compared to the control sequences.

Example 18

Application of MNAzymes to Detect Targets Including Small Molecules Such as Adenosine 5'-Triphosphate Aptamers are single-stranded DNA or RNA molecules evolved in vitro from large pools of random-sequence oligonucleotides for their capacity to bind targets with high affinity and specificity. Aptamers have been selected for their ability to specifically bind to many types of targets including proteins, carbohydrates, lipids, nucleotides, whole cells and viruses. In this example, an aptamer sequence was incorporated at the end of a partzyme (apta-partzyme) in a configuration whereby an active MNAzyme was only formed in the presence of the target. There are several ways of achieving this goal, including the strategies outlined in FIG. 4 and the strategy used in the following example which is illustrated in FIG. 20.

The nucleic acid oligonucleotides required for the MNAzyme detection strategy illustrated in FIG. 20 include; a standard partzyme;
a) an apta-partzyme which is a partzyme with an aptamer incorporated into one of its ends;
b) an assembly facilitator which is an oligonucleotide which binds to both the apta-partzyme and the partzyme enabling assembly of an active MNAzyme;
c) a reporter probe substrate; and
d) an inhibitor oligonucleotide which hybridises to the apta-partzyme in a region which spans at least part of the aptamer sequence and part of the substrate binding arm of the partzyme sequence.

In the absence of a target that binds to the aptamer (left hand panel FIG. 20), the inhibitor oligonucleotide binds to the apta-partzyme thus blocking binding (and cleavage) of the reporter probe substrate. In the presence of a target that binds to the aptamer (right hand panel FIG. 20), the target binds to the aptamer sequence of the apta-partzyme, preventing the binding of the inhibitor oligonucleotide and allowing binding and cleavage of the reporter probe substrate. As such, MNAzymes can only form and cause fluorescent signal generation in the presence of target.

The strategy was demonstrated using detection of a small molecule, ATP. The 27 nucleotide long aptamer sequence used in this example has been previously reported as being highly specific for binding of ATP and dATP (Achenbach, 2005; Huizenga and Szostak, 1995).

18.1. Partzyme Oligonucleotides, Assembly and Inhibitory Oligonucleotides

In this example the ATP aptamer sequence was placed adjacent to the substrate arm of apta-partzyme A (FIG. 20). The sensor arms of apta-partzyme A and partzyme B were designed to bind an assembly facilitator. The sequences of apta-partzyme AtpA2/1 and partzyme Atp B3/1 (FIG. 21) are shown below (5' to 3'). In the following sequences the bases in bold hybridize with the assembly facilitator, based underlined form part of the catalytic core of the assembled MNAzyme, and bases in italics hybridize to the substrate. In addition, bases in plain text in partzyme AtpA2/1 indicate DNA aptamer sequences that bind to ATP or dATP.

SEQ ID NO: 103 Apta-Partzyme A2 AtpA2/1:
AACGTACACTGCACGCGGTCGAAATAGTGAGTACCTGGGGGAGTATTGCG
GAGGAAGGT SEQ ID NO: 104 Partzyme B3 AtpB3/1:
CATCTCTTCTCCGAGCGTCTGTACCGTGTAC

The sequence of the assembly facilitator is shown below (5' to 3'):

SEQ ID NO: 105 Assembly facilitator AtpC/1:
GTACACGGTACAGACCGTGCAGTGTACGTT

The sequence of the inhibitor oligonucleotide is shown below (5' to 3').

SEQ ID NO: 106 Inhibitor AtpR/1:
CCAGGTACTCACTATTT

18.2. Reporter Substrate

MNAzyme activity was monitored by cleavage of a dual-labelled nucleic acid reporter substrate. The reporter substrate for this example is SubBi-1-FB with the sequence, 5' to 3', as below. The lower case bases represent RNA and the upper case bases represent DNA. The underlined bases indicate the position of a 6-FAM moiety at the 5' end and a BHQ1 moiety at the 3' end. Changes in fluorescence due to cleavage of SubBi-1-FB at the ribonucleotide between the FAM and BHQ1 were monitored at 520 nm (FAM emission wavelength) with excitation at 490 nm (FAM excitation wavelength).

SEQ ID NO: 6 SubBi-1-FB:
ACTCAC<u>T</u>ATaGGAAGAGA<u>T</u>G

18.3. Targets

The target molecules for this example were adenosine 5'-triphosphate (ATP) and deoxyadenosine 5'-triphosphate (dATP). Guanosine 5'-triphosphate (GTP) and cytosine 5'-triphosphate (CTP) were used as negative controls. All molecules were purchased from Bioline. Nuclease-free water was used as a no target control.

18.4. Reaction Conditions

Detection of the target was measured by an increase in fluorescent signal caused by cleavage of the reporter substrate by the catalytically active MNAzyme. Reactions were initiated by the addition of substrate and the total volume of all reactions was 50 µL. Prior to substrate injection, all reactions were pre-incubated at 60° C. for 5 minutes (to reduce secondary structure). Reactions were conducted at 47° C. on a FLU-Ostar OPTIMA (BMG Biotech). Fluorescence for each reaction was read every 3 seconds for a total of 10 minutes. Each reaction contained a final concentration of 200 nM AtpA2/1, 200 nM AtpB3/1, 200 nM AtpC/1, 200 nM AtpR/1, 200 nM SubBi-1-FB, 25 mM $MgCl_2$, 50 mM Tris HCl pH 7.5 and 2 mM of either ATP, dATP, GTP, CTP or no target (water).

18.5. Results: Detection and Cleavage of SubBi-1-FB Reporter Substrate

Figure 21:
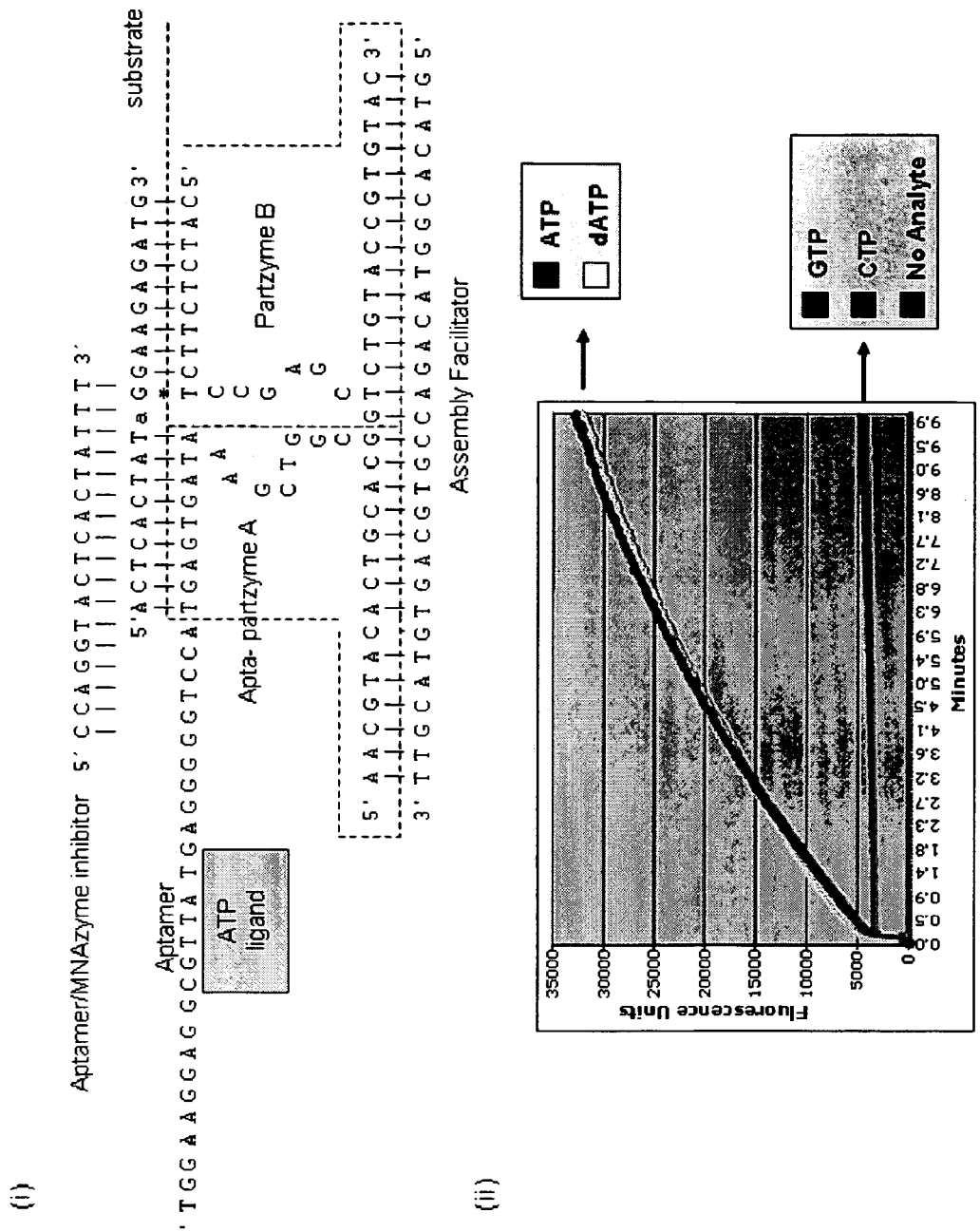
FIG. 21: MNAzyme detection of small molecules using an aptamer: An example of use of MNAzymes for detection of targets, specifically ATP, is depicted. The strategy illustrated in FIG. 20 was demonstrated using the example of detection of a small molecule, ATP. Panel (i) illustrates the sequences of the oligonucleotide components that were used for the detection of ATP. These comprise a partzyme (SEQ ID NO: 137), an aptapartzyme (SEQ ID NO: 103) (which incorporates an aptamer for binding ATP), an aptamer/MNAzyme assembly inhibitor (SEQ ID NO: 106), a reporter substrate (SEQ ID NO: 6) and an assembly facilitator (SEQ ID NO: 105). Panel (ii) SubBi-1-FB cleavage analysis shows the results obtained following incubation of the oligonucleotide components in the presence, or absence, of ATP and other nucleotides. An increase in fluorescence over time was observed in the presence of ATP, and dATP, but not in the presence of GTP or CTP. Further, no increase in fluorescence was observed in the absence of any target (water only control).

In the absence of ATP or dATP a low level of fluorescence was seen which did not increase over time, demonstrating that the inhibitor oligonucleotide was able to prevent the assembly of an active MNAzyme (FIG. 21). In the presence of ATP or dATP, the fluorescent signal was higher and it increased over time. This indicates that the inhibitor oligonucleotide was displaced by dATP and ATP and an active MNAzyme was formed. Assembly of the MNAzyme was target-dependent as the fluorescent signal in the presence of GTP and CTP was the same as in the absence of ATP or dATP i.e. in the no analyte water control. This example demonstrates that MNAzymes can be coupled to aptamers for the detection of targets which include both nucleic acid and non-nucleic acid targets, in an approach that is highly specific for the target.

One skilled in the art will recognise that the design of this strategy can be flexible. The aptamer can be incorporated into either end (5' or 3') of either of the two partzymes containing partial catalytic core sequences. As such, the inhibitor oligonucleotide can bind to the aptamer region and to either the substrate arm (that binds the reporter substrate) or the sensor arm (that binds the assembly facilitator). In the former design (FIG. 20; this example), the inhibitor blocks binding of the reporter substrate. In the latter design, the inhibitor would prevent binding of the assembly facilitator with the partzymes and therefore would prevent active MNAzyme formation.

The literature contains sequences for a large number of aptamers capable of detecting many types of targets. These include proteins, carbohydrates, lipids, prions, nucleotides, whole cells and viruses. Aptamers to all these types of targets could be linked to partzymes to detect a very diverse range of molecules. Reaction conditions (buffer, temperature, divalent cation concentration etc), which are compatible with both binding of targets to aptamers (or apta-partzymes) and cleavage of a reporter substrate by an MNAzyme, can be determined by empirical testing. Further, since aptamers are evolved in vitro under reaction conditions selected by the investigator it would possible to tailor molecular evolution to allow development of aptamers to any desired target that will bind under conditions compatible with MNAzyme cleavage. As MNAzymes are active over a very broad range of conditions, one skilled in the art could easily determine conditions compatible with MNAzyme cleavage.

Example 19

Use of MNAzymes for Detection of Single Base Mismatches

MNAzymes can be used to detect and quantify target nucleic acids in real time using in vitro target amplification methods such as PCR. MNAzymes can also be used to generate qualitative results, for example by detecting changes in nucleic acid sequences. MNAzyme-mediated target detection can occur via Watson-Crick base recognition of the sensor arms and the target sequence. In this example, MNAzymes are used to detect a single base mismatch by exploiting this requirement for complementarity between the partzyme sensor arm and the target nucleic acid sequence.

19.1. Partzyme Oligonucleotides

Figure 22:
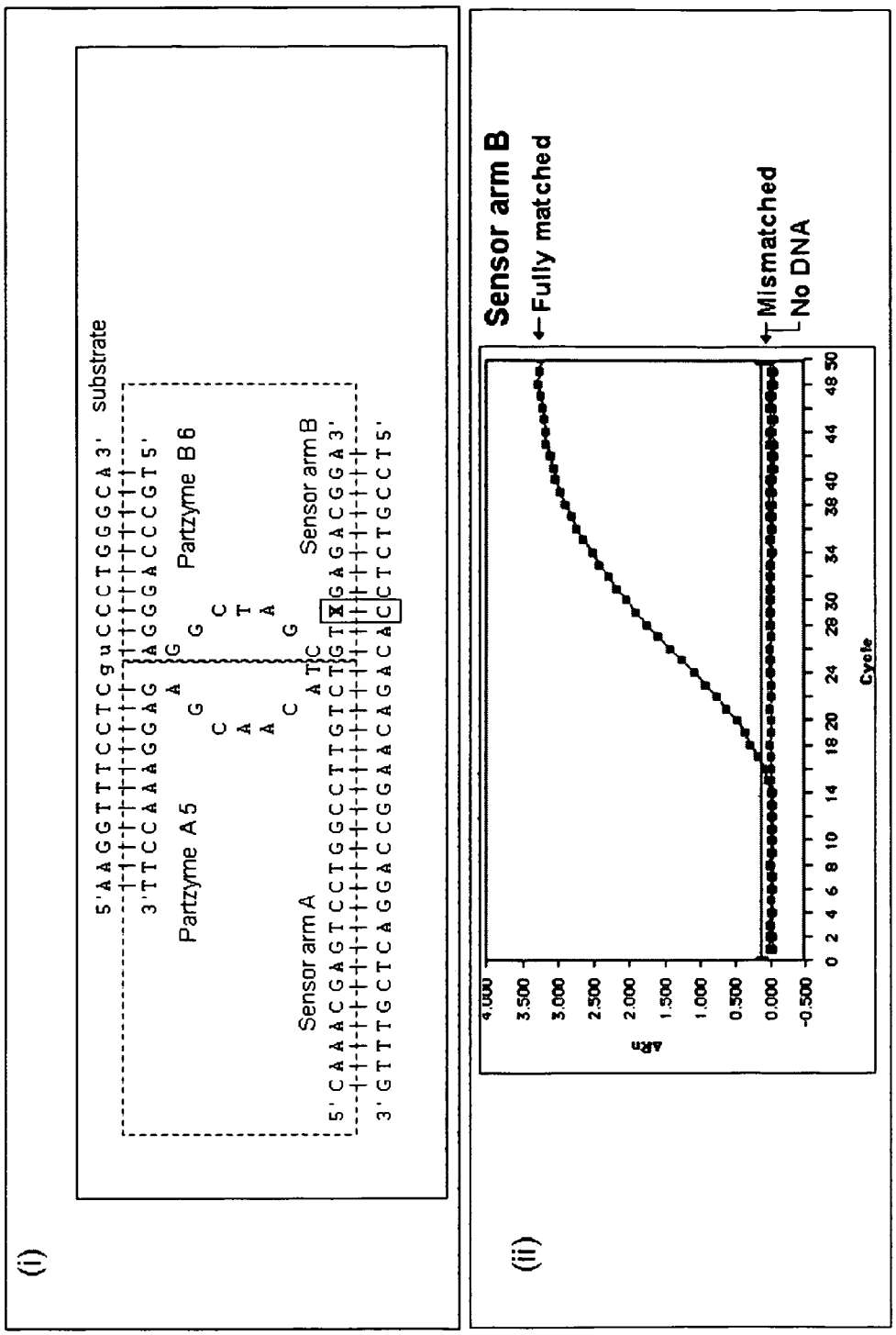
FIG. 22: Detection of single base mismatches using MNAzymes: An example of use of MNAzymes for detection of single base mismatches is depicted. Panel (i) illustrates the sequences of the oligonucleotide components that were used for the detection of single base mismatches in a RPLPO exon 5 target sequence (SEQ ID NO: 158). The oligonucleotide illustrated comprised two partzymes (A5 (SEQ ID NO: 160) and B6 (SEQ ID NO: 154)), which are based on MNAzyme design 7 (e.g. Example 20), and a reporter substrate (SEQ ID NO: 21). The third base (X) in the partzyme B sensor arm is either matched or mismatched with the target sequence. When X=G the partzyme and target are fully matched. When X=C there is a mismatch between the sensor arm and the target RPLPO. Panel (ii) shows the results obtained following PCR amplification and real time detection in reactions containing a partzyme B which is either fully matched, or is mismatched, with respect to the RPLPO target.

Partzyme oligonucleotides were designed to be either fully complementary to the target sequence, or mismatched with respect to the target sequence (FIG. 22(*i*)). The sequences of the fully matched partzyme A (RO5A5/2(22) -P), the fully matched partzyme B (RO5B6/2(11G)-P) and the mismatched partzyme B (RO5B6/2(11C)-P) are listed below (5' to 3'). In the following sequences the bases underlined form part of the catalytic core of the assembled MNAzyme, bases in bold hybridize with the target and bases in italics hybridize to the substrate. The mismatched base in partzyme RO5B6/2 (11C)-P is bold and underlined. The "-P" indicates 3' phosphorylation of the oligonucleotide.

```
SEQ ID NO: 107 Partzyme A5 RO5A5/2(22)-P:
CAAACGAGTCCTGGCCTTGTCTTACAACGAGAGGAAACCTT-P SEQ ID NO: 108 Partzyme B6 RO5B6/2(11G)-P:
TGCCCAGGGAGGCTAGCGTGGAGACGGA-P SEQ ID NO: 109 Partzyme B6 RO5B6/2(11C)-P:
TGCCCAGGGAGGCTAGCGTCGAGACGGA-P
```

19.2. Reporter Substrate

The reporter substrate used in this example was SubBi-2. In the current example, SubBi-2 was end labeled with a 6-FAM moiety at the 5' end, a BHQ1 moiety at the 3' end and designated SubBi-2-FB. Cleavage of SubBi-2-FB was monitored at 530 nm (FAM emission wavelength) with excitation at 485 nm (FAM excitation wavelength). The sequence of SubBi-2-FB is listed below (5' to 3'); the lower case bases represent RNA and the upper case bases represent DNA.

```
SEQ ID NO: 21 SubBi-2-FB:
AAGGTTTCCTCguCCCTGGGCA
```

19.3. PCR Primers for Amplification of RPLPO Exon 5

The target sequence for this example was generated by in vitro amplification of human genomic DNA using the oligonucleotide PCR primers listed below (5' to 3').

```
SEQ ID NO: 32 Primer 5RO5/1:
CATTCTATCATCAACGGGTA

SEQ ID NO: 110 Primer 3RO5/2:
AGCAGCCACAAAGGCAGA
```

19.4. Target Sequences and Controls

Human genomic DNA extracted from the human K562 cell line was used as template for amplification of the RPLPO gene. Nuclease-free (NF) water was used in place of genomic DNA as a no target control.

19.5. Reaction Components: Amplification and Detection of Target Sequence

Real time amplification and detection of the target sequence was performed in a total reaction volume of 25 µl. All reactions were conducted on an ABI 7700 thermocycler (Applied Biosystems). The cycling parameters were 95° C. for 7 minutes, 10 cycles of 95° C. for 15 seconds and 65° C. for 30 seconds (with a 1° C. decrease in temperature per cycle), and finally 50 cycles of 95° C. for 15 seconds and 47° C. for 30 seconds. The reactions contained 40 nM 5RO5/1, 200 nM of 3RO5/2, 200 nM RO5A5/2(22)-P and 200 nM RO5B6/2(11G)-P or 200 nM RO5B6/2(11C)-P, 200 nM SubBi-2-FB, 10 mM MgCl$_2$, 200 µM of each dNTP, 10 units Rnasin (Promega), 1×ROX reference (Invitrogen), 1×Immobuffer (Bioline), 1 unit of Immolase (Bioline) and either 100 ng genomic DNA template or NF-water.

19.6. Results: Single Base Mismatch Detection Using an MNAzyme

The MNAzyme comprising the fully matched sensor arm B showed an increase in fluorescence over time when the target sequence used was human genomic DNA amplified via PCR (FIG. 22(*ii*)). In contrast, the MNAzyme containing the mismatched sensor arm B showed a low level of fluorescence with the genomic target, similar to that seen in the no target control, and the fluorescence did not increase over time. Thus, the single mismatch, three bases from the partzyme A and B junction was sufficient to prevent the formation of the active MNAzyme.

This example demonstrates that MNAzymes can be used to detect single base mismatches between the target and sensor arms. Since MNAzymes are capable of detecting alterations as small as single base changes, it would be obvious to one skilled in the art that MNAzymes could also be used to discriminate sequence differing by small deletions or small insertions. In addition, larger alterations such as translocations associated with various cancer types, which result in fusion transcripts, could also be detected. These occur frequently in association with leukaemia, for example PML/RARα fusion transcripts are associated with acute promyelocytic leukaemia and bcr/abl fusion transcripts are associated with chronic granulocytic leukaemia.

While this example shows that single mismatches can be sufficient to prevent assembly of active MNAzyme, additional experiments demonstrated that not all single base mismatches completely disrupt MNAzyme assembly under all conditions. The capacity to discriminate single base mismatches depends on several factors including a) the stringency of the reaction conditions, which can be influenced by many factors including temperature, salt concentration, cation concentration, b) the type of mismatch, for example G/T mismatches versus C/C, c) the position of the mismatch within the partzyme arm, and d) the length of the partzyme arm.

Additional strategies can be used to increase the capacity of the MNAzyme to detectable single base polymorphisms. These include, for example, use of a truncated partzyme sensor arm as demonstrated in example 22.

Example 20

Testing MNAzyme Activity from a Series of Partzyme Pairs which Contain Variant Partial Catalytic Core Sequences Derived from the 10:23 Catalytic Core Multi-component nucleic acid enzymes (MNAzymes) can be made which incorporate partial sequences from a variety of in vitro evolved DNAzymes. Active MNAzymes, based on partial sequences from the 8:17 and 10:23 DNAzymes, have been demonstrated. Further, several alternative partzyme designs based on the 8:17 and 10:23 DNAzymes have been shown to either have (Examples 1, 3, FIGS. 9, 10 and 13), or lack (Example 1, FIG. 8), activity. This example further extends these studies and identifies both active and inactive partzyme sequences based on partial catalytic core sequences from the 10:23 DNAzyme. Further, the example provides a general protocol for the steps necessary to identify the optimal place(s) to split a catalytic core sequence such that, when the partial catalytic core sequences are incorporated into partzymes, functional active MNAzymes are generated.

20.1. Partzyme Oligonucleotides

The method in this example was used to investigate which positions within the 10:23 catalytic core sequence are suitable for splitting into partial catalytic core sequences which, upon incorporation into partzymes, result in functionally active MNAzymes. The 10:23 sequence was split at various points and then the two partial sequences were incorporated into a series of partzyme pairs which were designed to cleave a substrate in the presence of target (human RPLPO gene). The partial catalytic cores for each partzyme pair which were tested are shown in Table 22 with reference to the complete catalytic core sequence of the 10:23 DNAzyme (Santoro and Joyce, 1997).

TABLE 22

Bases and position in the 10:23 DNAzyme (SEQ ID NO: 49) and in a series of variant partzyme pairs where the bases at positions 1 to 15 of the core have been distributed differently between two partzymes A and B. Table 22 discloses the Partzyme A and B sequences as SEQ ID NOS 151, 167, 168, 175, 161, 172 and 176, respectively, in order of appearance.

| Position # | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 10:23 DNAzyme (Santro & Joyce, 1997) | G | G | C | T | A | G | C | T | A | C | A | A | C | G | A |
| Design 6 Partzyme A | | | | | | | | | A | C | A | A | C | G | A |
| A4:B5 Partzyme B (T8-A9) | G | G | C | T | A | G | C | T | | | | | | | |
| Design 7 Partzyme A | | | | | | | | | T | A | C | A | A | C | G | A |
| A5:B6 Partzyme B (C7-T8) | G | G | C | T | A | G | C | | | | | | | | |

TABLE 22-continued

Bases and position in the 10:23 DNAzyme (SEQ ID NO: 49) and in a series of variant partzyme pairs where the bases at positions 1 to 15 of the core have been distributed differently between two partzymes A and B. Table 22 discloses the Partzyme A and B sequences as SEQ ID NOS 151, 167, 168, 175, 161, 172 and 176, respectively, in order of appearance.

| Position # | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Design 8 Partzyme A | | | | | | | | | | | | A | C | G | A |
| A6:B7 Partzyme B (A11-A12) | G | G | C | T | A | G | C | T | A | C | A | | | | |
| Design 9 Partzyme A | | | | | | | | | | C | A | A | C | G | A |
| A7:B8 Partzyme B (A9-C10) | G | G | C | T | A | G | C | T | A | | | | | | |
| Design 10 Partzyme A | | | | | | | C | T | A | C | A | A | C | G | A |
| A8:B9 Partzyme B (G6-C7) | G | G | C | T | A | G | | | | | | | | | |
| Design 11 Partzyme A | | | | | | G | C | T | A | C | A | A | C | G | A |
| A9:B10 Partzyme B (A5-G6) | G | G | C | T | A | | | | | | | | | | |

All sequences are written 5' to 3'. The MNAzyme design and partzyme nomenclature is continued from the series in Table 3 and extended in this table to identify the location of the split within the core. For example, Design 6 is a 10:23 derived MNAzyme with partzyme A4 and partzyme B5 design (A4:B5), where the core has been split between T at position 8 and A at position 9 (T8-A9).

In this experiment the series of partzyme pairs were all synthesized with sensor arms designed to hybridise to exon 5 of the human RPLPO gene, and with substrate arms directed against the substrate, SubBi-2. The partzyme pairs used in this experiment were synthesized by Sigma-Proligo and their sequences are listed below (5' to 3'). The bases underlined form part of the catalytic core of the assembled MNAzyme, bases in bold hybridise with the nucleic acid target and bases in italics hybridise to the substrate. The "-P" indicates 3' phosphorylation of the oligonucleotide.

RPLPO Partzyme Pair A4:B5
SEQ ID NO: 147 RO5A4/2-P
CAAACGAGTCCTGGCCTTGTCT<u>ACAACGA</u>*GAGGAAACCTT*-P SEQ ID NO: 112 RO5B5(16)/2-P
*TGCCCAGGG*<u>AGGCTAGC</u>GTGGAGACGGATTACA-P RPLPO Partzyme Pair A5:B6
SEQ ID NO: 107 RO5A5/2(22)-P
CAAACGAGTCCTGGCCTTGTCT<u>TACAACGA</u>*GAGGAAACCTT*-P SEQ ID NO: 114 RO5B6(16)/2-P
*TGCCCAGGG*<u>AGGCTAGC</u>GTGGAGACGGATTACA-P RPLPO Partzyme Pair A6:B7
SEQ ID NO: 115 RO5A6(22)/2-P
CAAACGAGTCCTGGCCTTGTCT<u>ACGA</u>*GAGGAAACCTT*-P SEQ ID NO: 116 RO5B7(16)/2-P
*TGCCCAGGG*<u>AGGCTAGCTACA</u>GTGGAGACGGATTACA-P RPLPO Partzyme Pair A7:B8
SEQ ID NO: 117 RO5A7(22)/2-P
CAAACGAGTCCTGGCCTTGTCT<u>CAACGA</u>*GAGGAAACCTT*-P -continued

SEQ ID NO: 118 RO5B8(16)/2-P
TGCCCAGGGAGGCTAGCTAGTGGAGACGGATTACA-P

RPLPO Partzyme Pair A8:B9
SEQ ID NO: 119 RO5A8(22)/2-P
CAAACGAGTCCTGGCCTTGTCTCTACAACGAGAGGAAACCTT-P

SEQ ID NO: 120 RO5B9(16)/2-P
TGCCCAGGGAGGCTAGGTGGAGACGGATTACA-P

RPLPO Partzyme Pair A9:B10
SEQ ID NO: 121 RO5A9(22)/2-P
CAAACGAGTCCTGGCCTTGTCTGCTACAACGAGAGGAAACCTT-P

SEQ ID NO: 122 RO5B10(16)/2-P
TGCCCAGGGAGGCTAGTGGAGACGGATTACA-P 20.2. Reporter Substrate The reporter substrate for this example is SubBi-2 with the sequence, 5' to 3', as below. In the current example, SubBi-2 was end-labelled with a 6-FAM moiety at the 5' end and a BHQ1 moiety at the 3' end and was designated SubBi-2-FB. Cleavage of SubBi-2-FB was monitored at 530 nm (FAM emission wavelength) with excitation at 485 nm (FAM excitation wavelength). The lower case bases represent RNA and the upper case bases represent DNA.

SEQ ID NO: 21 SubBi-2-FB
AAGGTTTCCTCguCCCTGGGCA 20.3. PCR Primers for the Amplification of Exon 5 of the Human RPLPO Gene.

The sequences of the primers are shown, 5' to 3', below.

SEQ ID NO: 123 5' Primer 5RO5/2
GCTACCCAACTGTTGCATC

SEQ ID NO: 110 3' Primer 3RO5/2
AGCAGCCACAAAGGCAGA 20.4. Target Template

Human genomic DNA extracted from K562 cells was used as template in the PCR reaction.

20.5. Reaction Conditions

Real time amplification of the target sequence and detection of catalytic activity of the partzyme pairs was conducted in a 25 µL reaction cycled on an ABI 7700 thermocycler (Applied Biosystems). The cycling parameters were 95° C. for 7 minutes, 10 cycles of 95° C. for 15 seconds and 65° C. for 30 seconds (with a 1° C. decrease in temperature per cycle), and finally 50 cycles of 95° C. for 15 seconds and 50° C. for 30 seconds. Each reaction contained 0.04 µM 5RO5/1 and 0.2 µM of 3RO5/2, 10 mM $MgCl_2$, 50 µM each dNTP (dATP, dCTP, dGTP, dTTP), 1×Immobuffer (Bioline), 0.2 µM SubBi-2-FB, 1×Rox reference dye (Invitrogen), 10 Units of Rnasin (Progema) and 1 Unit of Immolase Polymerase (Bioline) and 100 ng of genomic DNA. In addition each reaction contained a pair of partzymes 0.2 µM of partzyme A and 0.2 µM of partzyme B (RPLPO Partzyme Pair A4:B5 or A5:B6 or A6:B7 or A7:B8 or A8:B9 or A9:B10).

20.6. Results

Using a real time MNAzyme-PCR method, catalytic activity was detected from three of the six RPLPO partzyme pairs. Partzyme pair A4:B5 and A5:B6 showed high levels of catalytic activity, allowing detection of target in ≦22 cycles (Table 23). The A7:B8 partzyme pair was also active, although less active than A4:B5 and A5:B6. No catalytic activity was detected from partzyme pairs A6:B7, A8:B9 or A9:BIO under the conditions of this experiment.

TABLE 23

Threshold Cycle (Ct) values obtained using various partzyme pairs

| Core Split (see table above, this example) | Ct | Comment |
|---|---|---|
| A4:B5 (T8-A9) | 19.3 | This combination of partial catalytic core sequences in these partzymes is compatible with formation of active MNAzymes. |
| A5:B6 (C7-T8) | 21.6 | This combination of partial catalytic core sequences in these partzymes is compatible with formation of active MNAzymes. |
| A6:B7 (A11-A12) | No signal at 50 cycles | This combination of partial catalytic core sequences in these partzymes is not compatible with formation of active MNAzymes under these experimental conditions. |
| A7:B8 (A9-C10) | 31.7 | This combination of partial catalytic core sequences in these partzymes is compatible with formation of active MNAzymes. |
| A8:B9 (G6-C7) | No signal at 50 cycles | This combination of partial catalytic core sequences in these partzymes is not compatible with formation of active MNAzymes under these experimental conditions. |
| A9:B10 (A5-G6) | No signal at 50 cycles | This combination of partial catalytic core sequences in these partzymes is not compatible with formation of active MNAzymes under these experimental conditions. |

The Ct values are averaged from triplicate reactions, when the threshold florescence level was set at 0.2 and the baseline background fluorescence was subtracted between cycles 1 and 14.

Example 21

Application of MNAzymes to Detect Protein Targets

As demonstrated in example 18, MNAzymes can be used to detect targets by incorporating aptamer sequences onto the end of a partzyme (apta-partzyme). In this example, the same MNAzyme detection strategy (FIG. 20) was used to detect the protein Taq polymerase using a 46 nucleotide long aptamer sequence which has been reported to bind Taq polymerase with high specificity (Yakimovich, 2003). The assembly facilitator and partzyme B oligonucleotide were the same as those used in the example 18 where ATP was detected using an MNAzyme.

21.1. Partzyme Oligonucleotides, Assembly and Inhibitory Oligonucleotides

In this example the Taq polymerase aptamer sequence was placed adjacent to the substrate arm of apta-partzyme A (FIG. 20). The sensor arms of apta-partzyme A and partzyme B were designed to bind an assembly facilitator. The sequences of apta-partzyme TaqA2/1 and partzyme AtpB3/1 are shown below (5' to 3'). In the following sequences the bases in bold hybridize with the assembly facilitator, based underlined form part of the catalytic core of the assembled MNAzyme, and bases in italics hybridize to the substrate. In addition, bases in plain text in apta-partzyme A2 TaqA2/1 indicate DNA aptamer sequences that bind to Taq polymerase.

SEQ ID NO: 124 Apta-Partzyme A2 TaqA2/1:
AACGTACACTGCACG<u>CGGTCGAAA</u>TAGTGAGTGCGGTCGGCTCGGGGCAT
TCTTAGCGTTTTGCCCCGAGCCGACCGC SEQ ID NO: 104 Partzyme B3 AtpB3/1:
*CATCTCTTCT*<u>CCGAGC</u>GTCTGTACCGTGTAC

The sequence of the assembly facilitator is shown below (5' to 3'):

SEQ ID NO: 105 Assembly facilitator AtpC/1:
GTACACGGTACAGACCGTGCAGTGTACGTT

The sequence of the inhibitor oligonucleotide is shown below (5' to 3').

SEQ ID NO: 125 Inhibitor TaqR/1:
TGCCCCGAGCCGACCGAACTCACTATTT

21.2. Reporter Substrate

MNAzyme activity is monitored by cleavage of a dual-labelled nucleic acid reporter substrate. The reporter substrate for this example is SubBi-1-FB with the sequence, 5' to 3', as below. The lower case bases represent RNA and the upper case bases represent DNA. The underlined bases indicate the position of a 6-FAM moiety at the 5' end and a BHQ1 moiety at the 3' end. Changes in fluorescence due to cleavage of SubBi-1-FB at the ribonucleotide between the FAM and BHQ1 were monitored at 520 nm (FAM emission wavelength) with excitation at 490 nm (FAM excitation wavelength).

SEQ ID NO: 6 SubBi-1-FB:
<u>A</u>CTCAC<u>T</u>A<u>T</u>aGGAAGAGA<u>TG</u>

21.3. Target

The target molecule in this example was Taq DNA Polymerase (Amersham Biosciences) and Klenow polymerase (Amersham Biosciences) was used as a negative control. Nuclease-free water was used as a "no target" control.

21.4. Reaction Conditions

Detection of the target sequence was measured by an increase in fluorescent signal caused by cleavage of the reporter substrate by the catalytically active MNAzyme. Reactions were initiated by the addition of substrate and the total volume of all reactions was 50 μL. Reactions were conducted at 40° C. on a FLUOstar OPTIMA (BMG Biotech). Fluorescence for each reaction was read every 6 seconds for a total of 15 minutes. Each reaction contained a final concentration of 200 nM TaqA2/1, 200 nM AtpB3/1, 200 nM AtpC/1, 200 nM TaqR/1, 200 nM SubBi-1-FB, 25 mM MgCl$_2$, 25 mM Tris HCl pH 6.8 and either 5 Units of Taq DNA polymerase or 5 Units of Klenow polymerase or no protein (water only).

21.5. Results: Detection and Cleavage of SubBi-1-FB Reporter Substrate

In the absence of Taq polymerase a low level of fluorescence was seen which only increased slightly over time, demonstrating that the inhibitor oligonucleotide was able to prevent the assembly of an active MNAzyme. In the presence of Taq polymerase, the fluorescent signal was higher and increased over time. This indicates that the inhibitor oligonucleotide was displaced by Taq polymerase and an active MNAzyme was formed. Assembly of the MNAzyme was target-dependent as the fluorescent signal in the presence of Klenow polymerase was similar to the signal in the absence of Taq polymerase ie. in the "no target" water control. This is consistent with the observations of Yakimovich et al (2003) who showed that the Taq polymerase aptamer sequence is specific for Taq polymerase and does not bind Klenow. This MNAzyme example above demonstrates that MNAzymes can be coupled to aptamers for the detection of specific proteins.

Example 22

Detection of a Single Nucleotide Polymorphism (SNP) Using a Truncated Partzyme and a Stabiliser Oligonucleotides MNAzyme-mediated target detection can occur via Watson-Crick base recognition of the partzyme sensor arms and the target sequence. In example 19, this requirement for complementarity was used to detect a single base mismatch between the partzyme sensor arm and the target nucleic acid sequence. In the following example, the requirement for complementarity was again exploited to detect a single nucleotide polymorphism (SNP) using a strategy that used a partzyme with a truncated sensor arm, which can be stabilised by a stabiliser oligonucleotide. The MNAzyme detection strategy used in this example is illustrated in FIG. 23 and the required oligonucleotides are described below:

a) standard partzyme;
b) a partzyme with a truncated sensor arm (eg 5 bases) which is designed to fully match one form of the SNP but not the other;
c) a stabiliser oligonucleotide (eg 15 bases), which hybridizes to the target adjacent to the truncated sensor arm of the partzyme.
The stabiliser is designed to facilitate MNAzyme assembly when the 5 nucleotide sensor arm is hybridized to the target; and
d) a reporter probe substrate.

22.1. Partzyme Oligonucleotides and Stabiliser Oligonucleotide

In this example, the sensor arm of partzyme B was designed to be only 5 nucleotides long and to discriminate a SNP occurring in the target oligonucleotide. The sensor arm of partzyme B was designed to hybridize to the "T" form of the SNP but not the "C" form of the SNP. The sequences of partzymes A and B and the stabiliser oligonucleotide are shown below (5' to 3'). In the following sequences the bases in bold hybridize with the target, bases underlined form part of the catalytic core of the assembled MNAzyme, and bases in italics hybridize to the substrate. The "-P" indicates 3' phosphorylation of the oligonucleotide.

SEQ ID NO: 126 Partzyme A4 XdA4/2-P:
ACTGGATGTCCATCTGTCTG<u>ACAACGA</u>*GAGGAAACCTT*-P SEQ ID NO: 127 Partzyme B5 XdB5/2-P:
*TGCCCAGGG*<u>AGGCTAGCT</u>TATAC-P SEQ ID NO: 128 Stabiliser XdF/2-P:
CTTCGTGAGGGTGAG-P

22.2. Reporter Substrate

The reporter substrate used in this example was SubBi-2. In the current example, SubBi-2 was end-labelled with a 6-FAM moiety at the 5' end, a BHQ1 moiety at the 3' end and designated SubBi-2-FB. Cleavage of SubBi-2-FB was monitored at 520 nm (FAM emission wavelength) with excitation at 490 nm (FAM excitation wavelength). The sequence of SubBi-2-FB is listed below (5' to 3'); the lower case bases represent RNA and the upper case bases represent DNA.

```
SEQ ID NO: 21 SubBi-2-FB:
AAGGTTTCCTCguCCCTGGGCA
```

22.3. Target

The target molecules for this example were synthetic oligonucleotides derived from the Xd gene. One of the targets corresponded to the "T" form of the SNP (XdC/2(52)) and was fully matched with the partzyme B sensor arm. The other target corresponded to the "C" form of the SNP and was mismatched to the partzyme B sensor arm. Synthetic oligonucleotides were ordered from Sigma-Proligo and nuclease-free water was used in place of target as a "no target" control. The sequences of both targets are listed below (5' to 3') with the SNP underlined.

```
SEQ ID NO: 129 Target XdC/2(52):
TGCCCCCTCACCCTCACGAAGGTATACAGACAGATGGACATCCAGTTGGT
GA SEQ ID NO: 130 Target (mismatch) XdC/2(1M52):
TGCCCCCTCACCCTCACGAAGGCATACAGACAGATGGACATCCAGTTGGT
GA
```

22.4. Reaction Conditions

Detection of the target sequence was measured by an increase in fluorescent signal caused by cleavage of the reporter substrate by the catalytically active MNAzyme. Reactions were initiated by the addition of substrate and the total volume of all reactions was 50 µL. Reactions were conducted at 55° C. on a FLUOstar OPTIMA (BMG Biotech). Fluorescence for each reaction was read every 2 seconds for a total of 5 minutes. All reactions contained 200 nM XdA4/2-P, 200 nM XdB5/2-P, 1×PCR Buffer II (Applied Biosystem) and 25 mM MgCl$_2$. In addition, the reaction contained oligonucleotides listed in Table 24

TABLE 24

Additional reagents in MNAzyme reactions.

| Reaction | Target | Stabiliser |
|---|---|---|
| A | 200 nM of XdC/2(52) | 200 nM of XdF/2-P |
| B | 200 nM of XdC/2(1M52): | 200 nM of XdF/2-P |
| C | 200 nM of XdC/2(52) | No stabiliser |
| D | No target | 200 nM of XdF/2-P |

22.5. Results: Detection and Cleavage of SubBi-2-FB Reporter Substrate

The MNAzyme showed an increase in fluorescence over time when the fully matched SNP template was used (Reaction A: FIG. 23). In contrast, when the template was mismatched (contained an SNP), the fluorescent signal did not increase over time (Reaction B: FIG. 23). Similarly, there was no increase in fluorescence in the absence of target oligonucleotide (Reaction D: FIG. 23). The presence of the stabiliser oligonucleotide was shown to be essential for stabilising the MNAzyme complex. A reaction containing all reaction components including fully matched target, but which lacked the stabiliser oligonucleotide, gave no increase in fluorescence over time (Reaction C: FIG. 23). As such, 5 bases of the sensor arm was insufficient to form a stable MNAzyme complex but the presence of a stabiliser oligonucleotide could compensate for the short length of the partzyme sensor arm (5 bases) and allow stable MNAzyme formation under stringent temperature conditions (55° C. in this example). The stabiliser oligonucleotide can be considered a third partzyme in this system, as it is required for stable MNAzyme formation.

This example demonstrates that MNAzymes can be used to discriminate between two targets that differ by as little as a SNP. Further, it demonstrates the application of partzymes with truncated sensor arms, and their use in combination with stabiliser oligonucleotides.

Example 23

Catalytic Activity of MNAzymes with Ribonucleotide Substitutions

Unlike ribozymes, DNAzymes have not been found to occur in nature. DNAzymes are evolved in vitro from large oligonucleotide libraries. The substitution of certain deoxyribonucleotides for certain ribonucleotides in known ribozymes has been attempted under certain conditions (McCall et al., 1992). Ribozymes that have been fully converted into DNA have no activity due to the conformational differences of RNA and DNA (Perreault et al., 1990). These studies demonstrate that RNA enzymes cannot be modified into working DNA enzymes by merely replacing ribonucleotides with deoxyribonucleotides. Experiments were performed to investigate the tolerance of MNAzymes to substitution of ribonucleotides for deoxyribonucleotides.

23.1. Partzyme Oligonucleotides

In this example, various partzymes were synthesized where one or more deoxyribonucleotides were replaced with ribonucleotides within the regions that constitute the partial catalytic core. Partzymes were synthesized which either had a single ribonucleotide substitution, or which had the entire partial catalytic core region replaced with ribonucleotides. Partzyme oligonucleotides A and B had sensor arms complementary to a region of exon 4 of the human RPLPO gene. The partzyme oligonucleotides are listed below, 5' to 3'. In the following sequences the bases underlined form part of the catalytic core of the assembled MNAzyme, the bases in bold hybridize to the target and bases in italics hybridize to the substrate. Bases in lower case represent RNA bases which have replaced DNA bases.

```
SEQ ID NO: 131 partzyme A (Control) RO4A5(18)/2-P
GGGCTGGTCATCCAGCAGTACAACGAGAGGAAACCTT-P SEQ ID NO: 132 partzyme B (Control) RO4B6 (19)/2-P
TGCCCAGGGAGGCTAGCGTGTTCGACAATGGCAGCA-P SEQ ID NO: 133 Partzyme A (ribo-14g):
RO4A5(18)/2-rG14-P
GGGCTGGTCATCCAGCAGTACAACgAGAGGAAACCTT-P SEQ ID NO: 134 Partzyme A (ribo-9a):
RO4A5(18)/2-rA9-P
GGGCTGGTCATCCAGCAGTaCAACGAGAGGAAACCTT-P SEQ ID NO: 135 Partzyme A (ribo x 8): RO4rA5(18)/2
GGGCTGGTCATCCAGCAGuacaacgaGAGGAAACCTT
```

-continued

SEQ ID NO: 136 Partzyme B (ribo x 7): RO4rB6(19)/2
TGCCCAGGGAggcuagcGTGTTCGACAATGGCAGCA

23.2. Reporter Substrate

The reporter substrate for this example was SubBi-2 with the sequence, 5' to 3', as below. In the current example, SubBi-2 was end-labelled with a 6-FAM moiety at the 5' end and a BHQ1 moiety at the 3' end and was designated SubBi-2-FB. Cleavage of SubBi-2-FB was monitored at 530 nm (FAM emission wavelength) with excitation at 485 nm (FAM excitation wavelength). In the following sequence the lower case bases represent RNA and the upper case bases represent DNA.

SEQ ID NO: 21 SubBi-2-FB:
AAGGTTTCCTCguCCCTGGGCA

23.3. Target Sequence

A synthetic DNA oligonucleotide was used as the target template in this experiment. The sequence of the target is shown below, 5' to 3'.

SEQ ID NO: 8 RO4/1Target
GCCATTGTCGAACACCTGCTGGATGACCAGC

23.4. Reaction Conditions

Analysis of the catalytic activity of various partzyme pairs was performed using a SmartCycler System thermocycler (Cepheid). The total reaction volumes were 25 µL and each reaction contained 1×PCR Buffer II (Applied Biosystems), 10 mM MgCl$_2$, 0.2 µM of SubBi-2-FB, 2 µM of RO4/1Target and a pair of A and B partzymes each at 2 µM. The partzyme pairs in each reaction were as in Table 24.

TABLE 24

Partzymes in various reactions.

| Reaction | Partzyme A | Partzyme B | Number of replicates |
|---|---|---|---|
| Control partzymes A and B (DNAonly) | RO4A5(18)/2-P | RO4B6(19)/2-P | 4 |
| Partzyme A (ribo - 9a) & control partzyme B | RO4A5(18)/2-rA9-P | RO4B6 (19)/2-P | 3 |
| Partzyme A (ribo - 14g) & control partzyme B | RO4A5(18)/2-rG14-P | RO4B6 (19)/2-P | 3 |
| Partzyme A (ribo × 8) & control partzyme B | RO4rA5(18)/2 | RO4B6 (19)/2-P | 3 |
| Control partzyme A and Partzyme B (ribo × 7) | RO4A5(18)/2-P | RO4rB6(19)/2 | 3 |
| Partzyme A (ribo × 8) & Partzyme B (ribo × 7) | RO4rA5(18)/2 | RO4rB6(19)/2 | 3 |

Reactions were incubated at 54° C. for 20 minutes and fluorescent data was collected at 12 second intervals. Since the starting fluorescence can vary for individual wells on the SmartCycler System thermocycler, the initial fluorescence value was subtracted from the fluorescence at each time point for each reaction to allow comparison between reactions in different wells.

23.5. Results: Catalytic Activity of MNAzymes with Ribonucleotide Substitutions within the Partzyme Partial Catalytic Core Sequences.

Catalytic cleavage of the substrate by MNAzymes composed of the various partzyme pairs was monitored as a change in fluorescence over time (Table 25).

TABLE 25

Results obtained using various partzyme combinations.

| Reaction | Result |
|---|---|
| Control Reaction with DNA only partzymes A and B | Rapid increase in fluorescence; fluorescence reached a plateau after 5 minutes of incubation. |
| Partzyme A (ribo - 9a) & control partzyme B | Increase in fluorescence; fluorescence had not yet reached a plateau after 20 minutes of incubation. |
| Partzyme A (ribo - 14g) & control partzyme B | Rapid increase in fluorescence; fluorescence reached a plateau after 5 minutes of incubation. |
| Partzyme A (ribo × 8) & control partzyme B | No increase in fluorescence over time. |
| Control partzyme A and Partzyme B (ribo × 7) | No increase in fluorescence over time. |
| Partzyme A (ribo × 8) & Partzyme B (ribo × 7) | No increase in fluorescence over time. |

The experiment shows that some ribonucleotide substitutions within the partial catalytic core of the partzymes are compatible with active MNAzyme formation. While the single substitution (partzyme A (ribo 14g)) had similar activity as the all DNA partzymes under these conditions, an alternative single substitution (partzyme A (ribo9a)), while still compatible with active MNAzyme formation, cleaved the substrate at a slower rate than the control. The MNAzyme did not tolerate substitution of all nucleotides in the partial catalytic core domain of either partzyme A and/or partzyme B.

Example 24

Activation of an MNAzyme by Release of a Tethered Partzymes as a Mechanism to Initiate a Signal Amplification Cascade

24.1. MNAzyme Mediated Signal Amplification Cascades

MNAzymes can be used to initiate signal amplification cascades. One strategy for such a signal amplification cascade is illustrated in FIG. 25. In the presence of the target, active MNAzyme 1 forms from partzymes which are free in solution. MNAzyme 1 cleaves its tethered substrate, Sub1, thus releasing partzyme components for MNAzyme 2. Once free, these partzymes hybridize with the assembly facilitator and form MNAzyme 2 which cleaves substrate Sub 2. Dual labeled Sub 2, which is free in solution, is cleaved by MNAzyme 2 and fluorescent signal is generated. In addition, MNAzyme 2 cleaves tethered Sub 2 releasing partzymes, which have the same sensor arms as MNAzyme 2 and when hybridized to the assembly facilitator, form MNAzyme 3. (The assembly facilitator can either be tethered or can be free in solution). Since MNAzyme 3 shares the same substrate arms as MNAzyme 1, it can also cleave tethered Sub1, thus releasing more partzyme components for MNAzyme 2. This results in a cascade of enzymatic generation of the components (partzymes) for more enzymes (MNAzymes) and concomitant signal amplification.

24.2. Activation of Tethered MNAzyme Capable of Cleaving Fluorescently Labeled Substrate This example demonstrates the first step of the signal amplification cascade as illustrated in FIG. 25. In this initiating step, target binds to partzymes, which are free in solution, and forms active MNAzyme 1. MNAzyme 1 cleaves its tethered substrate, Sub 1, thus releasing partzyme components for MNAzyme 2. Once free, these partzymes hybridize with the assembly facilitator and form MNAzyme 2. Dual labeled Sub 2-FQ (specifically SubBi-3-FB in this example), which is free in solution, is cleaved by MNAzyme 2 and fluorescent signal is generated.

24.3. Partzyme Oligonucleotides

In the following sequences the bases underlined form part of the catalytic core of the assembled MNAzyme, bases in bold hybridize with the target and bases in italics hybridize to the substrate. Bases that are both in italic and underlined represent the substrate sequences that are coupled to partzymes to be tethered. The "-P" indicates phosphorylation of the oligonucleotide and the "(Biotin)" indicates biotinylation of the oligonucleotide. The lower case bases represent RNA and the upper case bases represent DNA. All sequences listed below are written 5' to 3'.

The free in solution MNAzyme 1 partzymes were designed to specifically bind to exon 5 of the human RPLPO gene and the tethered MNAzyme 2 partzymes were designed to hybridize to the assembly facilitator.

SEQ ID NO: 147 Partzyme A4 RO5A4/2-P:
CAAACGAGTCCTGGCCTTGTCTACAACGAGA*GGAAACCTT*-P SEQ ID NO: 148 Partzyme B5 RO5B5/2-P:
*TGCCCAGGGA*GGCTAGCTGTGGAGACGGATTACACCTTC-P SEQ ID NO: 138 Tethered Substrate 1/Partzyme A4 RO4A4/3-5b:
(Biotin) AAAAAAAAGGTTTCCTC*gu*CCCTGGGCAGCTGGTCATCCAG

CAGACAACGAGGTTGTGCTG

SEQ ID NO: 139 Tethered Substrate 1/Partzyme B5 RO4B5/3-3b:
*CGGTTGGTGA*GGCTAGCTTGTTCGACAATGGCAAGGTTTCCTC*gu*CCCT GGGCAAAAAAA (Biotin)

24.4. Reporter Substrate

The reporter substrate (Sub 2; FIG. 25) for this example is SubBi-3 with the sequence, 5' to 3', as below. In the current example, SubBi-3 was end-labelled with a 6-FAM moiety at the 5' end and a BHQ1 moiety at the 3' end and was designated SubBi-3-FB. Cleavage of SubBi-3-FB was monitored at 516 nm (FAM emission wavelength) with excitation at 492 nm (FAM excitation wavelength). The lower case bases represent RNA and the upper case bases represent DNA.

SEQ ID NO: 31 SubBi-3-FB:
CAGCACAACC*gu*CACCAACCG 24.5. Synthetic Target and Facilitator Sequences In the following sequences, "(Biotin)" indicates biotinylation of the oligonucleotide.

SEQ ID NO: 140 Assembly facilitator RO4/2-3b:
GCCATTGTCGAACACCTGCTGGATGACCAGC-(Biotin)

SEQ ID NO: 141 RPLPO 5 synthetic target (RO5):
GAAGGTGTAATCCGTCTCCACAGACAAGGCCAGGACTCGTTTG 24.6. Tethering of Biotinylated Partzymes to Streptavidin-Coated Micro-Titer Plate Tethering of biotinylated partzymes and assembly facilitator was conducted at room temperature in a total reaction volume of 100 µl. The binding mix contained 200 nM of partzyme RO4A4/3-5b, 200 nM of partzyme RO4B5/3-3b and 200 nM of the assembly facilitator RO4/2-3b in Amressco PBS solution (without Ca+ and Mg+). Binding mix (100 µl) was aliquoted into each well of streptavidin coated micro-titer plate (Roche Diagnostics). Binding time was 30 minutes, followed by 3 washes using PBS, each with 15 minutes incubation before wash-off.

24.7. Cleavage of Tethered MNAzyme and Detection of Cleaved Fluorescently Labeled Substrate Cleavage of fluorescently labeled substrate, SubBi-3-FB was monitored isothermally at 55° C. for 4 minutes on the FluoStar Optima fluorometer (BMG LabTech) in a total reaction volume of 100 µL. Reactions contained 200 nM of partzyme RO5A4/2-P, 200 nM of the partzyme RO5B5/2-P, 200 nM of substrate SubBi-3-FB, 25 mM $MgCl_2$, 1×PCR Buffer II (Applied Biosystems) and 200 nM of synthetic RO5 target. Nuclease-free water was used instead of synthetic RO5 target for the "no target" controls. Reaction was initiated with addition of the substrate SubBi-3-FB.

24.8. Results: Change in Level of Fluorescence in the Presence of RO5 Target Versus "No Target" Control There is an increase in fluorescence in the presence of the RO5 target compared with reactions lacking target (water control). The change in fluorescence after 4 minutes was around 36,000 units in the presence of target, compared with <1,000 units for the no target control. This demonstrates the ability of MNAzyme 1 (made up of partzymes RO5A4/2-P and RO5B5/2-P) to cleave the tethered substrate and release the partzymes that make up MNAzyme 2. Further more, it demonstrates that once released, the partzymes can form an active MNAzyme complex with the assembly facilitator that is capable of substrate cleavage leading to signal generation.

Example 25

Direct Discrimination Between Methylated Cytosines and Cytosines in DNA

The use of a stabiliser arm with a partzyme that has truncated sensor arms was used to demonstrate the capacity of MNAzymes to detect single nucleotide polymorphisms (SNPs) present in target assembly facilitators (example 22). Under the experimental condition used in that example, a five base sensor arm was used as a probe for SNPs at 55° C., well above its expected melting temperature. Systems with stabiliser arms, and partzymes that have truncated sensor arms, are very sensitive to small changes in the target. This detection strategy can be further extended to directly discriminate between targets, which are either methylated or unmethylated at specific cytosine residues, without the need for prior bisulphite modification (see example 11).

The presence of 5-methylcytosine(s) increases the melting temperature of DNA by 1.3° C. per methylated base, relative to unmethylated cytosine(s). Thus, a partzyme with, for example, a five nucleotide long sensor arm would be able to bind a target containing three 5-methylcytosines at a temperature almost 4° C. higher than it would be able to bind an unmethylated target of the same sequence.

When partzymes, a stabiliser arm, and a substrate are incubated at a temperature, which is suitable for hybridization and MNAzyme formation in the presence of a methylated target, but which is too high for MNAzyme formation in the presence of an unmethylated target, a signal would be generated only in the presence of the methylated target.

This provides a new strategy for analysis of methylation patterns which can provide a method for detection of methylation bases as markers of cancer and other diseases.

Example 26

Use of MNAzymes to Induce a Colour Change in Response to a Target

Figure 24:
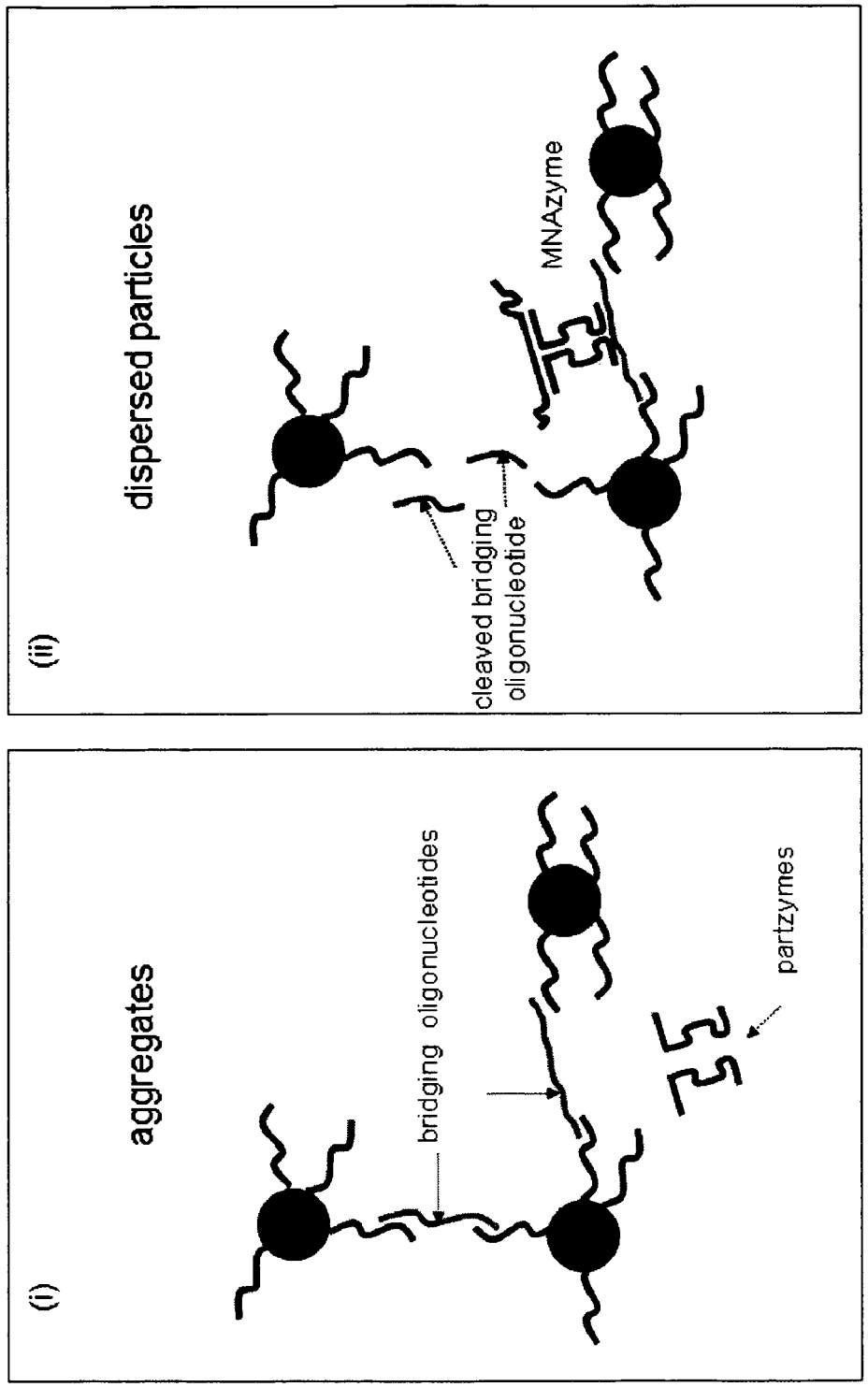
FIG. 24: Adaptation of MNAzyme detection to yield a colour-change reaction: The method uses nanoscale gold particles with attached oligonucleotides, which, when linked by bridging oligonucleotides, form a blue aggregate (panel i). The bridging oligonucleotides incorporate a substrate sequence. In the presence of target (panel ii), the MNAzyme assembles and cleaves the substrate sequence, releasing individual gold particles, and resulting in a blue to red colour change which is visible to the naked eye.

A strategy for using MNAzymes in a colourimetric format is illustrated in FIG. 24. In this approach, an MNAzyme substrate would be incorporated into a bridging oligonucleotide. The bridging oligonucleotide has complementarity to oligonucleotides attached to gold particles. If no assembly facilitator were present, the bridging oligonucleotide would remain intact and the gold particles would aggregate turning the reaction blue. If an assembly facilitator, for example a target nucleic acid, were present then active MNAzymes would assemble from partzymes present in solution, and cleave the substrate (and hence the bridging oligonucleotide). This would lead to dispersal of the gold particle aggregates which in turn would cause in a change in colour from blue to red.

This MNAzyme strategy provides a system that incorporates several generic components, and as such, it provides a method that can be rapidly adapted for any new target. This provides an advantage over other systems using DNAzymes and gold particles which require more complex molecules. In this MNAzyme strategy, the MNAzyme substrate and gold particles with attached oligonucleotides could be generic and used for analysis of any nucleic acid target. New analytical systems would merely require the synthesis of new partzymes with sensor arms complementary to the new target. Furthermore, the colourimetric reaction can also be used in conjunction with MNAzyme systems sensitive to activation by nucleic acids, proteins or other targets.

REFERENCES

Patents and Patent Publications:
PCT International Publication No. WO 99/45146
PCT International Publication No. 1B99/00848
PCT International Publication No. WO 99/50452
PCT International Publication No. WO 00/58505
PCT Application PCT/US96/02380 ("Asher")
U.S. Pat. No. 4,683,202
U.S. Pat. No. 4,683,195
U.S. Pat. No. 4,800,159
U.S. Pat. No. 5,176,995
U.S. Pat. No. 4,965,188
U.S. Pat. No. 6,140,055
U.S. Pat. No. 6,201,113
Other References:
Achenbach, J., Nutiu, R. and Li, Y. (2005) Structure-switching allosteric deoxyribozymes. Analytica Chimica Acta. 534(1): 41-51.
Adams, J. (1992) Biotin amplification of biotin and horseradish peroxidase signals in histochemical stains. J Histochem Cytochem. Oct;40(10): 1457-63.
Bobrow, M., Harris, T., Shaughnessy, K. and Litt, G. (1989) Catalyzed reporter deposition, a novel method of signal amplification. Application to immunoassays. J Immunol Methods. Dec 20(125(1-2)): 279-85.
Breaker, R. (1997) DNA enzymes. Nat Biotech. 15: 427-431.
Breaker, R.R. and Joyce, G.F. (1994) A DNA enzyme that cleaves RNA. Chem Biol. Dec; 1(4): 223-9.
Brown, A., Li, J., Pavot, C. and Lu, Y. (2003) A lead-dependent DNAzyme with a two-step mechanism. Biochem. Jun 17;42(23): 7152-61.
Cairns, M., King, A. and Sun, L. (2000) Nucleic acid mutation analysis using catalytic DNA. Nucl Acids Res. 28(3): e9.
Cairns, M., King, A. and Sun, L. (2003) Optimisation of the 10-23 DNAzyme-substrate pairing interactions enhanced RNA cleavage activity at purine-cytosine target sites. Nucl Acids Res. June 1; 31(11): 2883-9.
Carmi, N., Shultz, L. A. and Breaker, R. R. (1996) In vitro selection of self-cleaving DNAs. Chem Biol. 3(12): 1039-46.
Chehab, F. F., Doherty, M., Cai, S. P., Kan, Y. W., Cooper, S, and Rubin, E. M. (1987) Detection of sickle cell anaemia and thalassaemias [letter] [published erratum appears in Nature 1987 October 22-28; 329(6141):678]. Nature. 329 (6137): 293-4.
Chen, C., Ridzon, D., Broomer, A., Zhou, H., Barbisn, M., Lao, K. and Livak, K. (2005) MicroRNA quantitation by looped RT-PCR. AACR. poster.
Cheng, S., Merlino, G. T. and Pastan (1993) A versatile method for coupling of proteins to DNA:synthesis of a2-macroglobin-DNA conjugates. Nucleic Acid Research: 11, 659-669.
Compton, J. (1991) Nucleic acid sequence-based amplification. Nature. 350(6313): 91-2.
Cruz, R. P., Withers, J. B. and Li, Y. (2004) Dinucleotide junction cleavage versatility of 8-17 deoxyribozyme. Chem Biol. January; 11(1): 57-67.
Cuenoud, B. and Szostak, J. W. (1995) A DNA metalloenzyme with DNA ligase activity. Nature. 375(6532): 611-4.
Eigen, M. and Rigler, R. (1994) Sorting single molecules: application to diagnostics and evolutionary biotechnology. Proc Natl Acad Sci USA. 91(13): 5740-7.
Elghanian, R., Storhoff, J., Mucic, R., Letsinger, R. and Mirkin, C. (1997) Selective colorimetric detection of polynucleotides based on the distance-dependent optical properties of gold nanoparticles. Science. 277: 1078-1079.
Fahy, E., Kwoh, D. and Gingeras, T. (1991) Self-sustained sequence replication (3SR): an isothermal transcription-based amplification system alternative to PCR. PCR Methods Appl. August; 1(1): 25-33.
Hall, J. G., E is, P. S., Law, S. M., Reynaldo, L. P., Prudent, J. R., Marshall, D. J., Allawi, H. T., Mast, A. L., Dahlberg, J. E., Kwiatkowski, R. W., de Arruda, M., Neri, B. P. and Lyamichev, V. I. (2000) From the Cover: Sensitive detection of DNA polymorphisms by the serial invasive signal amplification reaction. Proc Natl Acad Sci USA. 97(15): 8272-8277.
Haseloff, J. and Gerlach, W. L. (1988) Simple RNA enzymes with new and highly specific endoribonucleases activities. Nature. August 18; 334(6183): 585-91.
Huizenga, D. and Szostak, J. (1995) A DNA aptamer that binds adenosine and ATP. Biochemistry. 34: 656-665

Illangasekare, M., Sanchez, G., Nickles, T. and Yarus, M. (1995) Aminoacyl-RNA synthesis catalyzed by an RNA. Science. 267(5198): 643-7.

Impey, H., Applegate, T., Haughton, M., Fuery, C., King, J. and Todd, A. (2000) Factors that influence deoxyribozyme cleavage during polymerase chain reaction. Anal Biochem. November 15; 286(2): 300-3.

Jonas, V., Alden, M., Curry, J., Kamisango, K., Knott, C., Lankford, R., Wolfe, J. and Moore, D. (1993) Detection and identification of *Mycobacterium tuberculosis* directly from sputum sediments by amplification of rRNA. Journal of Clinical Microbiology. 31: 2410-2416.

Kuwabara, T., Warashina, M., Nakayama, A., Ohkawa, J. and Taira, K. (1999) tRNA Val-heterodimeric maxizymes with high potential as geneinactivating agents: Simultaneous cleavage at two sites in HIV-1 tat mRNA in cultured cells. Proc Natl Acad Sci USA. 96(5): 1886-1891.

Kuwabara, T., Warashina, M. and Taira, K. (2000) Allosterically controllable maxizymes cleave mRNA with high efficiency and specificity. TIBTECH. November (18): 462-468.

Lee, J. F., Hesselberth, J. R., Meyers, L. A. and Ellington, A. D. (2004) Aptamer Database. Nucl Acids Res. 32(90001): D95-100.

Levy, M. and Ellington, A. (2003) Exponential growth by cross-catalytic cleavage of deoxyribozymogens. Proc Natl Acad Sci USA. 100(11): 6416-21.

Li, J., Zheng, W., Kwon, A. H. and Lu, Y. (2000) In vitro selection and characterization of a highly efficient Zn(II)-dependent RNA-cleaving deoxyribozyme. Nucl Acids Res. 28(2): 481-488.

Li, Y. and Sen, D. (1996) A catalytic DNA for porphyrin metallation [letter]. Nat Struct Biol. 3(9): 743-7.

Liu, J. and Lu, Y. (2004) Adenosine-dependent assembly of aptazyme-functionalized gold nanoparticles and its application as a colorimetric biosensor. Analytical Chemistry. 76: 1627-1632.

Lizardi, P., Huang, X., Zhu, Z., Bray-Ward, P., Thomas, D. and Ward, D. (1998) Mutation detection and single-molecule counting using isothermal rolling-circle amplification. Nat. Genet. July; 19(3): 225-32.

Lohse, P. A. and Szostak, J. W. (1996) Ribozyme-catalysed amino-acid transfer reactions. Nature. 381(6581): 442-4.

McCall, M., Hendry, P. and Jennings, P. (1992) Minimal Sequence Requirements for Ribozyme Activity. Proc Natl Acad Sci USA. 89(13): 5710-5714.

Mirkin, C., Letsinger, R., Mucic, R. and Storhoff, J. (1996) A DNA-based method for rationally assembling nanoparticles into macroscopic materials. Nature. 382: 607-609.

Nagamine, K., Kuzuhara, Y. and Notomi, T. (2002) Isolation of Single-Stranded DNA from Loop-Mediated Isothermal Amplification Products. Biochemical and Biophysical Research Communications. 290(4): 1195-1198.

Notomi, T., Okayama, H., Masubuchi, H., Yonekawa, T., Watanabe, K., Amino, N. and Hase, T. (2000) Loop-mediated isothermal amplification of DNA. Nucl Acids Res. June 15; 28(12): E63.

Oshima, K., Kawasaki, H., Soda, Y., Tani, K., Asano, S, and Taira, K. (2003) Maxizymes and Small Hairpin-Type RNAs That Are Driven by a tRNA Promoter Specifically Cleave a Chimeric Gene Associated with Leukemia in Vitro and in Vivo. Cancer Res. 63(20): 6809-6814.

Paul, N. and Joyce, G. (2004) Minimal self-replicating systems. Current Opinion in Chemical Biology. 8(6): 634-639.

Perreault, J., Labuda, D., Usman, N., Yang, J. and Cedergren, R. (1991) Relationship between 2'-hydroxyls and magnesium binding in the hammerhead RNA domain: a model for ribozyme catalysis. Biochemistry. 30(16): 4020-5.

Perreault, J., Wu, T., Cousineau, B., Ogilvie, K. and Cedergren, R. (1990) Mixed deoxyribo- and ribo-oligonucleotides with catalytic activity. Nature. 344(6266): 565-7.

Perriman, R., Delves, A. and Gerlach, W. L. (1992) Extended target-site specificity for a hammerhead ribozyme. Gene. 113(2): 157-63.

Raap, A., van de Corput, M., Vervenne, R., van Gijlswijk, R., Tanke, H. and Wiegant, J. (1995) Ultra-sensitive FISH using peroxidase-mediated deposition of biotin- or fluorochrome tyramides. Hum Mol Genet. April; 4(4): 529-34.

Raillard, S. A. and Joyce, G. F. (1996) Targeting sites within HIV-1 cDNA with a DNA-cleaving ribozyme. Biochemistry. 35(36): 11693-701.

Saiki, R. K., Scharf, S., Faloona, F., Mullis, K. B., Horn, G. T., Erlich, H. A. and Arnheim, N. (1985) Enzymatic amplification of beta-globin genomic sequences and restriction site analysis for diagnosis of sickle cell anemia. Science. 230(4732): 1350-4.

Santoro, S. and Joyce, G. (1997) A general purpose RNA cleaving DNA enzyme. Proc Natl Acad Sci USA. 94: 4262-4266.

Santoro, S. W. and Joyce, G. F. (1998) Mechanism and utility of an RNA-cleaving DNA enzyme. Biochem. 37(38): 13330-42.

Schubert, S., Furste, J., Werk, D., Grunert, H., Zeichhardt, H., Erdmann, V. and Kurreck, J. (2004) Gaining target access for deoxyribozymes. J Mol Biol. May 28; 339(2): 355-63.

Sidorov, A., Grasby, J. and Williams, D. (2004) Sequence-specific cleavage of RNA in the absence of divalent metal ions by a DNAzyme incorporating imidazolyl and amino functionalities. Nucl Acids Res. March 5; 32(4): 1591-601.

Silverman, S. (2004) Breaking up is easy to do (if you're a DNA enzyme that cleaves RNA). Chem Biol. January; 11(1): 7-8.

Tarasow, T. M., Tarasow, S. L. and Eaton, B. E. (1997) RNA-catalysed carbon-carbon bond formation. Nature. 389(6646): 54-7.

Todd, A. V., Fuery, C. J., Impey, H. L., Applegate, T. L. and Haughton, M. A. (2000) DzyNA-PCR: use of DNAzymes to detect and quantify nucleic acid sequences in a real-time fluorescent format. Clin Chem. May; 46(5): 625-630.

Urdea, M. (1993) Synthesis and characterization of branched DNA (bDNA) for direct and quantitative detection of CMV, HBV, HCV and HIV. Clin Chem. 39: 725-726.

van Gijlswijk, R., Zijimans, H., Wiegant, J., Bobrow, M., Erickson, T., Adler, K., Tanke, H. and Raap, A. (1997) Fluorochrome-labeled tyramides: use in immunocytochemistry and fluorescence in situ hybridization. J Histochem Cytochem. March; 45(3): 375-82.

Walker, G. T., Fraiser, M. S., Schram, J. L., Little, M. C., Nadeau, J. G. and Malinowski, D. P. (1992) Strand displacement amplification—an isothermal, in vitro DNA amplification technique. Nucl Acids Res. 20(7): 1691-6.

Warashina, M., Kuwabara, T., Nakamatsu, Y. and Taira, K. (1999) Extremely high and specific activity of DNA enzymes in cells with a Philadelphia chromosome. Chem Biol. April; 6(6): 237-50.

Yakimovich, O., Alekseev, Y., Maksimenko, A., Voronina, O. and Lunin, V. (2003) Influence of DNA aptamer structure on the specificity of binding to Taq DNA polymerase. Biochemistry (Moscow). 68(2): 228-235.

Zaborowska, Z., Furste, J., Erdmann, V. and Kurreck, J. (2002) Sequence requirements in the catalytic core of the "10-23" DNA enzyme. J Biol Chem. 277(43): 240617-22.

Zhang, S., Scharadin, N., Purohit, P. and Chasin, L. (2005) Aptamer-based multiplexed amplified real-time biochemical detector. Indiana Biosensor Symposium. Poster.

The invention claimed is:

1. A composition comprising at least two or more component oligonucleotides wherein at least a first component oligonucleotide and a second component oligonucleotide self-assemble in the presence of an MNAzyme assembly facilitator comprising a nucleic acid to form a catalytically active multi-component nucleic acid enzyme (MNAzyme), wherein each of said at least first and said second component oligonucleotides comprise a substrate arm portion, a catalytic core portion from SEQ ID NO:47 or 48, and a sensor arm portion;
wherein upon self-assembly, the sensor arm portion of said first and second component oligonucleotides act as sensor arms of the MNAzyme, the substrate arm portion of the first and second component oligonucleotides act as substrate arms of the MNAzyme, and the catalytic core portion of the first and second component oligonucleotides act as a catalytic core of the MNAzyme;
and wherein the sensor arms of the MNAzyme hybridize with said MNAzyme assembly facilitator so as to maintain the first and second component oligonucleotides in proximity for association of their respective catalytic core portions to form the catalytic core of the MNAzyme, said catalytic core capable of cleaving at least one substrate comprising a nucleic acid, and wherein said substrate arms of said MNAzyme hybridize to the substrate so that said catalytic core of said MNAzyme is capable of cleaving said substrate;
and wherein the catalytic core comprises deoxribonucleotides.

2. The composition of claim 1 wherein said nucleic acid is selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other noncoding RNAs, ribosomal RNA, derivatives thereof, amplicons, and any combination thereof.

3. The composition of claim 2, wherein the source of the nucleic acid is selected from the group consisting of synthetic, mammalian, human, animal, plant, fungal, bacterial, viral, archael and any combination thereof.

4. The composition of claim 2, wherein said nucleic acid is amplified.

5. The composition of claim 4 wherein said nucleic acid is amplified by one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

6. The composition of claim 1, further comprising at least a third component oligonucleotide which acts to stabilise at least one of said substrate arm portions or sensor arm portions by binding to the substrate or assembly facilitator adjacent to the substrate arm portion or sensor arm portion being stabilized.

7. The composition of claim 1, wherein the catalytic core portions of the first component oligonucleotide and the catalytic core portion of the second component oligonucleotide comprise SEQ ID NOS. 150 and 166; SEQ ID NOS. 151 and 167; SEQ ID NOS. 152 and 168.

8. The composition of claim 7, wherein the catalytic core portions of the first component oligonucleotide and the catalytic core portion of the second component oligonucleotide are SEQ ID NOS. 151 and 167.

9. The composition of claim 1, wherein the first or second component oligonucleotide further comprises an aptamer that binds to at least one inhibitor of said self assembly of said MNAzyme; wherein binding of a target analyte to the aptamer prevents binding of the inhibitor and allows assembly of the MNAzyme.

10. The composition of claim 1 wherein at least one of said component oligonucleotides or assembly facilitator or substrate or a combination thereof further comprises at least one aptamer or portion thereof.

11. The composition of claim 10 wherein said aptamer or portion thereof is comprised of at least one of nucleic acid, peptide, polypeptide or protein or a derivative or combination thereof.

12. The composition of claim 10 wherein at least one of said first or said second component oligonucleotides or said assembly facilitator or said substrate further comprises at least one portion of self complementary sequence capable of forming a hairpin structure.

13. The composition of claim 12 wherein said hairpin structure inhibits self assembly of said MNAzyme.

14. The composition of claim 13, wherein the hairpin structure includes an aptamer and said inhibition of self assembly is removed upon contact of the aptamer with a target analyte, as a result of the target analyte binding the aptamer and disrupting the hairpin.

15. The composition of claim 10 wherein said aptamer, or portion thereof, binds a target selected from the group consisting of nucleic acids, proteins, glycoproteins, lipids, lipoproteins, cells, viruses, bacteria, archaea, fungi, antibodies, metabolites, pathogens, toxins, contaminants, poisons, small molecules, polymers, metal ions, metal salts, prions, any derivatives, any portions, and combinations thereof.

16. The composition of claim 1 wherein said nucleic acid comprises at least one of a labeled nucleic acid, RNA, DNA, nucleic acid analogue, peptide nucleic acid, locked nucleic acid, peptide-nucleic acid chimera, or any combination thereof.

17. The composition of claim 1, wherein said substrate further comprises at least one nanoparticle or microparticle, or combination thereof.

18. The composition of claim 1 wherein said substrate is attached to an insoluble support or free in solution.

19. The composition of claim 1, wherein said substrate comprises a detectable portion and a quencher portion, wherein upon cleavage of said substrate by said MNAzyme, a detectable effect provided by said detectable portion is increased or decreased.

20. The composition of claim 1 wherein said cleavage of said substrate by said MNAzyme provides a detectable effect.

21. The composition of claim 20 wherein said detectable effect is detected by fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

22. The composition of claim 20 wherein said detectable effect is measured and wherein the magnitude of said measurement is indicative of the quantity of a target.

23. The composition of claim 1 wherein at least one of said component oligonucleotides, said assembly facilitator or said substrate comprises at least one nucleotide substitution or addition selected from the group consisting of 4-acetylcytidine, 5-(carboxyhydroxylmethyl)uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyl-5-methyluridine, 2'-O-methyluridine, wybutosine, 3-(3-amino-3-carboxypropyl)uridine, beta D-arabinosyl uridine, and beta D-arabinosyl thymidine.

24. A kit for assembling a plurality of MNAzymes, comprising (a) a plurality of pairs of first and second component oligonucleotides according to claim 1, each pair of first and second component oligonucleotides corresponding to each of a plurality of nucleic acid assembly facilitators, and (b) at least one nucleic acid substrate.

25. A method for making a plurality of multi-component nucleic acid enzymes (MNAzymes) that each recognize at least one assembly facilitator and cleave a substrate, the method comprising:
   (a) providing a plurality of nucleic acid assembly facilitators to be identified, detected or quantified,
   (b) designing two or more component oligonucleotides wherein at least a first component oligonucleotide and a second component oligonucleotide self-assemble in the presence of an assembly facilitator to form a catalytically active multi-component nucleic acid enzyme (MNAzyme), wherein each of the at least first and second component oligonucleotides comprise a substrate arm portion, a catalytic core portion from SEQ ID NO:47 or 48, and a sensor arm portion,
   wherein upon self-assembly, the sensor arm portion of the first and second component oligonucleotides form sensor arms of the MNAzyme, the substrate arm portion of the first and second component oligonucleotides form substrate arms of the MNAzyme, and the catalytic core portion of the first and second component oligonucleotides form a catalytic core of the MNAzyme;
   and wherein the sensor arms of the MNAzyme hybridize with a nucleic acid assembly facilitator so as to maintain the first and second component oligonucleotides in proximity for association of their respective catalytic core portions to form the catalytic core of the MNAzyme, said catalytic core capable of acting on at least one substrate, and wherein the substrate arms of the MNAzyme hybridize to a nucleic acid substrate so that the catalytic core of the MNAzyme can cleave said substrate;
   and wherein the catalytic core comprises deoxyribonucleotides;
   (c) altering said two or more component oligonucleotides such that the substrate arm portion and the catalytic core portion of the first and second component oligonucleotides is constant, and the sensor arm portion of at least one of the first and second component oligonucleotides is adapted to recognize another of the plurality of nucleic acid assembly facilitators, and
   (d) repeating the altering step for each of the plurality of nucleic acid assembly facilitators.

* * * * *